US006462049B1

(12) United States Patent
Ogura et al.

(10) Patent No.: US 6,462,049 B1
(45) Date of Patent: Oct. 8, 2002

(54) ETHYLENE DERIVATIVES AND PESTICIDES CONTAINING SAID DERIVATIVES

(75) Inventors: Tomoyuki Ogura; Hiroshi Murakami; Akira Numata; Rika Miyachi, all of Funabashi; Toshiro Miyake, Minamisaitama; Norihiko Mimori, Minamisaitama; Shinji Takii, Minamisaitama, all of (JP)

(73) Assignee: Nissan Chemical Industries, Ltd., Tokyo (JP)

( * ) Notice: Subject to any disclaimer, the term of this patent is extended or adjusted under 35 U.S.C. 154(b) by 0 days.

(21) Appl. No.: 09/492,321

(22) Filed: Jan. 27, 2000

Related U.S. Application Data

(60) Division of application No. 09/177,501, filed on Oct. 23, 1998, now Pat. No. 6,063,734, which is a continuation-in-part of application No. PCT/JP97/01440, filed on Apr. 24, 1997.

(30) Foreign Application Priority Data

Apr. 25, 1996 (JP) ........................................ HEI8-104878
Jun. 7, 1996 (JP) ........................................ HEI8-145802
Jun. 20, 1996 (JP) ........................................ HEI8-159346
Feb. 13, 1997 (JP) ........................................ HEI9-28916

(51) Int. Cl.[7] ..................... A61K 31/50; A61K 31/425; A61K 31/47; A61K 31/44; C07D 217/00
(52) U.S. Cl. ................. 514/254.02; 514/365; 514/307; 514/311; 514/342; 504/266; 504/138; 504/137; 546/139
(58) Field of Search ................................ 548/188, 186, 548/193; 514/365, 307, 311, 342, 254.02; 504/266, 130, 138, 136, 256; 546/139, 141, 152, 158, 269.7, 316, 367

(56) References Cited

U.S. PATENT DOCUMENTS

| | | | |
|---|---|---|---|
| 3,337,565 A | | 8/1967 | Bencze et al. |
| 3,337,566 A | | 8/1967 | Walker et al. |
| 4,600,712 A | | 7/1986 | Haken et al. |
| 4,988,818 A | * | 1/1991 | Lauer et al. |
| 5,064,844 A | | 11/1991 | O'Mahoney et al. |
| 5,364,860 A | * | 11/1994 | Bru-Maginez et al. |

FOREIGN PATENT DOCUMENTS

| | | |
|---|---|---|
| DE | 283 916 A5 | 10/1990 |
| EP | 0189960 | 8/1986 |
| EP | 0 706 758 A | 4/1996 |
| EP | 0842931 | 5/1998 |
| GB | 2051052 | 1/1981 |
| GB | 2051060 | 1/1981 |
| JP | 52-105167 | 9/1977 |
| JP | 53-92769 | 8/1978 |
| JP | A-57-502215 | 12/1982 |
| JP | A-59-219228 | 12/1984 |
| JP | A-60-11401 | 1/1985 |
| JP | A-60-11452 | 1/1985 |
| JP | A-60-209571 | 10/1985 |
| WO | WO 95/29591 | 11/1995 |
| WO | WO 97/40009 A | 10/1997 |
| WO | WO 98/42683 | 10/1998 |
| WO | WO 99/02507 | 1/1999 |

OTHER PUBLICATIONS

J. Entomol. Sci., (1987), 22(3), pp. 224–236.
J. Econ. Entomol., (1985), 78(6), pp. 1327–1330.
Phosphorus, Sulfur, and Silicon, (1992), 72, pp. 121–125.
Khim. Geterotsikl. Soedin., (1974), 4, pp. 500–502 (together with an English edition thereof).
Tet. Lett., (1996), 37(34), pp. 6213–6216.
Khim.–Farm. Zh., (1989), 23(6), pp. 695–696; abstract (English).
DD 240,544 A1; abstract (English).
V. Kantlehner et al., "Umsetzung von 2,5–Dimethyl–1,3, 4–thiadiazol mit Saurechloriden", *Chemiker–Zeitung*, vol. 113, pp. 125–127, (1989).
V. Kantlehner et al., "Umsetzung von 2,5–Dimethyl1–1,3, 4–thiadiazol mit Carbonsaureestern", *Chemiker–Zeitung*, vol. 113, pp. 217–219, (1989).
L. Zirngibl et al., Structure–Activity Relationships of 2–(1H–Imidazol–1–yl) vinyl Eters (Route to the New Broad–Spectrum Antifungal Agent Omoconazole); *Annals New York Academy of Sciences*, pp. 64–73.
Khim.–Farm. Zh., 22(10), (1988), pp. 1223–1225.
Chemical Abstracts, vol. 109, Abstract No. 93171 & Zh. Obshch. Khim., 57(10), (1987), pp. 2234–2249.
Chemical Abstracts, vol. 101, Abstract No. 211021 & Bull. Chem. Soc. Jpn., 57(8), (1984), pp. 2329–2330.
Chemical Abstracts, vol. 96, Abstract No. 217794 & Indian J. Chem., Sect. B, 21B(1), pp. 1–3.
SU 1,237,667 (English Abstract).
JP 60–220785 (English Abstract).
A. Alberola, "Production and Transformation of Carbanions Derived from C4α–Functionalized 3,5–Dimethylisothiazoles" *Gazzetta Chemica Italiana*, vol. 117, pp. 461–467, (1987).

(List continued on next page.)

*Primary Examiner*—D. Margaret Seaman
*Assistant Examiner*—Binta Robinson
(74) *Attorney, Agent, or Firm*—Oliff & Berridge, PLC

(57) ABSTRACT

Ethylene derivatives of formula (I):

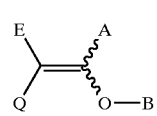

(I)

where Q is an unsubstituted or substituted phenyl or heterocyclic group, especially a 4-thiazolyl, 1- or 3-pyrazolyl, 1,3-oxazol-4-yl, phenyl or pyridyl group; E is a substituent such as a cyano group; A is a substituent such as a 4-pyrazolyl or thiazolyl group; and B is a substituent such as an alkylcarbonyl group. Agricultural chemicals and agents for preventing the attachment of aquatic organisms containing one or more such ethylene derivatives.

32 Claims, No Drawings

OTHER PUBLICATIONS

Ukr. Khim. Zh, (1987), 53, pp. 1085–1088 (English Abstract).

Geol., Khim. Biol. Nauki, (1986), 6, pp. 36–40, (English Abstract).

Geol., Khim biol. Nauki, (1984), 3, pp. 33–35, (English Abstract).

J. Prakt. Chem., (1974), 316, pp. 684–692, (English Abstract).

F. Eiden et al.; "Polycarbonylmethyl–Derivative: Reaktionen von 2–(3–Methyl–5–isoxazolyl)–1–phenylethanon" *Institut fur Pharmazie und Levensmittelchemie der Universitat Munchen,* pp. 242–251, (1985).

T. Eicher et al., "Zur Reaktion von Triafulvenen mit Isonitrilen, Eine einfache Synthese von diphenylsubstituierten funktionalisierten Cyclobuten–Derivaten und deren Folgeprodukten", *Universitat des Saarlandes,* pp. 619–626, (1987).

Ukr. Khim. Zh. (Russ. Ed.), 51(6), (1985), pp. 649–652.

A. Alberola et al., Produccion Y Transformacion De Carbaniones Derivados De 3,5–Dimetilisoxazoles Funcionalizados En C–4, *Universidad de Valladolid,* vol. 83, pp. 182–194, (1986).

* cited by examiner

US 6,462,049 B1

ETHYLENE DERIVATIVES AND PESTICIDES CONTAINING SAID DERIVATIVES

This application is a divisional of 09/177501 filed Oct. 23, 1998 now U.S. Pat. No. 6,063,734 which is CIP of PCT/JP97/01440 filed Apr. 24, 1997.

BACKGROUND OF THE INVENTION

1. Field of the Art

The present invention relates to novel ethylene derivatives, and also to agricultural chemicals and agents for preventing the attachment of aquatic organisms containing said derivatives as an active ingredient. The agricultural chemicals as referred to herein include insecticides, acaricides, nematocides, herbicides and fungicides, etc., and are especially pesticides in the field of agriculture, horticulture, stock farming and sanitation. The agent for preventing the attachment of aquatic organisms are chemicals for preventing the attachment of harmful aquatic organisms such as shells and algae to fishing nets, the bottoms of ships, marine equipment such as buoys, marine constructions, circulating water systems in thermal and atomic power plants, inlet channels for heat exchanger cooling water in chemical industry, underwater constructions and reservoirs.

2. Description of the Related Art

For acrylonitrile derivatives, Japanese Patent Application Laid-Open No. Sho 53-92769 discloses the use of 2'-chloro-3-hydroxy-2-(4-phenyl-2-thiazolyl)-cinnamoyl nitrile as an insecticide; and International Patent Application Laid-Open No. WO-95/29591 discloses its use as an aquatic adhesion inhibitor. Japanese Patent Application Laid-open No. Sho 60-11452 discloses the use of 2-(4-chlorophenyl)-3-(3-pyridyl)-3-oxopropionitrile as a herbicide and Japanese Patent Application Laid-open No. Sho 60-11401 discloses its use as a fungicide.

With the long-term use of insecticides and fungicides, recently, some pests have become resistant to chemicals and are often difficult to exterminate with conventional insecticides and fungicides. In addition, some insecticides are highly toxic and are prone to remain long, without being decomposed, to destroy the ecosystem. Accordingly, it is always expected to develop novel, low-toxic and low-persistent insecticides and fungicides.

On the other hand, in order to prevent the adhesion and growth of marine and freshwater aquatics, it is used antifouling coatings comprising organic tin compounds such as bis(tributyltin) oxide or copper compounds such as copper sulfate and cuprous oxide. However, organic tin compounds are highly toxic, though being effective in preventing the adhesion of aquatics, and are especially prone to accumulate in the bodies of fishes and shellfishes. As so promoting the environmental pollution, the use of those compounds is now under legal controls. Copper compounds are widely used in antifouling coatings for inlet channels and for the bottoms of ships. However, like tin compounds, copper compounds contain a copper as a heavy metal. Therefore, the use of copper compounds will bring about the environmental pollution in future, and agents for preventing the attachment of aquatic organisms comprising such copper compounds are not preferred. Under the above-mentioned situation, it has been desired agents for preventing the attachment of aquatic organisms that have few influences on the ecosystem and bring about little secondary pollution.

SUMMARY OF THE INVENTION

In order to solve the above-mentioned problems, the present inventors have assiduously studied to develop agricultural chemicals and agents for preventing the attachment of aquatic organisms which can exhibit excellent pesticidal activities even when used in small amounts, and which have few negative influences on non-targeted organisms such as mammals, fishes and useful insects, and, as a result, have found that the compounds mentioned hereinunder are highly safe and have excellent pesticidal activities and activities for preventing the attachment of aquatic organisms. On the basis of these findings, the present inventors have completed the present invention.

DETAILED DESCRIPTION OF THE INVENTION

Specifically, the present invention provides the following [1] to [25]

[1] Ethylene derivatives of a formula (I):
[wherein;
Q represents a phenyl group optionally substituted by G, a naphthyl group optionally substituted by G, or a heterocyclic group optionally substituted by R (said heterocyclic group being a thienyl, furyl, pyrrolyl, oxazolyl, isoxazolyl, thiazolyl, isothiazolyl, pyrazolyl, imidazolyl, 1,3,4-oxadiazolyl, 1,2,4-oxadiazolyl, 1,3,4-thiadiazolyl, 1,2,4-thiadiazolyl, 1,2,4-triazolyl, 1,2,3-thiadiazolyl, 1,2,3-triazolyl, 1,2,3,4-tetrazolyl, pyridinyl, pyrimidinyl, pyrazinyl, pyridazinyl, 1,3,5-triazinyl, 1,2,4-triazinyl, 1,2,4,5-tetrazinyl, pyrazolinyl, imidazolinyl, oxazolinyl, isoxazolinyl, thiazolinyl, imidazolinone, imidazolidinedione, 3(2H)-pyridazinone, benzothiazolyl, benzimidazolyl, indazolyl, benzoxazolyl, quinolyl, isoquinolyl, quinoxalinyl, phthalazinyl, cinnolinyl or quinazolinyl group);

A represents a phenyl group optionally substituted by W, a naphthyl group optionally substituted by W, or a heterocyclic group optionally substituted by Y (said heterocyclic group being a thienyl, furyl, pyrrolyl, oxazolyl, isoxazolyl, thiazolyl, isothiazolyl, pyrazolyl, imidazolyl, 1,3,4-oxadiazolyl, 1,2,4-oxadiazolyl, 1,3,4-thiadiazolyl, 1,2,4-thiadiazolyl, 1,2,4-triazolyl, 1,2,3-thiadiazolyl, 1,2,3-triazolyl, 1,2,3,4-tetrazolyl, pyridinyl, pyrimidinyl, pyrazinyl, pyridazinyl, 1,3,5-triazinyl, 1,2,4-triazinyl, pyrazolinyl, imidazolinyl, oxazolinyl, isoxazolinyl, thiazolinyl, 3(2H)-pyridazinone, benzothiazolyl, benzimidazolyl, indazolyl, benzoxazolyl, quinolyl, isoquinolyl, quinoxalinyl, phthalazinyl, cinnolinyl or quinazolinyl group);

provided that, (a) when Q is a thienyl group optionally substituted by R, a furyl group optionally substituted by R, a quinolyl group optionally substituted by R, or an isoquinolyl group optionally substituted by R, then A is a phenyl group optionally substituted by W, a naphthyl group optionally substituted by W, or a heterocyclic group optionally substituted by Y (said heterocyclic group being a pyrrolyl, oxazolyl, isoxazolyl, thiazolyl, isothiazolyl, pyrazolyl, imidazolyl, 1,3,4-oxadiazolyl, 1,2,4-oxadiazolyl, 1,3,4-thiadiazolyl, 1,2,4-thiadiazolyl, 1,2,4-triazolyl, 1,2,3-thiadiazolyl, 1,2,3-triazolyl, 1,2,3,4-tetrazolyl, pyrimidinyl, pyrazinyl, pyridazinyl, 1,3,5-triazinyl, 1,2,4-triazinyl, pyrazolinyl, imidazolinyl, oxazolinyl, isoxazolinyl, thiazolinyl, 3(2H)-pyridazinone, benzothiazolyl, benzimidazolyl, indazolyl, benzoxazolyl, quinoxalinyl, phthalazinyl, cinnolinyl or quinazolinyl group);

(b) when Q is a 2-thiazolyl group optionally substituted by R, then A is a naphthyl group optionally substituted by W, or a heterocyclic group optionally substituted by Y (said heterocyclic group being a thienyl, furyl, pyrrolyl, oxazolyl, isoxazolyl, thiazolyl, isothiazolyl, pyrazolyl, imidazolyl, 1,3,4-oxadiazolyl, 1,2,4-oxadiazolyl, 1,3,4-thiadiazolyl, 1,2,4-thiadiazolyl, 1,2,4-triazolyl, 1,2,3-thiadiazolyl, 1,2,3-triazolyl, 1,2,3,4-tetrazolyl, pyridinyl, pyrimidinyl, pyrazinyl, pyridazinyl, 1,3,5-triazinyl, 1,2,4-triazinyl, pyrazolinyl, imidazolinyl, oxazolinyl, isoxazolinyl, thiazolinyl, 3(2H)-pyridazinone, benzothiazolyl, benzimidazolyl, indazolyl, benzoxazolyl, quinolyl, isoquinolyl, quinoxalinyl, phthalazinyl, cinnolinyl or quinazolinyl group);

(c) when Q is a pyridyl group optionally substituted by R, then A is a heterocyclic group optionally substituted by Y (said heterocyclic group being a pyrrolyl, oxazolyl, isoxazolyl, thiazolyl, isothiazolyl, pyrazolyl, imidazolyl, 1,3,4-oxadiazolyl, 1,2,4-oxadiazolyl, 1,3,4-thiadiazolyl, 1,2,4-thiadiazolyl, 1,2,4-triazolyl, 1,2,3-thiadiazolyl, 1,2,3-triazolyl, 1,2,3,4-tetrazolyl, pyrazinyl, 1,3,5-triazinyl, 1,2,4-triazinyl, pyrazolinyl, imidazolinyl, oxazolinyl, isoxazolinyl, thiazolinyl, 3(2H)-pyridazinone, benzothiazolyl, benzimidazolyl, indazolyl, benzoxazolyl, quinoxalinyl, phthalazinyl, cinnolinyl or quinazolinyl group);

(d) when Q is an isothiazolyl group optionally substituted by R, a 1,2,3-triazolyl group optionally substituted by R, or a benzoxazolyl group optionally substituted by R, then A is a naphthyl group optionally substituted by W, or a heterocyclic group optionally substituted by Y (said heterocyclic group being a thienyl, furyl, pyrrolyl, oxazolyl, isoxazolyl, thiazolyl, isothiazolyl, pyrazolyl, imidazolyl, 1,3,4-oxadiazolyl, 1,2,4-oxadiazolyl, 1,3,4-thiadiazolyl, 1,2,4-thiadiazolyl, 1,2,4-triazolyl, 1,2,3-thiadiazolyl, 1,2,3-triazolyl, 1,2,3,4-tetrazolyl, pyridinyl, pyrimidinyl, pyrazinyl, pyridazinyl, 1,3,5-triazinyl, 1,2,4-triazinyl, pyrazolinyl, imidazolinyl, oxazolinyl, isoxazolinyl, thiazolinyl, 3(2H)-pyridazinone, benzothiazolyl, benzimidazolyl, indazolyl, benzoxazolyl, quinolyl, isoquinolyl, quinoxalinyl, phthalazinyl, cinnolinyl or quinazolinyl group);

(e) when Q is a 1,2,4-triazolyl group optionally substituted by R, then A is a heterocyclic group optionally substituted by Y (said heterocyclic group being a thienyl, furyl, pyrrolyl, oxazolyl, isoxazolyl, thiazolyl, isothiazolyl, pyrazolyl, imidazolyl, 1,3,4-oxadiazolyl, 1,2,4-oxadiazolyl, 1,3,4-thiadiazolyl, 1,2,4-thiadiazolyl, 1,2,4-triazolyl, 1,2,3-thiadiazolyl, 1,2,3-triazolyl, 1,2,3,4-tetrazolyl, pyrimidinyl, pyrazinyl, pyridazinyl, 1,3,5-triazinyl, 1,2,4-triazinyl, pyrazolinyl, imidazolinyl, oxazolinyl, isoxazolinyl, thiazolinyl, 3(2H)-pyridazinone, benzothiazolyl, benzimidazolyl, indazolyl, benzoxazolyl, quinolyl, isoquinolyl, quinoxalinyl, phthalazinyl, cinnolinyl or quinazolinyl group);

(f) when Q is a benzothiazolyl group optionally substituted by R, then A is a naphthyl group optionally substituted by W, or a heterocyclic group optionally substituted by Y (said heterocyclic group being a furyl, pyrrolyl, oxazolyl, isoxazolyl, thiazolyl, isothiazolyl, pyrazolyl, imidazolyl, 1,3,4-oxadiazolyl, 1,2,4-oxadiazolyl, 1,3,4-thiadiazolyl, 1,2,4-thiadiazolyl, 1,2,4-triazolyl, 1,2,3-thiadiazolyl, 1,2,3-triazolyl, 1,2,3,4-tetrazolyl, pyridinyl, pyrimidinyl, pyrazinyl, pyridazinyl, 1,3,5-triazinyl, 1,2,4-triazinyl, pyrazolinyl, imidazolinyl, oxazolinyl, isoxazolinyl, thiazolinyl, 3(2H)-pyridazinone, benzothiazolyl, benzimidazolyl, indazolyl, benzoxazolyl, quinolyl, isoquinolyl, quinoxalinyl, phthalazinyl, cinnolinyl or quinazolinyl group);

(g) when Q is a benzimidazolyl group optionally substituted by R, then A is a naphthyl group optionally substituted by W, or a heterocyclic group optionally substituted by Y (said heterocyclic group being a pyrrolyl, oxazolyl, isoxazolyl, thiazolyl, isothiazolyl, pyrazolyl, imidazolyl, 1,3,4-oxadiazolyl, 1,2,4-oxadiazolyl, 1,3,4-thiadiazolyl, 1,2,4-thiadiazolyl, 1,2,4-triazolyl, 1,2,3-thiadiazolyl, 1,2,3-triazolyl, 1,2,3,4-tetrazolyl, pyrazinyl, 1,3,5-triazinyl, 1,2,4-triazinyl, pyrazolinyl, imidazolinyl, oxazolinyl, isoxazolinyl, thiazolinyl, 3(2H)-pyridazinone, benzothiazolyl, benzimidazolyl, indazolyl, benzoxazolyl, quinolyl, isoquinolyl, quinoxalinyl, phthalazinyl, cinnolinyl or quinazolinyl group);

(h) when Q is a phenyl group optionally substituted by G, then A is a heterocyclic group optionally substituted by Y (said heterocyclic group being a pyrrolyl, oxazolyl, isoxazolyl, thiazolyl, isothiazolyl, pyrazolyl, 1,3,4-oxadiazolyl, 1,2,4-oxadiazolyl, 1,3,4-thiadiazolyl, 1,2,4-thiadiazolyl, 1,2,4-triazolyl, 1,2,3-thiadiazolyl, 1,2,3-triazolyl, 1,2,3,4-tetrazolyl, pyrazinyl, pyridazinyl, 1,3,5-triazinyl, 1,2,4-triazinyl, pyrazolinyl, imidazolinyl, oxazolinyl, isoxazolinyl, thiazolinyl, 3(2H)-pyridazinone, benzothiazolyl, benzimidazolyl, indazolyl, benzoxazolyl, quinoxalinyl, phthalazinyl, cinnolinyl or quinazolinyl group);

(i) when Q is a naphthyl group optionally substituted by G, then A is a heterocyclic group optionally substituted by Y (said heterocyclic group being a thienyl, pyrrolyl, oxazolyl, isoxazolyl, thiazolyl, isothiazolyl, pyrazolyl, imidazolyl, 1,3,4-oxadiazolyl, 1,2,4-oxadiazolyl, 1,3,4-thiadiazolyl, 1,2,4-thiadiazolyl, 1,2,4-triazolyl, 1,2,3-thiadiazolyl, 1,2,3-triazolyl, 1,2,3,4-tetrazolyl, pyridinyl, pyrimidinyl, pyrazinyl, pyridazinyl, 1,3,5-triazinyl, 1,2,4-triazinyl, pyrazolinyl, imidazolinyl, oxazolinyl, isoxazolinyl, thiazolinyl, 3(2H)-pyridazinone, benzothiazolyl, benzimidazolyl, indazolyl, benzoxazolyl, quinolyl, isoquinolyl, quinoxalinyl, phthalazinyl, cinnolinyl or quinazolinyl group);

B represents H, a $C_1$–$C_4$ alkyl group, a $C_1$–$C_4$ haloalkyl group, a $C_2$–$C_4$ alkoxyalkyl group, $CH_3SCH_2$, $CH_3OC_2H_4OCH_2$, a $C_1$–$C_4$ alkyl group substituted by a phenyl group optionally substituted by a halogen or a $C_1$–$C_4$ alkyl group, a $C_1$–$C_4$ alkyl group substituted by a benzoyl group optionally substituted by a halogen or a $C_1$–$C_4$ alkyl group, a tetrahydropyranyl group, $(CH_3)_3$ Si, a $C_1$–$C_4$ alkylsulfonyl group, a phenylsulfonyl group optionally substituted by a halogen or a $C_1$–$C_4$ alkyl group, —$SO_2CF_3$, a $C_1$–$C_4$ monoalkylaminosulfonyl group, a $C_2$–$C_8$ dialkylaminosulfonyl group, a phenylaminosulfonyl group, a $C_2$–$C_5$ monoalkylaminothiocarbonyl group, a $C_3$–$C_9$ dialkylaminothiocarbonyl group, a $C_2$–$C_5$ cyano alkyl group, a $C_3$–$C_9$ alkoxycarbonylalkyl group, —C(=O)$T^1$, —P(=O)$T^2T^3$, —P(=S)$T^2T^3$, an alkali Metal atom, an alkaline earth metal atom, or $NHT^4T^5T^6$;

provided that, when Q is a 2-thiazolyl or 2-benzothiazolyl group, then B is a $C_1$–$C_4$ alkyl group, a $C_1$–$C_4$ haloalkyl group, a $C_2$–$C_4$ alkoxyalkyl group, $CH_3SCH_2$, $CH_3OC_2H_4OCH_2$, a $C_1$–$C_4$ alkyl group substituted by a phenyl group optionally substituted by a halogen or a $C_1$–$C_4$ alkyl group, a $C_1$–$C_4$ alkyl group substituted by a benzoyl group optionally substituted by a halogen or a $C_1$–$C_4$ alkyl group, a tetrahydropyranyl group, $(CH_3)_3Si$, a $C_1$–$C_4$ alkylsulfonyl group, a phenylsulfonyl group optionally substituted by a halogen or a $C_1$–$C_4$ alkyl group, —$SO_2CF_3$, a $C_1$–$C_4$ monoalkylaminosulfonyl group, a $C_2$–$C_8$ dialkylaminosulfonyl group, a phenylaminosulfonyl group, a $C_2$–$C_5$ monoalkylaminothiocarbonyl group, a $C_3$–$C_9$ dialkylaminothiocarbonyl group, a $C_2$–$C_5$ cyanoalkyl group, a $C_3$–$C_9$ alkoxycarbonylalkyl group, —$C(=O)T^1$, —$P(=O)T^2T^3$, or —$P(=S)T^2T^3$;

E represents a heterocyclic group optionally substituted by a $C_1$–$C_4$ alkyl or $C_1$–$C_4$ haloalkyl group—(said heterocyclic group being a 2-oxazolyl, 2-thiazolyl, 2-imidazolyl, 1,2,4-triazol-3-yl, 1,2,4-oxadiazol-3-yl, 1,2,4-thiadiazol-3-yl, 1,3,4-oxadiazol-2-yl, 5-tetrazolyl, 2-oxazolinyl or 1,2,4,5-tetrazin-3-yl group)—or represents a halogen, a $C_2$–$C_4$ alkynyl group, a phenylethynyl group optionally substituted by Z, a $C_1$–$C_4$ haloalkyl group, CN, an isonitrile group, $NO_2$, $N_3$, CHO, a $C_2$–$C_5$ alkylcarbonyl group, a $C_2$–$C_5$ alkoxycarbonyl group, a $C_3$–$C_5$ alkenyloxycarbonyl group, a $C_2$–$C_4$ alkylaminocarbonyl group, a $C_3$–$C_9$ dialkylaminocarbonyl group, a benzoyl group optionally substituted by Z, an aminothiocarbonyl group, a $C_1$–$C_4$ alkylsulfenyl group, a $C_1$–$C_4$ alkylsulfinyl group, a $C_1$–$C_4$ alkylsulfonyl group, a phenylsulfenyl group optionally substituted by Z, a phenylsulfinyl group optionally substituted by Z, a phenylsulfonyl group optionally substituted by Z, —$P(=O)T^2T^3$, or —$P(=S)T^2T^3$.

G is a substituent freely selected from a halogen atom, a $C_1$–$C_{10}$ alkyl group, a $C_2$–$C_4$ cyanoalkyl group, a $C_1$–$C_4$ alkyl group substituted by a phenyl group optionally substituted by a halogen or a $C_1$–$C_4$ alkyl group, a $C_2$–$C_6$ alkenyl group, a $C_2$–$C_6$ alkynyl group, a $C_1$–$C_6$ haloalkyl group, a $C_2$–$C_6$ haloalkenyl group, a $C_2$–$C_6$ haloalkynyl group, a $C_3$–$C_6$ halocycloalkyl group, a $C_3$–$C_6$ cycloalkyl group optionally substituted by a $C_1$–$C_3$ alkyl group, a $C_1$–$C_{10}$ alkoxy group, a $C_2$–$C_6$ alkenyloxy group, a $C_2$–$C_6$ alkynyloxy group, a $C_1$–$C_4$ haloalkoxy group, a $C_2$–$C_6$ haloalkenyloxy group, a $C_2$–$C_6$ haloalkynyloxy group, a $C_1$–$C_4$ alkylsulfenyl group, a $C_1$–$C_4$ alkylsulfinyl group, a $C_1$–$C_4$ alkylsulfonyl group, a $C_2$–$C_6$ alkenylsulfenyl group, a $C_2$–$C_6$ alkenylsulfinyl group, a $C_2$–$C_6$ alkenylsulfonyl group, a $C_2$–$C_6$ alkynylsulfenyl group, a $C_2$–$C_6$ alkynylsulfinyl group, a $C_2$–$C_6$ alkynylsulfonyl group, a $C_1$–$C_4$ haloalkylsulfenyl group, a $C_1$–$C_4$ haloalkylsulfinyl group, a $C_1$–$C_4$ haloalkylsulfonyl group, a $C_2$–$C_4$ haloalkenylsulfenyl group, a $C_2$–$C_6$ haloalkenylsulfinyl group, a $C_2$–$C_6$ haloalkenylsulfonyl group, a $C_2$–$C_6$ haloalkynylsulfenyl group, a $C_2$–$C_6$ haloalkynylsulfinyl group, a $C_2$–$C_6$ haloalkynylsulfonyl group, CHO, $NO_2$, CN, —$NU^1U^2$, OH, a naphthyl group, a methoxygroup substituted by a phenyl group optionally substituted by a halogen or a $C_1$–$C_4$ alkyl group, a $C_2$–$C_7$ alkoxycarbonyl group, a $C_2$–$C_4$ alkoxyalkyl group, a $C_2$–$C_4$ alkylcarbonyl group, a $C_2$–$C_4$ haloalkylcarbonyl group, a $C_2$–$C_5$ alkylcarbonyloxy group, a $C_2$–$C_5$ haloalkylcarbonyloxy group, a $C_3$–$C_7$ dialkylaminocarbonyloxy group, a phenyl group optionally substituted by Z, a phenoxy group optionally substituted by Z, a benzoyl group optionally substituted by Z, a pyridyl group optionally substituted by Z, a pyridyloxy group optionally substituted by Z, a thienyl group optionally substituted by Z, a methylenedioxy group as bonded at the adjacent substituting positions, a halomethylenedioxy group as bonded at the adjacent substituting positions, and =N=$CT^7T^8$ (in which $T^7$ and $T^8$ each independently represent H, or a phenyl, benzyl or $C_1$–$C_6$ alkyl group, or $T^7$ and $T^8$, together with the carbon atom to which they are bonded, form a 5-, 6-, 7- or 8-membered ring), (provided that when the the substituent is two or more, then said substituents may be the same or different), and the number of the substituent, G, is 1, 2, 3 or 4; or G is an alkylene group as bonded to the adjacent substituting positions to form a 5-, 6-, 7- or 8-membered ring;

R is a substituent freely selected from a halogen atom, a $C_1$–$C_{10}$ alkyl group, a $C_1$–$C_4$ alkyl group substituted by a phenyl group optionally substituted by a halogen or a $C_1$–$C_4$ alkyl group, a $C_2$–$C_6$ alkenyl group, a $C_2$–$C_6$ alkynyl group, a $C_1$–$C_6$ haloalkyl group, a $C_2$–$C_6$ haloalkenyl group, a $C_2$–$C_6$ haloalkynyl group, a $C_3$–$C_6$ halocycloalkyl group, a $C_3$–$C_6$ cycloalkyl group optionally substituted by a $C_1$–$C_3$ alkyl group, a $C_1$–$C_6$ alkoxy group, a $C_2$–$C_6$ alkenyloxy group, a $C_2$–$C_6$ alkynyloxy group, a $C_1$–$C_4$ haloalkoxy group, a $C_2$–$C_6$ haloalkenyloxy group, a $C_2$–$C_6$ haloalkynyloxy group, a $C_1$–$C_4$ alkylsulfenyl group, a $C_1$–$C_4$ alkylsulfinyl group, a $C_1$–$C_4$ alkylsulfonyl group, a $C_2$–$C_6$ alkenylsulfenyl group, a $C_2$–$C_6$ alkenylsulfinyl group, a $C_2$–$C_6$ alkenylsulfonyl group, a $C_2$–$C_6$ alkynylsulfenyl group, a $C_2$–$C_6$ alkynylsulfinyl group, a $C_2$–$C_6$ alkynylsulfonyl group, a $C_1$–$C_4$ haloalkylsulfenyl group, a $C_1$–$C_4$ haloalkylsulfinyl group, a $C_1$–$C_4$ haloalkylsulfonyl group, a $C_2$–$C_6$ haloalkenylsulfenyl group, a $C_2$–$C_6$ haloalkenylsulfinyl group, a $C_2$–$C_6$ haloalkenylsulfonyl group, a $C_2$–$C_6$ haloalkynylsulfenyl group, a $C_2$–$C_6$ haloalkynylsulfinyl group, a $C_2$–$C_6$ haloalkynylsulfonyl group, $NO_2$, CN, —$NU^1U^2$, a phenoxy group, OH, a naphthyl group, a $C_2$–$C_7$ alkoxycarbonyl group, a $C_2$–$C_4$ alkoxyalkyl group, a $C_2$–$C_4$ alkylcarbonyl group, a $C_2$–$C_5$ alkylcarbonyloxy group, a $C_2$–$C_6$ haloalkylcarbonyloxy group, a benzoyl group optionally substituted by X, a phenyl group optionally substituted by X, a pyridyl group optionally substituted by X, a thienyl group optionally substituted by X, and —N=$CT^7T^8$, (provided that when the substituent is two or more, then said substituents may be the same or different), and the number of the substituents, R, is 1, 2, 3 or 4; or R is an alkylene group as bonded to the adjacent substituting positions to form a 5-, 6-, 7- or 8-membered ring;

Y is a substituent freely selected from a halogen atom, a $C_1$–$C_{10}$ alkyl group, a $C_1$–$C_6$ haloalkyl group, a $C_1$–$C_6$ alkoxy group, a $C_2$–$C_6$ alkenyloxy group, a $C_2$–$C_6$ alkynyloxy group, a $C_1$–$C_4$ haloalkoxy group, a $C_2$–$C_6$ haloalkenyloxy group, a $C_2$–$C_6$ haloalkynyloxy group, a $C_1$–$C_4$ alkylsulfenyl group, a $C_1$–$C_4$ alkylsulfinyl group, a $C_1$–$C_4$ alkylsulfonyl group, a $C_2$–$C_6$ alkenylsulfenyl group, a $C_2$–$C_6$ alkenylsulfinyl group, a $C_2$–$C_6$ alkenylsulfonyl group, a $C_2$–$C_6$ alkynylsulfenyl group, a $C_2$–$C_6$ alkynylsulfinyl group, a $C_2$–$C_6$ alkynylsulfonyl group, a $C_1$–$C_4$ haloalkylsulfenyl group, a $C_1$–$C_4$ haloalkylsulfinyl group, a $C_1$–$C_4$ haloalkylsulfonyl group, a $C_2$–$C_6$ haloalkenylsulfenyl group, a $C_2$–$C_6$ haloalkenylsulfinyl group, a $C_2$–$C_6$ haloalkenylsulfonyl group, a $C_2$–$C_6$ haloalkynylsulfenyl group, a $C_2$–$C_6$ haloalkynylsulfinyl group, a $C_2$–$C_6$ haloalkynylsulfonyl group, $NO_2$, CN, —$NU^1U^2$, OH, a $C_2$–$C_7$ alkoxycarbonyl group, a $C_2$–$C_4$ alkoxyalkyl group, a $C_2$–$C_5$ alkylcarbonyloxy group, a $C_2$–$C_5$ haloalkylcarbonyloxy group, a $C_3$–$C_7$ dialkylaminocarbonyloxy group, a phenyl group optionally substituted by X, and —N═$CT^7T^8$ (in which $T^7$ and $T^8$ each independently represent H, or a phenyl, benzyl or $C_1$–$C_6$ alkyl group, or $T^7$ and $T^8$ may, together with the carbon atom to which they are bonded, form a 5-, 6-, 7- or 8-membered ring), (provided that when the substituent is two or more, then said substituents may be the same or different), and the number of the substituent, Y, is 1, 2, 3 or 4; or Y is an alkylene groupas bonded to the adjacent substituting positions to form a 5-, 6-, 7- or 8-membered ring;

W is a substituent freely selected from a halogen atom, a $C_1$–$C_6$ alkyl group, a $C_1$–$C_4$ haloalkyl group, a $CC_1$–$C_4$alkoxy group, a $CC_1$–$C_4$ haloalkoxy group, a $CC_1$–$C_4$ alkylsulfenyl group, a $C_1$–$C_4$ alkylsulfinyl group, a $C_1$–$C_4$ alkylsulfonyl group, a $C_1$–$C_4$ haloalkylsulfenyl group, a $C_1$–$C_4$ haloalkylsulfinyl group, a $C_1$–$C_4$ haloalkylsulfonyl group, a $C_2$–$C_4$ alkenyl group, a $C_2$–$C_4$ haloalkenyl group, a $C_2$–$C_4$ alkenyloxy group, a $C_2$–$C_4$ haloalkenyloxy group, a $C_2$–$C_4$ alkenylsulfenyl group, a $C_2$–$C_4$ alkenylsulfinyl group, a $C_2$–$C_4$ alkenylsulfonyl group, a $C_2$–$C_4$ haloalkenylsulfenyl group, a $C_2$–$C_4$ haloalkenylsulfinyl group, a $C_2$–$C_4$ haloalkenylsulfonyl group, a $C_2$–$C_4$ alkynyl group, a $C_2$–$C_4$ haloalkynyl group, a $C_2$–$C_4$ alkynyloxy group, a $C_2$–$C_4$ haloalkynyloxy group, a $C_2$–$C_4$ alkynylsulfenyl group, a $C_2$–$C_4$ alkynylsulfinyl group, a $C_2$–$C_4$ alkynylsulfonyl group, a $C_2$–$C_4$ haloalkynylsulfenyl group, a $C_2$–$C_4$ haloalkynylsulfinyl group, a $C_2$–$C_4$ haloalkynylsulfonyl group, $NO_2$, CN, a formyl group, a $C_2$–$C_6$ alkoxycarbonyl group, a $C_2$–$C_6$ alkylcarbonyl group, a $C_2$–$C_6$ haloalkylcarbonyl group, a $C_2$–$C_6$ alkylcarbonyloxy group, and —$NU^1U^2$, (provided that when the substituent is two or more, then said substituents may be the same or different), and the number of the substituent, W, is 1, 2, 3 or 4;

$T^1$ represents a $C_1$–$C_{20}$ alkyl group, a $C_2$–$C_6$ alkenyl group, a $C_1$–$C_6$ haloalkyl group, a $C_1$–$C_4$ alkoxy-$C_1$–$C_4$ alkyl group, a $C_3$–$C_6$ halocycloalkyl group, a $C_1$–$C_4$ alkyl group substituted by a phenyl group optionally substituted by a halogen or a $C_1$–$C_4$ alkyl group, a $C_3$–$C_6$ cycloalkyl group optionally substituted by a $C_1$–$C_3$ alkyl group, a cycloalkyl group substituted by a phenyl group optionally substituted by a halogen or a $C_1$–$C_4$ alkyl group, a cyclopropyl group substituted by both a phenyl group optionally substituted by a halogen or a $C_1$–$C_4$ alkyl group and a $C_1$–$C_4$ alkyl group, a $C_3$–$C_4$ cycloalkyl group substituted by both a phenyl group optionally substituted by a halogen or a $C_1$–$C_4$ alkoxy group, and a halogen, a cyclopropyl group substituted by both a $C_2$–$C_4$ alkenyl group optionally substituted by a halogen, and a $C_1$–$C_4$ alkyl group, a $C_2$–$C_4$ alkenyl group substituted by a phenyl group optionally substituted by a halogen or a $C_1$–$C_4$ alkyl group, a $C_1$–$C_{12}$ alkoxy group, a $C_1$–$C_4$ haloalkoxy group, a $C_2$–$C_5$ alkenyloxy group, a $C_3$–$C_6$ cycloalkoxy group optionally substituted by a $C_1$–$C_3$ alkyl group, a benzyloxy group, a $C_2$–$C_5$ alkoxycarbonyl group, —$NU^1U^2$, a phenylamino group, a phenyl group optionally substituted by Z, a phenoxy group optionally substituted by Z, a phenylthio group optionally substituted by Z, a naphthyl group optionally substituted by Z, or a 5-membered or 6-membered heterocyclic group optionally substituted by Z, (said heterocyclic group being selected from thienyl, furyl, pyrrolyl, oxazolyl, isoxazolyl, thiazolyl, isothiazolyl, pyrazolyl, imidazolyl, 1,3,4-oxadiazolyl, 1,2,4-oxadiazolyl, 1,3,4-thiadiazolyl, 1,2,4-thiadiazolyl, 1,2,4-triazolyl, 1,2,3-thiadiazolyl, 1,2,3-triazolyl, 1,2,3,4-tetrazolyl, pyridinyl, pyrimidinyl, pyrazinyl, pyridazinyl, 1,3,5-triazinyl, 1,2,4-triazinyl, pyrazolinyl, imidazolinyl, oxazolinyl, isoxazolinyl, thiazolinyl and 3(2H)-pyridazinone groups);

$T^2$ and $T^3$ each independently represent OH, a phenyl group, a $C_1$–$C_6$ alkyl group, a $C_1$–$C_6$ alkoxy group, or a $C_1$–$C_4$ alkylsulfenyl group;

$T^4$, $T^5$ and $T^6$ each independently represent H, a $C_1$–$C_6$ alkyl group, a $C_1$–$C_6$ alkenyl group, a $C_3$–$C_6$ cycloalkyl group optionally substituted by a $C_1$–$C_3$ alkyl group, or a benzyl group; or any two of $T^4$, $T^5$ and $T^6$ may, together with the nitrogen atom to which they are bonded, form a 5-, 6-, 7- or 8-membered cyclic group optionally containing oxygen, nitrogen and/or sulfur atoms;

X and Z are independently substituents as freely selected from a halogen atom, a $C_1$–$C_4$ alkyl group, a $C_1$–$C_4$haloalkyl group, a $C_1$–$C_4$ alkoxy group, a $C_1$–$C_4$ haloalkoxy group, a $C_1$–$C_4$ alkylsulfenyl group, a $C_1$–$C_4$ alkylsulfinyl group, a $C_1$–$C_4$ alkylsulfonyl group, a $C_2$–$C_5$ alkenylsulfenyl group, a $C_2$–$C_5$ alkenylsulfinyl group, a $C_2$–$C_5$ alkenylsulfonyl group, a $C_1$–$C_4$ haloalkylsulfenyl group, a $C_1$–$C_4$ haloalkylsulfinyl group, a $C_1$–$C_4$ haloalkylsulfonyl group, $NO_2$, CN, CHO, OH, —$NU^1U^2$, a phenyl group, a phenoxy group, and a $C_2$–$C_5$ alkoxycarbonyl group, (provided that when the substituent is two or more, then said substituents may be the same or different), and the number of the substituent, X and Z, is 1, 2, 3, 4 or 5 each;

$T^7$ and $T^8$ each independently represent H, or a phenyl, benzyl or $C_1$–$C_6$ alkyl group, or $T^7$ and $T^8$ may, together with the carbon atom to which they are bonded, form a 5-, 6-, 7- or 8-membered ring; and $U^1$ and $U^2$ each independently represent H, a $C_1$–$C_6$ alkyl, $C_2$–$C_5$ alkylcarbonyl, phenyl or benzyl group, or $U^1$ and $U^2$ may, together with the nitrogen atom to which they are bonded, form a 5-, 6-, 7- or 8-membered ring.

[2] Ethylene derivatives of the above-mentioned [1], in which;

Q is a phenyl group optionally substituted by G, a naphthyl group optionally substituted by G, or a heterocyclic group optionally substituted by R, (said heterocyclic group being a thienyl, furyl, pyrrolyl, oxazolyl, isoxazolyl, thiazolyl, isothiazolyl, pyrazolyl, imidazolyl, 1,3,4-oxadiazolyl, 1,2,4-oxadiazolyl, 1,3,4-thiadiazolyl, 1,2,4-thiadiazolyl, 1,2,4-triazolyl, 1,2,3-triazolyl, 1,2,3,4-tetrazolyl, pyridinyl, pyrimidinyl, pyrazinyl, pyridazinyl, 1,3,5-triazinyl, 1,2,4-triazinyl, 1,2,4,5-tetrazinyl, pyrazolinyl, imidazolinyl, imidazolinone or imidazolidinedione group;

A is a phenyl group optionally substituted by W, a naphthyl group optionally substituted by W, or a heterocyclic group optionally substituted by Y, said heterocyclic group being a thienyl, furyl, pyrrolyl, oxazolyl, isoxazolyl, thiazolyl, isothiazolyl, pyrazolyl, imidazolyl, 1,3,4-oxadiazolyl, 1,2,4-oxadiazolyl, 1,3,4-thiadiazolyl, 1,2,4-thiadiazolyl, 1,2,4-triazolyl, 1,2,3-thiadiazolyl, 1,2,3-triazolyl, 1,2,3,4-tetrazolyl, pyridinyl, pyrimidinyl, pyrazinyl, pyridazinyl, 1,3,5-triazinyl, 1,2,4-triazinyl, pyrazolinyl or imidazolinyl group;

B is H, a $C_1$–$C_4$ alkyl group, a $C_1$–$C_4$ haloalkyl group, a $C_2$–$C_4$ alkoxyalkyl group, $CH_3OC_2H_4OCH_2$, a $C_1$–$C_4$ alkylsulfonyl group, a phenylsulfonyl group optionally substituted by a halogen or a $C_1$–$C_4$ alkyl group, —$SO_2CF_3$, a $C_2$–$C_8$ dialkylaminosulfonyl group, a $C_2$–$C_9$ dialkylaminothiocarbonyl group, a $C_3$–$C_9$ alkoxycarbonylalkyl group, —C(=O)$T^1$, —P(=O)$T^2T^3$, —P(=S)$T^2T^3$, an alkali metal atom, an alkaline earth metal atom, or $NHT^4T^5T^6$; and $T^1$ is a $C_1$–$C_{20}$ alkyl group, a $C_2$–$C_6$ alkenyl group, a $C_1$–$C_4$ haloalkyl group, a $C_1$–$C_4$ alkoxy-$C_1$–$C_4$ alkyl group, a $C_1$–$C_4$ alkyl group substituted by a phenyl group optionally substituted by a halogen or a $C_1$–$C_4$ alkyl group, a $C_3$–$C_6$ halocycloalkyl group, a $C_3$–$C_6$ cycloalkyl group optionally substituted by a $C_1$–$C_3$ alkyl group, a cycloalkyl group substituted by a phenyl group optionally substituted by a halogen or a $C_1$–$C_4$ alkyl group, a cyclopropyl group substituted by both a phenyl optionally substituted by a halogen or a $C_1$–$C_4$ alkyl group, and a $C_1$–$C_4$ alkyl group, a $C_3$–$C_4$ cycloalkyl group substituted by both a phenyl group optionally substituted by a halogen or a $C_1$–$C_4$ alkoxy group and a halogen, a cyclopropyl group substituted by both a $C_2$–$C_4$ alkenyl group optionally substituted by a halogen and a $C_1$–$C_4$ alkyl group, a $C_2$–$C_4$ alkenyl group substituted by a phenyl group optionally substituted by a halogen or a $C_1$–$C_4$ alkyl group, a $C_1$–$C_{12}$ alkoxy group, a $C_1$–$C_4$ haloalkoxy group, a $C_2$–$C_5$ alkenyloxy group, a $C_3$–$C_6$ cycloalkoxy group optionally substituted by a $C_1$–$C_3$ alkyl group, a benzyloxy group, a $C_2$–$C_5$ alkoxycarbonyl group, a phenyl group optionally substituted by Z, a phenoxy group optionally substituted by Z, a phenylthio group, a naphthyl group, or a heterocyclic group optionally substituted by Z, said heterocyclic group being selected from thienyl, furyl, oxazolyl, thiazolyl, pyrazolyl and pyridinyl groups.

[3] Ethylene derivatives of the above-mentioned [2], in which;

Q is a phenyl group optionally substituted by G, a naphthyl group optionally substituted by G, or a heterocyclic group optionally substituted by R, said heterocyclic group being

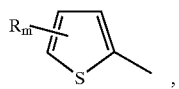
Q-1

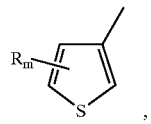
Q-2

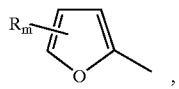
Q-3

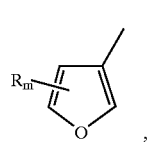
Q-4

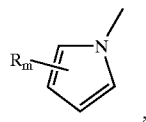
Q-5

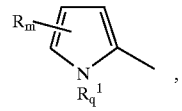
Q-6

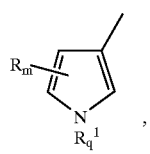
Q-7

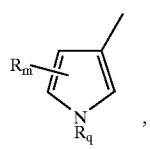
Q-8

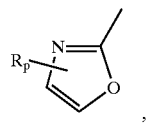
Q-9

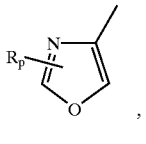
Q-10

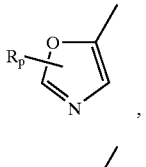
Q-11

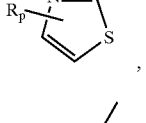
Q-12

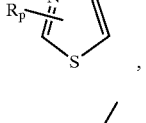
Q-13

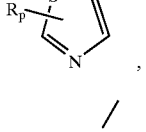
Q-14

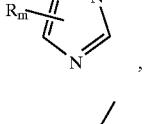
Q-15

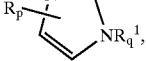
Q-16

-continued
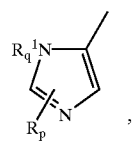 Q-17
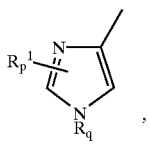 Q-18
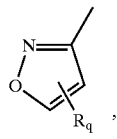 Q-19
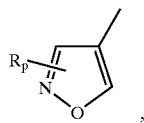 Q-20
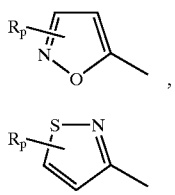 Q-21
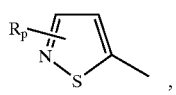 Q-22
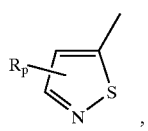 Q-23
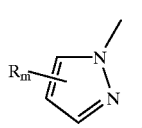 Q-24
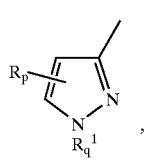 Q-25
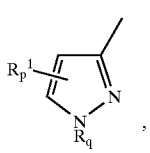 Q-26
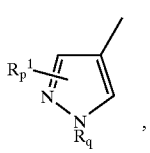 Q-27
Q-28
-continued
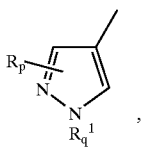 Q-29
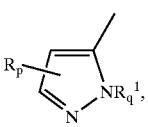 Q-30
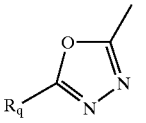 Q-31
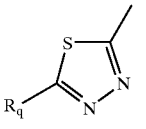 Q-32
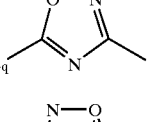 Q-33
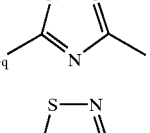 Q-34
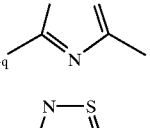 Q-35
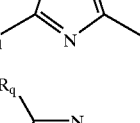 Q-36
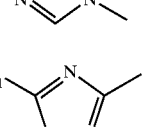 Q-37
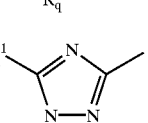 Q-38
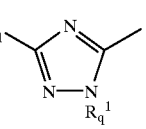 Q-39
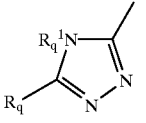 Q-40
Q-41

-continued
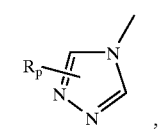, Q-42
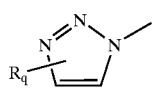, Q-43
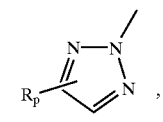, Q-44
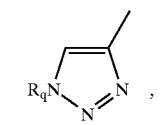, Q-45
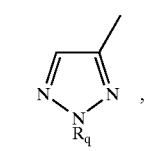, Q-46
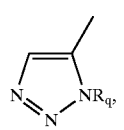, Q-47
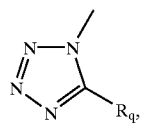, Q-48
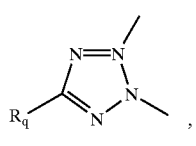, Q-49
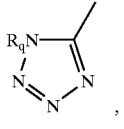, Q-50
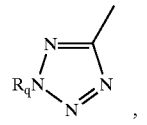, Q-51
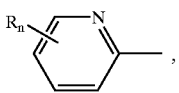, Q-52
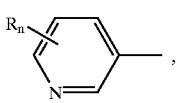, Q-53
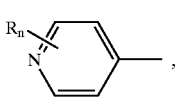, Q-54
-continued
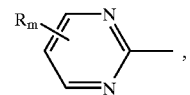, Q-55
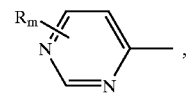, Q-56
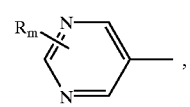, Q-57
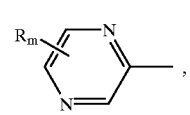, Q-58
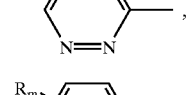, Q-59
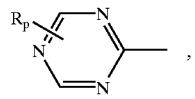, Q-60
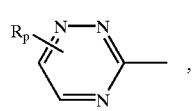, Q-61
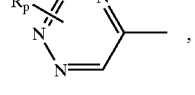, Q-62
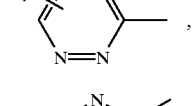, Q-63
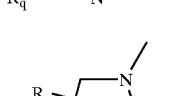, Q-64
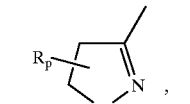, Q-65
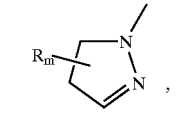, Q-66
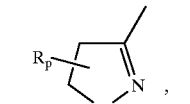, Q-67
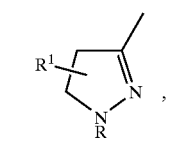, Q-68

-continued
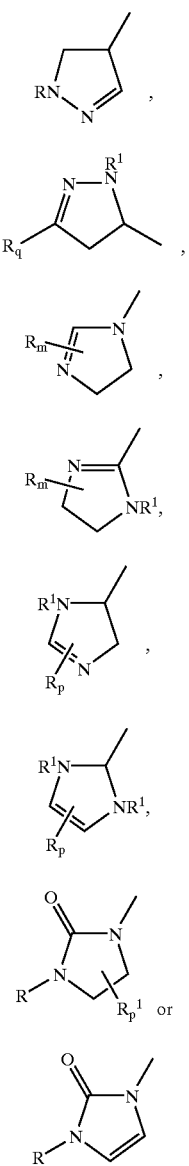
Q-69
Q-70
Q-71
Q-72
Q-73
Q-74
Q-75
Q-76
A is a phenyl group optionally substituted by W, a naphthyl group optionally substituted by W, or a heterocyclic group optionally substituted by Y, said heterocyclic group being
A-1
A-2
A-3
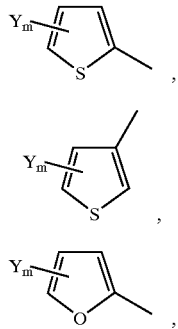
-continued
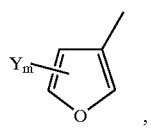 A-4
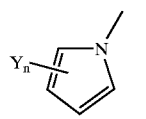 A-5
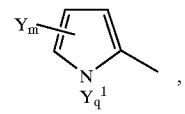 A-6
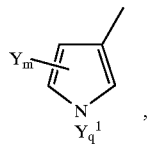 A-7
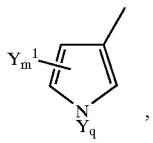 A-8
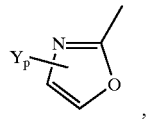 A-9
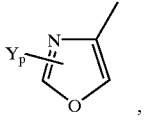 A-10
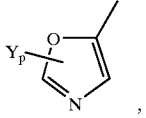 A-11
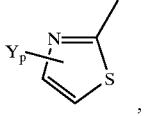 A-12
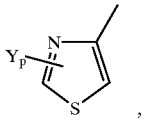 A-13
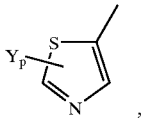 A-14

-continued

A-15, A-16, A-17, A-18, A-19, A-20, A-21, A-22, A-23, A-24, A-25, A-26

-continued

A-27, A-28, A-29, A-30, A-31, A-32, A-33, A-34, A-35, A-36, A-37, A-38

-continued
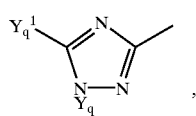, A-39
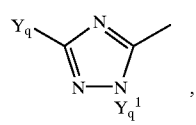, A-40
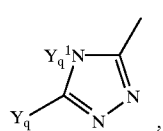, A-41
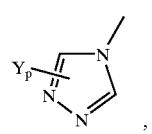, A-42
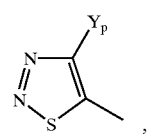, A-43
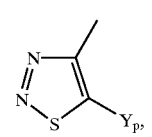, A-44
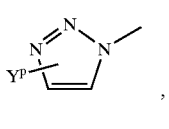, A-45
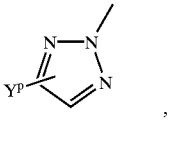, A-46
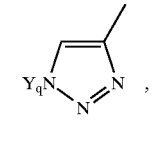, A-47
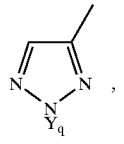, A-48
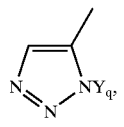, A-49
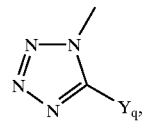, A-50
-continued
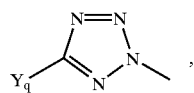, A-51
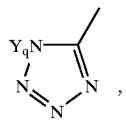, A-52
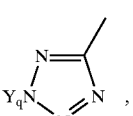, A-53
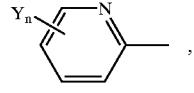, A-54
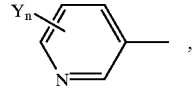, A-55
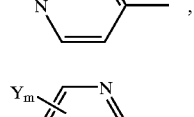, A-56
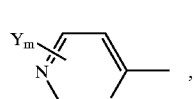, A-57
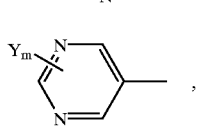, A-58
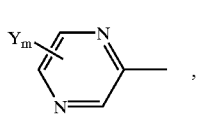, A-59
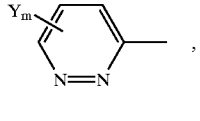, A-60
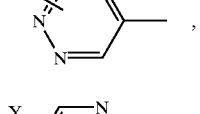, A-61
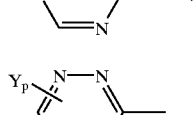, A-62
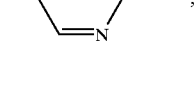, A-63
A-64

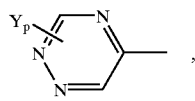
A-65

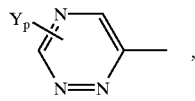
A-66

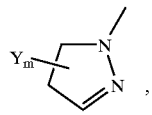
A-67

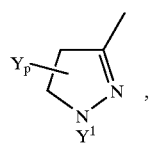
A-68

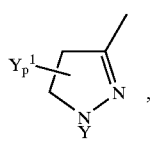
A-69

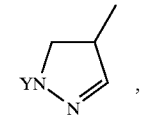
A-70

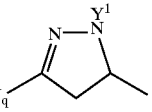
A-71

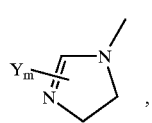
A-72

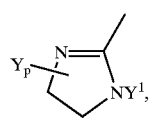
A-73

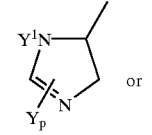
A-74

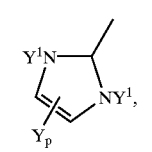
A-75 provided that, when (a) Q is any of Q-1, Q-2, Q-3 or Q-4, then A is a phenyl group optionally substituted by W, a naphthyl group optionally substituted by W, or a heterocyclic group optionally substituted by Y, (said heterocyclic group being any of A-5, A-6, A-7, A-8, A-9, A-10, A-11, A-12, A-13, A-14, A-15, A-16, A-17, A-18, A-19, A-20, A-21, A-22, A-23, A-24, A-25, A-26, A-27, A-28, A-29, A-30, A-31, A-32, A-33, A-34, A-35, A-36, A-37, A-38, A-39, A-40, A-41, A-42, A-43, A-44, A-45, A-46, A-47, A-48, A-49, A-50, A-51, A-52, A-53, A-57, A-58, A-59, A-60, A-61, A-62, A-63, A-64, A-65, A-66, A-67, A-68, A-69, A-70, A-71, A-72, A-73, A-74 or A-75), (b) when Q is Q-12, then A is a naphthyl group optionally substituted by W, or a heterocyclic group optionally substituted by Y, (said heterocyclic group being any of A-1, A-2, A-3, A-4, A-5, A-6, A-7, A-8, A-9, A-10, A-11, A-12, A-13, A-14, A-15, A-16, A-17, A-18, A-19, A-20, A-21, A-22, A-23, A-24, A-25, A-26, A-27, A-28, A-29, A-30, A-31, A-32, A-33, A-34, A-35, A-36, A-37, A-38, A-39, A-40, A-41, A-42, A-43, A-44, A-45, A-46, A-47, A-48, A-49, A-50, A-51, A-52, A-53, A-54, A-55, A-56, A-57, A-58, A-59, A-60, A-61, A-62, A-63, A-64, A-65, A-66, A-67, A-68, A-69, A-70, A-71, A-72, A-73, A-74 or A-75), (c) when Q is any of Q-52, Q-53 or Q-54, then A is a heterocyclic group optionally substituted by Y, (said heterocyclic group being any of A-5, A-6, A-7, A-8, A-9, A-10, A-11, A-12, A-13, A-14, A-15, A-16, A-17, A-18, A-19, A-20, A-21, A-22, A-23, A-24, A-25, A-26, A-27, A-28, A-29, A-30, A-31, A-32, A-33, A-34, A-35, A-36, A-37, A-38, A-39, A-40, A-41, A-42, A-43, A-44, A-45, A-46, A-47, A-48, A-49, A-50, A-51, A-52, A-53, A-60, A-63, A-64, A-65, A-66, A-67, A-68, A-69, A-70, A-71, A-72, A-73, A-74 or A-75), (d) when Q is any of Q-23, Q-24, Q-43, Q-44, Q-45, Q-46 or Q-49, then A is a naphthyl group optionally substituted by W, or a heterocyclic group optionally substituted by Y, (said heterocyclic group being any of A-1, A-2, A-3, A-4, A-5, A-6, A-7, A-8, A-9, A-10, A-11, A-12, A-13, A-14, A-15, A-16, A-17, A-18, A-19, A-20, A-21, A-22, A-23, A-24, A-25, A-26, A-27, A-28, A-29, A-30, A-31, A-32, A-33, A-34, A-35, A-36, A-37, A-38, A-39, A-40, A-41, A-42, A-43, A-44, A-45, A-46, A-47, A-48, A-49, A-50, A-51, A-52, A-53, A-54, A-55, A-56, A-57, A-58, A-59, A-60, A-61, A-62, A-63, A-64, A-65, A-66, A-67, A-68, A-69, A-70, A-71, A-72, A-73, A-74 or A-75), (e) when Q is any of Q-37, Q-38, Q-39, Q-40, Q-41 or Q-42, then A is a heterocyclic group optionally substituted by Y, (said heterocyclic group being any of A-1, A-2, A-3, A-4, A-5, A-6, A-7, A-8, A-9, A-10, A-11, A-12, A-13, A-14, A-15, A-16, A-17, A-18, A-19, A-20, A-21, A-22, A-23, A-24, A-25, A-26, A-27, A-28, A-29, A-30, A-31, A-32, A-33, A-34, A-35, A-36, A-37, A-38, A-39, A-40, A-41, A-42, A-43, A-44, A-45, A-46, A-47, A-48, A-49, A-50, A-51, A-52, A-53, A-57, A-58, A-59, A-60, A-61, A-62, A-63, A-64, A-65, A-66, A-67, A-68, A-69, A-70, A-71, A-72, A-73, A-74 or A-75), (f) when Q is a phenyl group optionally substituted by G, -then A is a heterocyclic group optionally substituted by Y, said heterocyclic group being any of A-5, A-6, A-7, A-8, A-9, A-10, A-11, A-12, A-13, A-14, A-i9, A-20, A-21, A-22, A-23, A-24, A-25, A-26, A-27, A-28, A-29, A-30, A-31, A-32, A-33, A-34, A-35, A-36, A-37, A-38, A-39, A-40, A-41, A-42, A-43, A-44, A-45, A-46, A-47, A-48, A-49, A-50, A-51, A-52, A-53, A-60, A-61, A-62, A-63, A-64, A-65, A-66, A-67, A-68, A-69, A-70, A-71, A-72, A-73, A-74 or A-75, (g) when Q is a naphthyl group optionally substituted by G, then A is a heterocyclic group optionally substituted by Y, (said heterocyclic group being any of A-1, A-2, A-5, A-6, A-7, A-8, A-9, A-10, A-11, A-12, A-13, A-14, A-15, A-16, A-17, A-18, A-19, A-20, A-21, A-22, A-23, A-24, A-25, A-26, A-27, A-28, A-29, A-30, A-31, A-32, A-33, A-34, A-35, A-36, A-37, A-38, A-39, A-40, A-41, A-42, A-43, A-44, A-45, A-46, A-47, A-48, A-49, A-50, A-51, A-52, A-53, A-54, A-55, A-56, A-57, A-58, A-59, A-60, A-61, A-62, A-63, A-64, A-65, A-66, A-67, A-68, A-69, A-70, A-71, A-72, A-73, A-74 or A-75, $R^1$ is selected from a halogen atom, a $C_1$–$C_{10}$ alkyl group, a $C_2$–$C_6$ alkenyl group, a $C_2$–$C_6$ alkynyl group, a $C_1$–$C_6$ haloalkyl group, a $C_1$–$C_6$ alkoxy group, a $C_2$–$C_6$ alkenyloxy group, $NO_2$, CN, —$NU^1U^2$, OH, a $C_2$–$C_7$ alkoxycarbonyl group, a $C_2$–$C_4$ alkoxyalkyl group, a $C_2$–$C_4$ alkylcarbonyl group, a phenyl group optionally substituted by X, a pyridyl group optionally substituted by X, a thienyl group optionally substituted by X, and —N=$CT^7T^8$ (in which $T^7$ and $T^8$ each independently represent H, a phenyl, benzyl or $C_1$–$C_6$ alkyl group, or $T^7$ and $T^8$ may, together with the carbon atom to which they are bonded, form a 5-, 6-, 7- or 8-membered ring); or may, together with the adjacent R, form a 5-, 6-, 7- or 8-membered ring as an alkylene group $Y^1$ is selected from a halogen atom, a $C_1$–$C_{10}$ alkyl group, a $C_1$–$C_6$ haloalkyl group, a $C_1$–$C_6$ alkoxy group, a $C_2$–$C_6$ alkenyloxy group, $NO_2$, CN, —$NU^1U^2$, OH, a $C_2$–$C_7$ alkoxycarbonyl group, a $C_2$–$C_4$ alkoxyalkyl group, a phenyl group optionally substituted by X, and —N=$CT^7T^8$ (in which $T^7$ and $T^8$ each independently represent H, or a phenyl, benzyl or $C_1$–$C_6$ alkyl group, or $T^7$ and $T^8$ may, together with the carbon atom to which they are bonded), form a 5-, 6-, 7- or 8-membered ring); or may, togeher with the adjacent $Y^1$, form a 5-, 6-, 7- or 8-membered ring an alkylene group;

X is a substituent of which the number is from 1 to 4 and which is freely selected from a halogen atom, a $C_1$–$C_4$ alkyl group, a $C_1$–$C_4$ haloalkyl group, a $C_1$–$C_4$ alkoxy group, a $C_1$–$C_4$ haloalkoxy group, a $C_1$–$C_4$ alkylsulfenyl group, a $C_1$–$C_4$ alkylsulfinyl group, a $C_1$–$C_4$ alkylsulfonyl group, a $C_2$–$C_5$ alkenylsulfenyl group, a $C_2$–$C_5$ alkenylsulfinyl group, a $C_2$–$C_5$ alkenylsulfonyl group, a $C_1$–$C_4$ haloalkylsulfenyl group, a $C_1$–$C_4$ haloalkylsulfinyl group, a $C_1$–$C_4$ haloalkylsulfonyl group, $NO_2$, CN, CHO, OH, —$NU^1U^2$, a phenyl group, a phenoxy group, and a $C_2$–$C_5$ alkoxycarbonyl group, (provided that when the number of the substituent, X, is two or more then said substituents may be the same or different);

Z is a substituent of which the number is from 1 to 4 and which is freely selected from a halogen atom, a $C_1$–$C_4$ alkyl group, a $C_1$–$C_4$ haloalkyl group, a $C_1$–$C_4$ alkoxy group, a $C_1$–$C_4$ haloalkoxy group, a $C_1$–$C_4$ alkylsulfenyl group, a $C_1$–$C_4$ alkylsulfinyl group, a $C_1$–$C_4$ alkylsulfonyl group, a $C_1$–$C_4$ alkenylsulfenyl group, a $C_1$–$C_4$ alkenylsulfinyl group, a $C_1$–$C_4$ alkenylsulfonyl group, $NO_2$, CN, —$NU^1U^2$, a phenyl group, a phenoxy group, and a $C_2$–$C_5$ alkoxycarbonyl group, (provided that when the number of the substituent, Z, is two or more, then said substituents may be the same or different);

m indicates the number of the substituents, and is 0, 1, 2 or 3;

n indicates the number of the substituents, and is 0, 1, 2, 3 or 4;

p indicates the number of the substituents, and is 0, 1, or 2;

q indicates the number of the substituents, and is 0 or 1; (provided that when m, n and p each are an integer of 2 or more, the substituents may be the same or different).

[4] Ethylene derivatives of the above-mentioned [2], in which E is CN.

[5] Ethylene derivatives of the above-mentioned [3], in which E is CN.

[6] Ethylene derivatives of the above-mentioned [2], in which E is a heterocyclic group optionally substituted by a $C_1$–$C_4$ alkyl or $C_1$–$C_4$ haloalkyl group—(said heterocyclic group being a 2-oxazolyl, 2-thiazolyl, 2-imidazolyl, 1,2,4-triazol-3-yl, 1,2,4-oxadiazol-3-yl, 1,2,4-thiadiazol-3-yl or 1,3,4-oxadiazol-2-yl group)—or is a halogen atom, a $C_2$–$C_4$ alkynyl group, a phenylethynyl group optionally substituted by Z, a $C_1$–$C_4$ haloalkyl group, CN, $NO_2$, $N_3$, CHO, a $C_2$–$C_5$ alkylcarbonyl group, a $C_2$–$C_5$ alkoxycarbonyl group, a $C_2$–$C_4$ alkylaminocarbonyl group, a $C_3$–$C_9$ dialkylaminocarbonyl group, a benzoyl group optionally substituted by Z, an aminothiocarbonyl group, a $C_1$–$C_4$ alkylsulfenyl group, a $C_1$–$C_4$ alkylsulfinyl group, a $C_1$–$C_4$ alkylsulfonyl group, a phenylsulfenyl group optionally substituted by Z, a phenylsulfinyl group optionally substituted by Z, a phenylsulfonyl group optionally substituted by Z, —P(=O)$T^2T^3$, or —P(=S)$T^2T^3$.

[7] Ethylene derivatives of the above-mentioned [3], in which E is a heterocyclic group optionally substituted by a $C_1$–$C_4$ alkyl or $C_1$–$C_4$ haloalkyl group—(said heterocyclic group being a 2-oxazolyl, 2-thiazolyl, 2-imidazolyl, 1,2,4-triazol-3-yl, 1,2,4-oxadiazol-3-yl, 1,2,4-thiadiazol-3-yl or 1,3,4-oxadiazol-2-yl group)—or is a halogen atom, a $C_2$–$C_4$ alkynyl group, a phenylethynyl group optionally substituted by Z, a $C_1$–$C_4$ haloalkyl group, CN, $NO_2$, $N_3$, CHO, a $C_2$–$C_5$ alkylcarbonyl group, a $C_2$–$C_5$ alkoxycarbonyl group, a $C_2$–$C_4$ alkylaminocarbonyl group, a $C_3$–$C_9$ dialkylaminocarbonyl group, a benzoyl group optionally substituted by Z, an aminothiocarbonyl group, a $C_1$–$C_4$ alkylsulfenyl group, a $C_1$–$C_4$ alkylsulfinyl group, a $C_1$–$C_4$ alkylsulfonyl group, a phenylsulfenyl group optionally substituted by Z, a phenylsulfinyl group optionally substituted by Z, a phenylsulfonyl group optionally substituted by Z, —P(=O)$T^2T^3$, or —P(=S)$T^2T^3$.

[8] Ethylene derivatives of the above-mentioned [4], in which Q is a phenyl group optionally substituted by G, an oxazolyl group optionally substituted by R, a thiazolyl group optionally substituted by R, a pyrazolyl group optionally substituted by R, a 1,2,3-triazolyl group optionally substituted by R, a pyridinyl group optionally substituted by R, or a pyrimidinyl group optionally substituted by R.

[9] Ethylene derivatives of the above-mentioned [8], in which Q is a phenyl group optionally substituted by G.

[10] Ethylene derivatives of the above-mentioned [8], in which Q is an oxazolyl group optionally substituted by R or a 1,2,3-triazolyl group optionally substituted by R.

[11] Ethylene derivatives of the above-mentioned [8], in which Q is a thiazolyl group optionally substituted by R.

[12] Ethylene derivatives of the above-mentioned [8], in which Q is a pyrazolyl group optionally substituted by R.

[13] Ethylene derivatives of the above-mentioned [5], in which Q is a phenyl group optionally substituted by G, or is Q-9, Q-10, Q-11, Q-12, Q-13, Q-14, Q-25, Q-26, Q-27, Q-28, Q-29, Q-30, Q-44, Q-45, Q-46, Q-47, Q-52, Q-53, Q-54, Q-55, Q-56 or Q-57.

[14] Ethylene derivatives of the above-mentioned [7], in which Q is a phenyl group optionally substituted by G, or is Q-9, Q-10, Q-11, Q-12, Q-13, Q-14, Q-25, Q-26, Q-27, Q-28, Q-29, Q-30, Q-44, Q-45, Q-46, Q-47, Q-52, Q-53, Q-54, Q-55, Q-56 or Q-57.

[15] Ethylene derivatives of the above-mentioned [13], in which Q is Q-10, Q-44, Q-45, Q-46 or Q-47.

[16] Ethylene derivatives of the above-mentioned [13], in which Q is Q-12, Q-13 or Q-14.

[17] Ethylene derivatives of the above-mentioned [13], in which Q is Q-25, 0-26, Q-27, Q-28, Q-29 or Q-30.

[18] Ethylene derivatives of the above-mentioned [13], in which Q is a phenyl group optionally substituted by G.

[19] Ethylene derivatives of the above-mentioned [2], in which A is a phenyl group optionally substituted by W, a thiazolyl group optionally substituted by Y, a pyrazolyl group optionally substituted by Y, a pyridinyl group optionally substituted by Y, or a pyrimidinyl group optionally substituted by Y.

[20] Ethylene derivatives of the above-mentioned [3], in which;

Q is a phenyl group optionally substituted by G, a naphthyl group, Q-31, Q-32, Q-33, Q-34, Q-35, Q-36, Q-37, Q-44, Q-45, Q-46, Q-49,

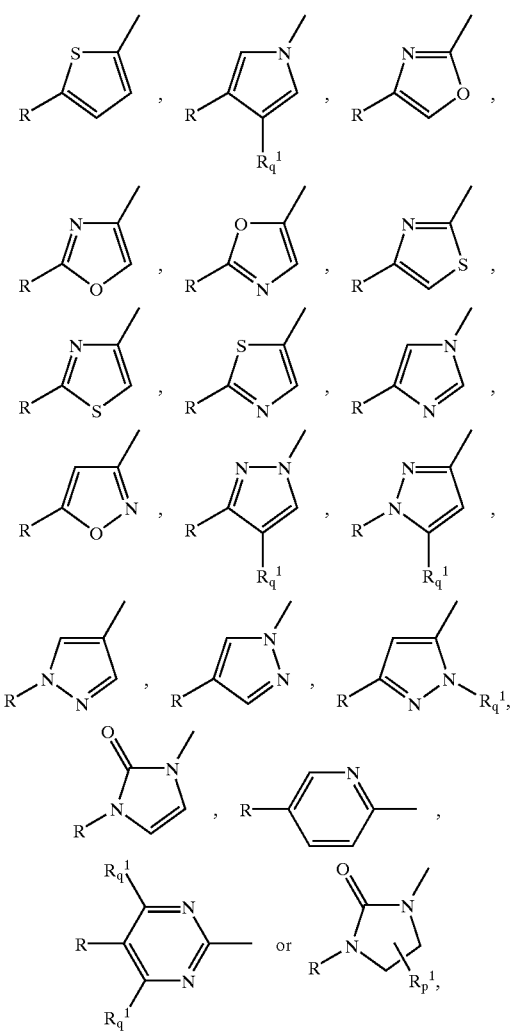

A is

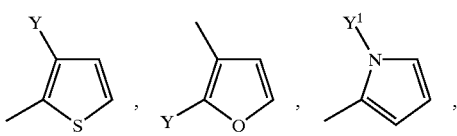

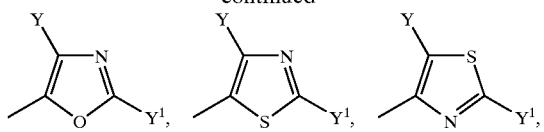

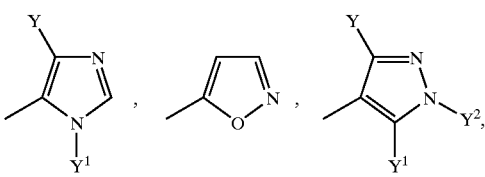

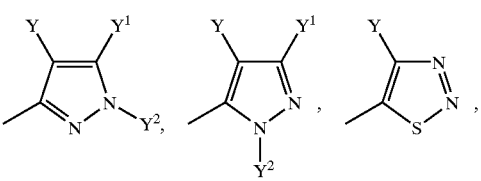

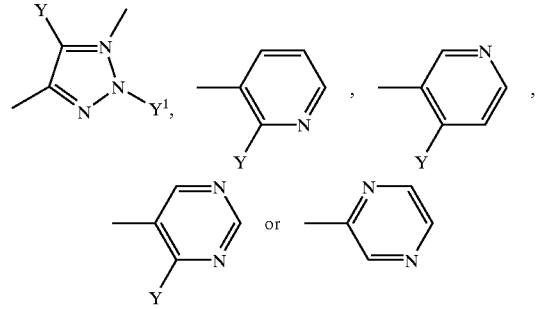

$Y^2$ i a halogen atom, a $C_1$–$C_4$ alkyl group, a $C_1$–$C_4$ haloalkyl group, a $C_1$–$C_4$ alkoxy group, $NO_2$, CN, or a $C_2$–$C_5$ alkoxycarbonyl group; and $Y^3$ is a halogen atom, a $C_1$–$C_4$ alkyl group, a $C_1$–$C_6$ haloalkyl group, a $C_2$–$C_4$ alkoxyalkyl group, or a phenyl group substituted by X.

[31] Ethylene derivatives of the above-mentioned [20], in which E is CN.

[22] Ethylene derivatives of the above-mentioned [20], in which E is a heterocyclic group optionally substituted by a $C_1$–$C_4$ alkyl or $C_1$–$C_4$ haloalkyl group—(said heterocyclic group being a 2-oxazolyl, 2-thiazolyl, 2-imidazolyl, 1,2,4-triazol-3-yl, 1,2,4-oxadiazol-3-yl, 1,2,4-thiadiazol-3-yl or 1,3,4-oxadiazol-2-yl group)—or is a halogen atom, a $C_2$–$C_4$ alkynyl group, a phenylethynyl group optionally substituted by Z, a $C_1$–$C_4$ haloalkyl group, CN, $NO_2$, $N_3$, CHO, a $C_2$–$C_5$ alkylcarbonyl group, a $C_2$–$C_5$ alkoxycarbonyl group, a $C_2$–$C_4$ alkylaminocarbonyl group, a $C_3$–$C_9$ dialkylaminocarbonyl group, a benzoyl group optionally substituted by Z, an aminothiocarbonyl group, a $C_1$–$C_4$ alkylsulfenyl group, a $C_1$–$C_4$ alkylsulfinyl group, a $C_1$–$C_4$ alkylsulfonyl group, a phenylsulfenyl group optionally substituted by Z, a phenylsulfinyl group optionally substituted by Z, a phenylsulfonyl group optionally substituted by Z, —P(=O)$T^2T^3$, or —P(=S)$T^2T^3$.

[23] Ethylene derivatives of the above-mentioned [1], which are selected from the following:

-continued

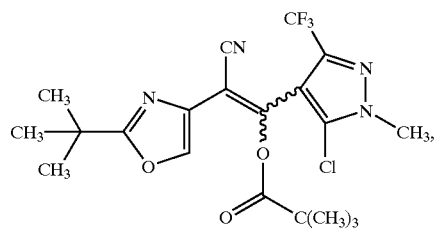 (13)
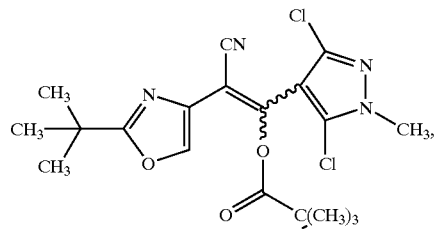 (14)
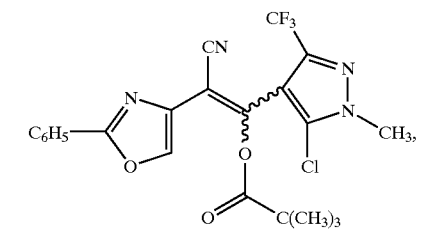 (15)
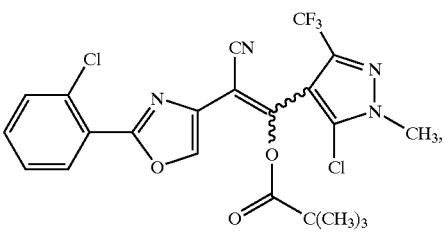 (16)
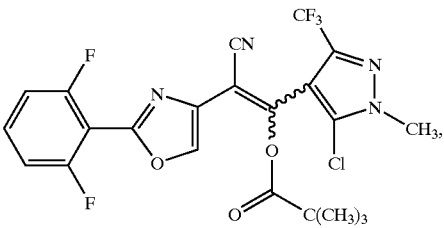 (17)
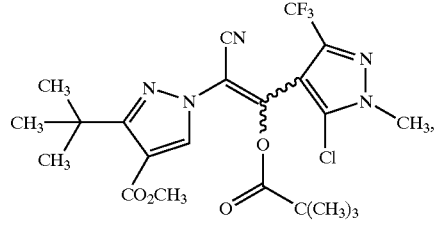 (18)
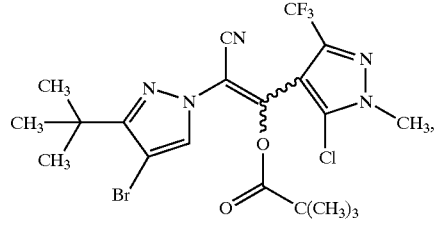 (19)
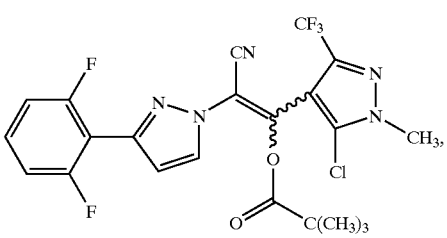 (20)
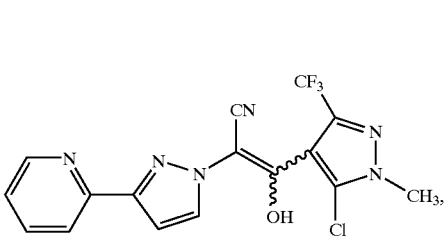 (21)
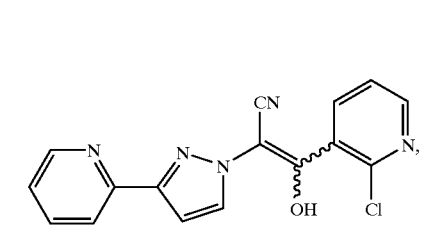 (22)
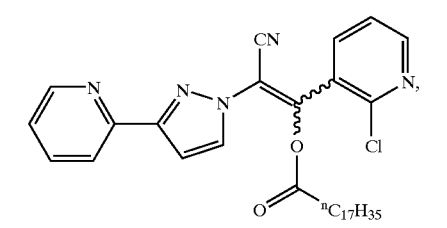 (23)
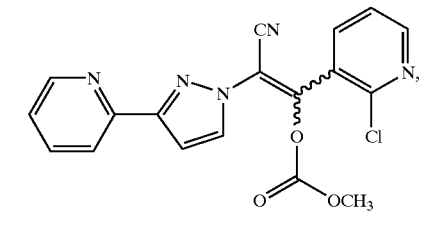 (24)
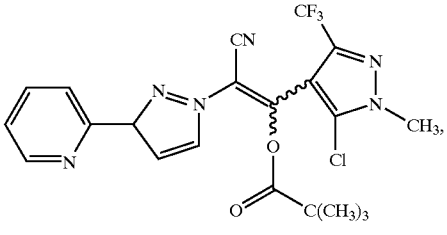 (25)
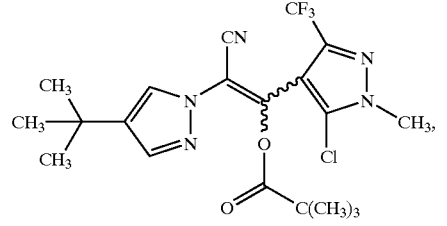 (26)

-continued

(27) 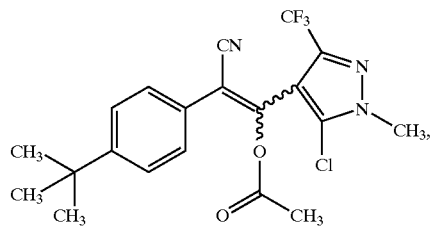

(28) 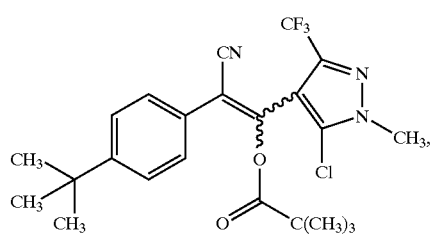

(29) 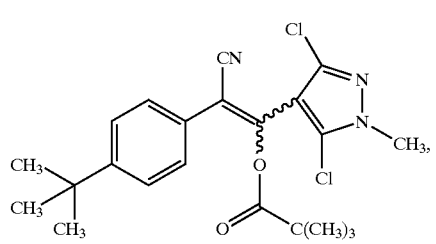

(30) 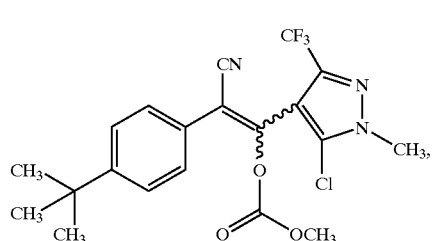

(31) 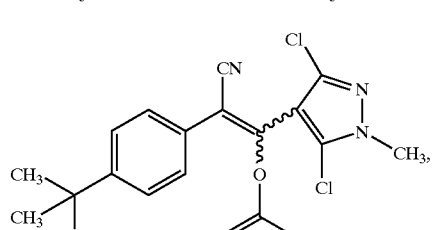

(32) 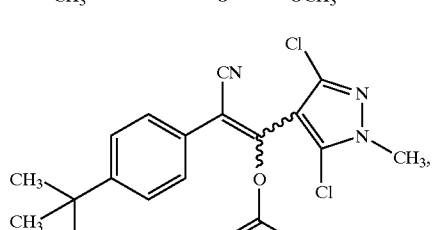

(33) 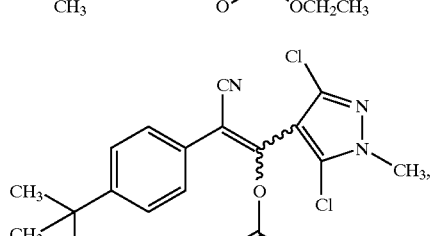

-continued

(34) 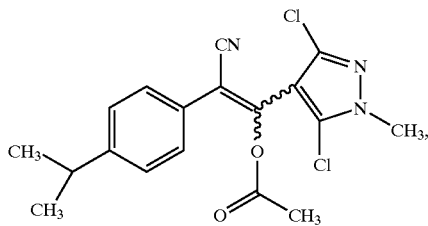

(35) 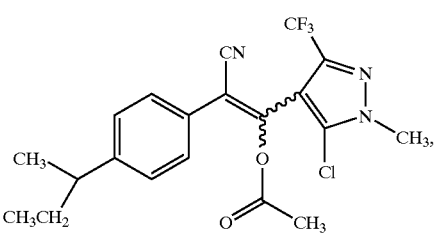

(36) 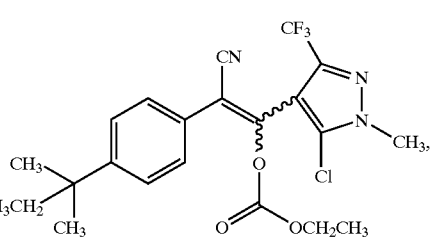

(37) 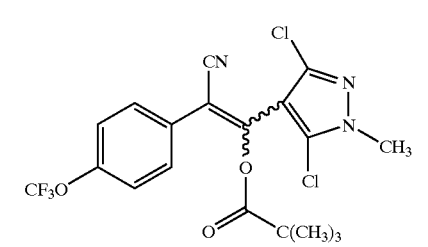

[24] An agricultural chemical comprising, as the active ingredient, one or more ethylene derivatives of the above-mentioned [1] to [23].

[25] An agent for preventing the attachment of aquatic organisms containing, as an active ingredient, one or more ethylene derivatives of the above-mentioned [1] to [23].

MODES OF CARRYING OUT THE INVENTION

The moiety —C(E)=C(OB)— of the compounds (I) of the present invention includes two isomers of E-form and Z-form, both of which are within the scope of the invention.

It will be understood that the compounds of formula (I) of the present invention where the substituent B is a hydrogen atom exist as tautomers to be represented by the following:

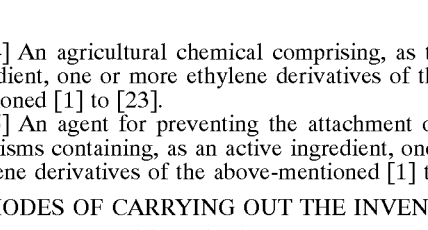

Although the compounds (I) will exist essentially as the enol-form (1'), they could be as the tautomer form (2) under some conditions. It should be understood that the present invention includes all these three tautomers and their mixtures.

Now, preferred embodiments of Q, A, B, E, G, R, $R^1$, Y, $Y^1$, $Y^2$, W, X, Z, $T^1$, $T^2$, $T^3$, $T^4$, $T^5$, $T^6$, $T^7$, $T^8$, $U^1$, $U^2$, m, n, p and q are referred to hereinunder.

The heterocyclic group for Q, A and B indicates the following meanings.

Specifically, thienyl is thiophen-2-yl or thiophen-3-yl; furyl is furan-2-yl or furan-3-yl; pyrrolyl is pyrrol-1-yl, pyrrol-2-yl or pyrrol-3-yl; oxazolyl is oxazol-2-yl, oxazol-3-yl, oxazol-4-yl or oxazol-5-yl; thiazolyl is thiazol-2-yl, thiazol-4-yl or thiazol-5-yl; imidazolyl is imidazol-1-yl, imidazol-2-yl or imidazol-4-yl; isoxazolyl is isoxazol-3-yl, isoxazol-4-yl or isoxazol-5-yl; isothiazolyl is isothiazol-3-yl, isothiazol-4-yl or isothiazol-5-yl; pyrazolyl is pyrazol-1-yl, pyrazol-3-yl, pyrazol-4-yl or pyrazol-5-yl; 1,3,4-oxadiazolyl is 1,3,4-oxadiazol-2-yl; 1,3,4-thiadiazolyl is 1,3,4-thiadiazol-2-yl; 1,2,4-oxadiazolyl is 1,2,4-oxadiazol-3-yl or 1,2,4-oxadiazol-5-yl; 1,2,4-thiadiazolyl is 1,2,4-thiadiazol-3-yl or 1,2,4-thiadiazol-5-yl; 1,2,4-triazolyl is 1,2,4-triazol-1-yl, 1,2,4-triazol-3-yl or 1,2,4-triazol-4-yl; 1,2,3-thiadiazolyl is 1,2,3-thiadiazol-4-yl or 1,2,3-thiadiazol-5-yl; 1,2,3-triazolyl is 1,2,3-triazol-1-yl, 1,2,3-triazol-2-yl or 1,2,3-triazol-4-yl; 1,2,3,4-tetrazolyl is 1,2,3,4-tetrazol-1-yl, 1,2,3,4-tetrazol-2-yl or 1,2,3,4-tetrazol-5-yl; pyridinyl is pyridin-2-yl, pyridin-3-yl or pyridin-4-yl; pyrimidinyl is pyrimidin-2-yl, pyrimidin-4-yl or pyrimidin-5-yl; pyrazinyl is pyrazin-2-yl; pyridazinyl is pyridazin-3-yl or pyridazin-4-yl; 1,3,5-triazinyl is 1,3,5-triazin-2-yl; 1,2,4-triazinyl is 1,2,4-triazin-3-yl, 1,2,4-triazin5-yl or 1,2,4-triazin-6-yl; 1,2,4,5-tetrazinyl is 1,2,4,5-tetrazin-3-yl; pyrazolinyl is 3-pyrazolin-1-yl, 3-pyrazolin-3-yl, 3-pyrazolin-4-yl or 3-pyrazolin-5-yl; imidazolinyl is 1-imidazolin-3-yl, 1-imidazolin-2yl, 1-imidazolin-4-yl or 4-imidazolin-2-yl; oxazolinyl is 2-oxazolin-2-yl, 2-oxazolin-4-yl or 2-oxazolin-5-yl; isoxazolinyl is 2-isoxazolin-3-yl, 2-isoxazolin-4-yl or 2-isoxazolin-5-yl; thiazolinyl is 2-thiazolin-2-yl, 2-thiazolin-4-yl or 3-thiazolin-2-yl; imidazolidinon-yl is imidazolidin-2-on-1-yl; imidazolinon-yl is 2-imidazolinon-1-yl; and 3(2H)-pyridazinon-yl is 3(2H)-pyridazinon-2-yl, 3(2H)-pyridazinon-4-yl, 3(2H)-pyridazinon-5-yl or 3(2H)-pyridazinon-6-yl.

Preferred scope of Q is the following groups.

QI: phenyl, thienyl, furyl, pyrrolyl, oxazolyl, isoxazolyl, thiazolyl, isothiazolyl, pyrazolyl, imidazolyl, 1,3,4-oxadiazolyl, 1,2,4-oxadiazolyl, 1,3,4-thiadiazolyl, 1,2,4-thiadiazolyl, 1,2,4-triazolyl, 1,2,3-thiadiazolyl, 1,2,3-triazolyl, 1,2,3,4-tetrazolyl, pyridinyl, pyrimidinyl, pyrazinyl, pyridazinyl, 1,3,5-triazinyl, 1,2,4-triazinyl, 1,2,4,5-tetrazinyl.

QII: phenyl, thienyl, furyl, pyrrolyl, oxazolyl, isoxazolyl, thiazolyl, pyrazolyl, imidazolyl, 1,3,4-oxadiazolyl, 1,2,4-oxadiazolyl, 1,2,4-thiadiazolyl, 1,2,4-triazolyl, 1,2,3-triazolyl, 1,2,3,4-tetrazolyl, pyridinyl, pyrimidinyl.

QIII: phenyl, thienyl, oxazolyl, thiazolyl, pyrazolyl, pyridinyl, pyrimidinyl, 1,2,3-triazolyl.

QIV: phenyl.

QV: oxazolyl.

QVI: thiazolyl.

QVII: pyrazolyl.

QVIII: pyrimidinyl.

QIX: 1,2,3-triazolyl.

Preferred scope of A is the following groups.

AI: phenyl, thienyl, furyl, pyrrolyl, oxazolyl, isoxazolyl, thiazolyl, isothiazolyl, pyrazolyl, imidazolyl, 1,3,4-oxadiazolyl, 1,2,4-oxadiazolyl, 1,3,4-thiadiazolyl, 1,2,4-thiadiazolyl, 1,2,4-triazolyl, 1,2,3-thiadiazolyl, 1,2,3-triazolyl, 1,2,3,4-tetrazolyl, pyridinyl, pyrimidinyl, pyrazinyl, pyridazinyl, 1,3,5-triazinyl, 1,2,4-triazinyl.

AII: phenyl, thienyl, furyl, pyrrolyl, oxazolyl, isoxazolyl, thiazolyl, pyrazolyl, imidazolyl, 1,2,3-triazolyl, 1,2,3-thiadiazolyl, pyridinyl, pyrimidinyl, pyrazinyl, pyridazinyl.

AIII: phenyl, thiazolyl, pyrazolyl, pyridinyl, pyrimidinyl.

AIV: thiazolyl, pyrazolyl, pyridinyl.

AV: thiazolyl.

AVI: pyrazolyl.

AVII: pyridinyl

Preferred scope of B is the following groups.

BI: H, $C_1$–$C_4$ alkyl, $C_1$–$C_4$ haloalkyl, $C_2$–$C_4$ alkoxyalkyl, $CH_3OC_2H_4OCH_2$, $C_1$–$C_4$ alkylsulfonyl, phenylsulfonyl optionally substituted by halogen or $C_1$–$C_4$ alkyl, —$SO_2CF_3$, $C_2$–$C_8$ dialkylaminosulfonyl, $C_3$–$C_9$ dialkylaminothiocarbonyl, $C_3$–$C_9$ alkoxycarbonylalkyl, —C(=O)$T^1$, —P(=O)$T^2T^3$, —P(=S)$T^2T^3$, alkali metal, alkaline earth metal or $NHT^4T^5T^6$.

BII: H, $C_1$–$C_4$ alkyl, $C_1$–$C_4$ haloalkyl, $C_2$–$C_4$ alkoxyalkyl, $CH_3OC_2H_4OCH_2$, $C_1$–$C_4$ alkylsulfonyl, —$SO_2CF_3$, —C(=O)$T^1$, alkali metal, alkaline earth metal or $NHT^4T^5T$.

BIII: H, $C_1$–$C_4$ alkoxyalkyl, $C_2$–$C_4$ alkylsulfonyl, —$SO_2CF_3$, —C(=O)$T^1$, alkali metal, alkaline earth metal, $NHT^4T^5T^6$.

BIV: $C_2$–$C_4$ alkoxyalkyl, $C_1$–$C_4$ alkylsulfonyl, —$SO_2CF_3$, —C(=O)$T^1$, alkali metal, alkaline earth metal or $NHT^4T^5T^6$.

Preferred scope of E is the following grouips.

EI: halogen, $C_2$–$C_4$ alkynyl, phenylethynyl optionally substituted by Z, $C_1$–$C_4$ haloalkyl, CN, $NO_2$, $N_3$, CHO, $C_2$–$C_5$ alkylcarbonyl, $C_2$–$C_5$ alkoxycarbonyl, $C_2$–$C_4$ alkylaminocarbonyl, $C_3$–$C_9$ dialkylaminocarbonyl, benzoyl optionally substituted by Z, aminothiocarbonyl, $C_1$–$C_4$ alkylsulfenyl, $C_1$–$C_4$ alkylsulfinyl, $C_1$–$C_4$ alkylsulfonyl, phenylsulfenyl optionally substituted by Z, phenylsulfinyl optionally substituted by Z, phenylsulfonyl optionally substituted by Z, —P(=O)$T^2T^3$, —P(=S)$T^2T^3$.

EII: halogen, $C_2$–$C_4$ alkynyl, phenylethynyl optionally substituted by Z, CN, $C_2$–$C_5$ alkylcarbonyl, $C_2$–$C_5$ alkoxycarbonyl, $C_2$–$C_4$ alkylaminocarbonyl, $C_3$–$C_9$ dialkylaminocarbonyl, benzoyl optionally substituted by Z, aminothiocarbonyl, $C_1$–$C_4$ alkylsulfenyl, $C_1$–$C_4$ alkylsulfinyl, $C_1$–$C_4$ alkylsulfonyl, phenylsulfenyl optionally substituted by Z, phenylsulfinyl optionally substituted by Z, phenylsulfonyl optionally substituted by Z or —P(=O)$T^2T^3$.

EIII: CN.

Preferred scope of G is the following groups.

GI: substituents freely selected from halogen, $C_1$–$C_6$ alkyl, $C_2$–$C_4$ alkenyl, $C_2$–$C_4$ alkynyl, $C_1$–$C_4$ haloalkyl, $C_2$–$C_4$ haloalkenyl, $C_2$–$C_4$ haloalkynyl, $C_3$–$C_6$ cycloalkyl optionally substituted by $C_1$–$C_3$ alkyl, $C_1$–$C_6$ alkoxy, $C_2$–$C_4$ alkenyloxy, $C_2$–$C_4$ alkynyloxy, $C_1$–$C_4$ haloalkoxy, $C_2$–$C_4$ haloalkenyloxy, $C_2$–$C_4$ haloalkynyloxy, $C_1$–$C_4$ alkylsulfenyl, $C_1$–$C_4$ alkylsulfinyl, $C_1$–$C_4$ alkylsulfonyl, $C_2$–$C_4$ alkenylsulfenyl, $C_2$–$C_4$ alkenylsulfinyl, $C_2$–$C_4$ alkenylsulfonyl, $C_2$–$C_4$ alkynylsulfenyl, $C_2$–$C_4$ alkynylsulfinyl, $C_2$–$C_4$ alkynylsulfonyl, $C_1$–$C_4$ haloalkylsulfenyl, $C_1$–$C_4$ haloalkylsulfinyl, $C_1$–$C_4$ haloalkylsulfonyl, $C_2$–$C_4$ haloalkenylsulfenyl, $C_2$–$C_4$ haloalkenylsulfinyl, $C_2$–$C_4$ haloalkenylsulfonyl, $C_2$–$C_4$ haloalkynylsulfenyl, $C_2$–$C_4$ haloalkynylsulfinyl, $C_2$–$C_4$ haloalkynylsulfonyl, $NO_2$, CN, —$NU^1U^2$, methoxy substituted by phenyl optionally substituted by halogen or $C_1$–$C_4$ alkyl, $C_2$–$C_5$ alkoxycarbonyl, $C_2$–$C_4$ alkoxyalkyl, $C_2$–$C_4$ alkylcarbonyl, $C_2$–$C_4$ haloalkylcarbonyl, $C_2$–$C_5$ alkylcarbonyloxy, $C_2$–$C_5$ haloalkylcarbonyloxy, $C_3$–$C_7$ dialkylaminocarbonyloxy, phenyl optionally substituted by Z, phenoxy optionally substituted by Z, benzoyl optionally substituted by Z, pyridyl optionally substituted by Z, and pyridyloxy optionally substituted by Z (provided that when the substituent is two or more, said substituents may be the same or different) and the number of the substituent, G, is 1, 2, 3 or 4, or G is an alkylene group as bonded to the adjacent substituting positions to form a 5-, 6-, 7- or 8-membered ring.

GII: substituents freely selected from halogen, $C_1$–$C_6$ alkyl, $C_2$–$C_4$ alkenyl, $C_2$–$C_4$ alkynyl, $C_1$–$C_4$ haloalkyl, $C_3$–$C_6$ cycloalkyl optionally substituted by $C_1$–$C_3$ alkyl, $C_1$–$C_6$ alkoxy, $C_2$–$C_4$ alkenyloxy, $C_2$–$C_4$ alkynyloxy, $C_1$–$C_4$ haloalkoxy, $C_2$–$C_4$ haloalkenyloxy, $C_1$–$C_4$ alkylsulfenyl, $C_1$–$C_4$ alkylsulfinyl, $C_1$–$C_4$ alkylsulfonyl, $C_2$–$C_4$ alkenylsulfenyl, $C_2$–$C_4$ alkenylsulfinyl, $C_2$–$C_4$ alkenylsulfonyl, $C_2$–$C_4$ alkynylsulfenyl, $C_2$–$C_4$ alkynylsulfinyl, $C_2$–$C_4$ alkynylsulfonyl, $C_1$–$C_4$ haloalkylsulfenyl, $C_1$–$C_4$ haloalkylsulfinyl, $C_1$–$C_4$ haloalkylsulfonyl, $C_2$–$C_4$ haloalkenylsulfenyl, $C_2$–$C_4$ haloalkenylsulfinyl, $C_2$–$C_4$ haloalkenylsulfonyl, methoxy substituted by phenyl optionally substituted by halogen or $C_1$–$C_4$ alkyl, $C_2$–$C_6$ alkoxycarbonyl, $C_2$–$C_5$ alkylcarbonyloxy, $C_2$–$C_5$ haloalkylcarbonyloxy, phenoxy optionally substituted by Z, and pyridyloxy optionally substituted by Z (provided that the number of the substituent is two or more, said substituebts may be the same or different), and the number of the substituent, G, is 1, 2 or 3.

GIII: substituents freely selected from halogen, $C_1$–$C_6$ alkyl, $C_1$–$C_4$ haloalkyl, $C_3$–$C_6$ cycloalkyl optionally substituted by $C_1$–$C_3$ alkyl, $C_1$–$C_6$ alkoxy, $C_2$–$C_4$ alkenyloxy, $C_2$–$C_4$ alkynyloxy, $C_1$–$C_4$ haloalkoxy, $C_2$–$C_4$ haloalkenyloxy, $C_1$–$C_4$ alkylsulfenyl, $C_1$–$C_4$ alkylsulfinyl, $C_1$–$C_4$ alkylsulfonyl, $C_2$–$C_4$ alkenylsulfenyl, $C_2$–$C_4$ alkenylsulfinyl, $C_2$–$C_4$ alkenylsulfonyl, $C_2$–$C_4$ alkynylsulfenyl, $C_2$–$C_4$ alkynylsulfinyl, $C_2$–$C_4$ alkynylsulfonyl, $C_1$–$C_4$ haloalkylsulfenyl, $C_1$–$C_4$ haloalkylsulfinyl, $C_1$–$C_4$ haloalkylsulfonyl, $C_2$–$C_4$ haloalkenylsulfenyl, $C_2$–$C_4$ haloalkenylsulfinyl, $C_2$–$C_4$ haloalkenylsulfonyl, methoxy substituted by phenyl optionally substituted by halogen or $C_1$–$C_4$ alkyl, $C_2$–$C_6$ alkoxycarbonyl, $C_2$–$C_5$ alkylcarbonyloxy, phenoxy optionally substituted by Z, and pyridyloxy optionally substituted by Z (provided that when the substituent is two or more, said substituents may be the same or different), and the number of the substituent, G, is 1 or 2.

Preferred scope of R is the following group.

RI: substituents freely selected from halogen, $C_1$–$C_6$ alkyl, $C_1$–$C_3$ alkyl substituted by phenyl optionally substituted by halogen or $C_1$–$C_4$ alkyl, $C_1$–$C_6$ haloalkyl, $C_3$–$C_6$ cycloalkyl optionally substituted by $C_1$–$C_3$ alkyl, $C_1$–$C_4$ alkoxy, $C_2$–$C_4$ alkenyloxy, $C_2$–$C_4$ alkynyloxy, $C_1$–$C_4$ haloalkoxy, $C_2$–$C_4$ haloalkenyloxy, $C_2$–CA haloalkynyloxy, $C_1$–$C_4$ alkylsulfenyl, $C_1$–$C_4$ alkylsulfinyl, $C_1$–$C_4$ alkylsulfonyl, $C_2$–$C_4$ alkenylsulfenyl, $C_2$–$C_4$ alkenylsulfinyl, $C_2$–$C_4$ alkenylsulfonyl, $C_2$–$C_4$ alkynylsulfenyl, $C_2$–$C_4$ alkynylsulfinyl, $C_2$–$C_4$ alkynylsulfonyl, $C_1$–$C_4$ haloalkylsulfenyl, $C_1$–$C_4$ haloalkylsulfinyl, $C_1$–$C_4$ haloalkylsulfonyl, $C_2$–$C_4$ haloalkenylsulfenyl, $C_2$–$C_4$ haloalkenylsulfinyl, $C_2$–$C_4$ haloalkenylsulfonyl, $NO_2$, CN, —$NU^1U^2$, naphthyl, $C_2$–$C_4$ alkoxycarbonyl, $C_2$–$C_4$ alkoxyalkyl, phenyl optionally substituted by X, pyridyl optionally substituted by X, and thienyl optionally substituted by X (provided that when the substituent is two or more, said substituents may be the same or different), and the number of the substituent, R, is 1, 2 or 3, or R is an alkylene group as bonded to the adjacent substituting positions to form a 5-, 6-, 7- or 8-membered ring.

RII: substituents freely selected from halogen, $C_1$–$C_6$ alkyl, $C_1$–$C_3$ alkyl substituted by phenyl optionally substituted by halogen or $C_1$–$C_4$ alkyl, $C_1$–$C_4$ haloalkyl, $C_3$–$C_6$ cycloalkyl optionally substituted by $C_1$–$C_3$ alkyl, $NO_2$, CN, —$NU^1U^2$, naphthyl, $C_2$–$C_4$ alkoxycarbonyl, $C_2$–$C_4$ alkoxyalkyl, phenyl optionally substituted by X, and pyridyl optionally substituted by X (provided that when the substituents is two or more, said substituents may be the same or different), and the number of the substituent, R, is 1, 2 or 3.

RIII: substituents freely selected from halogen, $C_1$–$C_6$ alkyl, $C_1$–$C_3$ alkyl substituted by phenyl optionally substituted by halogen or $C_1$–$C_4$ alkyl, $C_1$–$C_4$ haloalkyl, $C_3$–$C_6$ cycloalkyl optionally substituted by $C_1$–$C_3$ alkyl, $NO_2$, CN, —$NU^1U^2$, naphthyl, $C_2$–$C_4$ alkoxycarbonyl, phenyl optionally substituted by X, and pyridyl optionally substituted by X (provided that when the substituent is two or more, said substituents may be the same or different), and the number of the substituent, R, is 1 or 2.

Depending on the type of the heterocyclic group to be substituted by R, the number of R differs. For the group of 1,3,4-oxadiazolyl, 1,2,4-oxadiazolyl, 1,3,4-thiadiazolyl, 1,2,4-thiadiazolyl, 1,2,3-oxadiazolyl, 1,2,3-thiadiazolyl or 1,2,3,4-tetrazolyl, the number of R is 0 or 1, preferably 1. For the group of thiazolyl, oxazolyl, isoxazolyl, isothiazolyl, 1,3,4-triazolyl, 1,2,4-triazolyl, 1,2,3-triazolyl, 1,3,5-triazinyl, 1,2,4-triazinyl or 1,2,4-triazinyl, the number of R is an integer of from 0 to 2, preferably 1 or 2. For the group of thienyl, furyl, pyrazolyl, imidazolyl, pyrimidinyl, pyrazinyl or pyridazinyl, the number of R is an integer of from 0 to 3, preferably an integer of from 0 to 2, more preferably 1 or 2. For the group of pyrrolyl, pyridinyl, pyrazolinyl, imidazolinyl, oxazolinyl, isoxazolinyl or thiazolinyl, the number of R is an integer of from 0 to 4, preferably an integer of from 0 to 3, more preferably 1 or 2.

Preferred scope of Y is the following groups.

YI: substituents freely selected from halogen, $C_1$–$C_6$ alkyl, $C_1$–$C_4$ haloalkyl, $C_1$–$C_4$ alkoxy, $C_2$–$C_4$ alkenyloxy, $C_2$–$C_4$ alkynyloxy, $C_1$–$C_4$ haloalkoxy, $C_2$–$C_4$ haloalkenyloxy, $C_2$–$C_4$ haloalkynyloxy, $C_1$–$C_4$ alkylsulfenyl, $C_1$–$C_4$ alkylsulfinyl, $C_1$–$C_4$ alkylsulfonyl, $C_2$–$C_4$ alkenylsulfenyl, $C_2$–$C_4$ alkenylsulfinyl, $C_2$–$C_4$ alkenylsulfonyl, $C_2$–$C_4$ alkynylsulfenyl, $C_2$–$C_4$ alkynylsulfinyl, $C_2$–$C_4$ alkynylsulfonyl, $C_1$–$C_4$ haloalkylsulfenyl, $C_2$–$C_4$ haloalkylsulfinyl, $C_1$–$C_4$ haloalkylsulfonyl, $C_2$–$C_4$ haloalkenylsulfenyl, $C_1$–$C_4$ haloalkenylsulfinyl, $C_2$–$C_4$ haloalkenylsulfonyl, $C_2$–$C_4$ haloalkynylsulfenyl, $C_2$–$C_4$ haloalkynylsulfinyl, $C_2$–$C_4$ haloalkynylsulfonyl, $NO_2$, CN, —$NU^1U^2$, $C_2$–$C_4$ alkoxycarbonyl, $C_2$–$C_4$ alkoxyalkyl, $C_2$–$C_4$ alkylcarbonyloxy, $C_2$–$C_4$ haloalkylcarbonyloxy, and phenyl optionally substituted by X (provided that when the substituent is two or more, said substituents may be the same or different) and the number of the substituent, Y, is 1, 2 or 3.

YII: substituents freely selected from halogen, $C_1$–$C_4$ alkyl, $C_1$–$C_4$ haloalkyl, $C_1$–$C_4$ alkoxy, $C_1$–$C_4$ alkylsulfenyl, $C_1$–$C_4$ alkylsulfinyl, $C_1$–$C_4$ alkylsulfonyl, $C_1$–$C_4$ haloalkylsulfenyl, $C_1$–$C_4$ haloalkylsulfinyl, $C_1$–$C_4$ haloalkylsulfonyl, $NO_2$, CN, $C_2$–$C_4$ alkoxycarbonyl, and phenyl optionally substituted by X (provided that when the substituent is two or more, said substituents may be the same or different) and the number of the substituent, Y, is 1 or 2.

Depending on the type of the heterocyclic group to be substituted by Y, the number of Y differs. For the group of 1,3,4-oxadiazolyl, 1,2,4-oxadiazolyl, 1,3,4-thiadiazolyl, 1,2, 4-thiadiazolyl, 1,2,3-thiadiazolyl or 1,2,3,4-tetrazolyl, the number of Y is 0 or 1, preferably 1. For the group of thiazolyl, oxazolyl, isoxazolyl, isothiazolyl, 1,3,4-triazolyl, 1,2,4-triazolyl, 1,2,3-triazolyl, 1,3,5-triazinyl, 1,2,4-triazinyl or 1,2,4-triazinyl, the number of Y is an integer of from 0 to 2, preferably 1 or 2. For the group of thienyl, furyl, pyrazolyl, imidazolyl, pyrimidinyl, pyrazinyl or pyridazinyl, the number of Y is an integer of from 0 to 3, preferably an integer of from 0 to 2, more preferably 1 or 2. For the group of pyrrolyl, pyridinyl, pyrazolinyl, imidazolinyl, oxazolinyl, isoxazolinyl or thiazolinyl, the number of Y is an integer of from 0 to 4, preferably an integer of from 0 to 3, more preferably 1 or 2.

Preferred scope of W is the following group.

WI: substituents freely selected from halogen, $C_1$–$C_6$ alkyl, $C_1$–$C_4$ haloalkyl, $C_1$–$C_4$ alkoxy, $C_1$–$C_4$ haloalkoxy, $C_1$–$C_4$ alkylsulfenyl, $C_1$–$C_4$ alkylsulfinyl, $C_1$–$C_4$ alkylsulfonyl, $C_1$–$C_4$ haloalkylsulfenyl, $C_1$–$C_4$ haloalkylsulfinyl, $C_1$–$C_4$ haloalkylsulfonyl, $C_2$–$C_4$ alkenyloxy, $C_2$–$C_4$ haloalkenyloxy, $C_2$–$C_4$ alkenylsulfenyl, $C_2$–$C_4$ alkenylsulfinyl, $C_2$–$C_4$ alkenylsulfonyl, $C_2$–$C_4$ haloalkenylsulfenyl, $C_2$–$C_4$ haloalkenylsulfinyl, $C_2$–$C_4$ haloalkenylsulfonyl, $C_2$–$C_4$ alkynyloxy, $C_2$–$C_4$ alkynylsulfenyl, $C_2$–$C_4$ alkynylsulfinyl, $C_2$–$C_4$ alkynylsulfonyl, $NO_2$, CN, $C_2$–$C_4$ alkoxycarbonyl, $C_2$–$C_4$ alkylcarbonyl, $C_2$–$C_4$ haloalkylcarbonyl, $C_2$–$C_4$ alkylcarbonyloxy, and —$NU^1U^2$ (provided that when the substituent is two or more, said substituents are the same or different) and the number of the substituent, W, is 1, 2, 3 or 4.

WII: substituents freely selected from halogen, $C_1$–$C_4$ alkyl, $C_1$–$C_4$ haloalkyl, $C_1$–$C_4$ alkoxy, $C_1$–$C_4$ haloalkoxy, $C_1$–$C_4$ alkylsulfenyl, $C_1$–$C_4$ alkylsulfinyl, $C_1$–$C_4$ alkylsulfonyl, $C_1$–$C_4$ haloalkylsulfenyl, $C_1$–$C_4$ haloalkylsulfinyl, $C_1$–$C_4$ haloalkylsulfonyl, $C_2$–$C_4$ alkenyloxy, $C_2$–$C_4$ haloalkenyloxy, $C_2$–$C_4$ alkenylsulfenyl, $C_2$–$C_4$ alkenylsulfinyl, $C_2$–$C_4$ alkenylsulfonyl, $C_2$–$C_4$ alkynyloxy, $C_2$–$C_4$ alkynylsulfenyl, $C_2$–$C_4$ alkynylsulfinyl, $C_2$–$C_4$ alkynylsulfonyl, $NO_2$, and CN (provided that the substituent is two or more, said substituents may be the same or different) and the number of the substituent, W, is 1, 2 or 3.

WIII: substituents freely selected from halogen, $C_1$–$C_4$ alkyl, $C_1$–$C_4$ haloalkyl, $C_1$–$C_4$ alkoxy, $C_1$–$C_4$ haloalkoxy, $C_1$–$C_4$ alkylsulfenyl, $C_1$–$C_4$ alkylsulfinyl, $C_1$–$C_4$ alkylsulfonyl, $C_1$–$C_4$ haloalkylsulfenyl, $C_1$–$C_4$ haloalkylsulfinyl, $C_1$–$C_4$ haloalkylsulfonyl, $NO_2$, and CN (provided that when the substituent is two or more, the substituents may be the same or different) and the number of the substituent, W, is 1 or 2.

Preferred scope of $T^1$ is the following groups.

$T^1$I: $C_1$–$C_{18}$ alkyl, $C_2$–$C_6$ alkenyl, $C_1$–$C_4$ haloalkyl, $C_1$–$C_4$ alkoxy-$C_1$–$C_4$ alkyl, $C_1$–$C_4$ alkyl substituted by phenyl optionally substituted by halogen or $C_1$–$C_4$ alkyl, $C_3$–$C_6$ halocycloalkyl, $C_3$–$C_6$ cycloalkyl optionally substituted by $C_1$–$C_3$ alkyl, cycloalkyl substituted by phenyl optionally substituted by halogen or $C_1$–$C_4$ alkyl, $C_2$–$C_4$ alkenyl substituted by phenyl optionally substituted by halogen or $C_1$–$C_4$ alkyl, $C_1$–$C_{10}$ alkoxy, $C_1$–$C_4$ haloalkoxy, $C_2$–$C_5$ alkenyloxy, $C_3$–$C_6$ cycloalkoxy optionally substituted by $C_1$–$C_3$ alkyl, benzyloxy, $C_2$–$C_5$ alkoxycarbonyl, —$NU^1U^2$, phenyl optionally substituted by Z, phenoxy optionally substituted by Z, phenylthio optionally substituted by Z, naphthyl, and heterocyclic group optionally substituted by Z, (said heterocyclic group being selected from thienyl, furyl, pyrrolyl, oxazolyl, isoxazolyl, thiazolyl, pyrazolyl, imidazolyl, 1,3,4-oxadiazolyl, 1,2,4-oxadiazolyl, 1,3,4-thiadiazolyl, 1,2,4-thiadiazolyl, 1,2,4-triazolyl, 1,2,3-thiadiazolyl, 1,2,3-triazolyl, 1,2,3,4-tetrazolyl, pyridinyl, pyrimidinyl, pyrazinyl, pyridazinyl, 1,3,5-triazinyl and 1,2,4triazinyl groups).

$T^1$II: $C_1$–$C_{18}$ alkyl, $C_2$–$C_5$ alkenyl, $C_1$–$C_4$ haloalkyl, $C_2$–$C_4$ alkoxyalkyl, $C_1$–$C_4$ alkyl substituted by phenyl optionally substituted by halogen or $C_1$–$C_4$ alkyl, $C_3$–$C_6$ cycloalkyl optionally substituted by $C_1$–$C_3$ alkyl, cycloalkyl substituted by phenyl optionally substituted by halogen or $C_1$–$C_4$ alkyl, $C_2$–$C_4$ alkenyl substituted by phenyl optionally substituted by halogen or $C_1$–$C_4$ alkyl, $C_1$–$C_{10}$ alkoxy, $C_1$–$C_4$ haloalkoxy, $C_2$–$C_5$ alkenyloxy, $C_3$–$C_6$ cycloalkoxy, benzyloxy, $C_2$–$C_6$ alkoxycarbonyl, phenyl optionally substituted by Z, phenoxy optionally substituted by Z, phenylthio, naphthyl, and heterocyclic group optionally substituted by Z (said heterocyclic group being selected from thienyl, furyl, oxazolyl, thiazolyl, pyrazolyl and pyridinyl groups).

$T^1$III: $C_1$–$C_{17}$ alkyl, $C_2$–$C_6$ alkenyl, $C_1$–$C_4$ haloalkyl, $C_2$–$C_4$ alkoxyalkyl, $C_1$–$C_4$ alkyl substituted by phenyl, $C_3$–$C_6$ cycloalkyl optionally substituted by $C_1$–$C_3$ alkyl, cycloalkyl substituted by phenyl, $C_2$–$C_4$ alkenyl substituted by phenyl, $C_1$–$C_8$ alkoxy, $C_1$–$C_4$ haloalkoxy, $C_2$–$C_5$ alkenyloxy, $C_3$–$C_5$ cycloalkoxy, benzyloxy, $C_2$–$C_5$ alkoxycarbonyl, phenyl optionally substituted by Z, phenoxy optionally substituted by Z, phenylthio, naphthyl, pyrazolyl optionally substituted by Z or pyridinyl optionally substituted by Z.

Preferred scope of $T^2$ is the following groups.

$T^2$I: phenyl, $C_1$–$C_4$ alkyl, $C_1$–$C_4$ alkoxy or $C_1$–$C_4$ alkylsulfenyl.

Preferred scope of $T^3$ is the following groups.

$T^3$I: phenyl, $C_1$–$C_6$ alkyl, $C_1$–$C_6$ alkoxy or $C_1$–$C_4$ alkylsulfenyl.

Preferred scope of $T^4$ is the following groups.

$T^4$I: H, $C_1$–$C_4$ alkyl, $C_3$–$C_6$ cycloalkyl or benzyl. Also preferred is such that any two of $T^4$, $T^5$ and $T^6$, together with the nitrogen atom to which they are bonded, forms a 5-, 6- or 7-membered ring optionally having oxygen, nitrogen and/or sulfur atoms.

Preferred scope of $T^5$ is the following groups.

$T^5$I: H, $C_1$–$C_4$ alkyl, $C_3$–$C_6$ cycloalkyl or benzyl. Also, preferred is such that any two of $T^4$, $T^5$ and $T^6$, together with the nitrogen atom to which they are bonded, forms a 5-, 6- or 7-membered ring optionally having oxygen, nitrogen and/or sulfur atoms.

Preferred scope of $T^6$ is the following groups.

$T^8$I: H, $C_1$–$C_4$ alkyl, $C_3$–$C_6$ cycloalkyl or benzyl. Also, preferred is such that any two of $T^4_1$ $T^5$ and $T^6$, together with the nitrogen atom to which they are bonded, forms a 5-, 6- or 7-membered ring optionally having oxygen, nitrogen and/or sulfur atoms.

Preferred scope of X is the following groups.

XI: substituents freely selected from halogen, $C_1$–$C_4$ alkyl, $C_1$–$C_4$ haloalkyl, $C_1$–$C_4$ alkoxy, $C_1$–$C_4$ haloalkoxy, $C_1$–$C_4$ alkylsulfenyl, $C_1$–$C_4$ alkylsulfinyl, $C_1$–$C_4$ alkylsulfonyl, $C_2$–$C_5$ alkenylsulfenyl, $C_2$–$C_5$ alkenylsulfinyl, $C_2$–$C_5$ alkenylsulfonyl, $C_1$–$C_4$ haloalkylsulfenyl, $C_1$–$C_4$ haloalkylsulfinyl, $C_1$–$C_4$ haloalkylsulfonyl, $NO_2$, CN, —$NU^1U^2$ and $C_2$–$C_6$ alkoxycarbonyl (provided that the substituent is two or more, said substituents may be the same or different) and the substituent, X, is 1, 2 or 3.

XII: substituents freely selected from halogen, $C_1$–$C_4$ alkyl, $C_1$–$C_4$ haloalkyl, $C_1$–$C_4$ alkoxy, $C_1$–$C_4$ haloalkoxy, $C_1-C_4$ alkylsulfenyll $C_1-C_4$ alkylsulfinyl, $C_1-C_4$ alkylsulfonyl, $C_2-C_5$ alkenylsulfenyl, $C_1-C_4$ haloalkylsulfenyl, $C_1-C_4$ haloalkylsulfinyl, $C_1-C_4$ haloalkylsulfonyl, and $NO_2$ (provided that when the substituent is two or more, said substituents may be the same or different) and the number of the substituent, X, is 1, 2 or 3.

XIII: substituents freely selected from halogen, $C_1-C_4$ alkyl, $C_1-C_4$ haloalkyl, and $C_1-C_4$ alkoxy (provided that when the substituent is two or more, said substituents may be the same or different) and the number of the substituent, X, is 1 or 2.

Depending on the type of the ring to be substituted by X, the number of X differs. For phenyl, the number of X is an integer of from 0 to 5, preferably an integer of from 0 to 3, more preferably an integer of from 0 to 2. For pyridyl, the number of X is an integer of from 0 to 4, preferably 0, 1 or 2, more preferably 0 or 1. For thienyl, the number of X is an integer of from 0 to 3, preferably 0 or 1.

Preferred scope of Z is the following groups.

ZI: substituents freely selected from halogen, $C_1-C_4$ alkyl, $C_1-C_4$ haloalkyl, $C_1-C_4$ alkoxy, $C_1-C_4$ haloalkoxy, $C_1-C_4$ alkylsulfenyl, $C_1-C_4$ alkylsulfinyl, $C_1-C_4$ alkylsulfonyl, $C_2-C_5$ alkenylsulfenyl, $C_2-C_5$ alkenylsulfinyl, $C_2-C_5$ alkenylsulfonyl, $C_1-C_4$ haloalkylsulfenyl, $C_1-C_4$ haloalkylsulfinyl, $C_1-C_4$ haloalkylsulfonyl, $NO_2$, CN, —$NU^1U^2$ and $C_2-C_5$ alkoxycarbonyl (provided that when the substituent is two or more, said substituents may be the same or different) and the number of the substituent, Z, is 1, 2, 3 or 4.

ZII: substituents freely selected from halogen, $C_1-C_4$ alkyl, $C_1-C_4$ haloalkyl, $C_1-C_4$ alkoxy, $C_1-C_4$ haloalkoxy, $C_1-C_4$ alkylsulfenyl, $C_1-C_4$ alkylsulfinyl, $C_1-C_4$ alkylsulfonyl, $C_2-C_5$ alkenylsulfenyl, $C_2-C_5$ alkenylsulfinyl, $C_2-C_5$ alkenylsulfonyl, $C_1-C_4$ haloalkylsulfenyl, $C_1-C_4$ haloalkylsulfinyl and $C_1-C_4$ haloalkylsulfonyl (provided that when the substituent is two or more, said substituents may be the same or different) and the substituent, Z, is 1, 2, 3 or 4.

Depending on the type of the ring to be substituted by Z, the number of Z differs. For phenyl, the number of Z is an integer of from 0 to 5, preferably an integer of from 0 to 4, more preferably 0, 1, 2 or 3, even more preferably 0, 1 or 2. For naphthyl, the number of Z is an integer of from 0 to 7, preferably 0. Where the ring to be substituted by Z is a heterocyclic group, the number of the substituents of Z also differs depending on the type of the heterocyclic group. For the group of 1,3,4-oxadiazolyl, 1,2,4-oxadiazolyl, 1,3,4-thiadiazolyl, 1,2,4-thiadiazolyl, 1,2,3-oxadiazolyl, 1,2,3-thiadiazolyl, 1,2,3,4-tetrazolyl or 1,2,3,5-tetrazolyl, the number of Z is 0 or 1. For the group of thiazolyl, oxazolyl, isoxazolyl, isothiazolyl, 1,3,4-triazolyl, 1,2,4-triazolyl, 1,2,3-triazolyl, 1,3,5-triazinyl, 1,2,4-triazinyl or 1,2,4-triazinyl, the number of Z is an integer of from 0 to 2, preferably 1 or 2. For the group of thienyl, furyl, pyrazolyl, imidazolyl, pyrimidinyl, pyrazinyl or pyridazinyl, the number of Z is an integer of from 0 to 3, preferably an integer of from 0 to 2, more preferably 1 or 2. For the group of pyrrolyl, pyridinyl, pyrazolinyl, imidazolinyl, oxazolinyl, isoxazolinyl or thiazolinyl, the number of Z is an integer of from 0 to 4, preferably an integer of from 0 to 2, more preferably 1 or 2.

Preferred scope of $T^7$ is the following groups.

$T^7I$: H, phenyl, benzyl or $C_1-C_4$ alkyl. Also preferred is such that $T^7$ and $T^8$, together with the carbon atom to which they are bonded, form a 5-membered or 6-membered ring.

Preferred scope of $T^8$ is the following groups.

$T^8I$: phenyl, benzyl or $C_1-C_4$ alkyl. Also preferred is such that $T^7$ and $T^8$, together with the carbon atom to which they are bonded, form a 5-membered or 6-membered ring.

Preferred scope of $U^1$ is the following groups.

$U^1I$: H, $C_1-C_4$ alkyl or $C_2-C_5$ alkylcarbonyl. Also preferred is such that $U^1$ and $U^2$, together with nitrogen atom to which they are bonded, form a 5-, 6- or 7-membered ring.

Preferred scope of $U^2$ is the following groups.

$U^2I$: H, $C_1-C_4$ alkyl or $C_2-C_5$ alkylcarbonyl. Also preferred is such that $U^1$ and $U^2$, together with the carbon atom to which they are bonded, form a 5-, 6- or 7-membered ring.

Preferably, m is 1, 2, or 3, more preferably 1 or 2.

Preferably n is 0, 1, 2 or 3, more preferably 1 or 2.

Preferably, p is 1 or 2.

The above-mentioned preferred groups in the scopes of the preferred substituents can be optionally combined and show the scopes of the preferred compounds of the present invention. Hereinunder mentioned are especially preferred scopes.

Compounds of the invention comprising preferred substituents of QI, AI, BI, EI, GI, RI, YI, WI, $T^1I$, $T^2I$, $T^3I$, $T^4I$, $T^5I$, $T^6I$, XI, ZI, $T^7I$, $T^8I$, $U^1I$ and $U^2I$.

Compounds of the invention comprising preferred substituents of QI, AI, BI, EIII, GI, RI, YI, WI, $T^1I$, $T^2I$, $T^3I$, $T^4I$, $T^5I$, $T^6I$, XI, ZI, $T^7I$, $T^8I$, $U^1I$ and $U^2I$.

Compounds of the invention comprising preferred substituents of QII, AII, BI, EII, GI, RI, YI, WI, $T^1I$, $T^2I$, $T^3I$, $T^4I$, $T^5I$, $T^6I$, XI, ZI, $T^7I$, $T^8I$, $U^1I$ and $U^2I$.

Compounds of the invention comprising preferred substituents of QII, AII, BI, EIII, GI, RI, YI, WI, $T^1I$, $T^2I$, $T^3I$, $T^4I$, T5I, $T^6I$, XI, ZI, $T^7I$, $T^8I$, $U^1I$ and $U^2I$.

Compounds of the invention comprising preferred substituents of QIII, AIII, BI, EIII, GI, RI, YI, WI, TI, $T^2I$, $T^3I$, $T^4I$, $T^5 I$, $T^6I$, XI, ZI, $T^7I$, $T^8I$, $U^1I$ and $U^2I$.

Compounds of the invention comprising preferred substituents of QIII, AIII, BII, EIII, GII, RII, YII, WII, $T^1III$, $T^2I$, $T^3I$, $T^4I$, $T^5I$, $T^6I$, XII, ZII, $T^7I$, $T^8I$, $U^1I$ and $U^2I$.

Compounds of the invention comprising preferred substituents of QIII, AIII, BII, EIII, GIII, RIII, YII, WII, $T^1III$, $T^2I$, $T^3I$, $T^4I$, $T^5I$, $T^6I$, XIII, ZII, $T^7I$, $T^8I$, $U^1I$ and $U^2I$.

Compounds of the invention comprising preferred substituents of QVI, AIII, BIII, EIII, GIII, RIII, YII, WII, $T^1III$, $T^2I$, $T^3I$, $T^4I$, $T^5I$, $T^6I$, XIII, ZII, $T^7I$, $T^8I$, $U^1I$ and $U^2I$.

Compounds of the invention comprising preferred substituents of QIV, AIV, BIII, EIII, GIII, RIII, YII, WII, $T^1III$, $T^2I$, $T^3I$, $T^4I$, $T^5I$, $T^6I$, XIII, ZII, $T^7I$, $T^8I$, $U^1I$ and $U^2I$.

Compounds of the invention comprising preferred substituents of QVI, AIII, BIII, EIII, GIII, RIII, YII, WII, $T^1III$, $T^2I$, $T^3I$, $T^4I$, $T^5I$, $T^6I$, XIII, ZII, $T^7I$, $T^8I$, $U^1I$ and $U^2I$ .

Compounds of the invention comprising preferred substituents of QVI, AIII, BIII, EIII, GIII, RIII, YII, WII, $T^1III$, $T^2I$, $T^3I$, $T^4I$, $T^5I$, $T^6I$, XIII, ZII, $T^7I$, $T^8I$, $U^1I$ and $U^2I$.

Compounds of the invention comprising preferred substituents of QVI, AIV, BIII, EIII, GIII, RIII, YII, WII, $T^1III$, $T^2I$, $T^3I$, $T^4I$, $T^5I$, $T^6I$, XIII, ZII, $T^7I$, $T^8I$, $U^1I$ and $U^2I$.

Compounds of the invention comprising preferred substituents of QVII, AIII, BIII, EIII, GIII, RIII, YII, WII, $T^1III$, $T^2I$, $T^3I$, $T^4I$, $T^5I$, $T^6I$, XIII, ZII, $T^7I$, $T^8I$, $U^1I$ and $U^2I$.

Compounds of the invention comprising preferred substituents of QVII, AIII, BIII, EIII, GIII, RIII, YII, WII, $T^1III$, $T^2I$, $T^3I$, $T^4I$, $T^5I$, $T^6I$, XIII, ZII, $T^7I$, $T^8I$, $U^1I$ and $U^2I$.

Compounds of the invention comprising preferred substituents of QIX, AIII, BIII, EIII, GIII, RIII, YII, WII, $T^1III$, $T^2I$, $T^3I$, $T^4I$, $T^5I$, $T^6I$, XIII, ZII, $T^7I$, $T^8I$, $U^1I$ and $U^2I$.

Compounds of the invention comprising preferred substituents of QIII, AV, BIII, EIII, GIII, RIII, YII, WII, $T^1III$, $T^2I$, $T^3I$, $T^4I$, $T^5I$, $T^6I$, XIII, ZII, $T^7I$, $T^8I$, $U^1I$ and $U^2I$.

Compounds of the invention comprising preferred substituents of QIII, AVI, BIII, EIII, GIII, RIII, YII, WII, T$^1$III, T$^2$I, T$^3$I, T$^4$I, T$^5$I, T$^6$I, XIII, ZII, T$^7$I, T$^8$I, U$^1$I and U$^2$I.

Compounds of the invention comprising preferred substituents of QIII, AVII, BIII, EIII, GIII, RIII, YII, WII, T$^1$III, T$^2$I, T$^3$I, T$^4$I, T$^5$I, T$^6$I, XIII, ZII, T$^7$I, T$^8$I, U$^1$I and U$^2$I.

Now, specific examples of Q, A, B, E, G, R, R$^1$, Y, Y$^1$, Y$^2$, W, X, Z, T$^1$, T$^2$, T$^3$, T$^4$, T$^5$, T$^6$, T$^7$, T$^8$, U$^1$ and U$^2$, are mentioned below.

The halogen atom for E, G, R, R$^1$, W, X, Y, Y$^1$, Y$^2$, Y$^3$ and Z includes a fluorine atom, a chlorine atom, a bromine atom, and an iodine atom. Preferred are a fluorine atom, a chlorine atom and a bromine atom.

The alkyl group for B, G, R, R$^1$, T$^1$, T$^2$, T$^3$, T$^4$, T$^5$, T$^6$, T$^7$, T$^8$, U$^1$, U$^2$, W, X, Y, Y$^1$, Y$^2$, Y$^3$ and Z may be a straight chain or branched alkyl group having indicated carbon atoms, which includes, for example, methyl, ethyl, n-propyl, isopropyl, n-butyl, isobutyl, tert-butyl, sec-butyl, pentyl-1, pentyl-2, pentyl-3, 2-methylbutyl-1, 2-methylbutyl-2, 2-methylbutyl-3, 3-methylbutyl-1, 2,2-dimethylpropyl-1, hexyl-1, hexyl-2, hexyl-3, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl, 1-ethyl-2-methylpropyl, n-heptyl, n-octyl, n-nonyl, n-undecyl, n-dodecyl, n-tridecyl, n-tetradecyl, n-pentadecyl, n-hexadecyl, n-heptadecyl, n-octadecyl, n-nonadecyl and n-eicosyl groups.

The alkenyl group for G, R, R$^1$, T$^1$, T$^4$, T$^5$, T$^6$, Y$^1$ and W may be a straight chain or branched alkenyl group having indicated carbon atoms, which includes, for example, ethenyl, 1-propenyl, 2-propenyl, 1-butenyl, 2-butenyl, 3-butenyl, 1-methyl-2-propenyl, 2-methyl-2-propenyl, 1-pentenyl, 2-pentenyl, 3-pentenyl, 4-pentenyl, 1-methyl-2-butenyl, 2-methyl-2-butenyl, 3-methyl-2-butenyl, 1-methyl-3-butenyl, 2-methyl-3-butenyl, 3-methyl-3-butenyl, 1,1-dimethyl-2-propenyl, 1,2-dimethyl-2-propenyl, 1-ethyl-2-propenyl, 1-hexenyl, 2-hexenyl, 3-hexenyl, 4-hexenyl, 5-hexenyl, 1-methyl-2-pentenyl, 2-methyl-2-pentenyl, 3-methyl-2-pentenyl, 4-methyl-2-pentenyl, 1-methyl-3-pentenyl, 2-methyl-3-pentenyl, 3-methyl-3-pentenyl, 4-methyl-3-pentenyl, 1-methyl-4-pentenyl, 2-methyl-4-pentenyl, 3-methyl-4-pentenyl, 4-methyl-4-pentenyl, 1,1-dimethyl-2-butenyl, 1,1-dimethyl-3-butenyl, 1,2-dimethyl-2-butenyl, 1,2-dimethyl-3-butenyl, 1,3-dimethyl-2-butenyl, 1,3-dimethyl-3-butenyl, 2,3-dimethyl-2-butenyl, 2,3-dimethyl-3-butenyl, 3,3-dimethyl-2-butenyl, 1-ethyl-2-butenyl, 1-ethyl-3-butenyl, 2-ethyl-2-butenyl, 2-ethyl-3-butenyl, 1,1,2-trimethyl-2-propenyl and 1-ethyl-1-methyl-2-propenyl groups.

The alkynyl group for E, G, R, R$^1$, Y$^1$ and W may be a straight chain or branched alkynyl group having indicated carbon atoms, which includes, for example, ethynyl, 1-propynyl, 2-propynyl, 1-butynyl, 2-butynyl, 3-butynyl, 1-methyl-2-propynyl, 1-pentynyl, 2-pentynyl, 3-pentynyl, 4-pentynyl, 1-methyl-2-butynyl, 1-methyl-3-butynyl, 2-methyl-3-butynyl, hexynyl, 1-methyl-3-pentynyl, 1-methyl-4-pentynyl, 2-methyl-3-pentynyl, 2-methyl-4-pentynyl, 3-methyl-4-pentynyl, 4-methyl-2-pentynyl, 1,1-dimethyl-2-butynyl, 1,1-dimethyl-3-butynyl, 1,2-dimethyl-3-butynyl, 2,2-dimethyl-3-butynyl, 1-ethyl-2-butynyl, 1-ethyl-3-butynyl and 2-ethyl-3-butynyl groups.

The haloalkyl group for B, E, G, R, R$^1$, T$^1$, W, X, Y, Y$^1$, Y$^2$, Y$^3$ and Z may be a straight chain or branched haloalkyl group having indicated carbon atoms, which includes, for example, fluoromethyl, chloromethyl, bromomethyl, fluoroethyl, chloroethyl, bromoethyl, fluoro-n-propyl, chloro-n-propyl, difluoromethyl, chlorodifluoromethyl, trifluoromethyl, dichloromethyl, trichloromethyl, difluoroethyl, trifluoroethyl, trichloroethyl, chlorodifluoromethyl, bromodifluoromethyl, trifluorochloroethyl, hexafluoro-n-propyl, chlorobutyl, fluorobutyl, chloro-n-pentyl, fluoro-n-pentyl, chloro-n-hexyl and fluoro-n-hexyl groups.

The C$_3$–C$_6$ cycloalkyl group optionally substituted by a C$_1$–C$_3$ alkyl group for G, R, T$^1$, T$^4$, T$^5$ and T$^6$ includes, for example, cyclopropyl, 1-methylcyclopropyl, 2,2,3,3-tetramethylcyclopropyl, cyclobutyl, 1-ethylcyclobutyl, 1-n-butylcyclobutyl, cyclopentyl, 1-methylcyclopentyl, cyclohexyl, 1-methylcyclohexyl and 4-methylcyclohexyl groups.

The C$_1$–C$_4$ alkyl group substituted by a phenyl group optionally substituted by a halogen atom or a C$_1$–C$_4$ alkyl group for B, G, R and T$^1$ includes, for example, benzyl, 2-chlorobenzyl, 3-bromobenzyl, 4-chlorobenzyl, 4-methylbenzyl, 4-tert-butylbenzyl, 1-phenylethyl, 1-(3-chlorophenyl)ethyl, 2-phenylethyl, 1-methyl-1-phenylethyl, 1-(4-chlorophenyl)-1-methylethyl, 1-(3-chlorophenyl)-1-methylethyl, 1-phenylpropyl, 2-phenylpropyl, 3-phenylpropyl, 1-phenylpropyl, 2-phenylbutyl, 3-phenylbutyl, 4-phenylbutyl, 1-methyl-1-phenylpropyl, 1-methyl-2-phenylpropyl, 1-methyl-3-phenylpropyl, 2-methyl-2-phenylpropyl, 2-(4-chlorophenyl)-2-methylpropyl and 2-methyl-2-(3-methylphenyl)propyl groups.

For T$^1$, the C$_3$–C$_5$ cycloalkyl group substituted by a phenyl group optionally substituted by a halogen atom or a C$_1$–C$_4$ alkyl group includes, for example, 1-phenylcyclopropyl, 1-(3-chlorophenyl)cyclopropyl, 1-(4-chlorophenyl)cyclopropyl, 1-(4-bromophenyl)cyclopropyl, 1-(4-fluorophenyl)cyclopropyl, 1-(4-ethylphenyl)cyclopropyl, 1-(4-propylphenyl)cyclopropyl, 2-phenylcyclopropyl, 1-phenylcyclobutyl, 2-phenylcyclobutyl, 1-phenylcyclopentyl, 1-(4-chlorophenyl)cyclopentyl, 2-phenylcyclopentyl, 3-phenylcyclopentyl, 1-phenylcyclohexyl, 1-(3-fluorophenyl)cyclohexyl, 1-(4-chlorophenyl)cyclohexyl, 1-(4-tert-butylphenyl)cyclohexyl, 2-phenylcyclohexyl, 3-phenylcyclohexyl and 4-phenylcyclohexyl groups.

For T$^1$, the cyclopropyl group substituted by both a phenyl group optionally substituted by a halogen atom or a C$_1$–C$_4$ alkyl group and a C$_1$–C$_4$ alkyl group includes, for example, 2,2-dimethyl-1-phenylcyclopropyl, 1-(4-chlorophenyl)-2,2-dimethylcyclopropyl, 2,2-dimethyl-3-phenylcyclopropyl, 3-(3-chlorophenyl)-2,2-dimethylcyclopropyl, (4-chlorophenyl)-2,2-dimethyl-3-phenylcyclopropyl, (4-bromophenyl)-2,2-dimethyl-3-phenylcyclopropyl, 2,2-dimethyl-3-(4-methylphenyl)cyclopropyl and (4-tert-butylphenyl)-2,2-dimethyl-3-phenylcyclopropyl groups.

For T$^1$, the C$_3$–C$_4$ cycloalkyl group substituted by both a phenyl group optionally substituted by a halogen atom or a C$_1$–C$_4$ alkoxy group and a halogen atom includes, for example, 2,2-dichloro-1-phenylcyclopropyl, 2,2-dichloro-1-(3-chlorophenyl)cyclopropyl, 2,2-dichloro-1-(4-methoxyphenyl)cyclopropyl, 2,2-dichloro-1-(4-ethoxyphenyl)cyclopropyl, 2,2-dichloro-(4-1-propyloxyphenyl)cyclopropyl, 2,2-dichloro-1-(4-t-butylphenyl)cyclopropyl, 2,2-dichloro-1-(4-methoxyphenyl)-3-phenylcyclopropyl and 1-(4-ethoxyphenyl)-2,2,3,3-tetrafluorobutyl groups.

For T$^1$, the cyclopropyl group substituted by both a C$_2$–C$_4$ alkenyl group optionally substituted by a halogen atom, and a $C_1$–$C_4$ alkyl group includes, for example, 2,2-dimethyl-3-(2,2-dimethylethenyl)cyclopropyl, 3-(2,2-dibromoethenyl)-2,2-dimethylcyclopropyl, 3-(2,2-dichoroethenyl)-2,2-dimethylcyclopropyl and 3-(2,2-chlorotrifluoroethenyl)-2,2-dimethylcyclopropyl groups.

For $T^1$, the $C_3$–$C_5$ cycloalkoxy group optionally substituted by a $C_1$–$C_3$ alkyl group includes, for example, cyclopropoxy, cyclobutoxy, cyclopentoxy, cyclohexyloxy and 1-methylcyclopropoxy groups.

For $T^1$, the $C_2$–$C_4$ alkenyl group substituted by a phenyl group optionally substituted by a halogen atom or a $C_1$–$C_4$ alkyl group includes, for example, 1-phenylethenyl, 2-phenylethenyl, 2-(2-chlorophenyl)ethenyl, 2-(3-chlorophenyl)ethenyl, 2-(4-chlorophenyl)ethenyl, 2-(4-methylphenyl)ethenyl, 2-(2,6-difluorophenyl)ethenyl, 2-(2,5-dimethylphenyl)ethenyl, 1-methyl-2-phenylethenyl, 2-phenyl-1-propenyl, 2-(4-bromophenyl)-1-propenyl and 2-(2,4,6-trimethylphenyl)-1-propenyl groups.

The alkoxy group for G, R, $T^1$, $T^2$, $T^3$, $R^1$, W, X, Y, $Y^1$, $Y^2$ and Z may be a straight chain or branched alkoxy group having indicated carbon atoms, which includes, for example, methoxy, ethoxy, n-propoxy, isopropoxy, n-butoxy, isobutoxy, sec-butoxy, tert-butoxy, n-pentyloxy, 1-methylbutyloxy, 2-methylbutyloxy, 3-methylbutyloxy, 1,1-dimethylpropoxy, 1,2-dimethylpropoxy, 2,2-dimethylpropoxy, 1-ethylpropyloxy, n-hexyloxy, 1-methylpentyloxy, 2-methylpentyloxy, 3-methylpentyloxy, 4-methylpentyloxy, 1,1-dimethylbutyloxy, 1,2-dimethylbutyloxy, 1,3-dimethylbutyloxy, 2,2-dimethylbutyloxy, 2,3-dimethylbutyloxy, 3,3-dimethylbutyloxy, 1-ethylbutyloxy, 2-ethylbutyloxy, 1,1,2-trimethylpropyloxy, 1,2,2-trimethylpropyloxy, 1-ethyl-1-methylpropyloxy, 1-ethyl-2-methylpropyloxy, n-heptyloxy, n-octyloxy, n-nonyloxy and n-decyloxy groups.

The $C_3$–$C_5$ halocycloalkyl group for G, R and $T^1$ includes, for example, fluorocyclopropyl, difluorocyclopropyl, chlorocyclopropyl, dichlorocyclopropyl, 1-methyl-2,2-dichlorocyclopropyl, chlorocyclobutyl, dichlorocyclobutyl, chlorocyclopentyl, dichlorocyclopentyl, chlorocyclohexyl, dichlorocyclohexyl and tetrafluorocyclobutyl groups.

The group —$NU^1U^2$ for G, R, $R^1$, $T^1$, W, X, Y, $Y^1$ and Z includes, for example, methylamino, ethylamino, n-propylamino, isopropylamino, n-butylamino, isobutylamino, sec-butylamino, tert-butylamino, n-pentylamino, 1-methylbutylamino, 2-methylbutylamino, 3-methylbutylamino, 1,1-dimethylpropylamino, 1,2-dimethylpropylamino, 2,2-dimethylpropylamino, 1-ethylpropylamino, n-hexylamino, 1-methylpentylamino, 2-methylpentylamino, 3-methylpentylamino, 4-methylpentylamino, 1,1-dimethylbutylamino, 1,2-dimethylbutylamino, 1,3-dimethylbutylamino, 2,2-dimethylbutylamino, 2,3-dimethylbutylamino, 3,3-dimethylbutylamino, 1-ethylbutylamino, 2-ethylbutylamino, 1,1,2-trimethylpropylamino, 1,2,2-trimethylpropylamino, 1-ethyl-1-methylpropylamino, 1-ethyl-2-methylpropylamino, dimethylamino, diethylamino, di-n-propylamino, diisopropylamino, di-n-butylamino, di-sec-butylamino, diisobutylamino, di-n-pentylamino, di-n-hexylamino, methylethylamino, methylpropylamino, methylisopropylamino, methylbutylamino, methyl-sec-butylamino, methylisobutylamino, methyl-tert-butylamino, methylpentylamino, methylhexylamino, ethylpropylamino, ethylisopropylamino, ethylbutylamino, ethyl-sec-butylamino, ethyl-isobutylamino, ethylpentylamino, ethylhexylamino, phenylamino, benzylamino, N-methylacetamido, N-ethylacetamido, N-phenylacetamido and N-acetylacetamido groups, to which is applied the indicated scope of the carbon atoms constituting it.

The $C_2$–$C_5$ alkoxycarbonyl group for E, G, R, $R^1$, $T^1$, W, X, Y, $Y^1$, $Y^2$ and Z includes, for example, methoxycarbonyl, ethoxycarbonyl, n-propoxycarbonyl, iso-propoxycarbonyl, n-butoxycarbonyl, sec-butoxycarbonyl, iso-butoxycarbonyl and tert-butoxycarbonyl groups.

The $C_1$–$C_4$ haloalkoxy group for G, R, $T^1$, W, X, Y and Z may be a straight chain or branched $C_1$–$C_4$ haloalkoxy group, including, for example, fluoromethoxy, difluoromethoxy, trifluoromethoxy, chlorodifluoromethoxy, bromodifluoromethoxy, dichlorofluoromethoxy, chloromethoxy, dichloromethoxy, trichloromethoxy, bromomethoxy, fluoroethoxy, chloroethoxy, bromoethoxy, difluoroethoxy, trifluoroethoxy, tetrafluoroethoxy, pentafluoroethoxy, trichloroethoxy, trifluorochloroethoxy, fluoropropoxy, chloropropoxy, bromopropoxy, fluorobutoxy, chlorobutoxy, fluoro-iso-propoxy and chloro-iso-propoxy groups.

The $C_1$–$C_4$ alkylsulfenyl group for E, G, R, $T^2$, $T^3$, W, X, Y and Z includes, for example, methylthio, ethylthio, n-propylthio, iso-propylthio, n-butylthio, iso-butylthio, sec-butylthio and tert-butylthio groups.

The $C_1$–$C_4$ alkylsulfinyl group for E, G, R, X, W, Y and Z includes, for example, methylsulfinyl, ethylsulfinyl, n-propylsulfinyl, iso-propylsulfinyl, n-butylsulfinyl, iso-butylsulfinyl, sec-butylsulfinyl and tert-butylsulfinyl groups.

The $C_1$–$C_4$ alkylsulfonyl group for B, E, G, R, W, X, Y and Z includes, for example, methylsulfonyl, ethylsulfonyl, n-propylsulfonyl, iso-propylsulfonyl, n-butylsulfonyl, iso-butylsulfonyl, sec-butylsulfonyl and tert-butylsulfonyl groups.

The $C_2$–$C_4$ alkoxyalkyl group for B, G, R, $R^1$, $T^1$, Y, $Y^1$ and $Y^2$ includes, for example, $C_1$–$C_3$ alkoxy-methyl, $C_1$–$C_2$ alkoxy-ethyl, methoxyethoxymethyl and methoxypropyl groups.

The $C_2$–$C_6$ alkylcarbonyl group for E, G, R, $R^1$, $U^1$, $U^2$, $Y^1$, $Y^2$ and W includes, for example, acetyl, propionyl, butanoyl and iso-butanoyl groups.

The $C_2$–$C_6$ haloalkylcarbonyl group for G and W includes, for example, chloroacetyl, trifluoroacetyl, 3,3,3-trifluoropropionyl and pentafluoropropionyl groups.

The $C_2$–$C_5$ haloalkylcarbonyloxy group for G, R and Y includes, for example, chloroacetyloxy, trifluoroacetyloxy, 3,3,3-trifluoropropionyloxy and pentafluoropropionyloxy groups.

The $C_3$–$C_7$ dialkylaminocarbonyloxy group for G and Y includes, for example, dimethylaminocarbonyloxy, diethylaminocarbonyloxy and di-i-propylaminocarbonyloxy groups.

The naphthyl group for R, Y, Z and $T^1$ includes, for example, 1-naphthyl and 2-naphthyl groups.

The pyridyl group optionally substituted by Z for G and $T^1$ includes, for example, 2-pyridyl, 3-pyridyl and 4-pyridyl groups all optionally substituted by Z. Preferred are 2-pyridyl and 3-pyridyl groups both optionally substituted by Z; and more preferred is a 2-pyridyl group optionally substituted by Z.

The pyridyloxy group optionally substituted by Z for G and $T^1$ includes, for example, 2-pyridyloxy, 3-pyridyloxy and 4-pyridyloxy groups all optionally substituted by Z.

The pyridyl group optionally substituted by X for R and $R^1$ includes, for example, 2-pyridyl, 3-pyridyl and 4-pyridyl groups all optionally substituted by X. Preferred are 2-pyridyl and 3-pyridyl groups both optionally substituted by X; and more preferred is a 2-pyridyl group optionally substituted by X.

The pyridyloxy group optionally substituted by X for R and $R^1$ includes, for example, 2-pyridyloxy, 3-pyridyloxy and 4-pyridyloxy groups all optionally substituted by X.

The thienyl group optionally substituted by X for R and $R^1$ includes, for example, 2-thienyl and 3-thienyl groups both optionally substituted by X.

The thienyl group optionally substituted by Z for G and $Y^1$ includes, for example, 2-thienyl and 3-thienyl groups both optionally substituted by Z.

The group —N=$CT^7T^8$ for G, R, $R^1$, Y and $Y^1$ indicates an alkylidenamino group, a benzylidenamino group, an arylidenamino group or a cycloalkylidenamino group, including, for example, methylidenamino, ethylidenamino, propylidenamino, isopropylidenamino, 4-methyl-2-pentylidenamino, cyclopentylidenamino and cyclohexylidenamino groups.

The $C_2$–$C_4$ alkylaminocarbonyl group for E includes, for example, methylaminocarbonyl, ethylaminocarbonyl and n-propylaminocarbonyl groups.

The $C_3$–$C_6$ dialkylaminocarbonyl group for E includes, for example, dimethylaminocarbonyl, diethylaminocarbonyl, di-n-propylaminocarbonyl, di-isopropylaminocarbonyl and di-n-butylaminocarbonyl groups.

The $C_1$–$C_4$ alkylaminosulfonyl group for B includes, for example, methylaminosulfonyl, ethylaminosulfonyl, n-propylaminosulfonyl, isopropylaminosulfonyl and n-butylaminosulfonyl groups.

The $C_2$–$C_8$ dialkylaminosulfonyl group for B includes, for example, dimethylaminosulfonyl, diethylaminosulfonyl, di-n-propylaminosulfonyl, di-isopropylaminosulfonyl and di-n-butylaminosulfonyl groups.

The $C_2$–$C_5$ alkylaminothiocarbonyl group for B includes, for example, methylaminothiocarbonyl, ethylaminothiocarbonyl, n-propylaminothiocarbonyl, isopropylaminothiocarbonyl and n-butylaminothiocarbonyl groups.

The $C_3$–$C_9$ dialkylaminothiocarbonyl group for B includes, for example, dimethylaminothiocarbonyl, diethylaminothiocarbonyl, di-n-propylaminothiocarbonyl, di-isopropylaminothiocarbonyl and di-n-butylaminothiocarbonyl groups.

The $C_1$–$C_4$ alkyl group substituted by a benzoyl group optionally substituted by a halogen atom or a $C_1$–$C_4$ alkyl group for B includes, for example, phenacyl, 2-fluorophenacyl, 3-chlorophenacyl, 4-bromophenacyl, 2-methylphenacyl, 3-ethylphenacyl, 4-i-propylphenacyl and 4-t-butylphenacyl groups.

The phenylsulfonyl group optionally substituted by a halogen atom or a $C_1$–$C_4$ alkyl group for B includes, for example, 2-fluorophenylsulfonyl, 4-fluorophenylsulfonyl, 2-chlorophenylsulfonyl, 4-chlorophenylsulfonyl, 4-bromophenylsulfonyl, 2,5-dichlorophenylsulfonyl, pentafluorophenylsulfonyl, 4-methylphenylsulfonyl, 2-methylphenylsulfonyl, 4-t-butylphenylsulfonyl, 2,5-dimethylphenylsulfonyl, 2,4-dimethylphenylsulfonyl, 2,4,6-trimethylphenylsulfonyl and 2,4,6-tri-i-propylphenylsulfonyl groups.

The $C_2$–$C_5$ cyanoalkyl group for G and B includes, for example, cyanomethyl, 2-cyanoethyl, 3-cyanopropyl and 1-cyano-1-methylethyl groups.

The $C_3$–$C_9$ alkoxycarbonylalkyl group for B may be a straight chain or branched one, including, for example, methoxycarbonylmethyl, ethoxycarbonylmethyl, n-propoxycarbonylmethyl, i-propoxycarbonylmethyl, n-butoxycarbonylmethyl, i-butoxycarbonylmethyl, t-butoxycarbonylmethyl, n-hexyloxycarbonylmethyl, n-heptyloxycarbonylmethyl, 1-methoxycarbonylethyl, 1-ethoxycarbonylethyl, 1-n-butoxyethyl, 2-methoxycarbonylethyl, 2-ethoxycarbonylethyl, 1-methoxycarbonylpropyl, 3-ethoxycarbonylpropyl, 4-methoxycarbonylbutyl, 6-ethoxycarbonylhexyl, 1-methoxycarbonyl-1-methylethyl, 1-iso-propoxycarbonyl-1-methylethyl and 1-ethoxycarbonyl-2-methylpropyl groups.

The alkali metal for B includes, for example, lithium sodium and potassium.

The alkaline earth metal for B includes, for example, magnesium, calcium, strontium and barium. Preferred are magnesium, calcium and barium.

The ammonium group of $NHT^4T^5T^6$ for B includes, for example, ammonium, monomethylammonium, dimethylammonium, trimethylammonium, diethylammonium, triethylammonium, di-isopropylammonium, di-isopropylethylammonium, hexylmethylammonium, cyclopropylmethylammonium, cyclohexylmethylammonium, allylmethylammonium, benzylmethylammonium and 4-methylcyclohexylethylammonium groups. Any two of $T^4$, $T^5$ and $T^6$ may form, along with the nitrogen atom to which they are bonded, a heterocyclic, 5-, 6-, 7- or 8-membered ammonium group optionally having oxygen, nitrogen and/or sulfur atoms.

The methoxy group substituted by a phenyl group optionally substituted by a halogen atom or a $C_1$–$C_4$ alkyl group for G includes, for example, benzyloxy, 2-chlorobenzyloxy, 3-chlorobenzyloxy, 4-chlorobenzyloxy, 3-methylbenzyloxy, 4-t-butylbenzyloxy, 2,6-difluorobenzyloxy and 2-fluoro-4-chlorobenzyloxy groups.

The heterocyclic, 5-, 6-, 7- or 8-membered ammonium group optionally having oxygen, nitrogen and/or sulfur atoms, which is formed by two of $T^4$, $T^5$ and $T^6$ along with the nitrogen atom to which they are bonded, includes, for example, pyrrolidine, pyrazolidine, imidazolidine, oxazolidine, isoxazolidine, thiazolidine, piperidine, piperazine, morpholine, thiamorpholine, hexamethylenimine and heptamethylenimine groups. The haloalkylsulfenyl group for G, R, W, X, Y and Z may be a straight chain or branched $C_1$–$C_4$ haloalkylthio group, including, for example, fluoromethylthio, chlorodifluoromethylthio, bromodifluoromethylthio, trifluoromethylthio, trichloromethylthio, 2,2,2-trifluoroethylthio, 1,1,2,2-tetrafluoroethylthio, fluoroethylthio, pentafluoroethylthio and fluoro-iso-propylthio groups.

The haloalkylsulfinyl group for G, R, W, X, Y and Z may be a straight chain or branched, $C_1$–$C_4$ haloalkylsulfinyl group, including, for example, fluoromethylsulfinyl, chlorodifluoromethylsulfinyl, bromodifluoromethylsulfinyl, trifluoromethylsulfinyl, trichloromethylsulfinyl, 2,2,2-trifluoroethylsulfinyl, 1,1,2,2-tetrafluoroethylsulfinyl, fluoroethylsulfinyl, pentafluoroethylsulfinyl and fluoro-iso-propylsulfinyl groups.

The haloalkylsulfonyl group for G, R, W, X, Y and Z may be a straight chain or branched, $C_1$–$C_4$ haloalkylsulfonyl group, including, for example, fluoromethylsulfonyl, chlorodifluoromethylsulfonyl, bromodifluoromethylsulfonyl, trifluoromethylsulfonyl, trichloromethylsulfonyl, 2,2,2-trifluoroethylsulfonyl, 1,1,2,2-tetrafluoroethylsulfonyl, fluoroethylsulfonyl, pentafluoroethylsulfonyl and fluoro-isopropylsulfonyl groups.

The haloalkenyl group for G, R, T¹ and W may be a straight chain or branched $C_1$–$C_4$ haloalkenyl group, including, for example, 2-chloroethenyl, 2-bromoethenyl and 2,2-dichloroethenyl groups.

The alkenyloxy group for G, R, R¹, T¹, W, Y and Y¹ may be a straight chain or branched $C_2$–$C_4$ alkenyloxy group, including, for example, allyloxy, 2-propenyloxy, 2-butenyloxy and 2-methyl-2-propenyloxy groups.

The haloalkenyloxy group for G, R, W and Y may be a straight chain or branched $C_2$–$C_4$ haloalkenyloxy group, including, for example, 3-chloro-2-propenyloxy, 3,3-dichloro-2-propenyloxy, 4-chloro-2-butenyloxy, 4,4-dichloro-3-butenyloxy and 4,4-difluoro-3-butenyloxy groups.

The alkenylsulfenyl group for G, R, W, X, Y and Z may be a straight chain or branched $C_2$–$C_4$ alkenylsulfenyl group, including, for example, allylsulfenyl, 2-propenylsulfenyl, 2-butenylsulfenyl and 2-methyl-2-propenylsulfenyl groups.

The alkenylsulfinyl group for G, R, W, X, Y and Z may be a straight chain or branched $C_2$–$C_4$ alkenylsulfinyl group, including, for example, allylsulfinyl, 2-propenylsulfinyl, 2-butenylsulfinyl and 2-methyl-2-propenylsulfinyl groups.

The alkenylsulfonyl group for G, R, W, X, Y and Z may be a straight chain or branched $C_2$–$C_4$ alkenylsulfonyl group, including, for example, allylsulfonyl, 2-propenylsulfonyl, 2-butenylsulfonyl and 2-methyl-2-propenylsulfonyl groups.

The haloalkenylsulfenyl group for G, R, W and Y may be a straight chain or branched $C_2$–$C_4$ haloalkenylsulfenyl group, including, for example, 3-chloro-2-propenylsulfenyl, 4-chloro-2-butenylsulfenyl, 3,3-dichloro-2-propenylsulfenyl, 4,4-dichloro-3-butenylsulfenyl and 4,4-difluoro-3-butenylsulfenyl groups.

The haloalkenylsulfinyl group for G, R, W and Y may be a straight chain or branched $C_2$–$C_4$ haloalkenylsulfinyl group, including, for example, 3-chloro-2-propenylsulfinyl, 3,3-dichloro-2-propenylsulfinyl, 4-chloro-2-butenylsulfinyl, 4,4-dichloro-3-butenylsulfinyl and 4,4-difluoro-3-butenylsulfinyl groups.

The haloalkenylsulfonyl group for G, R, W and Y may be a straight chain or branched $C_2$–$C_4$ haloalkenylsulfonyl group, including, for example, 3-chloro-2-propenylsulfonyl, 3,3-dichloro-2-propenylsulfonyl, 4-chloro-2-butenylsulfonyl, 4,4-dichloro-3-butenylsulfonyl and 4,4-difluoro-3-butenylsulfonyl groups.

The $C_2$–$C_4$ haloalkynyl group for G, R and W includes, for example, chloroethynyl, bromoethynyl, iodoethynyl, 3-chloro-1-propynyl and 3-bromo-1-butynyl groups.

The $C_2$–$C_4$ alkynyloxy group for G, R, W and Y includes, for example, 2-propynyloxy, 2-butynyloxy and 1-methyl-2-propynyloxy groups.

The $C_2$–$C_4$ haloalkynyloxy group for G, R, W and Y includes, for example, 3-chloro-2-propynyloxy, 3-bromo-2-propynyloxy and 3-iodo-2-propynyloxy groups.

The $C_2$–$C_6$ alkynylsulfenyl group for G, R, W and Y includes, for example, 2-propynylsulfenyl, 2-butynylsulfenyl and 1-methyl-2-propynylsulfenyl groups.

The $C_2$–$C_6$ alkynylsulfinyl group for G, R, W and Y includes, for example, 2-propynylsulfinyl, 2-butynylsulfinyl and 1-methyl-2-propynylsulfinyl groups.

The $C_2$–$C_6$ alkynylsulfonyl group for G, R, W and Y includes, for example, 2-propynylsulfonyl, 2-butynylsulfonyl and 1-methyl-2-propynylsulfonyl groups.

The $C_2$–$C_6$ haloalkynylsulfenyl group for G, R, W and Y includes, for example, 3-chloro-2-propynylsulfenyl, 3-bromo-2-propynylsulfenyl and 3-iodo-2-propynylsulfenyl groups.

The $C_2$–$C_6$ haloalkynylsulfinyl group for G, R, W and Y includes, for example, 3-chloro-2-propynylsulfinyl, 3-bromo-2-propynylsulfinyl and 3-iodo-2-propynylsulfinyl groups.

The $C_2$–$C_6$ haloalkynylsulfonyl group for G, R, W and Y includes, for example, 3-chloro-2-propynylsulfonyl, 3-bromo-2-propynylsulfonyl and 3-iodo-2-propynylsulfonyl groups.

The $C_2$–$C_4$ alkylcarbonyloxy group for G, R, W and Y includes, for example, acetoxy, propanoyloxy, butanoyloxy and isopropylcarbonyloxy groups.

The benzoyl group optionally substituted by X for E and G includes, for example, benzoyl, 2-chlorobenzoyl, 3-chlorobenzoyl, 4-chlorobenzoyl, 4-bromobenzoyl, 4-fluorobenzoyl, 3-methylbenzoyl, 4-methylbenzoyl, 4-tert-butylbenzoyl and 3,4-dichlorobenzoyl groups.

Even at low concentration, the compounds of the present invention effectively prevent various pests, which include, for example, so-called agricultural insect pests that injure agricultural and horticultural crops and trees, so-called livestock insect pests that live on livestock and poultry, so-called sanitary insect pests that have various negative influences on the human living environment including houses, so-called stored products insect pests that injure grains stored in storehouses, and also acarids, nematodes, molluscs and crustaceans that live in the same sites as above and injure those mentioned above.

Examples of insect pests, acarids, nematodes, molluscs and crustaceans capable of being exterminated by the compounds of the present invention are mentioned below, which, however, are not limitative.

Insect pests of Lepidoptera, such as rice stem borer (*Chilo suppressalis* Walker), rice leafroller (*Cnaphalocrocis medinalis* Guenée), green rice caterpillar (Naranga aenescens Moore), rice skipper (*Parnara guttata* Bremer et Gvey), diamond back moths (*Plutella xylostella* Linné), cabbage armyworms (*Mamestra brassicae* Linné), common white (*Pieris rapae crucivora* Boisduval), turnip moth (*Agrotis segetum* Denis et Schiffermüller), common cutworm (*Spodptera litura* Fabricius), beet armyworm (*Spodoptera exigua* Hübner), smaller tea tortrix (Adoxophyes sp.), oriental tea tortrix (*Homona magnanima* Diakonoff), peach fruit moth (*Carposina niponensis* Walsingham), oriental fruit moth (*Grapholita molesta* Busck), summer fruit tortrix (*Adoxophyes orana fasciata* Walsingham), apple leafminers (*Phyllonorycter ringoniella* Matsumura), corn earworm (*Helicoverpa zea* Boddie), tobacco bad worms (*Heliothis virescens* Fabricius), European corn borer (*Ostrinia nubilalis* Hübner), fall armyworm (*Spodoptera frugiperda* J. E. Smith), Codling moth moth (*Cydia pomonella* Linné), fall webworms (*Hyphantria cunea* Drury), etc.;

Insect pests of Hemiptera, such as green rice leafhopper (*Nephotettix cincticeps* Uhler), brown rice planthoppers (*Nilaparvata lugens* Stal), green peach aphid (*Myzus persicae* Sulzer), cotton aphid (*Aphis gossypii* Glover), greenhouse whitefly (*Trialeurodes vaporariorum* Westwood), sweetpotato white fly (*Bemisia tabaci* Gennadius), pear psylla (*Psylla pyricola* Förster), azalea lace bug (*Stephanitis pyrioides* Scott), arrowhead scale (*Unaspis yanonensis* Kuwana), comstock mealybug (*Pseudococcus comstocki* Kuwana), red wax scale (*Ceroplastes rubens* Maskell), brown-marmorated stinkbug (*Halyomorpha mista* Uhler), cabbage bug (*Eurydema rugosam* Motschulsky), bed bug (*Cimex lectularius* Linné), etc.;

Insect pests of *Coleoptera*, such as twenty-eight-spotted ladybird (*Henosepilachna vigintioctopunctata* Fabricius), cupreous chafers (*Anomala cuprea* Hope), ricewater weevil (*Lissorhoptrus oryzophilus* Kuschel), sweetpotato weevil (*Cylas formicarius* Fabricius), cucurbit leaf beetle (*Aulacophora femoralis* Motschulsky), striped flea beetle (*Phyllotreta striolata* Fablicius), white-spotted longicorn beetle (*Anoplophora malasiaca* Thomson), pine sawyers (*Monochamus alternatus* Hope), corn rootworms (Diabrotica spp.), rice weevil (*Sitophilus zeamais* Motschulsky), lesser rice weevil (*Sitophilus oryzae* Linné), granary weevils (*Sitophilus granarius* Linné), red four beetle (*Tribolium castaneum* Herbst), etc.;

Insect pests of *Diptera*, such as legume leafminer (*Liriomyza trifolii* Burgess), seedcorn maggot (*Delia platura* Meigen), Hessia fly (*Mayetiola destructor* Say), melon fly (*Dacus* (*Zengodacus*) *cucurbitae* Coquillett), Mediterranear fruit fly (*Ceratitis capitata* Wiedemann), house flies (*Musca domestica* Linné), stable fly (*Stomoxys calcitrans* Linné), Sheep ked (*Melophagus orinus*), common cattle grub (*Hypoderm lineatum* devillers), nothern cattle grub (*Hypoderma boris* Linné), sheep botfly (*Oestrus ovis* Linné), tsetse fly (*Golossina* palpalis Robineau-Desvoidy), common gnat (*Culex pipiens pallens* Coquillett), yellow-fever mosquitoes (*Aedes aegypti* Linné), *Anopheles culicifacies*), etc.

Insect pests of *Hymenoptera*, such as cabbage sawfly (*Athalis rosae ruficornis* Jakovlev), pine sawfly (*Neodiprion sertifer* Geoffroy), chestnut sawfly (*Apethymus kuri* Takeuchi), etc.;

Insect pests of *Thysanoptera*, such as melon thrips (*Thrips palmi* Karny), onion thrips (*Thrips tabaci* Lindeman), western flower thrips (*Frankliniella occidentalis* Pergande), flower thrip (*Frankliniella intonsa* Trybom), yellow tea thrip (*Scirtothrips dorsalis* Hood), etc.;

Insect pests of *Dictyoptera*, such as smokybrown cockroache (*Periplaneta fuliginosa* Serville), Japanese cockroach (*Periplaneta japonica* Karny), German cockroaches (*Blattella germanica* Linne), etc.;

Insect pests of *Orthoptera*, such as oriental migratory locust (*Locusta migratoria* Linné), rice grasshopper (*Oxya yezoensis* Shiraki), desert locust (*Schistocerca gregaria* Forskål), etc.;

Insect pests of *Isoptera*, such as Formosan subterranean termit (*Coptotermes formosanus* Shiraki), (*Reticulitermes* (*Leucotermes*) *speratus* Kolbe), (*Odontotermes formosanus* Shirakif), etc.;

Insect pests of *Siphonaptera*, such as cat fleas (*Ctenocephalides felis* Bouché), human fleas (*Pulex irritans* Linné), oriental rat flea (*Xenopsylla cheopis* Rothschild), etc.;

Insect pests of *Mallophaga*, such as Chicken bodylouse (*Menacanthus stramineus* Nitsch), cattle biting louse (*Bovicola bovis* Linné), etc.;

Insect pests of *Anoplura*, such as short-nosed cattle louse (*Haematopinus eurysternus* Nitzsh), hog louse (*Haematopinus suis* Linné), longnosed cattle louse (*Linognathus vituli* Linné), little cattle louse (*Solenopotes capillatus* Enderlein), etc.

Pests of TETRANYCHIDAE, such as citrus red mite (*Panonychus citri* McGregor), European red mite (*Panonychus ulmi* Kock), two-spotted spider mite (*Tetranychus urticae* Koch), Kanzawa spinder mite (*Tetranychus kanzawai* Kishida), etc.;

Pests of ERIOPHYDAE, such as pink citrus rust mite (*Aculops pelekassi* Keifor), pear rust mite (*Epitrimerus pyri* Nalepa), dry bulb mite (*Aceria tulipae* Keiter), pink tea mite (*Acaphylla theae* watt), etc.;

Pests of TARSONEMIDAE, such as broad mites (*Polyphagotarsonemus latus* Banks), cyclamen mite, strawberry mite (*Steneotarsonemus pallidus* Banks), etc.;

Pests of ACARIDAE, such as mold mite, copra mite, forage mite (*Tyrophagus putrescetiae* Schrank), bulb mite (*Rhizoglyphus robini* Claparede), etc.;

Pests of VARROIDAE, such as bee brood mite (*Varroa jacobsoni* Oudemans), etc.;

Pests of Ixodidae, such as bull ticks (*Boophilus microplus* Canestrini), (*Haemaphysalis longicornis* Neumann), etc.;

Pests of Sarcoptidae, such as sarcoptes mange mite (*Sarcaptes scabiei* Linné), etc.;

Nematodes, such as southern root-knot nematode (*Meloidogyne incognita* Kofoid et White), northern root-knot nematode (*Meloidogyne hapla* Chitwood), Cobb root-lesion nematode (*Pratylenchus penetraus* Cobb), walnut root-lesion nematode (*Pratylenchus vulnus* Allen et Jensen), potato cyst nematode (*Globodera rostochiensis* Wollenweber), pine wood nematode (*Bursaphelenchus xylophilus* Steiner et Buhrer), etc.;

Mollusca, such as apple snail (*Pomacea canaliculata* Lamarck), (*Incilaria pilineata* Benson), (*Acusta despecta sieboldiana* Pfeiffer), (*Euhadra peliomphala* Pfeiffer), pillbug (*Armadillidium vulgare* Latreille), etc.;

Crustaceans, such as pillbug (*Armadillidium vulgare* Latreille), etc.

The plant diseases to be controlled by the compounds of the present invention are as follows:

Blast (*Pyricularia oryzae*), Helminthosporium leaf spot (*Cochliobolus miyabeanus*) and Sheath blight (*Rhizoctonia solani*) of rice, Powdery mildew (*Erysiphe graminis* f. sp. *hordei*, f. sp. *tritici*), Leaf stripe (*Pyrenophora graminea*), Net blotch (*Pyrenophora teres*), Fusarium blight (*Gibberella zeae*), yellow rust, black stem rust and brown rust (*Puccinia striiformis, P. graminis, P. recondita* and *P. hordei*), Snow blight and snow mold (*Typhula sp., Micronectriella nivais*), Loose smut (*Ustilago tritici, U. nuda*), Eyespot (*Pseudocercorsporella herpotrichoides*), Scald and leaft blotch (*Rhynchosporium secalis*), Speckled blotch (*Septoria tritici*), and Glume blotch (*Leptosphaeria nodorum*) of barley and wheat, Melanose (*Diaporthe citri*), Scab (*Elsinoe fawcetti*), and Common green mold and blue mold (*Penicillium digitatum, P. italicum*) of citrus fruit, Blossom blight (*Sclerotinia mali*), Canker (*Valsa mali*), Powder mildew (*Podosphaera leucotricha*), Alternaria leaft spot (*Alternaria mali*) and Scab (*Venturia inaequalis*) of apple, Scab (*Venturia nashicola*), Black spot (*Alternaria Kikuchiana*) and Rust (*Gymnosporangium haraeanum*) of pear, Brown rot (*Sclerotinia cinerea*), Scab (*Cladosporium carpophilum*), and Phomopsis rot (*Phomopsis sp.*) of peach, Downy mildew (*Plasmopara viticola*), Anthracnose (*Elsinoe ampelina*), Ripe rot (*Glomerella cingulata*), Powdery mildew (*Uncinula necator*) and Rust (*Phakopsora ampelopsidis*) of grape, Anthracnose (*Gloesporium kaki*), Powdery mildew (*Phyllactinia kakicola*), Angular leaf spot (*Cercospora* kaki), and Circular leaf spot (*Mycosphaerella nawae*) of persimmon,

Downy mildew (*Pseudoperenospora cubensis*), Anthracnose (*Colletotrichum lagenarium*), Powdery mildew (*phaerotheca fuliginea*), and Gummy stem blight (*Mycosphaerella melonis*) of cucurbit, Late blight (*Phytophthora infestans*), Early blight (*Alternaria solani*) and Leaf mold (*Cladosporium fulvam*) of tomato.

Brown spot (*Phomopsis vexans*) and Powdery mildew (*Erysiphe cichoracoarum*) of egg plant, Alternaria leaft spot (*Alternaria japonica*) and white spot (*Cerocosporella brassicae*) of vegetable of the family crucifers.

Rust (*Puccinia allii*) of welsh onion.

Purple seed stain (*Cercospora kikuchii*), Sphaceloma scab (*Elsinoe glycines*) and Pot and stem blight (*Diaporthe phaseololum*) of soybean, Anthracnose (*Collectorichum lindemuthianum*) of kidney bean.

Leaf spot (*Mycosphaerella personatum*) and Brown leaf spot (*Cercospora arachidicola*) of peanut, Powdery mildew (*Erysiphe pisi*) of garden pea, Early blight (*Alternaria solani*) of potato, Powdery mildew (*Sphaerotheca humuli*) of strawberry, Net blister blight (*Exobasidium reticulatum*) and White scab (*Elsinoe leucospila*) of tea, Brown spot (*Alternaria longipes*), Powdery mildew (*Erysiphe cichoracearum*) and Anthracnose (*Colletotrichum tabacum*) of tobacco, Cercospora leaft spot (*Cercospora beticola*) of sugar beat, Black spot (*Diplocarpon rosae*) and Powdery mildew (*Sphaerotheca pannosa*) of rose, Leaf spot (*Septoria chrysanthemiindici*) and Rust (*Puccinia horiana*) of chrysanthemum, Gray mold (*Botrytis cinerea*) of various kinds of crops, and, Sclerotinia rot (*Sclerotinia sclerotiorum*) of various kinds of crops.

In addition, the compounds of the present invention are effective in preventing the attachment of aquatic organisms, even at extremely low concentrations. Aquatic organisms to which the invention is directed are, for example, shellfishes and algae, such as mussel, barnacle, oyster, hydrozoan, hydra, Serpula, ascidian, seamoss, Bagula, mud pond snail, sea lettuce, green laver, Ectocarpus, etc.

Specifically, the compounds of the present invention can effectively exterminate various pests and phytopathogenic microbes of, for example, Orthoptera, Hemiptera, Lepidoptera, Coleoptera, Hymenoptera, Diptera, Temitidae, and also mites and louses, even when used at low concentrations. In addition, the compounds of the invention are effective in preventing the attachment of various aquatic organisms living in sea water and fresh water to aquatic constructions, etc. On the other hand, the compounds of the present invention contains useful compounds that have few negative influences on mammals, fishes, shellfishes and useful insects.

Of the compounds of the invention, those having CN as E can be produced according to the following methods (Scheme 1).

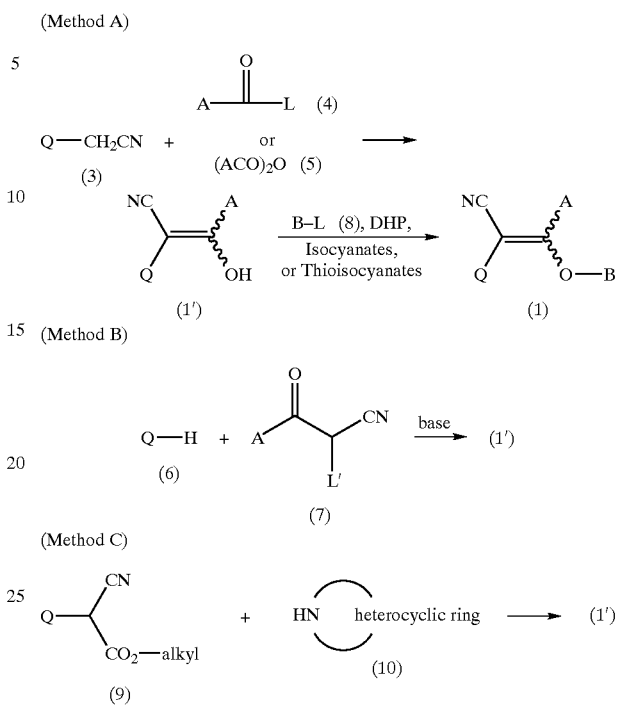

In (Scheme 1), Q, A and B have the same meanings as defined above; L represents a suitable leaving group, such as a chlorine atom, a bromine atom, an iodine atom, an alkoxy group having from 1 to 4 carbon atoms, a phenoxy group, an alkylsulfonyloxy group having from 1 to 4 carbon. atoms, a benzenesulfonyloxy group, a toluenesulfonyloxy group a phenoxy group, a 1-pyrazolyl. group or a 1-imidazolyl group; L' represents a halogen atom; and alkyl represents an alkyl group preferably having from 1 to 4 carbon atoms.

Method A in (Scheme 1) is to react an acetonitrile derivative of formula (3) with an acid chloride, ester or amide of formula (4) or with an acid anhydride of formula (5) to give compounds (1') of the present invention. The compound (1') of the invention is optionally reacted with an alkyl halide, an alkyl sulfonate, a trimethylsilyl halide, a sulfonyl chloride, a sulfamoyl chloride, a thiocarbamoyl chloride, an acid chloride or an ester of formula (8) to be converted into compounds (1) of the invention. Depending on the type of B in the compounds (1) of the invention, the compound (1') is reacted with a dihydropyran, an isocyanate or a thioisocyanate to give the compounds (1). In Method A, if the compound of formula (4) or (5) is used in an excessive amount, the compounds (1) can be directly obtained without isolating the compounds (1').

Where Q is bonded to the acrylonitrile moiety via a nitrogen atom, compounds (1') may be produced according to Method B. Method B is to react a heterocyclic compound of formula (6) with a halogenocyanoketone derivative of formula (7) to give compounds (1') of the invention.

Where A is bonded to the acrylonitrile moiety via a nitrogen atom, compounds (1') may be produced according to Method C. Method C is to react a cyanoacetic acid derivative of formula (9) with a heterocyclic compound of formula (10) to give compounds (1') of the invention. As the case may be, the compound of formula (9) will be prepared by reacting an acetonitrile derivative of formula (3), such as that used in Method A, with a carbonic acid ester in the presence of a base.

Of the compounds of the invention, those where E is

Scheme 2:

(Method D)

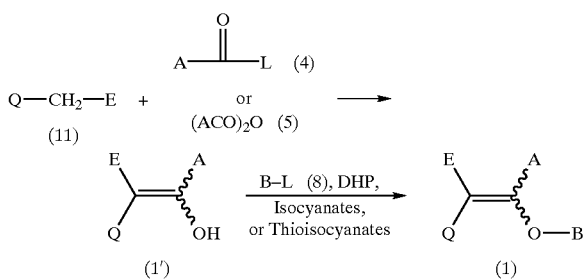

(Method E)

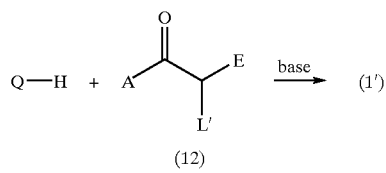

(Method F)

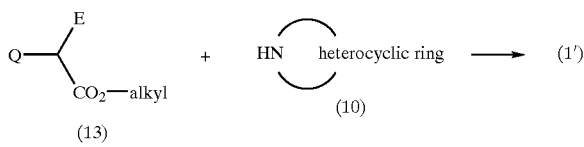

In (Scheme 2), Q, A, E, B, L, L' and alkyl have the same meanings as above.

Method D in (Scheme 2) is to react a compound of formula (11) with an acid chloride, ester or amide of formula (4) or with an acid anhydride of formula (5) to give the compounds (1') of the present invention. The compound (1') of the invention is optionally reacted with an alkyl halide, an alkyl sulfonate, a trimethylsilyl halide, a sulfonyl chloride, a sulfamoyl chloride, a thiocarbamoyl chloride, an acid chloride or an ester of formula (8) to be converted into the compounds (1) of the invention. Depending on the type of B in the compounds (1) of the invention, the compound (1') is reacted with a dihydropyran, an isocyanate or a thioisocyanate to give the compounds (1). In Method A, if the compound of formula (4) or (5) is used in an excessive amount, the compounds (1) can be directly obtained without isolating the compounds (1').

Where Q is bonded to the ethylene moiety via a nitrogen atom, the compounds (1') may be produced according to Method E. Method E is to react a heterocyclic compound of formula (6) with a compound of formula (12) in the presence of a base to give compounds (1') of the invention.

Where A is bonded to the ethylene moiety via a nitrogen atom, the compounds (1') may be produced according to Method F. Method F is to react a compound of formula (13) with a heterocyclic compound of formula (10) through dealcoholation to give the compounds (1') of the invention. As the case may be, the compound of formula (13) will be prepared by reacting a compound of formula (11), such as that used in Method D, with a carbonic acid ester in the presence of a base.

If desired, the compounds (1') where E is an alkoxycarbonyl group may be hydrolyzed, decarboxylated and halogenated to give the compounds of the invention where E is a halogen atom. As the case may be, the compounds of the invention where E is a halogen atom may be reacted with a nucleophilic reagent corresponding to E (e.g., triester phosphates, alkyl mercaptans, thiophenols, metal acetylides, metal cyanides, metal azides, nitrites) to give different compounds of the invention. Also as the case may be, the compounds to be obtained through decarboxylation of the compounds (1') where E is an alkoxycarbonyl group may be reacted with an electrophilic reagent under basic conditions to give the compounds of the invention.

As the case may be, the processes of (Scheme 1) and (Scheme 2) are preferably effected in the presence of a base. The base to be used includes, for example, alkali metal alkoxides such as sodium ethoxide, sodium methoxide and t-butoxy potassium; alkali metal hydroxides such as sodium hydroxide and potassium hydroxide; alkali metal carbonates such as sodium carbonate and potassium carbonate; organic bases such as triethylamine, pyridine and DBU; organic lithium compounds such as butyl lithium; lithium amides such as lithium diisopropylamide and lithium bistrimethylsilylamide; and sodium hydride.

The reactions of (Scheme 1) and (Scheme 2) may be effected in a solvent that is inert to the reaction. The solvent includes, for example, lower alcohols such as methanol and ethanol; aromatic hydrocarbons such as benzene and toluene; etherd such as diethyl ether, tetrahydrofuran, 1,4-dioxane, 1,2-dimethoxyethane and 1,2-diethoxyethane; halogenated hydrocarbons such as methylene chloride, chloroform and 1,2-dichloroethane; amides such as dimethylformamide and dimethylacetamide; acetonitrile; dimethylsulfoxide; and mixed solvents of these. As the case may be, also employable are mixed solvent comprising said solvents and water. Also as the case may be, a quaternary ammonium salt such as tetra-n-butylammonium bromide may be added to the reaction system as a catalyst to obtain good results. The reaction temperature may be freely settled within a range between −30° C. and 200° C. Preferably, the reaction temperature falls between 0° C. and 150° C., or between 0° C. and the boiling point of the solvent if used. The base may be used in an amount of from 0.05 to 10 equivalents, preferably from 0.05 to 3 equivalents, of the reaction substrate.

The compounds of the present invention may be separated from reaction mixtures according to any ordinary methods. If the purification of the compounds of the invention is needed, they can be separated and purified by any ordinary methods of, for example, recrystallization or column chromatography.

Of the compounds of the invention, those having an asymmetric carbon atom include optically-active compounds of (+) form and (−) form.

Methods of producing the compounds (3) to be used in (Scheme 1) are referred to hereinunder. The compounds (3) can be produced according to the following (Scheme 3).

Scheme 3:

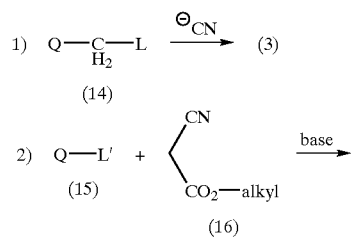

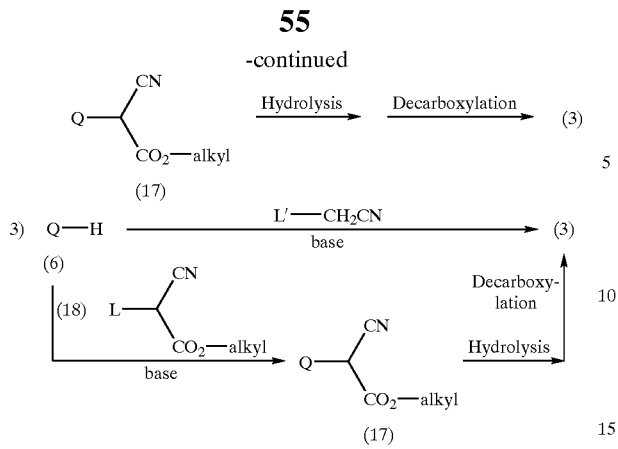

1) A benzyl halide, a benzyl alkylsulfonate, a benzyl arylsulfonate, a halomethyl-heterocyclic compound, an alkylsulfonyloxymethyl-heterocyclic compound or an arylsulfonyloxymethyl-heterocyclic compound of formula (14) is reacted with a suitable cyanating reagent to give compounds (3). Alternatively, a phenylacetic acid derivative or a heterocyclic acetic acid derivative is converted into the corresponding amide derivative, which is then dehydrated to give compounds (3).

2) A heterocyclic halide (15) is condensed with a cyanoacetate (16) in the presence of a base to give a compound (17), which is then hydrolyzed and decarboxylated to give compounds (3).

3) To obtain compounds (3) where Q is bonded to the ethylene moiety via a nitrogen atom, a heterocyclic derivative (6) where the nitrogen atom of Q is unsubstituted is reacted with a haloacetonitrile derivative in the presence of a base. Alternatively, the compound (6) is reacted with a compound (18) in the presence of a base to give a compound (17), said compound (18) being obtained through halogenation of a cyanoacetate, and thereafter the compound (17) is hydrolyzed and decarboxylated to obtain the compounds (3).

The compounds (11) to be used in (Scheme 2) can be produced in the same manner as in the production of the compounds (3) mentioned above.

The compounds (7) to be used in (Scheme 1) can be produced by condensing a benzoic acid halide or heterocyclic carboxylic acid halide with a cyanoacetate in the presence of a base followed by halogenating the resulting condensate.

The above-mentioned halomethyl-heterocyclic compounds, alkylsulfonyloxymethyl-heterocyclic compounds and arylsulfonyloxymethyl-heterocyclic compounds can be derived from heterocyclic methane derivatives or heterocyclic carboxylate derivatives that are produced according to ordinary methods (see Alan R. Katritzky, and Charles W. Rees; Comprehensive Heterocyclic Chemistry, Vol. 2, Vol. 3, Vol. 4, Vol. 5 or Vol. 6). To produce the compounds (14) where Q is an oxazol-4-yl or thiazol-4-yl group, a carboxylic acid amide or thioamide can be reacted with 1,3-dichloro-2-propanone.

Examples of the compounds of the present invention are shown in Table 1 to Table 14 below. The abbreviations in these Tables are for the meanings mentioned below:

Me: methyl group, Et: ethyl group, Pr: propyl group, Bu: butyl group, Pen: pentyl group, Hex: hexyl group, Hep: heptyl group, Oct: octyl group, Non: nonyl group, Dec: decyl group, Ph: phenyl group, n: normal, i: iso, sec: secondary, t: tertiary, c: cyclo.

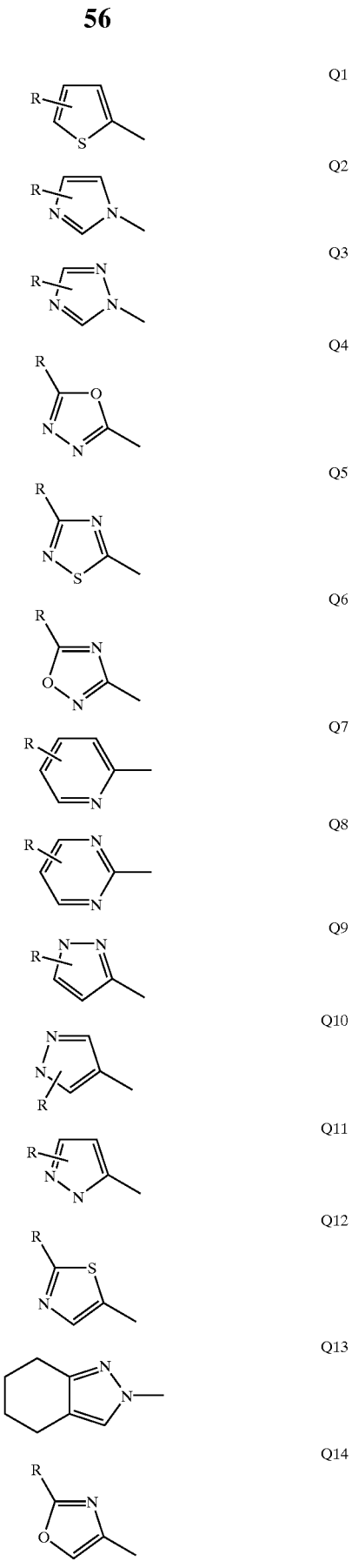

-continued
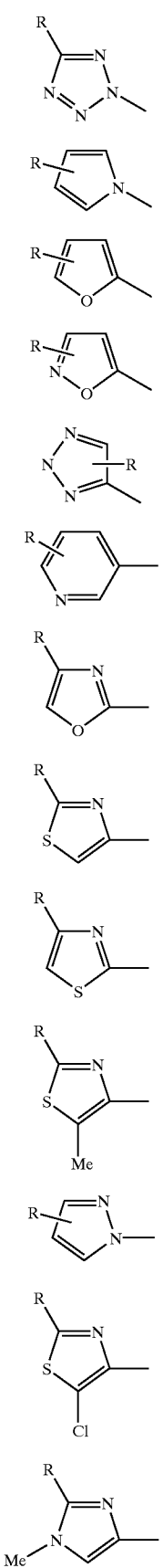
| | |
|---|---|
| Q15 | |
| Q16 | |
| Q17 | |
| Q18 | |
| Q19 | |
| Q20 | |
| Q21 | |
| Q22 | |
| Q23 | |
| Q24 | |
| Q25 | |
| Q26 | |
| Q27 | |
-continued
| | |
|---|---|
| 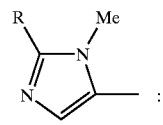 | Q28 |
| 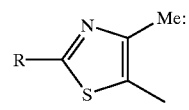 | Q29 |
| 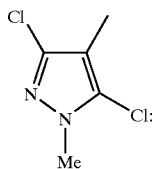 | A1 |
| 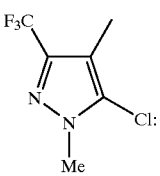 | A2 |
| 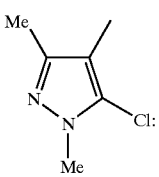 | A3 |
| 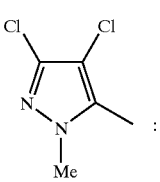 | A4 |
| 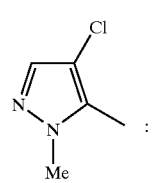 | A5 |
| 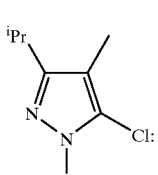 | A6 |
| 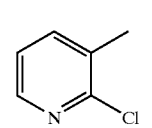 | A-7 |
| 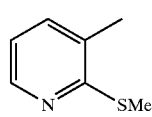 | A8 |

-continued
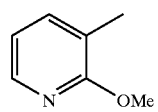 A9
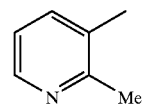 A10
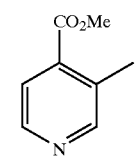 A11
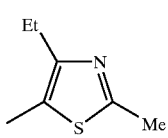 A12
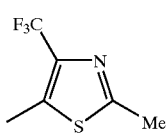 A13
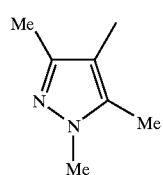 A14
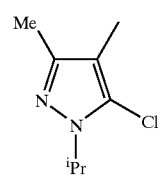 A15
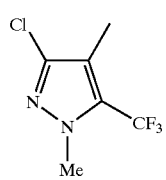 A16
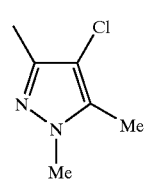 A17
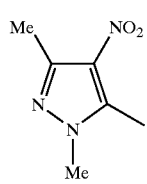 A18
-continued
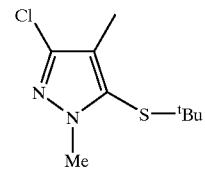 A19
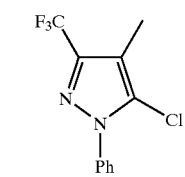 A20
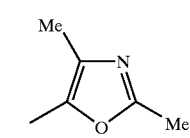 A21
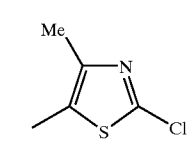 A22
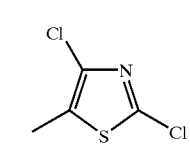 A23
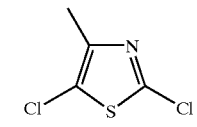 A24
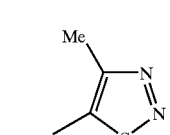 A25
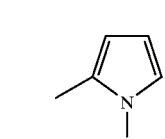 A26
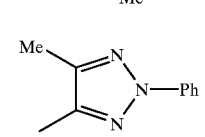 A27
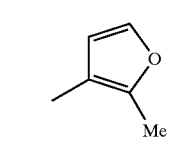 A28
A29

-continued
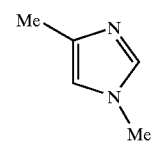 A30
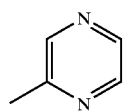 A31
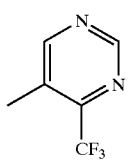 A32
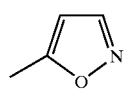 A33
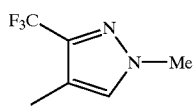 A34
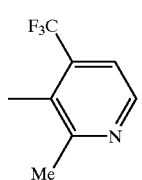 A35
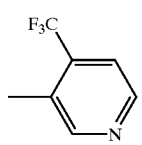 A36
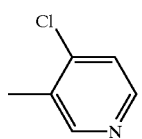 A37
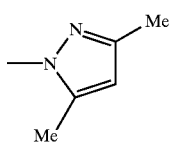 A38
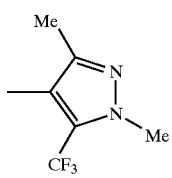 A39
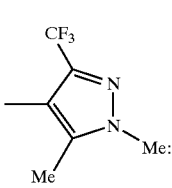 A40
-continued
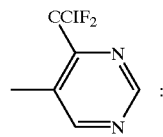 A41
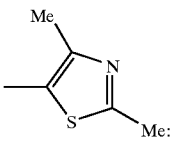 A42
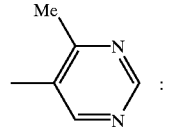 A43
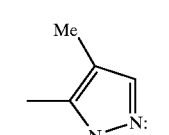 A44
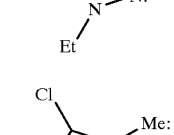 A45
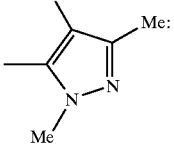 A46
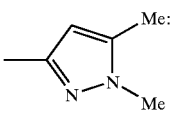 A47
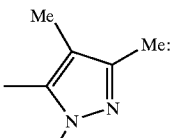 A48
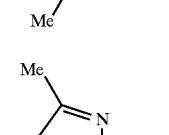 A49
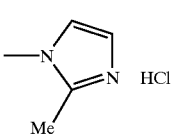 A50

-continued
A51
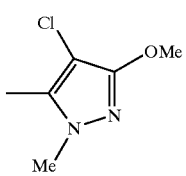
A52
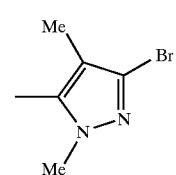
B1
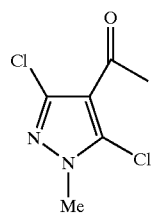
B2
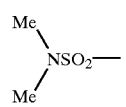
B3 CH₃OCH₂—
B4 CF₃SO₂—
B5 CH₃SO₂—
B6
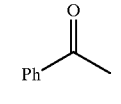
B7
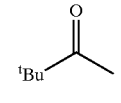
B8
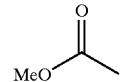
B9 Et₃⁺NH
B10
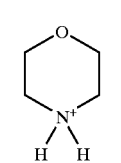
B11 ⁿBu₃⁺NH
B12
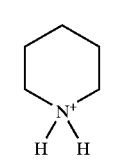
B13 Me₃Si—
-continued
B14
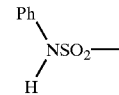
B15
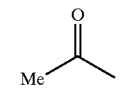
B16
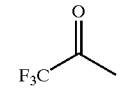
B17
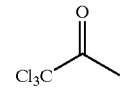
B18
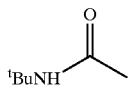
B19
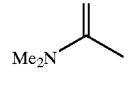
B20
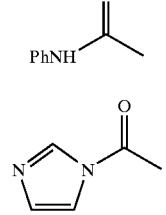
B21
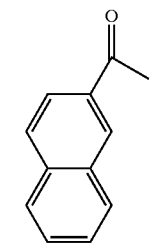
B22
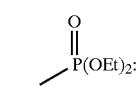
B23
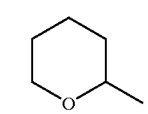
B24 CH₃O(CH₂)₂OCH₂—:
B25
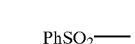
B26 PhSO₂—
B27
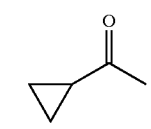

-continued
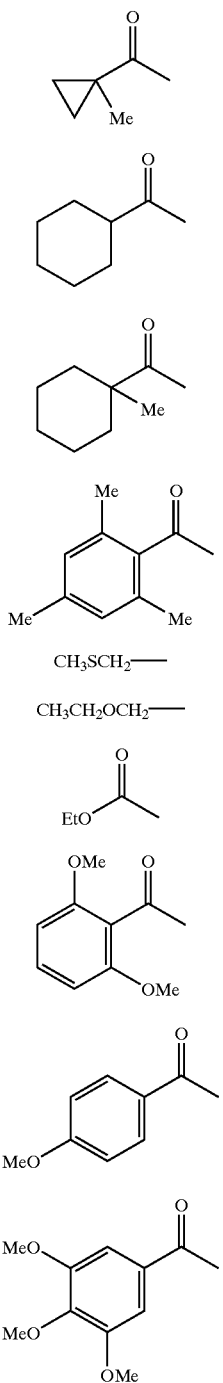
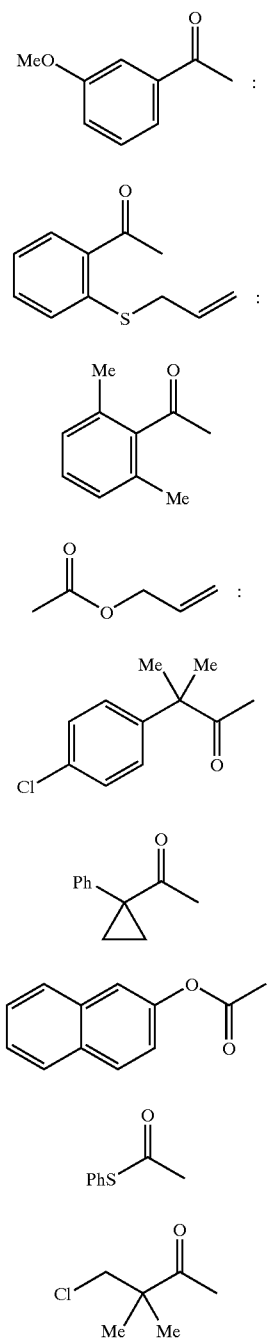
TABLE 1
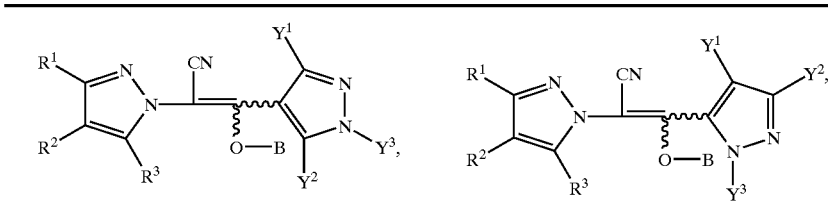

TABLE 1-continued
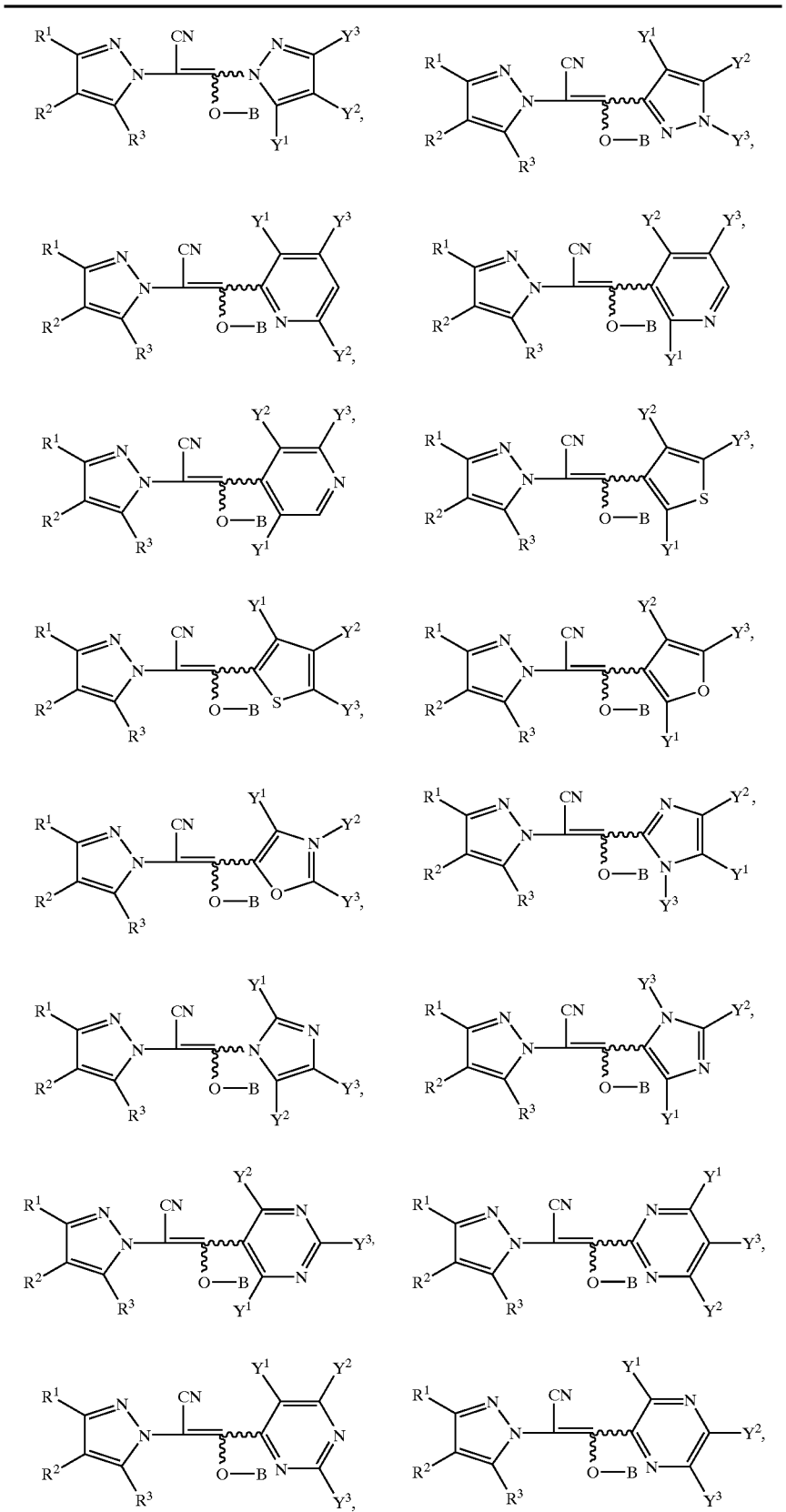

TABLE 1-continued
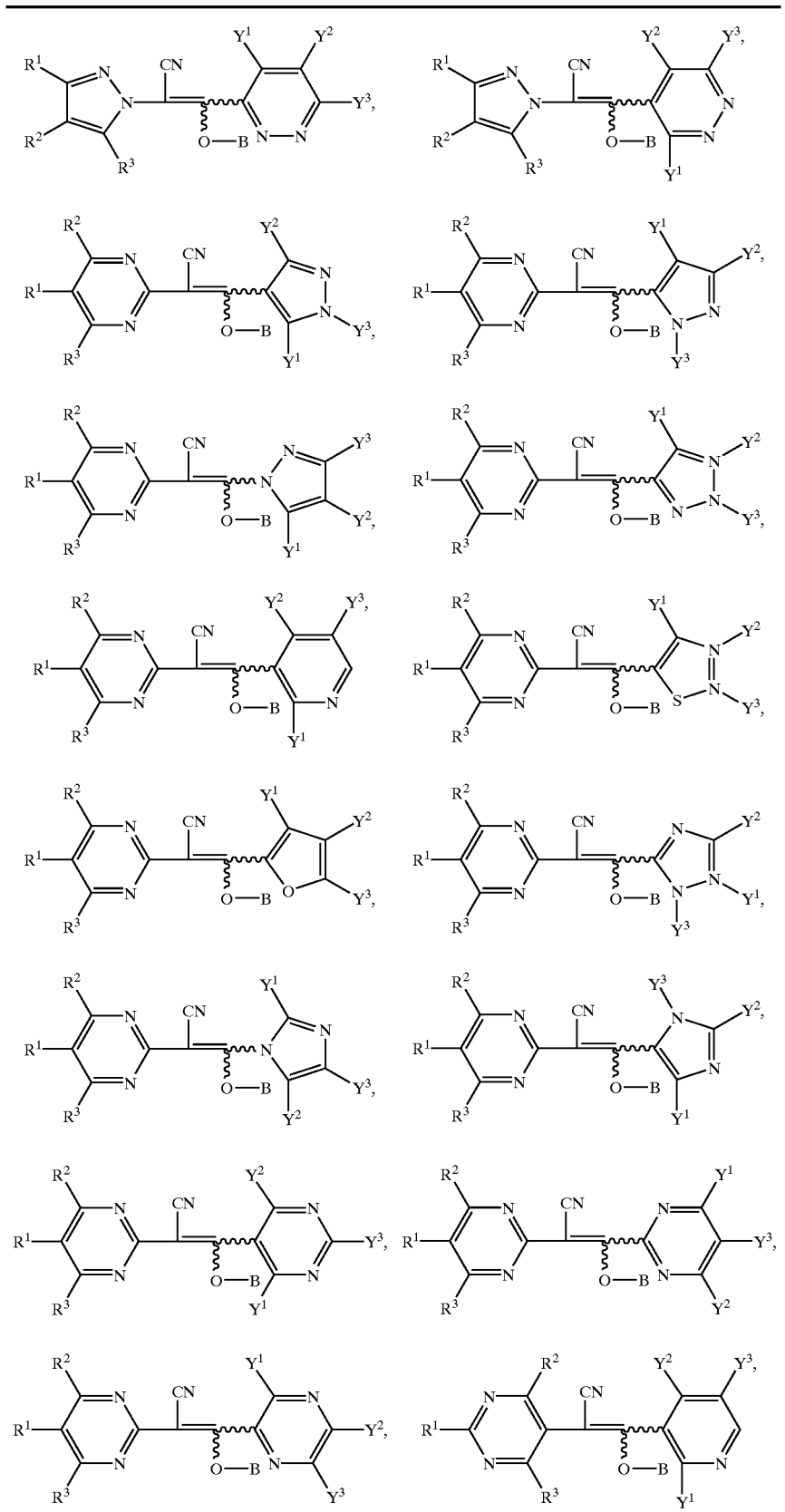

TABLE 1-continued

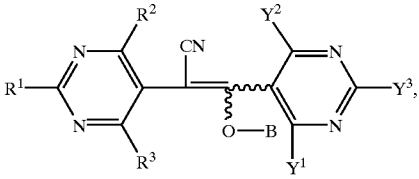

| R¹ | R² | R³ | B | Y¹ | Y² | Y³ |
|---|---|---|---|---|---|---|
| 2,6-F₂—Ph | H | H | H | H | H | H |
| 2,6-F₂—Ph | H | H | H | H | Cl | H |
| 2,6-F₂—Ph | H | H | H | H | Me | H |
| 2,6-F₂—Ph | H | H | H | H | OMe | H |
| 2,6-F₂—Ph | H | H | H | H | SMe | H |
| 2,6-F₂—Ph | H | H | H | H | OCF₃ | H |
| 2,6-F₂—Ph | H | H | H | H | CF₃ | H |
| 2,6-F₂—Ph | H | H | H | H | CO₂Me | H |
| 2,6-F₂—Ph | H | H | H | H | H | Me |
| 2,6-F₂—Ph | H | H | H | Me | H | Me |
| 2,6-F₂—Ph | H | H | H | Me | H | CF₃ |
| 2,6-F₂—Ph | H | H | H | Me | H | H |
| 2,6-F₂—Ph | H | H | H | Me | Me | Me |
| 2,6-F₂—Ph | H | H | H | Me | Me | H |
| 2,6-F₂—Ph | H | H | H | Me | Cl | Me |
| 2,6-F₂—Ph | H | H | H | Me | Cl | H |
| 2,6-F₂—Ph | Cl | H | H | Me | Cl | Me |
| 2,6-F₂—Ph | H | H | H | Et | Me | Me |
| 2,6-F₂—Ph | H | H | H | Et | H | H |
| 2,6-F₂—Ph | H | H | H | nPr | Me | Me |
| 2,6-F₂—Ph | H | H | H | iPr | Me | Me |
| 2,6-F₂—Ph | H | H | H | iPr | Cl | Me |
| 2,6-F₂—Ph | H | H | H | nBu | Me | Me |
| 2,6-F₂—Ph | H | H | H | tBu | Me | Me |
| 2,6-F₂—Ph | H | H | H | Cl | Me | Me |
| 2,6-F₂—Ph | H | H | H | Cl | Me | H |
| 2,6-F₂—Ph | H | H | H | Cl | H | Me |
| 2,6-F₂—Ph | H | H | H | Cl | H | CF₃ |
| 2,6-F₂—Ph | H | H | H | Cl | H | H |
| 2,6-F₂—Ph | Me | H | H | Cl | H | H |
| 2,6-F₂—Ph | Cl | H | H | Cl | H | H |
| 2,6-F₂—Ph | NO₂ | H | H | Cl | H | H |
| 2,6-F₂—Ph | CO₂Me | H | H | Cl | H | H |
| 2,6-F₂—Ph | CO₂Et | H | H | Cl | H | H |
| 2,6-F₂—Ph | H | H | H | Cl | Cl | Me |
| 2,6-F₂—Ph | Me | H | H | Cl | Cl | Me |
| 2,6-F₂—Ph | H | Me | H | Cl | Cl | Me |
| 2,6-F₂—Ph | H | Cl | H | Cl | Cl | Me |

TABLE 1-continued

| | | | | | | |
|---|---|---|---|---|---|---|
| 2,6-F$_2$—Ph | Cl | H | H | Cl | Cl | Me |
| 2,6-F$_2$—Ph | Cl | Cl | H | Cl | Cl | Me |
| 2,6-F$_2$—Ph | Cl | Cl | Bl | Cl | Cl | Me |
| 2,6-F$_2$—Ph | Ph | H | H | Cl | Cl | Me |
| 2,6-F$_2$—Ph | H | Ph | H | Cl | Cl | Me |
| 2,6-F$_2$—Ph | CF$_3$ | H | H | Cl | Cl | Me |
| 2,6-F$_2$—Ph | H | CF$_3$ | H | Cl | Cl | Me |
| 2,6-F$_2$—Ph | cPr | H | H | Cl | Cl | Me |
| 2,6-F$_2$—Ph | H | cPr | H | Cl | Cl | Me |
| 2,6-F$_2$—Ph | OMe | H | H | Cl | Cl | Me |
| 2,6-F$_2$—Ph | H | OMe | H | Cl | Cl | Me |
| 2,6-F$_2$—Ph | NH$_2$ | H | H | Cl | Cl | Me |
| 2,6-F$_2$—Ph | H | NH$_2$ | H | Cl | Cl | Me |
| 2,6-F$_2$—Ph | NHMe | H | H | Cl | Cl | Me |
| 2,6-F$_2$—Ph | H | NHMe | H | Cl | Cl | Me |
| 2,6-F$_2$—Ph | NMe$_2$ | H | H | Cl | Cl | Me |
| 2,6-F$_2$—Ph | H | NMe$_2$ | H | Cl | Cl | Me |
| 2,6-F$_2$—Ph | NO$_2$ | H | H | Cl | Cl | Me |
| 2,6-F$_2$—Ph | H | NO$_2$ | H | Cl | Cl | Me |
| 2,6-F$_2$—Ph | CN | H | H | Cl | Cl | Me |
| 2,6-F$_2$—Ph | H | CN | H | Cl | Cl | Me |
| 2,6-F$_2$—Ph | OH | H | H | Cl | Cl | Me |
| 2,6-F$_2$—Ph | H | OH | H | Cl | Cl | Me |
| 2,6-F$_2$—Ph | CO$_2$Me | H | H | Cl | Cl | Me |
| 2,6-F$_2$—Ph | H | CO$_2$Me | H | Cl | Cl | Me |
| 2,6-F$_2$—Ph | CO$_2$Et | H | H | Cl | Cl | Me |
| 2,6-F$_2$—Ph | H | H | H | Cl | Cl | H |
| 2,6-F$_2$—Ph | H | H | H | Cl | Cl | CF$_3$ |
| 2,6-F$_2$—Ph | H | H | H | Cl | Cl | CF$_2$H |
| 2,6-F$_2$—Ph | H | H | H | Cl | Cl | CH$_2$OMe |
| 2,6-F$_2$—Ph | H | H | H | Cl | Cl | COMe |
| 2,6-F$_2$—Ph | H | H | H | Cl | Cl | Ph |
| 2,6-F$_2$—Ph | H | H | H | Cl | Cl | CH$_2$Ph |
| 2,6-F$_2$—Ph | H | H | H | Cl | CF$_3$ | Me |
| 2,6-F$_2$—Ph | H | H | H | Br | Me | Me |
| 2,6-F$_2$—Ph | H | H | H | Me | Br | Me |
| 2,6-F$_2$—Ph | H | H | H | Me | Br | H |
| 2,6-F$_2$—Ph | H | H | H | Br | H | H |
| 2,6-F$_2$—Ph | H | H | H | OMe | Me | Me |
| 2,6-F$_2$—Ph | H | H | H | Me | OMe | Me |
| 2,6-F$_2$—Ph | H | H | H | OMe | H | H |
| 2,6-F$_2$—Ph | H | H | H | H | OMe | H |
| 2,6-F$_2$—Ph | H | H | H | Cl | OMe | Me |
| 2,6-F$_2$—Ph | H | H | H | OCF$_3$ | Me | Me |
| 2,6-F$_2$—Ph | H | H | H | OCF$_3$ | Cl | Me |
| 2,6-F$_2$—Ph | H | H | H | OCF$_3$ | H | H |
| 2,6-F$_2$—Ph | H | H | H | Me | OCF$_3$ | Me |
| 2,6-F$_2$—Ph | H | H | H | Cl | OCF$_3$ | Me |
| 2,6-F$_2$—Ph | H | H | H | SMe | Cl | Me |
| 2,6-F$_2$—Ph | H | H | H | Me | SMe | Me |
| 2,6-F$_2$—Ph | H | H | H | Cl | SMe | Me |
| 2,6-F$_2$—Ph | H | H | H | SMe | H | H |
| 2,6-F$_2$—Ph | H | H | H | SOMe | Cl | Me |
| 2,6-F$_2$—Ph | H | H | H | Cl | SOMe | Me |
| 2,6-F$_2$—Ph | H | H | H | SOMe | H | H |
| 2,6-F$_2$—Ph | H | H | H | SO$_2$Me | Cl | Me |
| 2,6-F$_2$—Ph | H | H | H | Cl | SO$_2$Me | Me |
| 2,6-F$_2$—Ph | H | H | H | SO$_2$Me | H | H |
| 2,6-F$_2$—Ph | H | H | H | CF$_3$ | Me | Me |
| 2,6-F$_2$—Ph | H | H | H | CF$_3$ | Cl | H |
| 2,6-F$_2$—Ph | H | H | H | CF$_3$ | Cl | Me |
| 2,6-F$_2$—Ph | Me | H | H | CF$_3$ | Cl | Me |
| 2,6-F$_2$—Ph | Cl | H | H | CF$_3$ | Cl | Me |
| 2,6-F$_2$—Ph | Br | H | H | CF$_3$ | Cl | Me |
| 2,6-F$_2$—Ph | CF$_3$ | H | H | CF$_3$ | Cl | Me |
| 2,6-F$_2$—Ph | NO$_2$ | H | H | CF$_3$ | Cl | Me |
| 2,6-F$_2$—Ph | CN | H | H | CF$_3$ | Cl | Me |
| 2,6-F$_2$—Ph | CO$_2$Me | H | H | CF$_3$ | Cl | Me |
| 2,6-F$_2$—Ph | CO$_2$Et | H | H | CF$_3$ | Cl | Me |
| 2,6-F$_2$—Ph | H | H | H | CF$_3$ | Cl | CF$_3$ |
| 2,6-F$_2$—Ph | H | H | H | CF$_3$ | Cl | CF$_2$H |
| 2,6-F$_2$—Ph | H | H | H | CF$_3$ | Cl | CH$_2$OMe |
| 2,6-F$_2$—Ph | H | H | H | CF$_3$ | Cl | COCH$_3$ |
| 2,6-F$_2$—Ph | H | H | H | CF$_3$ | H | Me |
| 2,6-F$_2$—Ph | H | H | H | CF$_3$ | H | H |
| 2,6-F$_2$—Ph | H | H | H | CF$_3$ | Br | Me |
| 2,6-F$_2$—Ph | H | H | H | CF$_3$ | SMe | Me |
| 2,6-F$_2$—Ph | H | H | H | CF$_3$ | SOMe | Me |
| 2,6-F$_2$—Ph | H | H | H | CF$_3$ | SO$_2$Me | Me |

TABLE 1-continued

| | | | | | | |
|---|---|---|---|---|---|---|
| 2,6-F$_2$—Ph | H | H | H | CF$_3$ | CF$_3$ | Me |
| 2,6-F$_2$—Ph | H | H | H | CF$_3$ | NO$_2$ | Me |
| 2,6-F$_2$—Ph | H | H | H | CF$_3$ | CN | Me |
| 2,6-F$_2$—Ph | H | H | H | CF$_3$ | NHMe | Me |
| 2,6-F$_2$—Ph | H | H | H | CF$_3$ | NMe$_2$ | Me |
| 2,6-F$_2$—Ph | H | H | H | CF$_3$ | Ph | Me |
| 2,6-F$_2$—Ph | H | H | H | CF$_3$ | CH$_2$Ph | Me |
| 2,6-F$_2$—Ph | H | H | H | CF$_3$ | OPh | Me |
| 2,6-F$_2$—Ph | H | H | H | CF$_3$ | OH | Me |
| 2,6-F$_2$—Ph | H | H | H | CF$_3$ | CO$_2$Me | Me |
| 2,6-F$_2$—Ph | H | H | H | CF$_3$ | OMe | Me |
| 2,6-F$_2$—Ph | H | H | H | CF$_3$ | OCF$_3$ | Me |
| 2,6-F$_2$—Ph | H | H | H | CF$_3$ | OCF$_2$H | Me |
| 2,6-F$_2$—Ph | H | H | H | CF$_3$ | OCF$_2$H | CF$_2$H |
| 2,6-F$_2$—Ph | H | H | H | NO$_2$ | CF$_3$ | Me |
| 2,6-F$_2$—Ph | H | H | H | NO$_2$ | Cl | Me |
| 2,6-F$_2$—Ph | H | H | H | NO$_2$ | Me | Me |
| 2,6-F$_2$—Ph | H | H | H | NO$_2$ | H | H |
| 2,6-F$_2$—Ph | H | H | H | Cl | NO$_2$ | Me |
| 2,6-F$_2$—Ph | H | H | H | CN | CF$_3$ | Me |
| 2,6-F$_2$—Ph | H | H | H | CN | Cl | Me |
| 2,6-F$_2$—Ph | H | H | H | CN | Me | Me |
| 2,6-F$_2$—Ph | H | H | H | CN | H | H |
| 2,6-F$_2$—Ph | H | H | H | Cl | CN | Me |
| 2,6-F$_2$—Ph | H | H | H | Br | CN | Me |
| 2,6-F$_2$—Ph | H | H | H | NHMe | Me | Me |
| 2,6-F$_2$—Ph | H | H | H | NHMe | Cl | Me |
| 2,6-F$_2$—Ph | H | H | H | NHMe | H | H |
| 2,6-F$_2$—Ph | H | H | H | Cl | NHMe | Me |
| 2,6-F$_2$—Ph | H | H | H | NMe$_2$ | Me | Me |
| 2,6-F$_2$—Ph | H | H | H | NMe$_2$ | Cl | Me |
| 2,6-F$_2$—Ph | H | H | H | NMe$_2$ | H | H |
| 2,6-F$_2$—Ph | H | H | H | Cl | NMe$_2$ | Me |
| 2,6-F$_2$—Ph | H | H | H | Ph | Cl | Me |
| 2,6-F$_2$—Ph | H | H | H | Ph | H | H |
| 2,6-F$_2$—Ph | H | H | H | Cl | Ph | Me |
| 2,6-F$_2$—Ph | H | H | H | CH$_2$Ph | Me | Me |
| 2,6-F$_2$—Ph | H | H | H | CH$_2$Ph | H | H |
| 2,6-F$_2$—Ph | H | H | H | Cl | CH$_2$Ph | Me |
| 2,6-F$_2$—Ph | H | H | H | OPh | Cl | Me |
| 2,6-F$_2$—Ph | H | H | H | OPh | H | H |
| 2,6-F$_2$—Ph | H | H | H | Cl | OPh | Me |
| 2,6-F$_2$—Ph | H | H | H | OH | Me | Me |
| 2,6-F$_2$—Ph | H | H | H | OH | H | H |
| 2,6-F$_2$—Ph | H | H | H | Cl | OH | Me |
| 2,6-F$_2$—Ph | H | H | H | CO$_2$Me | Me | Me |
| 2,6-F$_2$—Ph | H | H | H | CO$_2$Me | Cl | Me |
| 2,6-F$_2$—Ph | H | H | H | CO$_2$Me | H | H |
| 2,6-F$_2$—Ph | H | H | H | cPr | Me | Me |
| 2,6-F$_2$—Ph | H | H | H | cPr | Cl | Me |
| 2,6-F$_2$—Ph | H | H | B1 | Cl | Cl | Me |
| 2,6-F$_2$—Ph | Cl | H | B1 | Cl | Cl | Me |
| 2,6-F$_2$—Ph | H | H | B2 | Cl | Cl | Me |
| 2,6-F$_2$—Ph | H | H | B3 | Cl | Cl | Me |
| 2,6-F$_2$—Ph | H | H | B4 | Cl | Cl | Me |
| 2,6-F$_2$—Ph | Cl | H | B4 | Cl | Cl | Me |
| 2,6-F$_2$—Ph | Cl | Me | B4 | Cl | Cl | Me |
| 2,6-F$_2$—Ph | NO$_2$ | H | B4 | Cl | Cl | Me |
| 2,6-F$_2$—Ph | CO$_2$Me | H | B4 | Cl | Cl | Me |
| 2,6-F$_2$—Ph | CO$_2$Et | H | B4 | Cl | Cl | Me |
| 2,6-F$_2$—Ph | H | H | B5 | Cl | Cl | Me |
| 2,6-F$_2$—Ph | Cl | H | B5 | Cl | Cl | Me |
| 2,6-F$_2$—Ph | H | H | B6 | Cl | Cl | Me |
| 2,6-F$_2$—Ph | Cl | H | B6 | Cl | Cl | Me |
| 2,6-F$_2$—Ph | NO$_2$ | H | B6 | Cl | Cl | Me |
| 2,6-F$_2$—Ph | CO$_2$Me | H | B6 | Cl | Cl | Me |
| 2,6-F$_2$—Ph | CO$_2$Et | H | B6 | Cl | Cl | Me |
| 2,6-F$_2$—Ph | H | H | B7 | Cl | Cl | Me |
| 2,6-F$_2$—Ph | Cl | H | B7 | Cl | Cl | Me |
| 2,6-F$_2$—Ph | NO$_2$ | H | B7 | Cl | Cl | Me |
| 2,6-F$_2$—Ph | CO$_2$Me | H | B7 | Cl | Cl | Me |
| 2,6-F$_2$—Ph | CO$_2$Et | H | B7 | Cl | Cl | Me |
| 2,6-F$_2$—Ph | H | H | B8 | Cl | Cl | Me |
| 2,6-F$_2$—Ph | H | H | B9 | Cl | Cl | Me |
| 2,6-F$_2$—Ph | H | H | B10 | Cl | Cl | Me |
| 2,6-F$_2$—Ph | H | H | B11 | Cl | Cl | Me |
| 2,6-F$_2$—Ph | H | H | B12 | Cl | Cl | Me |
| 2,6-F$_2$—Ph | H | H | B13 | Cl | Cl | Me |
| 2,6-F$_2$—Ph | H | H | B14 | Cl | Cl | Me |

TABLE 1-continued

| | | | | | | |
|---|---|---|---|---|---|---|
| 2,6-F$_2$—Ph | H | H | B15 | Cl | Cl | Me |
| 2,6-F$_2$—Ph | H | H | B16 | Cl | Cl | Me |
| 2,6-F$_2$—Ph | H | H | B17 | Cl | Cl | Me |
| 2,6-F$_2$—Ph | H | H | B18 | Cl | Cl | Me |
| 2,6-F$_2$—Ph | H | H | B19 | Cl | Cl | Me |
| 2,6-F$_2$—Ph | H | H | B20 | Cl | Cl | Me |
| 2,6-F$_2$—Ph | H | H | B21 | Cl | Cl | Me |
| 2,6-F$_2$—Ph | H | H | B22 | Cl | Cl | Me |
| 2,6-F$_2$—Ph | H | H | B23 | Cl | Cl | Me |
| 2,6-F$_2$—Ph | H | H | B24 | Cl | Cl | Me |
| 2,6-F$_2$—Ph | H | H | B25 | Cl | Cl | Me |
| 2,6-F$_2$—Ph | H | H | B26 | Cl | Cl | Me |
| 2,6-F$_2$—Ph | H | H | B27 | Cl | Cl | Me |
| 2,6-F$_2$—Ph | H | H | B28 | Cl | Cl | Me |
| 2,6-F$_2$—Ph | H | H | B29 | Cl | Cl | Me |
| 2,6-F$_2$—Ph | H | H | B30 | Cl | Cl | Me |
| 2,6-F$_2$—Ph | H | H | B31 | Cl | Cl | Me |
| 2,6-F$_2$—Ph | H | H | B32 | Cl | Cl | Me |
| 2,6-F$_2$—Ph | H | H | B33 | Cl | Cl | Me |
| 2,6-F$_2$—Ph | H | H | B34 | Cl | Cl | Me |
| 2,6-F$_2$—Ph | H | H | Na | Cl | Cl | Me |
| 2,6-F$_2$—Ph | H | H | K | Cl | Cl | Me |
| 2,6-F$_2$—Ph | H | H | B1 | CF$_3$ | Cl | Me |
| 2,6-F$_2$—Ph | H | H | B2 | CF$_3$ | Cl | Me |
| 2,6-F$_2$—Ph | H | H | B3 | CF$_3$ | Cl | Me |
| 2,6-F$_2$—Ph | H | H | B4 | CF$_3$ | Cl | Me |
| 2,6-F$_2$—Ph | Me | H | B4 | CF$_3$ | Cl | Me |
| 2,6-F$_2$—Ph | Cl | H | B4 | CF$_3$ | Cl | Me |
| 2,6-F$_2$—Ph | NO$_2$ | H | B4 | CF$_3$ | Cl | Me |
| 2,6-F$_2$—Ph | CO$_2$Me | H | B4 | CF$_3$ | Cl | Me |
| 2,6-F$_2$—Ph | CO$_2$Et | H | B4 | CF$_3$ | Cl | Me |
| 2,6-F$_2$—Ph | H | H | B5 | CF$_3$ | Cl | Me |
| 2,6-F$_2$—Ph | Cl | H | B5 | CF$_3$ | Cl | Me |
| 2,6-F$_2$—Ph | H | H | B6 | CF$_3$ | Cl | Me |
| 2,6-F$_2$—Ph | Me | H | B6 | CF$_3$ | Cl | Me |
| 2,6-F$_2$—Ph | Cl | H | B6 | CF$_3$ | Cl | Me |
| 2,6-F$_2$—Ph | NO$_2$ | H | B6 | CF$_3$ | Cl | Me |
| 2,6-F$_2$—Ph | CO$_2$Me | H | B6 | CF$_3$ | Cl | Me |
| 2,6-F$_2$—Ph | CO$_2$Et | H | B6 | CF$_3$ | Cl | Me |
| 2,6-F$_2$—Ph | H | H | B7 | CF$_3$ | Cl | Me |
| 2,6-F$_2$—Ph | Me | H | B7 | CF$_3$ | Cl | Me |
| 2,6-F$_2$—Ph | Cl | H | B7 | CF$_3$ | Cl | Me |
| 2,6-F$_2$—Ph | NO$_2$ | H | B7 | CF$_3$ | Cl | Me |
| 2,6-F$_2$—Ph | CO$_2$Me | H | B7 | CF$_3$ | Cl | Me |
| 2,6-F$_2$—Ph | CO$_2$Et | H | B7 | CF$_3$ | Cl | Me |
| 2,6-F$_2$—Ph | H | H | B8 | CF$_3$ | Cl | Me |
| 2,6-F$_2$—Ph | H | H | B9 | CF$_3$ | Cl | Me |
| 2,6-F$_2$—Ph | H | H | B10 | CF$_3$ | Cl | Me |
| 2,6-F$_2$—Ph | H | H | B11 | CF$_3$ | Cl | Me |
| 2,6-F$_2$—Ph | H | H | B12 | CF$_3$ | Cl | Me |
| 2,6-F$_2$—Ph | H | H | B13 | CF$_3$ | Cl | Me |
| 2,6-F$_2$—Ph | H | H | B14 | CF$_3$ | Cl | Me |
| 2,6-F$_2$—Ph | H | H | B15 | CF$_3$ | Cl | Me |
| 2,6-F$_2$—Ph | H | H | B16 | CF$_3$ | Cl | Me |
| 2,6-F$_2$—Ph | H | H | B17 | CF$_3$ | Cl | Me |
| 2,6-F$_2$—Ph | H | H | B18 | CF$_3$ | Cl | Me |
| 2,6-F$_2$—Ph | H | H | B19 | CF$_3$ | Cl | Me |
| 2,6-F$_2$—Ph | H | H | B20 | CF$_3$ | Cl | Me |
| 2,6-F$_2$—Ph | H | H | B21 | CF$_3$ | Cl | Me |
| 2,6-F$_2$—Ph | H | H | B22 | CF$_3$ | Cl | Me |
| 2,6-F$_2$—Ph | H | H | B23 | CF$_3$ | Cl | Me |
| 2,6-F$_2$—Ph | H | H | B24 | CF$_3$ | Cl | Me |
| 2,6-F$_2$—Ph | H | H | B25 | CF$_3$ | Cl | Me |
| 2,6-F$_2$—Ph | H | H | B26 | CF$_3$ | Cl | Me |
| 2,6-F$_2$—Ph | H | H | B27 | CF$_3$ | Cl | Me |
| 2,6-F$_2$—Ph | H | H | B28 | CF$_3$ | Cl | Me |
| 2,6-F$_2$—Ph | H | H | B29 | CF$_3$ | Cl | Me |
| 2,6-F$_2$—Ph | H | H | B30 | CF$_3$ | Cl | Me |
| 2,6-F$_2$—Ph | H | H | B31 | CF$_3$ | Cl | Me |
| 2,6-F$_2$—Ph | H | H | B32 | CF$_3$ | Cl | Me |
| 2,6-F$_2$—Ph | H | H | B33 | CF$_3$ | Cl | Me |
| 2,6-F$_2$—Ph | H | H | B34 | CF$_3$ | Cl | Me |
| 2,6-F$_2$—Ph | H | H | Na | CF$_3$ | Cl | Me |
| 2,6-F$_2$—Ph | H | H | K | CF$_3$ | Cl | Me |
| 2,6-F$_2$—Ph | H | H | B1 | Cl | H | H |
| 2,6-F$_2$—Ph | H | H | B2 | Cl | H | H |
| 2,6-F$_2$—Ph | H | H | B3 | Cl | H | H |
| 2,6-F$_2$—Ph | H | H | B4 | Cl | H | H |
| 2,6-F$_2$—Ph | Me | H | B4 | Cl | H | H |

TABLE 1-continued

| | | | | | | |
|---|---|---|---|---|---|---|
| 2,6-F₂—Ph | Cl | H | B4 | Cl | H | H |
| 2,6-F₂—Ph | NO₂ | H | B4 | Cl | H | H |
| 2,6-F₂—Ph | CO₂Me | H | B4 | Cl | H | H |
| 2,6-F₂—Ph | CO₂Et | H | B4 | Cl | H | H |
| 2,6-F₂—Ph | H | H | B5 | Cl | H | H |
| 2,6-F₂—Ph | H | H | B6 | Cl | H | H |
| 2,6-F₂—Ph | NO₂ | H | B6 | Cl | H | H |
| 2,6-F₂—Ph | H | H | B7 | Cl | H | H |
| 2,6-F₂—Ph | Me | H | B7 | Cl | H | H |
| 2,6-F₂—Ph | Cl | H | B7 | Cl | H | H |
| 2,6-F₂—Ph | NO₂ | H | B7 | Cl | H | H |
| 2,6-F₂—Ph | CO₂Me | H | B7 | Cl | H | H |
| 2,6-F₂—Ph | CO₂Et | H | B7 | Cl | H | H |
| 2,6-F₂—Ph | H | H | B8 | Cl | H | H |
| 2,6-F₂—Ph | H | H | B9 | Cl | H | H |
| 2,6-F₂—Ph | H | H | B10 | Cl | H | H |
| 2,6-F₂—Ph | H | H | B11 | Cl | H | H |
| 2,6-F₂—Ph | H | H | B12 | Cl | H | H |
| 2,6-F₂—Ph | H | H | B13 | Cl | H | H |
| 2,6-F₂—Ph | H | H | B14 | Cl | H | H |
| 2,6-F₂—Ph | H | H | B15 | Cl | H | H |
| 2,6-F₂—Ph | H | H | B16 | Cl | H | H |
| 2,6-F₂—Ph | H | H | B17 | Cl | H | H |
| 2,6-F₂—Ph | H | H | B18 | Cl | H | H |
| 2,6-F₂—Ph | H | H | B19 | Cl | H | H |
| 2,6-F₂—Ph | H | H | B20 | Cl | H | H |
| 2,6-F₂—Ph | H | H | B21 | Cl | H | H |
| 2,6-F₂—Ph | H | H | B22 | Cl | H | H |
| 2,6-F₂—Ph | H | H | B23 | Cl | H | H |
| 2,6-F₂—Ph | H | H | B24 | Cl | H | H |
| 2,6-F₂—Ph | H | H | B25 | Cl | H | H |
| 2,6-F₂—Ph | H | H | B26 | Cl | H | H |
| 2,6-F₂—Ph | H | H | B27 | Cl | H | H |
| 2,6-F₂—Ph | H | H | B28 | Cl | H | H |
| 2,6-F₂—Ph | H | H | B29 | Cl | H | H |
| 2,6-F₂—Ph | H | H | B30 | Cl | H | H |
| 2,6-F₂—Ph | H | H | B31 | Cl | H | H |
| 2,6-F₂—Ph | H | H | B32 | Cl | H | H |
| 2,6-F₂—Ph | H | H | B33 | Cl | H | H |
| 2,6-F₂—Ph | H | H | B34 | Cl | H | H |
| 2,6-F₂—Ph | H | H | Na | Cl | H | H |
| 2,6-F₂—Ph | H | H | K | Cl | H | H |
| tBu | H | H | H | H | H | Me |
| tBu | H | H | H | Me | H | Me |
| tBu | H | H | H | Me | H | CF₃ |
| tBu | H | H | B7 | Me | H | H |
| tBu | H | H | H | Me | Me | Me |
| tBu | H | H | H | Me | Cl | Me |
| tBu | Cl | H | H | Me | Cl | Me |
| tBu | H | H | H | Et | Me | Me |
| tBu | H | H | B8 | Et | H | H |
| tBu | H | H | H | Cl | Me | Me |
| tBu | H | H | H | Cl | Me | H |
| tBu | H | H | H | Cl | H | Me |
| tBu | H | H | H | Cl | H | CF₃ |
| tBu | H | H | H | Cl | H | H |
| tBu | Me | H | B7 | Cl | H | H |
| tBu | Cl | H | B7 | Cl | H | H |
| tBu | NO₂ | H | B7 | Cl | H | H |
| tBu | CO₂Me | H | B7 | Cl | H | H |
| tBu | CO₂Et | H | B7 | Cl | H | H |
| tBu | H | H | H | Cl | Cl | Me |
| tBu | Me | H | H | Cl | Cl | Me |
| tBu | Cl | H | H | Cl | Cl | Me |
| tBu | CF₃ | H | H | Cl | Cl | Me |
| tBu | cPr | H | H | Cl | Cl | Me |
| tBu | OMe | H | H | Cl | Cl | Me |
| tBu | NO₂ | H | H | Cl | Cl | Me |
| tBu | CN | H | H | Cl | Cl | Me |
| tBu | CO₂Me | H | H | Cl | Cl | Me |
| tBu | CO₂Et | H | H | Cl | Cl | Me |
| tBu | H | H | H | Cl | Cl | H |
| tBu | H | H | H | Cl | Cl | CF₃ |
| tBu | H | H | H | Cl | Cl | CF₂H |
| tBu | H | H | H | Cl | Cl | CH₂OMe |
| tBu | H | H | H | Cl | Cl | COMe |
| tBu | H | H | H | Cl | CF₃ | Me |
| tBu | H | H | H | Br | Me | Me |
| tBu | H | H | H | Me | Br | Me |

TABLE 1-continued

| | | | | | | |
|---|---|---|---|---|---|---|
| tBu | H | H | H | Me | Br | H |
| tBu | H | H | B34 | Br | H | H |
| tBu | H | H | H | OMe | Me | Me |
| tBu | H | H | H | Me | OMe | Me |
| tBu | H | H | H | OMe | H | H |
| tBu | H | H | H | Cl | OMe | Me |
| tBu | H | H | H | $OCF_3$ | Me | Me |
| tBu | H | H | H | $OCF_3$ | Cl | Me |
| tBu | H | H | H | $OCF_3$ | H | H |
| tBu | H | H | H | Me | $OCF_3$ | Me |
| tBu | H | H | H | Cl | $OCF_3$ | Me |
| tBu | H | H | H | SMe | Cl | Me |
| tBu | H | H | H | Me | SMe | Me |
| tBu | H | H | H | Cl | SMe | Me |
| tBu | H | H | B7 | SMe | H | H |
| tBu | H | H | H | $CF_3$ | Me | Me |
| tBu | H | H | H | $CF_3$ | Cl | H |
| tBu | H | H | H | $CF_3$ | Cl | Me |
| tBu | Me | H | H | $CF_3$ | Cl | Me |
| tBu | Cl | H | H | $CF_3$ | Cl | Me |
| tBu | Br | H | H | $CF_3$ | Cl | Me |
| tBu | $CF_3$ | H | H | $CF_3$ | Cl | Me |
| tBu | $NO_2$ | H | H | $CF_3$ | Cl | Me |
| tBu | CN | H | H | $CF_3$ | Cl | Me |
| tBu | $CO_2Me$ | H | H | $CF_3$ | Cl | Me |
| tBu | $CO_2Et$ | H | H | $CF_3$ | Cl | Me |
| tBu | H | H | H | $CF_3$ | Cl | $CF_3$ |
| tBu | H | H | H | $CF_3$ | Cl | $CF_2H$ |
| tBu | H | H | H | $CF_3$ | Cl | $CH_2OMe$ |
| tBu | H | H | H | $CF_3$ | Cl | $COCH_3$ |
| tBu | H | H | H | $CF_3$ | H | Me |
| tBu | H | H | H | $CF_3$ | H | H |
| tBu | H | H | H | $CF_3$ | Br | Me |
| tBu | H | H | H | $CF_3$ | SMe | Me |
| tBu | H | H | H | $CF_3$ | SOMe | Me |
| tBu | H | H | H | $CF_3$ | $SO_2Me$ | Me |
| tBu | H | H | H | $CF_3$ | $CF_3$ | Me |
| tBu | H | H | H | $CF_3$ | $NO_2$ | Me |
| tBu | H | H | H | $CF_3$ | CN | Me |
| tBu | H | H | H | $CF_3$ | NHMe | Me |
| tBu | H | H | H | $CF_3$ | $NMe_2$ | Me |
| tBu | H | H | H | $CF_3$ | OH | Me |
| tBu | H | H | H | $CF_3$ | $CO_2Me$ | Me |
| tBu | H | H | H | $CF_3$ | OMe | Me |
| tBu | H | H | H | $CF_3$ | $OCF_3$ | Me |
| tBu | H | H | H | $CF_3$ | $OCF_2H$ | Me |
| tBu | H | H | H | $CF_3$ | $OCF_2H$ | $CF_2H$ |
| tBu | H | H | H | $NO_2$ | Cl | Me |
| tBu | H | H | H | $NO_2$ | Me | Me |
| tBu | H | H | H | $NO_2$ | H | H |
| tBu | H | H | H | Cl | $NO_2$ | Me |
| tBu | H | H | H | CN | Cl | Me |
| tBu | H | H | H | CN | Me | Me |
| tBu | H | H | H | CN | H | H |
| tBu | H | H | H | Cl | CN | Me |
| tBu | H | H | H | $NMe_2$ | H | H |
| tBu | H | H | H | Cl | $NMe_2$ | Me |
| tBu | H | H | H | OH | Me | Me |
| tBu | H | H | H | OH | H | H |
| tBu | H | H | H | Cl | OH | Me |
| tBu | H | H | H | $CO_2Me$ | Me | Me |
| tBu | H | H | H | $CO_2Me$ | Cl | Me |
| tBu | H | H | H | $CO_2Me$ | H | H |
| tBu | H | H | B1 | Cl | Cl | Me |
| tBu | Cl | H | B1 | Cl | Cl | Me |
| tBu | H | H | B2 | Cl | Cl | Me |
| tBu | H | H | B3 | Cl | Cl | Me |
| tBu | H | H | B4 | Cl | Cl | Me |
| tBu | Me | H | B4 | Cl | Cl | Me |
| tBu | Cl | H | B4 | Cl | Cl | Me |
| tBu | $NO_2$ | H | B4 | Cl | Cl | Me |
| tBu | $CO_2Me$ | H | B4 | Cl | Cl | Me |
| tBu | $CO_2Et$ | H | B4 | Cl | Cl | Me |
| tBu | H | H | B5 | Cl | Cl | Me |
| tBu | H | H | B6 | Cl | Cl | Me |
| tBu | Cl | H | B6 | Cl | Cl | Me |
| tBu | H | H | B7 | Cl | Cl | Me |
| tBu | Me | H | B7 | Cl | Cl | Me |
| tBu | Cl | H | B7 | Cl | Cl | Me |

TABLE 1-continued

| | | | | | | |
|---|---|---|---|---|---|---|
| tBu | NO₂ | H | B7 | Cl | Cl | Me |
| tBu | CO₂Me | H | B7 | Cl | Cl | Me |
| tBu | CO₂Et | H | B7 | Cl | Cl | Me |
| tBu | H | H | B8 | Cl | Cl | Me |
| tBu | H | H | B9 | Cl | Cl | Me |
| tBu | H | H | B10 | Cl | Cl | Me |
| tBu | H | H | B11 | Cl | Cl | Me |
| tBu | H | H | B12 | Cl | Cl | Me |
| tBu | H | H | B13 | Cl | Cl | Me |
| tBu | H | H | B14 | Cl | Cl | Me |
| tBu | H | H | B15 | Cl | Cl | Me |
| tBu | H | H | B16 | Cl | Cl | Me |
| tBu | H | H | B17 | Cl | Cl | Me |
| tBu | H | H | B18 | Cl | Cl | Me |
| tBu | H | H | B19 | Cl | Cl | Me |
| tBu | H | H | B20 | Cl | Cl | Me |
| tBu | H | H | B21 | Cl | Cl | Me |
| tBu | H | H | B22 | Cl | Cl | Me |
| tBu | H | H | B23 | Cl | Cl | Me |
| tBu | H | H | B24 | Cl | Cl | Me |
| tBu | H | H | B25 | Cl | Cl | Me |
| tBu | H | H | B26 | Cl | Cl | Me |
| tBu | H | H | B27 | Cl | Cl | Me |
| tBu | H | H | B28 | Cl | Cl | Me |
| tBu | H | H | B29 | Cl | Cl | Me |
| tBu | H | H | B30 | Cl | Cl | Me |
| tBu | H | H | B31 | Cl | Cl | Me |
| tBu | H | H | B32 | Cl | Cl | Me |
| tBu | H | H | B33 | Cl | Cl | Me |
| tBu | H | H | B34 | Cl | Cl | Me |
| tBu | H | H | Na | Cl | Cl | Me |
| tBu | H | H | K | Cl | Cl | Me |
| tBu | H | H | B1 | CF₃ | Cl | Me |
| tBu | H | H | B2 | CF₃ | Cl | Me |
| tBu | H | H | B3 | CF₃ | Cl | Me |
| tBu | H | H | B4 | CF₃ | Cl | Me |
| tBu | Me | H | B4 | CF₃ | Cl | Me |
| tBu | Cl | H | B4 | CF₃ | Cl | Me |
| tBu | NO₂ | H | B4 | CF₃ | Cl | Me |
| tBu | CO₂Me | H | B4 | CF₃ | Cl | Me |
| tBu | CO₂Et | H | B4 | CF₃ | Cl | Me |
| tBu | H | H | B5 | CF₃ | Cl | Me |
| tBu | H | H | B6 | CF₃ | Cl | Me |
| tBu | Cl | H | B6 | CF₃ | Cl | Me |
| tBu | H | H | B7 | CF₃ | Cl | Me |
| tBu | Me | H | B7 | CF₃ | Cl | Me |
| tBu | Cl | H | B7 | CF₃ | Cl | Me |
| tBu | NO₂ | H | B7 | CF₃ | Cl | Me |
| tBu | CO₂Me | H | B7 | CF₃ | Cl | Me |
| tBu | CO₂Et | H | B7 | CF₃ | Cl | Me |
| tBu | H | H | B8 | CF₃ | Cl | Me |
| tBu | H | H | B9 | CF₃ | Cl | Me |
| tBu | H | H | B10 | CF₃ | Cl | Me |
| tBu | H | H | B11 | CF₃ | Cl | Me |
| tBu | H | H | B12 | CF₃ | Cl | Me |
| tBu | H | H | B13 | CF₃ | Cl | Me |
| tBu | H | H | B14 | CF₃ | Cl | Me |
| tBu | H | H | B15 | CF₃ | Cl | Me |
| tBu | H | H | B16 | CF₃ | Cl | Me |
| tBu | H | H | B17 | CF₃ | Cl | Me |
| tBu | H | H | B18 | CF₃ | Cl | Me |
| tBu | H | H | B19 | CF₃ | Cl | Me |
| tBu | H | H | B20 | CF₃ | Cl | Me |
| tBu | H | H | B21 | CF₃ | Cl | Me |
| tBu | H | H | B22 | CF₃ | Cl | Me |
| tBu | H | H | B23 | CF₃ | Cl | Me |
| tBu | H | H | B24 | CF₃ | Cl | Me |
| tBu | H | H | B25 | CF₃ | Cl | Me |
| tBu | H | H | B26 | CF₃ | Cl | Me |
| tBu | H | H | B27 | CF₃ | Cl | Me |
| tBu | H | H | B28 | CF₃ | Cl | Me |
| tBu | H | H | B29 | CF₃ | Cl | Me |
| tBu | H | H | B30 | CF₃ | Cl | Me |
| tBu | H | H | B31 | CF₃ | Cl | Me |
| tBu | H | H | B32 | CF₃ | Cl | Me |
| tBu | H | H | B33 | CF₃ | Cl | Me |
| tBu | H | H | B34 | CF₃ | Cl | Me |
| tBu | H | H | Na | CF₃ | Cl | Me |
| tBu | H | H | K | CF₃ | Cl | Me |

TABLE 1-continued

| | | | | | | |
|---|---|---|---|---|---|---|
| tBu | H | H | B1 | Cl | H | H |
| tBu | H | H | B2 | Cl | H | H |
| tBu | H | H | B3 | Cl | H | H |
| tBu | H | H | B4 | Cl | H | H |
| tBu | H | H | B5 | Cl | H | H |
| tBu | H | H | B6 | Cl | H | H |
| tBu | H | H | B7 | Cl | H | H |
| tBu | H | H | B8 | Cl | H | H |
| tBu | H | H | B9 | Cl | H | H |
| tBu | H | H | B10 | Cl | H | H |
| tBu | H | H | B11 | Cl | H | H |
| tBu | H | H | B12 | Cl | H | H |
| tBu | H | H | B13 | Cl | H | H |
| tBu | H | H | B14 | Cl | H | H |
| tBu | H | H | B15 | Cl | H | H |
| tBu | H | H | B16 | Cl | H | H |
| tBu | H | H | B17 | Cl | H | H |
| tBu | H | H | B18 | Cl | H | H |
| tBu | H | H | B19 | Cl | H | H |
| tBu | H | H | B20 | Cl | H | H |
| tBu | H | H | B21 | Cl | H | H |
| tBu | H | H | B22 | Cl | H | H |
| tBu | H | H | B23 | Cl | H | H |
| tBu | H | H | B24 | Cl | H | H |
| tBu | H | H | B25 | Cl | H | H |
| tBu | H | H | B26 | Cl | H | H |
| tBu | H | H | B27 | Cl | H | H |
| tBu | H | H | B28 | Cl | H | H |
| tBu | H | H | B29 | Cl | H | H |
| tBu | H | H | B30 | Cl | H | H |
| tBu | H | H | B31 | Cl | H | H |
| tBu | H | H | B32 | Cl | H | H |
| tBu | H | H | B33 | Cl | H | H |
| tBu | H | H | B34 | Cl | H | H |
| tBu | H | H | Na | Cl | H | H |
| tBu | H | H | K | Cl | H | H |
| 2-pyridyl | H | H | H | H | H | Me |
| 2-pyridyl | H | H | H | Me | H | Me |
| 2-pyridyl | H | H | H | Me | H | $CF_3$ |
| 2-pyridyl | H | H | B7 | Me | H | H |
| 2-pyridyl | H | H | H | Me | Me | Me |
| 2-pyridyl | H | H | H | Me | Cl | Me |
| 2-pyridyl | Cl | H | H | Me | Cl | Me |
| 2-pyridyl | H | H | H | Et | Me | Me |
| 2-pyridyl | H | H | H | Et | H | H |
| 2-pyridyl | H | H | H | Cl | Me | Me |
| 2-pyridyl | H | H | H | Cl | Me | H |
| 2-pyridyl | H | H | H | Cl | H | Me |
| 2-pyridyl | H | H | H | Cl | H | $CF_3$ |
| 2-pyridyl | H | H | B7 | Cl | H | H |
| 2-pyridyl | Me | H | B7 | Cl | H | H |
| 2-pyridyl | Cl | H | B7 | Cl | H | H |
| 2-pyridyl | $CF_3$ | H | B7 | Cl | H | H |
| 2-pyridyl | cPr | H | B7 | Cl | H | H |
| 2-pyridyl | OMe | H | B7 | Cl | H | H |
| 2-pyridyl | $NO_2$ | H | B7 | Cl | H | H |
| 2-pyridyl | CN | H | B7 | Cl | H | H |
| 2-pyridyl | $CO_2Me$ | H | B7 | Cl | H | H |
| 2-pyridyl | $CO_2Et$ | H | B7 | Cl | H | H |
| 2-pyridyl | H | H | H | Cl | Cl | Me |
| 2-pyridyl | Me | H | H | Cl | Cl | Me |
| 2-pyridyl | Cl | H | H | Cl | Cl | Me |
| 2-pyridyl | $CF_3$ | H | H | Cl | Cl | Me |
| 2-pyridyl | cPr | H | H | Cl | Cl | Me |
| 2-pyridyl | OMe | H | H | Cl | Cl | Me |
| 2-pyridyl | $NO_2$ | H | H | Cl | Cl | Me |
| 2-pyridyl | CN | H | H | Cl | Cl | Me |
| 2-pyridyl | $CO_2Me$ | H | H | Cl | Cl | Me |
| 2-pyridyl | $CO_2Et$ | H | H | Cl | Cl | Me |
| 2-pyridyl | H | H | H | Cl | Cl | H |
| 2-pyridyl | H | H | H | Cl | Cl | $CF_3$ |
| 2-pyridyl | H | H | H | Cl | Cl | $CF_2H$ |
| 2-pyridyl | H | H | H | Cl | Cl | $CH_2OMe$ |
| 2-pyridyl | H | H | H | Cl | Cl | COMe |
| 2-pyridyl | H | H | H | Cl | $CF_3$ | Me |
| 2-pyridyl | H | H | H | Br | Me | Me |
| 2-pyridyl | H | H | H | Me | Br | Me |
| 2-pyridyl | H | H | H | Me | Br | H |
| 2-pyridyl | H | H | H | Br | H | H |

TABLE 1-continued

| | | | | | | |
|---|---|---|---|---|---|---|
| 2-pyridyl | H | H | H | OMe | Me | Me |
| 2-pyridyl | H | H | H | Me | OMe | Me |
| 2-pyridyl | H | H | B7 | OMe | H | H |
| 2-pyridyl | H | H | H | Cl | OMe | Me |
| 2-pyridyl | H | H | H | $OCF_3$ | Me | Me |
| 2-pyridyl | H | H | H | $OCF_3$ | Cl | Me |
| 2-pyridyl | H | H | B7 | $OCF_3$ | H | H |
| 2-pyridyl | H | H | H | Me | $OCF_3$ | Me |
| 2-pyridyl | H | H | H | Cl | $OCF_3$ | Me |
| 2-pyridyl | H | H | H | SMe | Cl | Me |
| 2-pyridyl | H | H | H | Me | SMe | Me |
| 2-pyridyl | H | H | H | Cl | SMe | Me |
| 2-pyridyl | H | H | B7 | SMe | H | H |
| 2-pyridyl | H | H | H | $CF_3$ | Me | Me |
| 2-pyridyl | H | H | H | $CF_3$ | Cl | H |
| 2-pyridyl | H | H | H | $CF_3$ | Cl | Me |
| 2-pyridyl | Me | H | H | $CF_3$ | Cl | Me |
| 2-pyridyl | Cl | H | H | $CF_3$ | Cl | Me |
| 2-pyridyl | Br | H | H | $CF_3$ | Cl | Me |
| 2-pyridyl | $CF_3$ | H | H | $CF_3$ | Cl | Me |
| 2-pyridyl | $NO_2$ | H | H | $CF_3$ | Cl | Me |
| 2-pyridyl | CN | H | H | $CF_3$ | Cl | Me |
| 2-pyridyl | $CO_2Me$ | H | H | $CF_3$ | Cl | Me |
| 2-pyridyl | $CO_2Et$ | H | H | $CF_3$ | Cl | Me |
| 2-pyridyl | H | H | H | $CF_3$ | Cl | $CF_3$ |
| 2-pyridyl | H | H | H | $CF_3$ | Cl | $CF_2H$ |
| 2-pyridyl | H | H | H | $CF_3$ | Cl | $CH_2OMe$ |
| 2-pyridyl | H | H | H | $CF_3$ | Cl | $COCH_3$ |
| 2-pyridyl | H | H | H | $CF_3$ | H | Me |
| 2-pyridyl | H | H | H | $CF_3$ | H | H |
| 2-pyridyl | H | H | H | $CF_3$ | Br | Me |
| 2-pyridyl | H | H | H | $CF_3$ | SMe | Me |
| 2-pyridyl | H | H | H | $CF_3$ | SOMe | Me |
| 2-pyridyl | H | H | H | $CF_3$ | $SO_2Me$ | Me |
| 2-pyridyl | H | H | H | $CF_3$ | $CF_3$ | Me |
| 2-pyridyl | H | H | H | $CF_3$ | $NO_2$ | Me |
| 2-pyridyl | H | H | H | $CF_3$ | CN | Me |
| 2-pyridyl | H | H | H | $CF_3$ | NHMe | Me |
| 2-pyridyl | H | H | H | $CF_3$ | $NMe_2$ | Me |
| 2-pyridyl | H | H | H | $CF_3$ | OH | Me |
| 2-pyridyl | H | H | H | $CF_3$ | $CO_2Me$ | Me |
| 2-pyridyl | H | H | H | $CF_3$ | OMe | Me |
| 2-pyridyl | H | H | H | $CF_3$ | $OCF_3$ | Me |
| 2-pyridyl | H | H | H | $CF_3$ | $OCF_2H$ | Me |
| 2-pyridyl | H | H | H | $CF_3$ | $OCF_2H$ | $CF_2H$ |
| 2-pyridyl | H | H | H | $NO_2$ | Cl | Me |
| 2-pyridyl | H | H | H | $NO_2$ | Me | Me |
| 2-pyridyl | H | H | B7 | $NO_2$ | H | H |
| 2-pyridyl | H | H | H | Cl | $NO_2$ | Me |
| 2-pyridyl | H | H | H | CN | Cl | Me |
| 2-pyridyl | H | H | H | CN | Me | Me |
| 2-pyridyl | H | H | H | CN | H | H |
| 2-pyridyl | H | H | H | Cl | CN | Me |
| 2-pyridyl | H | H | H | $NMe_2$ | H | H |
| 2-pyridyl | H | H | H | Cl | $NMe_2$ | Me |
| 2-pyridyl | H | H | H | OH | Me | Me |
| 2-pyridyl | H | H | H | OH | H | H |
| 2-pyridyl | H | H | H | Cl | OH | Me |
| 2-pyridyl | H | H | H | $CO_2Me$ | Me | Me |
| 2-pyridyl | H | H | H | $CO_2Me$ | Cl | Me |
| 2-pyridyl | H | H | H | $CO_2Me$ | H | H |
| 2-pyridyl | H | H | B1 | Cl | Cl | Me |
| 2-pyridyl | H | H | B2 | Cl | Cl | Me |
| 2-pyridyl | H | H | B3 | Cl | Cl | Me |
| 2-pyridyl | H | H | B4 | Cl | Cl | Me |
| 2-pyridyl | H | H | B5 | Cl | Cl | Me |
| 2-pyridyl | H | H | B6 | Cl | Cl | Me |
| 2-pyridyl | H | H | B7 | Cl | Cl | Me |
| 2-pyridyl | Cl | H | B7 | Cl | Cl | Me |
| 2-pyridyl | H | H | B8 | Cl | Cl | Me |
| 2-pyridyl | H | H | B9 | Cl | Cl | Me |
| 2-pyridyl | H | H | B10 | Cl | Cl | Me |
| 2-pyridyl | H | H | B11 | Cl | Cl | Me |
| 2-pyridyl | H | H | B12 | Cl | Cl | Me |
| 2-pyridyl | H | H | B13 | Cl | Cl | Me |
| 2-pyridyl | H | H | B14 | Cl | Cl | Me |
| 2-pyridyl | H | H | B15 | Cl | Cl | Me |
| 2-pyridyl | H | H | B16 | Cl | Cl | Me |
| 2-pyridyl | H | H | B17 | Cl | Cl | Me |

TABLE 1-continued

| | | | | | | |
|---|---|---|---|---|---|---|
| 2-pyridyl | H | H | B18 | Cl | Cl | Me |
| 2-pyridyl | H | H | B19 | Cl | Cl | Me |
| 2-pyridyl | H | H | B20 | Cl | Cl | Me |
| 2-pyridyl | H | H | B21 | Cl | Cl | Me |
| 2-pyridyl | H | H | B22 | Cl | Cl | Me |
| 2-pyridyl | H | H | B23 | Cl | Cl | Me |
| 2-pyridyl | H | H | B24 | Cl | Cl | Me |
| 2-pyridyl | H | H | B25 | Cl | Cl | Me |
| 2-pyridyl | H | H | B26 | Cl | Cl | Me |
| 2-pyridyl | H | H | B27 | Cl | Cl | Me |
| 2-pyridyl | H | H | B28 | Cl | Cl | Me |
| 2-pyridyl | H | H | B29 | Cl | Cl | Me |
| 2-pyridyl | H | H | B30 | Cl | Cl | Me |
| 2-pyridyl | H | H | B31 | Cl | Cl | Me |
| 2-pyridyl | H | H | B32 | Cl | Cl | Me |
| 2-pyridyl | H | H | B33 | Cl | Cl | Me |
| 2-pyridyl | H | H | B34 | Cl | Cl | Me |
| 2-pyridyl | H | H | Na | Cl | Cl | Me |
| 2-pyridyl | H | H | K | Cl | Cl | Me |
| 2-pyridyl | H | H | B1 | $CF_3$ | Cl | Me |
| 2-pyridyl | H | H | B2 | $CF_3$ | Cl | Me |
| 2-pyridyl | H | H | B3 | $CF_3$ | Cl | Me |
| 2-pyridyl | H | H | B4 | $CF_3$ | Cl | Me |
| 2-pyridyl | Cl | H | B4 | $CF_3$ | Cl | Me |
| 2-pyridyl | $CO_2Me$ | H | B4 | $CF_3$ | Cl | Me |
| 2-pyridyl | H | H | B5 | $CF_3$ | Cl | Me |
| 2-pyridyl | H | H | B6 | $CF_3$ | Cl | Me |
| 2-pyridyl | H | H | B7 | $CF_3$ | Cl | Me |
| 2-pyridyl | Cl | H | B7 | $CF_3$ | Cl | Me |
| 2-pyridyl | $NO_2$ | H | B7 | $CF_3$ | Cl | Me |
| 2-pyridyl | $CO_2Me$ | H | B7 | $CF_3$ | Cl | Me |
| 2-pyridyl | H | H | B8 | $CF_3$ | Cl | Me |
| 2-pyridyl | H | H | B9 | $CF_3$ | Cl | Me |
| 2-pyridyl | H | H | B10 | $CF_3$ | Cl | Me |
| 2-pyridyl | H | H | B11 | $CF_3$ | Cl | Me |
| 2-pyridyl | H | H | B12 | $CF_3$ | Cl | Me |
| 2-pyridyl | H | H | B13 | $CF_3$ | Cl | Me |
| 2-pyridyl | H | H | B14 | $CF_3$ | Cl | Me |
| 2-pyridyl | H | H | B15 | $CF_3$ | Cl | Me |
| 2-pyridyl | H | H | B16 | $CF_3$ | Cl | Me |
| 2-pyridyl | H | H | B17 | $CF_3$ | Cl | Me |
| 2-pyridyl | H | H | B18 | $CF_3$ | Cl | Me |
| 2-pyridyl | H | H | B19 | $CF_3$ | Cl | Me |
| 2-pyridyl | H | H | B20 | $CF_3$ | Cl | Me |
| 2-pyridyl | H | H | B21 | $CF_3$ | Cl | Me |
| 2-pyridyl | H | H | B22 | $CF_3$ | Cl | Me |
| 2-pyridyl | H | H | B23 | $CF_3$ | Cl | Me |
| 2-pyridyl | H | H | B24 | $CF_3$ | Cl | Me |
| 2-pyridyl | H | H | B25 | $CF_3$ | Cl | Me |
| 2-pyridyl | H | H | B26 | $CF_3$ | Cl | Me |
| 2-pyridyl | H | H | B27 | $CF_3$ | Cl | Me |
| 2-pyridyl | H | H | B28 | $CF_3$ | Cl | Me |
| 2-pyridyl | H | H | B29 | $CF_3$ | Cl | Me |
| 2-pyridyl | H | H | B30 | $CF_3$ | Cl | Me |
| 2-pyridyl | H | H | B31 | $CF_3$ | Cl | Me |
| 2-pyridyl | H | H | B32 | $CF_3$ | Cl | Me |
| 2-pyridyl | H | H | B33 | $CF_3$ | Cl | Me |
| 2-pyridyl | H | H | B34 | $CF_3$ | Cl | Me |
| 2-pyridyl | H | H | Na | $CF_3$ | Cl | Me |
| 2-pyridyl | H | H | K | $CF_3$ | Cl | Me |
| 2-pyridyl | H | H | B1 | Cl | H | H |
| 2-pyridyl | H | H | B2 | Cl | H | H |
| 2-pyridyl | H | H | B3 | Cl | H | H |
| 2-pyridyl | H | H | B4 | Cl | H | H |
| 2-pyridyl | Me | H | B4 | Cl | H | H |
| 2-pyridyl | Cl | H | B4 | Cl | H | H |
| 2-pyridyl | $NO_2$ | H | B4 | Cl | H | H |
| 2-pyridyl | $CO_2Me$ | H | B4 | Cl | H | H |
| 2-pyridyl | $CO_2Et$ | H | B4 | Cl | H | H |
| 2-pyridyl | H | H | B5 | Cl | H | H |
| 2-pyridyl | H | H | B6 | Cl | H | H |
| 2-pyridyl | $NO_2$ | H | B6 | Cl | H | H |
| 2-pyridyl | H | H | B7 | Cl | H | H |
| 2-pyridyl | Me | H | B7 | Cl | H | H |
| 2-pyridyl | Cl | H | B7 | Cl | H | H |
| 2-pyridyl | $NO_2$ | H | B7 | Cl | H | H |
| 2-pyridyl | $CO_2Me$ | H | B7 | Cl | H | H |
| 2-pyridyl | $CO_2Et$ | H | B7 | Cl | H | H |
| 2-pyridyl | H | H | B8 | Cl | H | H |

TABLE 1-continued

| | | | | | | |
|---|---|---|---|---|---|---|
| 2-pyridyl | H | H | B9 | Cl | H | H |
| 2-pyridyl | H | H | B10 | Cl | H | H |
| 2-pyridyl | H | H | B11 | Cl | H | H |
| 2-pyridyl | H | H | B12 | Cl | H | H |
| 2-pyridyl | H | H | B13 | Cl | H | H |
| 2-pyridyl | H | H | B14 | Cl | H | H |
| 2-pyridyl | H | H | B15 | Cl | H | H |
| 2-pyridyl | H | H | B16 | Cl | H | H |
| 2-pyridyl | H | H | B17 | Cl | H | H |
| 2-pyridyl | H | H | B18 | Cl | H | H |
| 2-pyridyl | H | H | B19 | Cl | H | H |
| 2-pyridyl | H | H | B20 | Cl | H | H |
| 2-pyridyl | H | H | B21 | Cl | H | H |
| 2-pyridyl | H | H | B22 | Cl | H | H |
| 2-pyridyl | H | H | B23 | Cl | H | H |
| 2-pyridyl | H | H | B24 | Cl | H | H |
| 2-pyridyl | H | H | B25 | Cl | H | H |
| 2-pyridyl | H | H | B26 | Cl | H | H |
| 2-pyridyl | H | H | B27 | Cl | H | H |
| 2-pyridyl | H | H | B28 | Cl | H | H |
| 2-pyridyl | H | H | B29 | Cl | H | H |
| 2-pyridyl | H | H | B30 | Cl | H | H |
| 2-pyridyl | H | H | B31 | Cl | H | H |
| 2-pyridyl | H | H | B32 | Cl | H | H |
| 2-pyridyl | H | H | B33 | Cl | H | H |
| 2-pyridyl | H | H | B34 | Cl | H | H |
| 2-pyridyl | H | H | Na | Cl | H | H |
| 2-pyridyl | H | H | K | Cl | H | H |
| 3-pyridyl | H | H | H | Cl | Cl | Me |
| 3-pyridyl | H | H | H | $CF_3$ | Cl | Me |
| 3-pyridyl | H | H | H | Cl | H | H |
| 3-pyridyl | H | H | B4 | Cl | H | H |
| 3-pyridyl | H | H | B7 | Cl | H | H |
| 4-pyridyl | H | H | H | Cl | Cl | Me |
| 4-pyridyl | H | H | H | $CF_3$ | Cl | Me |
| 4-pyridyl | H | H | H | Cl | H | H |
| 4-pyridyl | H | H | B4 | Cl | H | H |
| 4-pyridyl | H | H | B7 | Cl | H | H |
| 3-Me-pyridin-2-yl | H | H | H | Cl | Cl | Me |
| 2-F-Ph | H | H | H | Me | H | Me |
| 2-F-Ph | H | H | H | Me | Me | Me |
| 2-F-Ph | H | H | H | Me | Cl | Me |
| 2-F-Ph | H | H | H | Cl | H | H |
| 2-F-Ph | H | H | H | Cl | H | Me |
| 2-F-Ph | H | H | H | Cl | H | $CF_3$ |
| 2-F-Ph | H | H | H | Cl | Cl | Me |
| 2-F-Ph | Cl | H | H | Cl | Cl | Me |
| 2-F-Ph | H | H | B7 | OMe | H | H |
| 2-F-Ph | H | H | B7 | SMe | H | H |
| 2-F-Ph | H | H | H | $CF_3$ | Me | Me |
| 2-F-Ph | H | H | H | $CF_3$ | Cl | Me |
| 2-F-Ph | Cl | H | H | $CF_3$ | Cl | Me |
| 2-F-Ph | H | H | H | $CF_3$ | H | Me |
| 2-F-Ph | H | H | B1 | Cl | Cl | Me |
| 2-F-Ph | Cl | H | B1 | Cl | Cl | Me |
| 2-F-Ph | H | H | B3 | Cl | Cl | Me |
| 2-F-Ph | Cl | H | B4 | Cl | Cl | Me |
| 2-F-Ph | H | H | B6 | Cl | Cl | Me |
| 2-F-Ph | H | H | B7 | Cl | Cl | Me |
| 2-F-Ph | Cl | H | B7 | Cl | Cl | Me |
| 2-F-Ph | H | H | B9 | Cl | Cl | Me |
| 2-F-Ph | H | H | B20 | Cl | Cl | Me |
| 2-F-Ph | H | H | B24 | Cl | Cl | Me |
| 2-F-Ph | H | H | B2 | $CF_3$ | Cl | Me |
| 2-F-Ph | H | H | B3 | $CF_3$ | Cl | Me |
| 2-F-Ph | H | H | B4 | $CF_3$ | Cl | Me |
| 2-F-Ph | Cl | H | B4 | $CF_3$ | Cl | Me |
| 2-F-Ph | H | H | B6 | $CF_3$ | Cl | Me |
| 2-F-Ph | H | H | B7 | $CF_3$ | Cl | Me |
| 2-F-Ph | Cl | H | B7 | $CF_3$ | Cl | Me |
| 2-F-Ph | H | H | B9 | $CF_3$ | Cl | Me |
| 2-F-Ph | H | H | B20 | $CF_3$ | Cl | Me |
| 2-F-Ph | H | H | B24 | $CF_3$ | Cl | Me |
| 2-F-Ph | H | H | B6 | Cl | H | H |
| 2-F-Ph | H | H | B7 | Cl | H | H |
| 3-F-Ph | H | H | H | Cl | Cl | Me |
| 3-F-Ph | Cl | H | H | Cl | Cl | Me |
| 3-F-Ph | H | H | H | $CF_3$ | Cl | Me |

TABLE 1-continued

| | | | | | | |
|---|---|---|---|---|---|---|
| 3-F-Ph | Cl | H | H | CF₃ | Cl | Me |
| 4-F-Ph | H | H | H | Cl | Cl | Me |
| 4-F-Ph | Cl | H | H | Cl | Cl | Me |
| 4-F-Ph | H | H | H | CF₃ | Cl | Me |
| 4-F-Ph | Cl | H | H | CF₃ | Cl | Me |
| 2,3-F₂—Ph | H | H | H | Cl | Cl | Me |
| 2,3-F₂—Ph | H | H | H | CF₃ | Cl | Me |
| 2,4-F₂—Ph | H | H | H | Cl | Cl | Me |
| 2,4-F₂—Ph | H | H | H | CF₃ | Cl | Me |
| 2,5-F₂—Ph | H | H | H | Cl | Cl | Me |
| 2,5-F₂—Ph | H | H | H | CF₃ | Cl | Me |
| Ph | H | H | H | Me | H | Me |
| Ph | H | H | H | Me | Me | Me |
| Ph | H | H | H | Me | Cl | Me |
| Ph | H | H | B7 | Cl | H | H |
| Ph | H | H | H | Cl | H | Me |
| Ph | H | H | H | Cl | H | CF₃ |
| Ph | H | H | H | Cl | Cl | Me |
| Ph | Cl | H | H | Cl | Cl | Me |
| Ph | H | H | B7 | OMe | H | H |
| Ph | H | H | B7 | SMe | H | H |
| Ph | H | H | H | CF₃ | Me | Me |
| Ph | H | H | H | CF₃ | Cl | Me |
| Ph | Cl | H | H | CF₃ | Cl | Me |
| Ph | H | H | B7 | CF₃ | H | Me |
| Ph | H | H | B1 | Cl | Cl | Me |
| Ph | Cl | H | B1 | Cl | Cl | Me |
| Ph | H | H | B3 | Cl | Cl | Me |
| Ph | Cl | H | B4 | Cl | Cl | Me |
| Ph | H | H | B6 | Cl | Cl | Me |
| Ph | H | H | B7 | Cl | Cl | Me |
| Ph | Cl | H | B7 | Cl | Cl | Me |
| Ph | H | H | B9 | Cl | Cl | Me |
| Ph | H | H | B20 | Cl | Cl | Me |
| Ph | H | H | B24 | Cl | Cl | Me |
| Ph | H | H | B2 | CF₃ | Cl | Me |
| Ph | H | H | B3 | CF₃ | Cl | Me |
| Ph | H | H | B4 | CF₃ | Cl | Me |
| Ph | Cl | H | B4 | CF₃ | Cl | Me |
| Ph | H | H | B6 | CF₃ | Cl | Me |
| Ph | H | H | B7 | CF₃ | Cl | Me |
| Ph | Cl | H | B7 | CF₃ | Cl | Me |
| Ph | H | H | B9 | CF₃ | Cl | Me |
| Ph | H | H | B20 | CF₃ | Cl | Me |
| Ph | H | H | B24 | CF₃ | Cl | Me |
| Ph | H | H | B6 | Cl | H | H |
| Ph | H | H | B7 | Cl | H | H |
| 3,4-F₂—Ph | H | H | H | Cl | Cl | Me |
| 3,4-F₂—Ph | H | H | H | CF₃ | Cl | Me |
| 3,5-F₂—Ph | H | H | H | Cl | Cl | Me |
| 3,5-F₂—Ph | H | H | H | CF₃ | Cl | Me |
| 2-Cl—Ph | H | H | H | Me | H | Me |
| 2-Cl—Ph | H | H | H | Me | Me | Me |
| 2-Cl—Ph | H | H | H | Me | Cl | Me |
| 2-Cl—Ph | H | H | H | Cl | H | H |
| 2-Cl—Ph | H | H | H | Cl | H | Me |
| 2-Cl—Ph | H | H | H | Cl | H | CF₃ |
| 2-Cl—Ph | H | H | H | Cl | Cl | Me |
| 2-Cl—Ph | Cl | H | H | Cl | Cl | Me |
| 2-Cl—Ph | H | H | H | OMe | H | H |
| 2-Cl—Ph | H | H | H | SMe | H | H |
| 2-Cl—Ph | H | H | H | CF₃ | Me | Me |
| 2-Cl—Ph | H | H | H | CF₃ | Cl | Me |
| 2-Cl—Ph | Cl | H | H | CF₃ | Cl | Me |
| 2-Cl—Ph | H | H | H | CF₃ | H | Me |
| 2-Cl—Ph | H | H | B1 | Cl | Cl | Me |
| 2-Cl—Ph | Cl | H | B1 | Cl | Cl | Me |
| 2-Cl—Ph | H | H | B3 | Cl | Cl | Me |
| 2-Cl—Ph | Cl | H | B4 | Cl | Cl | Me |
| 2-Cl—Ph | H | H | B6 | Cl | Cl | Me |
| 2-Cl—Ph | H | H | B7 | Cl | Cl | Me |
| 2-Cl—Ph | Cl | H | B7 | Cl | Cl | Me |
| 2-Cl—Ph | H | H | B9 | Cl | Cl | Me |
| 2-Cl—Ph | H | H | B20 | Cl | Cl | Me |
| 2-Cl—Ph | H | H | B24 | Cl | Cl | Me |
| 2-Cl—Ph | H | H | B2 | CF₃ | Cl | Me |
| 2-Cl—Ph | H | H | B3 | CF₃ | Cl | Me |
| 2-Cl—Ph | H | H | B4 | CF₃ | Cl | Me |
| 2-Cl—Ph | Cl | H | B4 | CF₃ | Cl | Me |

TABLE 1-continued

| | | | | | | |
|---|---|---|---|---|---|---|
| 2-Cl—Ph | H | H | B6 | CF₃ | Cl | Me |
| 2-Cl—Ph | H | H | B7 | CF₃ | Cl | Me |
| 2-Cl—Ph | Cl | H | B7 | CF₃ | Cl | Me |
| 2-Cl—Ph | H | H | B9 | CF₃ | Cl | Me |
| 2-Cl—Ph | H | H | B20 | CF₃ | Cl | Me |
| 2-Cl—Ph | H | H | B24 | CF₃ | Cl | Me |
| 2-Cl—Ph | H | H | B6 | Cl | H | H |
| 2-Cl—Ph | H | H | B7 | Cl | H | H |
| 3-Cl—Ph | H | H | H | Cl | Cl | Me |
| 3-Cl—Ph | Cl | H | H | Cl | Cl | Me |
| 3-Cl—Ph | H | H | H | CF₃ | Cl | Me |
| 3-Cl—Ph | Cl | H | H | CF₃ | Cl | Me |
| 4-Cl—Ph | H | H | H | Cl | Cl | Me |
| 4-Cl—Ph | Cl | H | H | Cl | Cl | Me |
| 4-Cl—Ph | H | H | H | CF₃ | Cl | Me |
| 4-Cl—Ph | Cl | H | H | CF₃ | Cl | Me |
| 2,3-Cl₂—Ph | H | H | H | Cl | Cl | Me |
| 2,3-Cl₂—Ph | H | H | H | CF₃ | Cl | Me |
| 2,4-Cl₂—Ph | H | H | H | Cl | Cl | Me |
| 2,4-Cl₂—Ph | H | H | H | CF₃ | Cl | Me |
| 2,5-Cl₂—Ph | H | H | H | Cl | Cl | Me |
| 2,5-Cl₂—Ph | H | H | H | CF₃ | Cl | Me |
| 2,6-Cl₂—Ph | H | H | H | Me | H | Me |
| 2,6-Cl₂—Ph | H | H | H | Me | Me | Me |
| 2,6-Cl₂—Ph | H | H | H | Me | Cl | Me |
| 2,6-Cl₂—Ph | H | H | B7 | Cl | H | H |
| 2,6-Cl₂—Ph | H | H | H | Cl | H | Me |
| 2,6-Cl₂—Ph | H | H | H | Cl | H | CF₃ |
| 2,6-Cl₂—Ph | H | H | H | Cl | Cl | Me |
| 2,6-Cl₂—Ph | Cl | H | H | Cl | Cl | Me |
| 2,6-Cl₂—Ph | H | H | B7 | OMe | H | H |
| 2,6-Cl₂—Ph | H | H | B7 | SMe | H | H |
| 2,6-Cl₂—Ph | H | H | H | CF₃ | Me | Me |
| 2,6-Cl₂—Ph | H | H | H | CF₃ | Cl | Me |
| 2,6-Cl₂—Ph | Cl | H | H | CF₃ | Cl | Me |
| 2,6-Cl₂—Ph | H | H | H | CF₃ | H | Me |
| 2,6-Cl₂—Ph | H | H | B1 | Cl | Cl | Me |
| 2,6-Cl₂—Ph | Cl | H | B1 | Cl | Cl | Me |
| 2,6-Cl₂—Ph | H | H | B3 | Cl | Cl | Me |
| 2,6-Cl₂—Ph | Cl | H | B4 | Cl | Cl | Me |
| 2,6-Cl₂—Ph | H | H | B6 | Cl | Cl | Me |
| 2,6-Cl₂—Ph | H | H | B7 | Cl | Cl | Me |
| 2,6-Cl₂—Ph | Cl | H | B7 | Cl | Cl | Me |
| 2,6-Cl₂—Ph | H | H | B9 | Cl | Cl | Me |
| 2,6-Cl₂—Ph | H | H | B20 | Cl | Cl | Me |
| 2,6-Cl₂—Ph | H | H | B24 | Cl | Cl | Me |
| 2,6-Cl₂—Ph | H | H | B2 | CF₃ | Cl | Me |
| 2,6-Cl₂—Ph | H | H | B3 | CF₃ | Cl | Me |
| 2,6-Cl₂—Ph | H | H | B4 | CF₃ | Cl | Me |
| 2,6-Cl₂—Ph | Cl | H | B4 | CF₃ | Cl | Me |
| 2,6-Cl₂—Ph | H | H | B6 | CF₃ | Cl | Me |
| 2,6-Cl₂—Ph | H | H | B7 | CF₃ | Cl | Me |
| 2,6-Cl₂—Ph | Cl | H | B7 | CF₃ | Cl | Me |
| 2,6-Cl₂—Ph | H | H | B9 | CF₃ | Cl | Me |
| 2,6-Cl₂—Ph | H | H | B20 | CF₃ | Cl | Me |
| 2,6-Cl₂—Ph | H | H | B24 | CF₃ | Cl | Me |
| 2,6-Cl₂—Ph | H | H | B8 | Cl | H | H |
| 2,6-Cl₂—Ph | H | H | B15 | Cl | H | H |
| 3,4-Cl₂—Ph | H | H | H | Cl | Cl | Me |
| 3,4-Cl₂—Ph | H | H | H | CF₃ | Cl | Me |
| 3,5-Cl₂—Ph | H | H | H | Cl | Cl | Me |
| 3,5-Cl₂—Ph | H | H | H | CF₃ | Cl | Me |
| 2-Me—Ph | H | H | H | Cl | Cl | Me |
| 2-Me—Ph | H | H | H | CF₃ | Cl | Me |
| 2,6-Me₂—Ph | H | H | H | Cl | Cl | Me |
| 2,6-Me₂—Ph | H | H | H | CF₃ | Cl | Me |
| 2-MeO—Ph | H | H | H | Cl | Cl | Me |
| 2-MeO—Ph | H | H | H | CF₃ | Cl | Me |
| 2-MeO—Ph | Cl | H | H | CF₃ | Cl | Me |
| 2-CF₃O—Ph | H | H | H | Cl | Cl | Me |
| 2-CF₃O—Ph | H | H | H | CF₃ | Cl | Me |
| 2-SMe—Ph | H | H | H | Cl | Cl | Me |
| 2-SMe—Ph | H | H | H | CF₃ | Cl | Me |
| 2-SOMe—Ph | H | H | H | Cl | Cl | Me |
| 2-SOMe—Ph | H | H | H | CF₃ | Cl | Me |
| 2-SO₂Me—Ph | H | H | H | Cl | Cl | Me |
| 2-SO₂Me—Ph | H | H | H | CF₃ | Cl | Me |
| 2-CF₃—Ph | H | H | H | Cl | Cl | Me |
| 2-CF₃—Ph | H | H | H | CF₃ | Cl | Me |

TABLE 1-continued

| | | | | | | |
|---|---|---|---|---|---|---|
| 2-NO$_2$—Ph | H | H | H | Cl | Cl | Me |
| 2-NO$_2$—Ph | H | H | H | CF$_3$ | Cl | Me |
| 2-CN—Ph | H | H | H | Cl | Cl | Me |
| 2-CN—Ph | H | H | H | CF$_3$ | Cl | Me |
| 2-NHMe—Ph | H | H | H | Cl | Cl | Me |
| 2-NHMe—Ph | H | H | H | CF$_3$ | Cl | Me |
| 2-NMe$_2$—Ph | H | H | H | Cl | Cl | Me |
| 2-NMe$_2$—Ph | H | H | H | CF$_3$ | Cl | Me |
| 4-CH$_2$Ph—Ph | H | H | H | Cl | Cl | Me |
| 4-OPh—Ph | H | H | H | Cl | Cl | Me |
| 2-OH—Ph | H | H | H | Cl | Cl | Me |
| 2-OH—Ph | H | H | H | CF$_3$ | Cl | Me |
| 2-CO$_2$Me—Ph | H | H | H | Cl | Cl | Me |
| 2-CO$_2$Me—Ph | H | H | H | CF$_3$ | Cl | Me |
| 2-CO$_2$Et—Ph | H | H | H | Cl | Cl | Me |
| 2-CO$_2$Et—Ph | H | H | H | CF$_3$ | Cl | Me |
| H | CO$_2$Et | Ph | H | Cl | Cl | Me |
| Cl | CO$_2$Et | H | H | Cl | Cl | Me |
| Me | Ph | H | H | Cl | Cl | Me |
| Et | Me | H | H | Cl | Cl | Me |
| nPr | H | H | H | Cl | Cl | Me |
| iPr | H | H | H | Cl | Cl | Me |
| iPr | H | H | H | CF$_3$ | Cl | Me |
| nBu | H | H | H | Cl | Cl | Me |
| nBu | H | H | H | CF$_3$ | Cl | Me |
| iBu | H | H | H | Cl | Cl | Me |
| iBu | H | H | H | CF$_3$ | Cl | Me |
| iBu | H | H | B7 | Cl | Cl | Me |
| iBu | H | H | B7 | CF$_3$ | Cl | Me |
| secBu | H | H | H | Cl | Cl | Me |
| secBu | H | H | H | CF$_3$ | Cl | Me |
| 2,2-Me$_2$-propyl | H | H | H | Cl | Cl | Me |
| nHex | H | H | H | Cl | Cl | Me |
| ethenyl | H | H | H | Cl | Cl | Me |
| 1-propenyl | H | H | H | Cl | Cl | Me |
| 1-propenyl | H | H | H | CF$_3$ | Cl | Me |
| ethynyl | H | H | H | Cl | Cl | Me |
| 1-propynyl | H | H | H | Cl | Cl | Me |
| 1-propynyl | H | H | H | CF$_3$ | Cl | Me |
| CF$_3$ | H | H | H | Cl | Cl | Me |
| CF$_3$ | H | H | H | CF$_3$ | Cl | Me |
| C$_2$F$_5$ | H | H | H | Cl | Cl | Me |
| C$_2$F$_5$ | H | H | H | CF$_3$ | Cl | Me |
| 2,2-Cl$_2$-cPr | H | H | H | Cl | Cl | Me |
| 2,2-Cl$_2$-cPr | H | H | H | CF$_3$ | Cl | Me |
| cPr | H | H | H | Cl | Cl | Me |
| cPr | H | H | H | CF$_3$ | Cl | Me |
| 1-Me-cPr | H | H | H | Cl | Cl | Me |
| 1-Me-cPr | H | H | H | CF$_3$ | Cl | Me |
| cHex | H | H | H | Cl | Cl | Me |
| cHex | H | H | H | CF$_3$ | Cl | Me |
| OMe | H | H | H | Cl | Cl | Me |
| OtBu | H | H | H | Cl | Cl | Me |
| OtBu | H | H | H | CF$_3$ | Cl | Me |
| OCF$_3$ | H | H | H | Cl | Cl | Me |
| OCF$_3$ | H | H | H | CF$_3$ | Cl | Me |
| StBu | H | H | H | Cl | Cl | Me |
| StBu | H | H | H | CF$_3$ | Cl | Me |
| SOtBu | H | H | H | Cl | Cl | Me |
| SOtBu | H | H | H | CF$_3$ | Cl | Me |
| SO$_2$tBu | H | H | H | Cl | Cl | Me |
| SO$_2$tBu | H | H | H | CF$_3$ | Cl | Me |
| NO$_2$ | H | H | H | Cl | Cl | Me |
| NO$_2$ | H | H | H | CF$_3$ | Cl | Me |
| CN | H | H | H | Cl | Cl | Me |
| CN | H | H | H | CF$_3$ | Cl | Me |
| NH$_2$ | H | H | H | Cl | Cl | Me |
| NH$_2$ | H | H | H | CF$_3$ | Cl | Me |
| NHMe | H | H | H | Cl | Cl | Me |
| NHMe | H | H | H | CF$_3$ | Cl | Me |
| NMe$_2$ | H | H | H | Cl | Cl | Me |
| NMe$_2$ | H | H | H | CF$_3$ | Cl | Me |
| CH$_2$Ph | H | H | H | Cl | Cl | Me |
| CH$_2$Ph | H | H | H | CF$_3$ | Cl | Me |
| OPh | H | H | H | Cl | Cl | Me |
| OPh | H | H | H | CF$_3$ | Cl | Me |
| OH | H | H | H | Cl | Cl | Me |
| OH | H | H | H | CF$_3$ | Cl | Me |
| naphthyl-1 | H | H | H | Cl | Cl | Me |

TABLE 1-continued

| | | | | | | |
|---|---|---|---|---|---|---|
| naphthyl-1 | H | H | H | $CF_3$ | Cl | Me |
| naphthyl-2 | H | H | H | Cl | Cl | Me |
| naphthyl-2 | H | H | H | $CF_3$ | Cl | Me |
| $CO_2Me$ | H | H | H | Cl | Cl | Me |
| $CO_2Me$ | H | H | H | $CF_3$ | Cl | Me |
| $CO_2Et$ | H | H | H | Cl | Cl | Me |
| $CO_2Et$ | H | H | H | $CF_3$ | Cl | Me |
| 2-thienyl | H | H | H | Cl | Cl | Me |
| 2-thienyl | H | H | H | $CF_3$ | Cl | Me |
| $CH_2OMe$ | H | H | H | Cl | Cl | Me |
| $COCH_3$ | H | H | H | Cl | Cl | Me |
| —N=$CMe_2$ | H | H | H | Cl | Cl | Me |
| —N=$CMe_2$ | H | H | H | $CF_3$ | Cl | Me |
| —$(CH_2)_3$— | | H | H | Cl | Cl | Me |
| —$(CH_2)_3$— | | H | H | $CF_3$ | Cl | Me |
| —$(CH_2)_4$— | | H | H | Cl | Cl | Me |
| —$(CH_2)_4$— | | H | H | $CF_3$ | Cl | Me |

TABLE 2

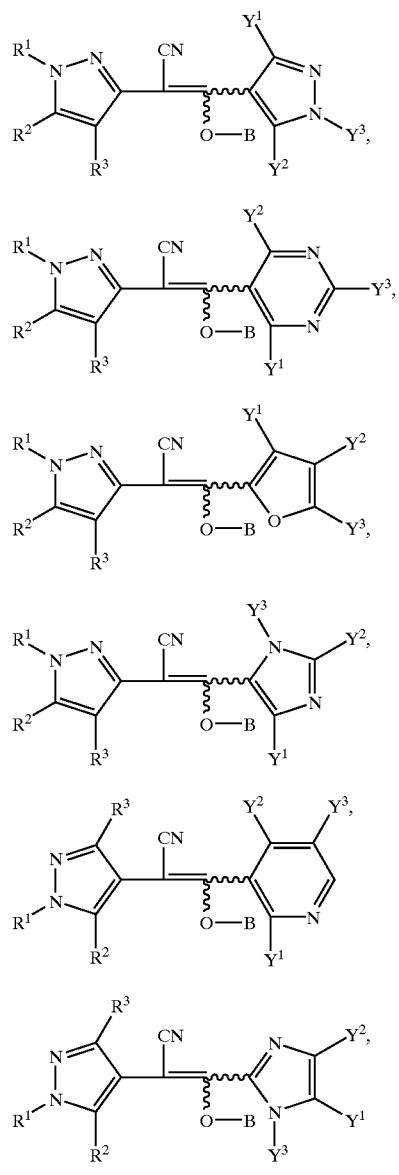

TABLE 2-continued

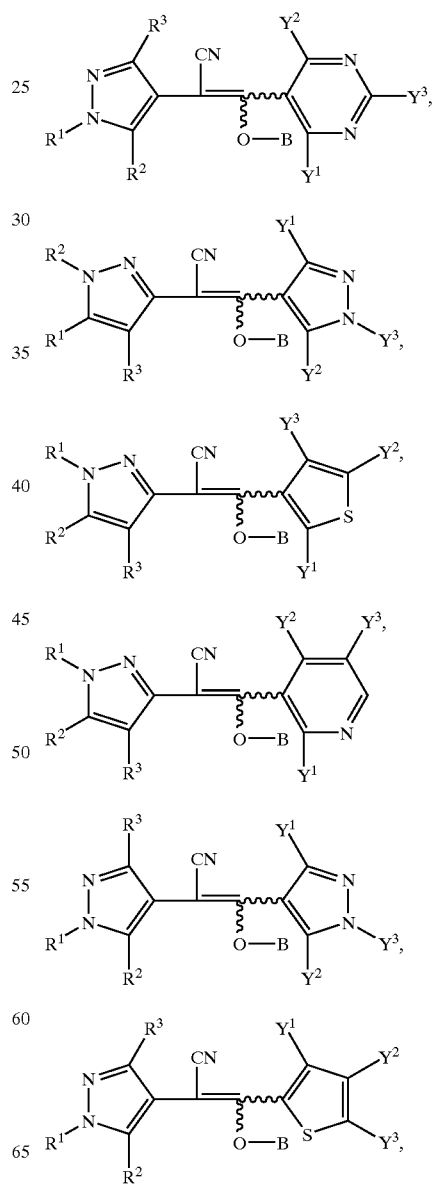

TABLE 2-continued
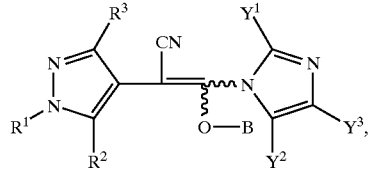
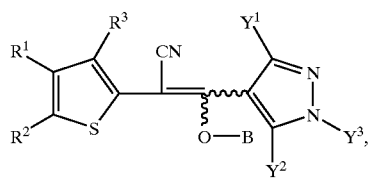
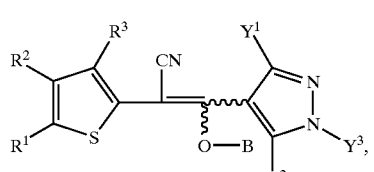
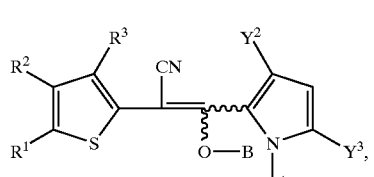
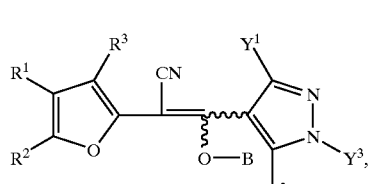
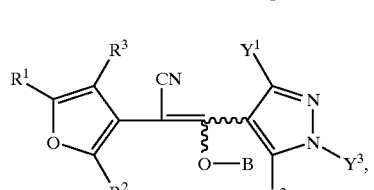
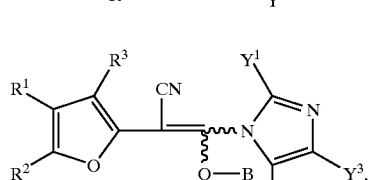
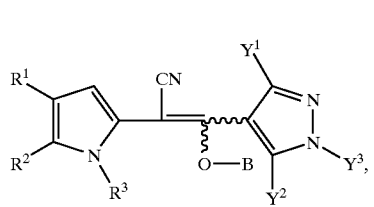
TABLE 2-continued
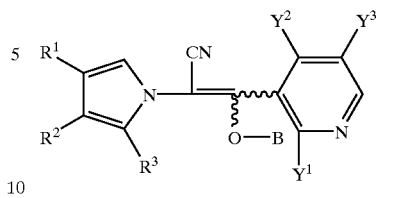
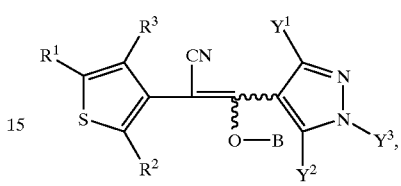
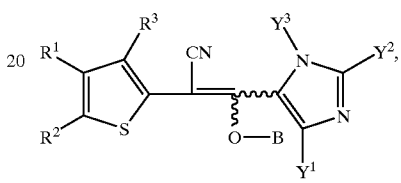
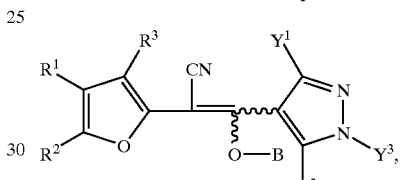
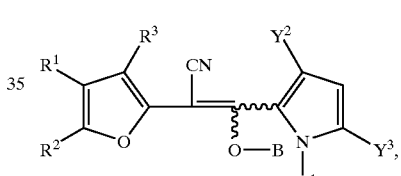
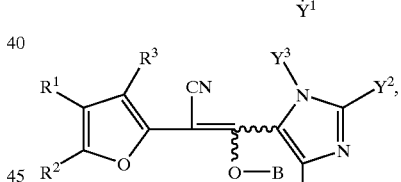
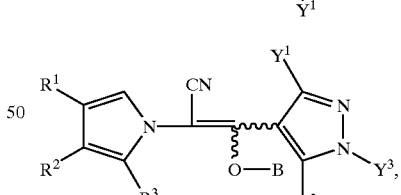
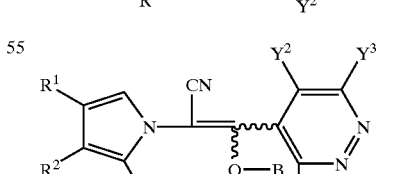
| | $R^1$ | $R^2$ | $R^3$ | B | $Y^1$ | $Y^2$ | $Y^3$ |
|---|---|---|---|---|---|---|---|
| | 2,6-F$_2$-Ph | H | H | H | Me | H | Me |
| | 2,6-F$_2$-Ph | H | H | H | Me | H | CF$_3$ |
| | 2,6-F$_2$-Ph | H | H | H | Me | H | H |

TABLE 2-continued

| | | | | | |
|---|---|---|---|---|---|
| 2,6-F$_2$-Ph | H | H | H | Me | Me | Me |
| 2,6-F$_2$-Ph | H | H | H | Me | Cl | Me |
| 2,6-F$_2$-Ph | Cl | H | H | Me | Cl | Me |
| 2,6-F$_2$-Ph | H | H | H | Et | Me | Me |
| 2,6-F$_2$-Ph | H | H | H | Cl | Me | Me |
| 2,6-F$_2$-Ph | H | H | H | Cl | H | Me |
| 2,6-F$_2$-Ph | H | H | H | Cl | H | CF$_3$ |
| 2,6-F$_2$-Ph | H | H | H | Cl | H | H |
| 2,6-F$_2$-Ph | Me | H | H | Cl | H | H |
| 2,6-F$_2$-Ph | Cl | H | H | Cl | H | H |
| 2,6-F$_2$-Ph | H | H | H | Cl | Cl | Me |
| 2,6-F$_2$-Ph | Me | H | H | Cl | Cl | Me |
| 2,6-F$_2$-Ph | H | Cl | H | Cl | Cl | Me |
| 2,6-F$_2$-Ph | Cl | H | H | Cl | Cl | Me |
| 2,6-F$_2$-Ph | CF$_3$ | H | H | Cl | Cl | Me |
| 2,6-F$_2$-Ph | OMe | H | H | Cl | Cl | Me |
| 2,6-F$_2$-Ph | NH$_2$ | H | H | Cl | Cl | Me |
| 2,6-F$_2$-Ph | NHMe | H | H | Cl | Cl | Me |
| 2,6-F$_2$-Ph | NMe$_2$ | H | H | Cl | Cl | Me |
| 2,6-F$_2$-Ph | NO$_2$ | H | H | Cl | Cl | Me |
| 2,6-F$_2$-Ph | CN | H | H | Cl | Cl | Me |
| 2,6-F$_2$-Ph | OH | H | H | Cl | Cl | Me |
| 2,6-F$_2$-Ph | CO$_2$Me | H | H | Cl | Cl | Me |
| 2,6-F$_2$-Ph | CO$_2$Et | H | H | Cl | Cl | Me |
| 2,6-F$_2$-Ph | H | H | H | Cl | Cl | CF$_3$ |
| 2,6-F$_2$-Ph | H | H | H | Cl | Cl | CF$_2$H |
| 2,6-F$_2$-Ph | H | H | H | Cl | Cl | CH$_2$OMe |
| 2,6-F$_2$-Ph | H | H | H | Cl | Cl | COMe |
| 2,6-F$_2$-Ph | H | H | H | Cl | CF$_3$ | Me |
| 2,6-F$_2$-Ph | H | H | H | Br | Me | Me |
| 2,6-F$_2$-Ph | H | H | H | Me | Br | Me |
| 2,6-F$_2$-Ph | H | H | H | Me | OMe | Me |
| 2,6-F$_2$-Ph | H | H | H | OMe | H | H |
| 2,6-F$_2$-Ph | H | H | H | OCF$_3$ | H | H |
| 2,6-F$_2$-Ph | H | H | H | SMe | H | H |
| 2,6-F$_2$-Ph | H | H | H | CF$_3$ | Me | Me |
| 2,6-F$_2$-Ph | H | H | H | CF$_3$ | Cl | Me |
| 2,6-F$_2$-Ph | Me | H | H | CF$_3$ | Cl | Me |
| 2,6-F$_2$-Ph | Cl | H | H | CF$_3$ | Cl | Me |
| 2,6-F$_2$-Ph | Br | H | H | CF$_3$ | Cl | Me |
| 2,6-F$_2$-Ph | CF$_3$ | H | H | CF$_3$ | Cl | Me |
| 2,6-F$_2$-Ph | NO$_2$ | H | H | CF$_3$ | Cl | Me |
| 2,6-F$_2$-Ph | CN | H | H | CF$_3$ | Cl | Me |
| 2,6-F$_2$-Ph | CO$_2$Me | H | H | CF$_3$ | Cl | Me |
| 2,6-F$_2$-Ph | CO$_2$Et | H | H | CF$_3$ | Cl | Me |
| 2,6-F$_2$-Ph | H | H | H | CF$_3$ | Cl | CF$_3$ |
| 2,6-F$_2$-Ph | H | H | H | CF$_3$ | Cl | CF$_2$H |
| 2,6-F$_2$-Ph | H | H | H | CF$_3$ | Cl | CH$_2$OMe |
| 2,6-F$_2$-Ph | H | H | H | CF$_3$ | Cl | COCH$_3$ |
| 2,6-F$_2$-Ph | H | H | H | CF$_3$ | H | Me |
| 2,6-F$_2$-Ph | H | H | H | CF$_3$ | Br | Me |
| 2,6-F$_2$-Ph | H | H | H | CF$_3$ | NO$_2$ | Me |
| 2,6-F$_2$-Ph | H | H | H | CF$_3$ | CN | Me |
| 2,6-F$_2$-Ph | H | H | H | CF$_3$ | NHMe | Me |
| 2,6-F$_2$-Ph | H | H | H | CF$_3$ | NMe$_2$ | Me |
| 2,6-F$_2$-Ph | H | H | H | CF$_3$ | CO$_2$Me | Me |
| 2,6-F$_2$-Ph | H | H | H | CF$_3$ | OMe | Me |
| 2,6-F$_2$-Ph | H | H | H | CF$_3$ | OCF$_2$H | CF$_2$H |
| 2,6-F$_2$-Ph | H | H | H | Cl | NO$_2$ | Me |
| 2,6-F$_2$-Ph | H | H | H | Cl | CN | Me |
| 2,6-F$_2$-Ph | H | H | H | CO$_2$Me | Me | Me |
| 2,6-F$_2$-Ph | H | H | B1 | Cl | Cl | Me |
| 2,6-F$_2$-Ph | H | H | B2 | Cl | Cl | Me |
| 2,6-F$_2$-Ph | H | H | B3 | Cl | Cl | Me |
| 2,6-F$_2$-Ph | H | H | B4 | Cl | Cl | Me |
| 2,6-F$_2$-Ph | H | H | B5 | Cl | Cl | Me |
| 2,6-F$_2$-Ph | H | H | B6 | Cl | Cl | Me |
| 2,6-F$_2$-Ph | H | H | B7 | Cl | Cl | Me |
| 2,6-F$_2$-Ph | H | H | B8 | Cl | Cl | Me |
| 2,6-F$_2$-Ph | H | H | B9 | Cl | Cl | Me |
| 2,6-F$_2$-Ph | H | H | B10 | Cl | Cl | Me |
| 2,6-F$_2$-Ph | H | H | B11 | Cl | Cl | Me |
| 2,6-F$_2$-Ph | H | H | B12 | Cl | Cl | Me |
| 2,6-F$_2$-Ph | H | H | B13 | Cl | Cl | Me |
| 2,6-F$_2$-Ph | H | H | B14 | Cl | Cl | Me |
| 2,6-F$_2$-Ph | H | H | B15 | Cl | Cl | Me |
| 2,6-F$_2$-Ph | H | H | B16 | Cl | Cl | Me |
| 2,6-F$_2$-Ph | H | H | B17 | Cl | Cl | Me |
| 2,6-F$_2$-Ph | H | H | B18 | Cl | Cl | Me |
| 2,6-F$_2$-Ph | H | H | B19 | Cl | Cl | Me |
| 2,6-F$_2$-Ph | H | H | B20 | Cl | Cl | Me |
| 2,6-F$_2$-Ph | H | H | B21 | Cl | Cl | Me |
| 2,6-F$_2$-Ph | H | H | B22 | Cl | Cl | Me |
| 2,6-F$_2$-Ph | H | H | B23 | Cl | Cl | Me |
| 2,6-F$_2$-Ph | H | H | B24 | Cl | Cl | Me |
| 2,6-F$_2$-Ph | H | H | B25 | Cl | Cl | Me |
| 2,6-F$_2$-Ph | H | H | B26 | Cl | Cl | Me |
| 2,6-F$_2$-Ph | H | H | B27 | Cl | Cl | Me |
| 2,6-F$_2$-Ph | H | H | B28 | Cl | Cl | Me |
| 2,6-F$_2$-Ph | H | H | B29 | Cl | Cl | Me |
| 2,6-F$_2$-Ph | H | H | B30 | Cl | Cl | Me |
| 2,6-F$_2$-Ph | H | H | B31 | Cl | Cl | Me |
| 2,6-F$_2$-Ph | H | H | B32 | Cl | Cl | Me |
| 2,6-F$_2$-Ph | H | H | B33 | Cl | Cl | Me |
| 2,6-F$_2$-Ph | H | H | B34 | Cl | Cl | Me |
| 2,6-F$_2$-Ph | H | H | Na | Cl | Cl | Me |
| 2,6-F$_2$-Ph | H | H | K | Cl | Cl | Me |
| 2,6-F$_2$-Ph | H | H | B2 | CF$_3$ | Cl | Me |
| 2,6-F$_2$-Ph | H | H | B3 | CF$_3$ | Cl | Me |
| 2,6-F$_2$-Ph | H | H | B4 | CF$_3$ | Cl | Me |
| 2,6-F$_2$-Ph | H | H | B5 | CF$_3$ | Cl | Me |
| 2,6-F$_2$-Ph | H | H | B6 | CF$_3$ | Cl | Me |
| 2,6-F$_2$-Ph | H | H | B7 | CF$_3$ | Cl | Me |
| 2,6-F$_2$-Ph | H | H | B8 | CF$_3$ | Cl | Me |
| 2,6-F$_2$-Ph | H | H | B9 | CF$_3$ | Cl | Me |
| 2,6-F$_2$-Ph | H | H | B10 | CF$_3$ | Cl | Me |
| 2,6-F$_2$-Ph | H | H | B11 | CF$_3$ | Cl | Me |
| 2,6-F$_2$-Ph | H | H | B12 | CF$_3$ | Cl | Me |
| 2,6-F$_2$-Ph | H | H | B13 | CF$_3$ | Cl | Me |
| 2,6-F$_2$-Ph | H | H | B14 | CF$_3$ | Cl | Me |
| 2,6-F$_2$-Ph | H | H | B15 | CF$_3$ | Cl | Me |
| 2,6-F$_2$-Ph | H | H | B16 | CF$_3$ | Cl | Me |
| 2,6-F$_2$-Ph | H | H | B17 | CF$_3$ | Cl | Me |
| 2,6-F$_2$-Ph | H | H | B18 | CF$_3$ | Cl | Me |
| 2,6-F$_2$-Ph | H | H | B19 | CF$_3$ | Cl | Me |
| 2,6-F$_2$-Ph | H | H | B20 | CF$_3$ | Cl | Me |
| 2,6-F$_2$-Ph | H | H | B21 | CF$_3$ | Cl | Me |
| 2,6-F$_2$-Ph | H | H | B22 | CF$_3$ | Cl | Me |
| 2,6-F$_2$-Ph | H | H | B23 | CF$_3$ | Cl | Me |
| 2,6-F$_2$-Ph | H | H | B24 | CF$_3$ | Cl | Me |
| 2,6-F$_2$-Ph | H | H | B25 | CF$_3$ | Cl | Me |
| 2,6-F$_2$-Ph | H | H | B26 | CF$_3$ | Cl | Me |
| 2,6-F$_2$-Ph | H | H | B27 | CF$_3$ | Cl | Me |
| 2,6-F$_2$-Ph | H | H | B28 | CF$_3$ | Cl | Me |
| 2,6-F$_2$-Ph | H | H | B29 | CF$_3$ | Cl | Me |
| 2,6-F$_2$-Ph | H | H | B30 | CF$_3$ | Cl | Me |
| 2,6-F$_2$-Ph | H | H | B31 | CF$_3$ | Cl | Me |
| 2,6-F$_2$-Ph | H | H | B32 | CF$_3$ | Cl | Me |
| 2,6-F$_2$-Ph | H | H | B33 | CF$_3$ | Cl | Me |
| 2,6-F$_2$-Ph | H | H | B34 | CF$_3$ | Cl | Me |
| 2,6-F$_2$-Ph | H | H | Na | CF$_3$ | Cl | Me |
| 2,6-F$_2$-Ph | H | H | K | CF$_3$ | Cl | Me |
| 2,6-F$_2$-Ph | H | H | B7 | Cl | H | H |
| 2,6-F$_2$-Ph | H | H | B9 | Cl | H | H |
| 2,6-F$_2$-Ph | H | H | B10 | Cl | H | H |
| 2,6-F$_2$-PhPh | H | H | B11 | Cl | H | H |
| tBu | H | H | H | Me | H | Me |
| tBu | H | H | H | Me | H | CF$_3$ |
| tBu | H | H | H | Me | H | H |
| tBu | H | H | H | Me | Me | Me |
| tBu | H | H | H | Me | Cl | Me |
| tBu | Cl | H | H | Me | Cl | Me |
| tBu | H | H | H | Cl | Me | Me |
| tBu | H | H | H | Cl | H | Me |
| tBu | H | H | H | Cl | H | CF$_3$ |
| tBu | H | H | H | Cl | H | H |
| tBu | H | H | H | Cl | Cl | Me |
| tBu | Me | H | H | Cl | Cl | Me |
| tBu | Cl | H | H | Cl | Cl | Me |
| tBu | NO$_2$ | H | H | Cl | Cl | Me |
| tBu | CO$_2$Me | H | H | Cl | Cl | Me |
| tBu | CO$_2$Et | H | H | Cl | Cl | Me |
| tBu | H | H | H | Cl | Cl | CF$_3$ |
| tBu | H | H | H | Cl | Cl | CF$_2$H |
| tBu | H | H | H | Cl | Cl | CH$_2$OMe |
| tBu | H | H | H | Cl | Cl | COMe |
| tBu | H | H | H | Cl | CF$_3$ | Me |
| tBu | H | H | H | Br | Me | Me |

TABLE 2-continued

| | | | | | | |
|---|---|---|---|---|---|---|
| tBu | H | H | H | Me | Br | Me |
| tBu | H | H | H | OMe | H | H |
| tBu | H | H | H | CF$_3$ | Me | Me |
| tBu | H | H | H | CF$_3$ | Cl | Me |
| tBu | Me | H | H | CF$_3$ | Cl | Me |
| tBu | Cl | H | H | CF$_3$ | Cl | Me |
| tBu | NO$_2$ | H | H | CF$_3$ | Cl | Me |
| tBu | CO$_2$Me | H | H | CF$_3$ | Cl | Me |
| tBu | CO$_2$Et | H | H | CF$_3$ | Cl | Me |
| tBu | H | H | H | CF$_3$ | Cl | CF$_3$ |
| tBu | H | H | H | CF$_3$ | Cl | CF$_2$H |
| tBu | H | H | H | CF$_3$ | Cl | CH$_2$OMe |
| tBu | H | H | H | CF$_3$ | Cl | COCH$_3$ |
| tBu | H | H | H | CF$_3$ | H | Me |
| tBu | H | H | H | CF$_3$ | NO$_2$ | Me |
| tBu | H | H | H | CF$_3$ | NHMe | Me |
| tBu | H | H | H | CF$_3$ | NMe$_2$ | Me |
| tBu | H | H | H | NO$_2$ | Me | Me |
| tBu | H | H | H | CN | Cl | Me |
| tBu | H | H | H | CN | Me | Me |
| tBu | H | H | H | Cl | CN | Me |
| tBu | H | H | H | CO$_2$Me | Me | Me |
| tBu | H | H | H | CO$_2$Me | Cl | Me |
| tBu | H | H | B1 | Cl | Cl | Me |
| tBu | Cl | H | B1 | Cl | Cl | Me |
| tBu | H | H | B2 | Cl | Cl | Me |
| tBu | H | H | B3 | Cl | Cl | Me |
| tBu | H | H | B4 | Cl | Cl | Me |
| tBu | H | H | B5 | Cl | Cl | Me |
| tBu | H | H | B6 | Cl | Cl | Me |
| tBu | H | H | B7 | Cl | Cl | Me |
| tBu | H | H | B8 | Cl | Cl | Me |
| tBu | H | H | B9 | Cl | Cl | Me |
| tBu | H | H | B10 | Cl | Cl | Me |
| tBu | H | H | B11 | Cl | Cl | Me |
| tBu | H | H | B12 | Cl | Cl | Me |
| tBu | H | H | B13 | Cl | Cl | Me |
| tBu | H | H | B14 | Cl | Cl | Me |
| tBu | H | H | B15 | Cl | Cl | Me |
| tBu | H | H | B16 | Cl | Cl | Me |
| tBu | H | H | B17 | Cl | Cl | Me |
| tBu | H | H | B18 | Cl | Cl | Me |
| tBu | H | H | B19 | Cl | Cl | Me |
| tBu | H | H | B20 | Cl | Cl | Me |
| tBu | H | H | B21 | Cl | Cl | Me |
| tBu | H | H | B22 | Cl | Cl | Me |
| tBu | H | H | B23 | Cl | Cl | Me |
| tBu | H | H | B24 | Cl | Cl | Me |
| tBu | H | H | B25 | Cl | Cl | Me |
| tBu | H | H | B26 | Cl | Cl | Me |
| tBu | H | H | B27 | Cl | Cl | Me |
| tBu | H | H | B28 | Cl | Cl | Me |
| tBu | H | H | B29 | Cl | Cl | Me |
| tBu | H | H | B30 | Cl | Cl | Me |
| tBu | H | H | B31 | Cl | Cl | Me |
| tBu | H | H | B32 | Cl | Cl | Me |
| tBu | H | H | B33 | Cl | Cl | Me |
| tBu | H | H | B34 | Cl | Cl | Me |
| tBu | H | H | Na | Cl | Cl | Me |
| tBu | H | H | K | Cl | Cl | Me |
| tBu | H | H | B2 | CF$_3$ | Cl | Me |
| tBu | H | H | B3 | CF$_3$ | Cl | Me |
| tBu | H | H | B4 | CF$_3$ | Cl | Me |
| tBu | H | H | B5 | CF$_3$ | Cl | Me |
| tBu | H | H | B6 | CF$_3$ | Cl | Me |
| tBu | H | H | B7 | CF$_3$ | Cl | Me |
| tBu | H | H | B8 | CF$_3$ | Cl | Me |
| tBu | H | H | B9 | CF$_3$ | Cl | Me |
| tBu | H | H | B10 | CF$_3$ | Cl | Me |
| tBu | H | H | B11 | CF$_3$ | Cl | Me |
| tBu | H | H | B12 | CF$_3$ | Cl | Me |
| tBu | H | H | B13 | CF$_3$ | Cl | Me |
| tBu | H | H | B14 | CF$_3$ | Cl | Me |
| tBu | H | H | B15 | CF$_3$ | Cl | Me |
| tBu | H | H | B16 | CF$_3$ | Cl | Me |
| tBu | H | H | B17 | CF$_3$ | Cl | Me |
| tBu | H | H | B18 | CF$_3$ | Cl | Me |
| tBu | H | H | B19 | CF$_3$ | Cl | Me |
| tBu | H | H | B20 | CF$_3$ | Cl | Me |
| tBu | H | H | B21 | CF$_3$ | Cl | Me |
| tBu | H | H | B22 | CF$_3$ | Cl | Me |
| tBu | H | H | B23 | CF$_3$ | Cl | Me |
| tBu | H | H | B24 | CF$_3$ | Cl | Me |
| tBu | H | H | B25 | CF$_3$ | Cl | Me |
| tBu | H | H | B26 | CF$_3$ | Cl | Me |
| tBu | H | H | B27 | CF$_3$ | Cl | Me |
| tBu | H | H | B28 | CF$_3$ | Cl | Me |
| tBu | H | H | B29 | CF$_3$ | Cl | Me |
| tBu | H | H | B30 | CF$_3$ | Cl | Me |
| tBu | H | H | B31 | CF$_3$ | Cl | Me |
| tBu | H | H | B32 | CF$_3$ | Cl | Me |
| tBu | H | H | B33 | CF$_3$ | Cl | Me |
| tBu | H | H | B34 | CF$_3$ | Cl | Me |
| tBu | H | H | Na | CF$_3$ | Cl | Me |
| tBu | H | H | K | CF$_3$ | Cl | Me |
| tBu | H | H | B7 | Cl | H | H |
| tBu | H | H | B8 | Cl | H | H |
| tBu | H | H | B15 | Cl | H | H |
| tBu | H | H | B17 | Cl | H | H |
| tBu | H | H | B18 | Cl | H | H |
| tBu | H | H | B34 | Cl | H | H |
| 2-pyridyl | H | H | H | Me | H | Me |
| 2-pyridyl | H | H | H | Me | H | CF$_3$ |
| 2-pyridyl | H | H | B7 | Me | H | H |
| 2-pyridyl | H | H | H | Me | Me | Me |
| 2-pyridyl | H | H | H | Me | Cl | Me |
| 2-pyridyl | H | H | H | Cl | Me | Me |
| 2-pyridyl | H | H | H | Cl | H | Me |
| 2-pyridyl | H | H | H | Cl | H | CF$_3$ |
| 2-pyridyl | H | H | H | Cl | H | H |
| 2-pyridyl | Cl | H | H | Cl | H | H |
| 2-pyridyl | CO$_2$Me | H | H | Cl | H | H |
| 2-pyridyl | CO$_2$Et | H | H | Cl | H | H |
| 2-pyridyl | H | H | H | Cl | Cl | Me |
| 2-pyridyl | H | H | H | Cl | CF$_3$ | Me |
| 2-pyridyl | H | H | H | Br | Me | Me |
| 2-pyridyl | H | H | H | Me | Br | Me |
| 2-pyridyl | H | H | B7 | OMe | H | H |
| 2-pyridyl | H | H | H | CF$_3$ | Me | Me |
| 2-pyridyl | H | H | H | CF$_3$ | Cl | Me |
| 2-pyridyl | H | H | H | CF$_3$ | H | Me |
| 2-pyridyl | H | H | B7 | CF$_3$ | H | H |
| 2-pyridyl | H | H | B1 | Cl | Cl | Me |
| 2-pyridyl | H | H | B3 | Cl | Cl | Me |
| 2-pyridyl | H | H | B7 | Cl | Cl | Me |
| 2-pyridyl | H | H | B3 | CF$_3$ | Cl | Me |
| 2-pyridyl | H | H | B7 | CF$_3$ | Cl | Me |
| 2-pyridyl | H | H | B3 | Cl | H | H |
| 2-pyridyl | H | H | B4 | Cl | H | H |
| 2-pyridyl | H | H | B5 | Cl | H | H |
| 2-pyridyl | H | H | B6 | Cl | H | H |
| 2-pyridyl | H | H | B7 | Cl | H | H |
| 2-pyridyl | H | H | B8 | Cl | H | H |
| 2-pyridyl | H | H | B9 | Cl | H | H |
| 2-pyridyl | H | H | B10 | Cl | H | H |
| 2-pyridyl | H | H | B11 | Cl | H | H |
| 2-pyridyl | H | H | B15 | Cl | H | H |
| 2-pyridyl | H | H | B16 | Cl | H | H |
| 2-pyridyl | H | H | B17 | Cl | H | H |
| 2-pyridyl | H | H | B28 | Cl | H | H |
| 2-pyridyl | H | H | B30 | Cl | H | H |
| 2-pyridyl | H | H | B31 | Cl | H | H |
| 2-pyridyl | H | H | B32 | Cl | H | H |
| 2-pyridyl | H | H | B34 | Cl | H | H |
| 3-pyridyl | H | H | H | Cl | Cl | Me |
| 3-pyridyl | H | H | H | Cl | H | H |
| 4-pyridyl | H | H | H | Cl | Cl | Me |
| 4-pyridyl | H | H | H | Cl | H | H |
| 2-F-Ph | H | H | H | Cl | H | H |
| 2-F-Ph | H | H | H | Cl | Cl | Me |
| 2-F-Ph | H | H | B7 | OMe | H | H |
| 2-F-Ph | H | H | B7 | SMe | H | H |
| 2-F-Ph | H | H | H | CF$_3$ | H | Me |
| 2-F-Ph | H | H | H | CF$_3$ | H | Me |
| 2-F-Ph | H | H | B1 | Cl | Cl | Me |
| 2-F-Ph | H | H | B3 | Cl | Cl | Me |
| 2-F-Ph | H | H | B6 | Cl | Cl | Me |
| 2-F-Ph | H | H | B7 | Cl | Cl | Me |

TABLE 2-continued

| | | | | | | |
|---|---|---|---|---|---|---|
| 2-F-Ph | Cl | H | B7 | Cl | Cl | Me |
| 2-F-Ph | H | H | B3 | CF₃ | Cl | Me |
| 2-F-Ph | H | H | B6 | CF₃ | Cl | Me |
| 2-F-Ph | H | H | B7 | CF₃ | Cl | Me |
| 2-F-Ph | Cl | H | B7 | CF₃ | Cl | Me |
| 2-F-Ph | H | H | B7 | Cl | H | H |
| 3-F-Ph | H | H | H | Cl | Cl | Me |
| 3-F-Ph | H | H | H | CF₃ | Cl | Me |
| 4-F-Ph | H | H | H | Cl | Cl | Me |
| 4-F-Ph | H | H | H | CF₃ | Cl | Me |
| 2,3-F₂-Ph | H | H | H | Cl | Cl | Me |
| 2,4-F₂-Ph | H | H | H | Cl | Cl | Me |
| 2,5-F₂-Ph | H | H | H | Cl | Cl | Me |
| Ph | H | H | H | Cl | H | H |
| Ph | H | H | H | Cl | Cl | Me |
| Ph | H | H | H | OMe | H | H |
| Ph | H | H | H | SMe | H | H |
| Ph | H | H | H | CF₃ | Cl | Me |
| Ph | H | H | H | CF₃ | H | Me |
| Ph | H | H | B1 | Cl | Cl | Me |
| Ph | H | H | B3 | Cl | Cl | Me |
| Ph | H | H | B6 | Cl | Cl | Me |
| Ph | H | H | B7 | Cl | Cl | Me |
| Ph | Cl | H | B7 | Cl | Cl | Me |
| Ph | H | H | B3 | CF₃ | Cl | Me |
| Ph | H | H | B6 | CF₃ | Cl | Me |
| Ph | H | H | B7 | CF₃ | Cl | Me |
| Ph | Cl | H | B7 | CF₃ | Cl | Me |
| Ph | H | H | B7 | Cl | H | H |
| Ph | H | H | H | Cl | Cl | Me |
| Ph | H | H | H | Cl | Cl | Me |
| 2-Cl-Ph | H | H | H | Cl | H | H |
| 2-Cl-Ph | H | H | H | Cl | Cl | Me |
| 2-Cl-Ph | H | H | H | OMe | H | H |
| 2-Cl-Ph | H | H | H | SMe | H | H |
| 2-Cl-Ph | H | H | H | CF₃ | Cl | Me |
| 2-Cl-Ph | H | H | H | CF₃ | H | Me |
| 2-Cl-Ph | H | H | B1 | Cl | Cl | Me |
| 2-Cl-Ph | H | H | B3 | Cl | Cl | Me |
| 2-Cl-Ph | H | H | B6 | Cl | Cl | Me |
| 2-Cl-Ph | H | H | B7 | Cl | Cl | Me |
| 2-Cl-Ph | Cl | H | B7 | Cl | Cl | Me |
| 2-Cl-Ph | H | H | B3 | CF₃ | Cl | Me |
| 2-Cl-Ph | H | H | B6 | CF₃ | Cl | Me |
| 2-Cl-Ph | H | H | B7 | CF₃ | Cl | Me |
| 2-Cl-Ph | Cl | H | B7 | CF₃ | Cl | Me |
| 2-Cl-Ph | H | H | B7 | Cl | H | H |
| 3-Cl-Ph | H | H | H | Cl | Cl | Me |
| 4-Cl-Ph | H | H | H | Cl | Cl | Me |
| 2,3-Cl₂-Ph | H | H | H | Cl | Cl | Me |
| 2,4-Cl₂-Ph | H | H | H | Cl | Cl | Me |
| 2,5-Cl₂-Ph | H | H | H | Cl | Cl | Me |
| 2,6-Cl₂-Ph | H | H | H | Cl | H | H |
| 2,6-Cl₂-Ph | H | H | H | Cl | Cl | Me |
| 2,6-Cl₂-Ph | H | H | H | OMe | H | H |
| 2,6-Cl₂-Ph | H | H | H | SMe | H | H |
| 2,6-Cl₂-Ph | H | H | H | CF₃ | Cl | Me |
| 2,6-Cl₂-Ph | H | H | H | CF₃ | H | Me |
| 2,6-Cl₂-Ph | H | H | B1 | Cl | Cl | Me |
| 2,6-Cl₂-Ph | H | H | B3 | Cl | Cl | Me |
| 2,6-Cl₂-Ph | H | H | B6 | Cl | Cl | Me |
| 2,6-Cl₂-Ph | H | H | B7 | Cl | Cl | Me |
| 2,6-Cl₂-Ph | Cl | H | B7 | Cl | Cl | Me |
| 2,6-Cl₂-Ph | H | H | B3 | CF₃ | Cl | Me |
| 2,6-Cl₂-Ph | H | H | B6 | CF₃ | Cl | Me |
| 2,6-Cl₂-Ph | H | H | B7 | CF₃ | Cl | Me |
| 2,6-Cl₂-Ph | Cl | H | B7 | CF₃ | Cl | Me |
| 2,6-Cl₂-Ph | H | H | B7 | Cl | H | H |
| 3,4-Cl₂-Ph | H | H | H | Cl | Cl | Me |
| 3,5-Cl₂-Ph | H | H | H | Cl | Cl | Me |
| 2-Me-Ph | H | H | H | Cl | Cl | Me |
| 2-Me-Ph | H | H | H | CF₃ | Cl | Me |
| 2,6-Me₂-Ph | H | H | H | Cl | Cl | Me |
| 2,6-Me₂-Ph | H | H | H | CF₃ | Cl | Me |
| 2-MeO-Ph | H | H | H | Cl | Cl | Me |
| 2-MeO-Ph | H | H | H | CF₃ | Cl | Me |
| 2-CF₃O-Ph | H | H | H | Cl | Cl | Me |
| 2-SMe-Ph | H | H | H | Cl | Cl | Me |
| 2-SOMe-Ph | H | H | H | Cl | Cl | Me |
| 2-SO₂Me-Ph | H | H | H | Cl | Cl | Me |
| 2-CF₃-Ph | H | H | H | Cl | Cl | Me |
| 2-NO₂-Ph | H | H | H | Cl | Cl | Me |
| 2-CN-Ph | H | H | H | Cl | Cl | Me |
| 2-NHMe-Ph | H | H | H | Cl | Cl | Me |
| 2-NMe₂-Ph | H | H | H | Cl | Cl | Me |
| 4-benzyl-Ph | H | H | H | Cl | Cl | Me |
| 4-phenoxy-Ph | H | H | H | Cl | Cl | Me |
| 2-OH-Ph | H | H | H | Cl | Cl | Me |
| 2-CO₂Me-Ph | H | H | H | Cl | Cl | Me |
| 2-CO₂Et-Ph | H | H | H | Cl | Cl | Me |
| H | CO₂Et | Ph | H | Cl | Cl | Me |
| Me | Ph | H | H | Cl | Cl | Me |
| Et | Me | H | H | Cl | Cl | Me |
| nPr | H | H | H | Cl | Cl | Me |
| iPr | H | H | H | Cl | Cl | Me |
| iPr | H | H | H | CF₃ | Cl | Me |
| nBu | H | H | H | Cl | Cl | Me |
| nBu | H | H | H | CF₃ | Cl | Me |
| iBu | H | H | H | Cl | Cl | Me |
| iBu | H | H | H | CF₃ | Cl | Me |
| iBu | H | H | B7 | Cl | Cl | Me |
| iBu | H | H | B7 | CF₃ | Cl | Me |
| iBu | H | H | H | Cl | H | H |
| secBu | H | H | H | Cl | Cl | Me |
| secBu | H | H | H | CF₃ | Cl | Me |
| 2,2-Me₂-propyl | H | H | H | Cl | Cl | Me |
| nHex | H | H | H | Cl | Cl | Me |
| ethenyl | H | H | H | Cl | Cl | Me |
| 1-propenyl | H | H | H | Cl | Cl | Me |
| 1-propenyl | H | H | H | CF₃ | Cl | Me |
| ethynyl | H | H | H | Cl | Cl | Me |
| 1-propynyl | H | H | H | Cl | Cl | Me |
| CF₃ | H | H | H | Cl | Cl | Me |
| CHF₂ | H | H | H | Cl | Cl | Me |
| C₂F₅ | H | H | H | Cl | Cl | Me |
| 2,2-Cl₂-cPr | H | H | H | Cl | Cl | Me |
| 2,2-Cl₂-cPr | H | H | H | CF₃ | Cl | Me |
| cPr | H | H | H | Cl | Cl | Me |
| cPr | H | H | H | CF₃ | Cl | Me |
| 1-Me-cPr | H | H | H | Cl | Cl | Me |
| 1-Me-cPr | H | H | H | CF₃ | Cl | Me |
| cHex | H | H | H | Cl | Cl | Me |
| cHex | H | H | H | CF₃ | Cl | Me |
| CH₂Ph | H | H | H | Cl | Cl | Me |
| naphthyl-1 | H | H | H | Cl | Cl | Me |
| naphthyl-1 | H | H | H | CF₃ | Cl | Me |
| naphthyl-2 | H | H | H | Cl | Cl | Me |
| CO₂Me | H | H | H | Cl | Cl | Me |
| CO₂Et | H | H | H | Cl | Cl | Me |
| 2-thienyl | H | H | H | Cl | Cl | Me |
| CH₂OMe | H | H | H | Cl | Cl | Me |
| CH₂OEt | H | H | H | Cl | Cl | Me |
| COCH₃ | H | H | H | Cl | Cl | Me |
| COtBu | H | H | H | Cl | Cl | Me |

TABLE 3

TABLE 3-continued
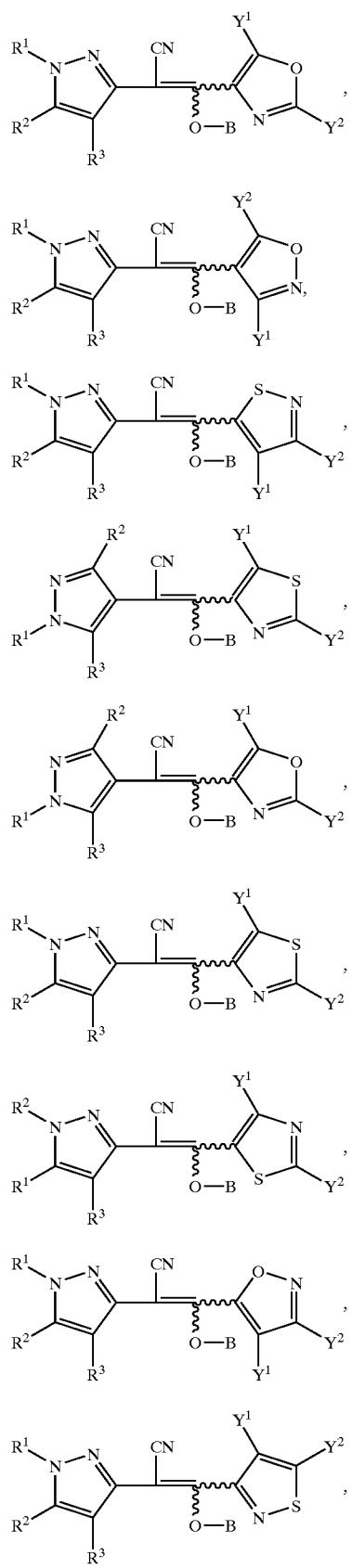
TABLE 3-continued
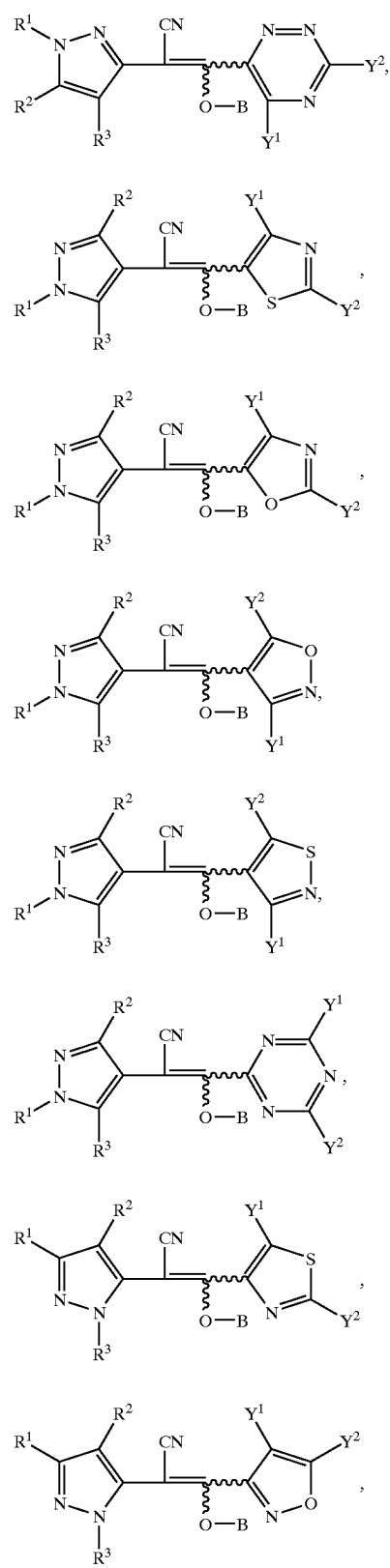

TABLE 3-continued

| R¹ | R² | R³ | B | Y¹ | Y² |
|---|---|---|---|---|---|
| 2,6-F₂Ph | H | H | H | Me | Me |
| 2,6-F₂Ph | H | H | H | Et | Me |
| 2,6-F₂Ph | Me | H | H | Et | Me |
| 2,6-F₂Ph | Cl | H | H | Et | Me |
| 2,6-F₂Ph | H | Cl | H | Et | Me |
| 2,6-F₂Ph | H | H | H | Cl | Cl |
| 2,6-F₂Ph | H | H | H | Cl | Me |
| 2,6-F₂Ph | H | H | H | Cl | CF₃ |
| 2,6-F₂Ph | H | H | H | Me | Cl |
| 2,6-F₂Ph | H | H | H | Br | Me |
| 2,6-F₂Ph | H | H | H | Me | Br |
| 2,6-F₂Ph | H | H | H | Me | CF₃ |
| 2,6-F₂Ph | H | H | H | OMe | Me |
| 2,6-F₂Ph | H | H | H | OCF₃ | Me |
| 2,6-F₂Ph | H | H | H | SMe | Me |
| 2,6-F₂Ph | H | H | H | CO₂Me | Me |
| 2,6-F₂Ph | H | H | H | CO₂Et | Me |
| 2,6-F₂Ph | H | H | H | CF₃ | Me |
| 2,6-F₂Ph | H | H | H | CF₃ | H |
| 2,6-F₂Ph | H | H | B3 | CF₃ | Me |
| 2,6-F₂Ph | H | H | B6 | CF₃ | Me |
| 2,6-F₂Ph | H | H | B7 | CF₃ | Me |
| 2,6-F₂Ph | Cl | H | B7 | CF₃ | Me |
| tBu | H | H | H | Me | Me |
| tBu | H | H | H | Et | Me |
| tBu | H | H | H | Cl | Cl |
| tBu | H | H | H | Cl | Me |
| tBu | H | H | H | Me | Cl |
| tBu | H | H | H | Cl | CF₃ |
| tBu | H | H | H | Br | Me |
| tBu | H | H | H | Me | Br |
| tBu | H | H | H | Me | CF₃ |
| tBu | H | H | H | OMe | Me |
| tBu | H | H | H | OCF₃ | Me |
| tBu | H | H | H | SMe | Me |
| tBu | H | H | H | CO₂Me | Me |
| tBu | H | H | H | CO₂Et | Me |
| tBu | H | H | H | CF₃ | Me |
| tBu | Me | H | H | CF₃ | Me |
| tBu | Cl | H | H | CF₃ | Me |
| tBu | Br | H | H | CF₃ | Me |
| tBu | CF₃ | H | H | CF₃ | Me |
| tBu | NO₂ | H | H | CF₃ | Me |
| tBu | CN | H | H | CF₃ | Me |
| tBu | CO₂Me | H | H | CF₃ | Me |
| tBu | CO₂Et | H | H | CF₃ | Me |
| tBu | H | H | H | CF₃ | H |
| tBu | H | H | H | CF₃ | Br |
| tBu | H | H | H | CF₃ | NO₂ |
| tBu | H | H | H | CF₃ | CN |
| tBu | H | H | H | CF₃ | NHMe |
| tBu | H | H | H | CF₃ | NMe₂ |
| tBu | H | H | H | CF₃ | CO₂Me |
| tBu | H | H | B2 | CF₃ | Me |
| tBu | H | H | B3 | CF₃ | Me |
| tBu | H | H | B4 | CF₃ | Me |
| tBu | H | H | B5 | CF₃ | Me |
| tBu | H | H | B6 | CF₃ | Me |
| tBu | H | H | B7 | CF₃ | Me |
| tBu | Cl | H | B7 | CF₃ | Me |
| tBu | H | H | B8 | CF₃ | Me |
| tBu | H | H | B9 | CF₃ | Me |
| tBu | H | H | B10 | CF₃ | Me |
| tBu | H | H | B11 | CF₃ | Me |
| tBu | H | H | B12 | CF₃ | Me |

TABLE 3-continued

| | | | | | |
|---|---|---|---|---|---|
| tBu | H | H | B13 | CF₃ | Me |
| tBu | H | H | B14 | CF₃ | Me |
| tBu | H | H | B15 | CF₃ | Me |
| tBu | H | H | B16 | CF₃ | Me |
| tBu | H | H | B17 | CF₃ | Me |
| tBu | H | H | B18 | CF₃ | Me |
| tBu | H | H | B19 | CF₃ | Me |
| tBu | H | H | B20 | CF₃ | Me |
| tBu | H | H | B21 | CF₃ | Me |
| tBu | H | H | B22 | CF₃ | Me |
| tBu | H | H | B23 | CF₃ | Me |
| tBu | H | H | B24 | CF₃ | Me |
| tBu | H | H | B25 | CF₃ | Me |
| tBu | H | H | B26 | CF₃ | Me |
| tBu | H | H | B27 | CF₃ | Me |
| tBu | H | H | B28 | CF₃ | Me |
| tBu | H | H | B29 | CF₃ | Me |
| tBu | H | H | B30 | CF₃ | Me |
| tBu | H | H | B31 | CF₃ | Me |
| tBu | H | H | B32 | CF₃ | Me |
| tBu | H | H | B33 | CF₃ | Me |
| tBu | H | H | B34 | CF₃ | Me |
| tBu | H | H | Na | CF₃ | Me |
| tBu | H | H | K | CF₃ | Me |
| 2-pyridyl | H | H | H | Me | Me |
| 2-pyridyl | H | H | H | Et | Me |
| 2-pyridyl | H | H | H | Cl | Cl |
| 2-pyridyl | H | H | H | Cl | Me |
| 2-pyridyl | H | H | H | Cl | CF₃ |
| 2-pyridyl | H | H | H | Me | Cl |
| 2-pyridyl | H | H | H | Br | Me |
| 2-pyridyl | H | H | H | Me | Br |
| 2-pyridyl | H | H | H | Me | CF₃ |
| 2-pyridyl | H | H | H | OMe | Me |
| 2-pyridyl | H | H | H | OCF₃ | Me |
| 2-pyridyl | H | H | H | SMe | Me |
| 2-pyridyl | H | H | H | CO₂Me | Me |
| 2-pyridyl | H | H | H | CO₂Et | Me |
| 2-pyridyl | H | H | H | CF₃ | Me |
| 2-pyridyl | H | H | H | CF₃ | H |
| 2-pyridyl | H | H | B3 | CF₃ | Me |
| 2-pyridyl | H | H | B6 | CF₃ | Me |
| 2-pyridyl | H | H | B7 | CF₃ | Me |
| 3-pyridyl | H | H | H | CF₃ | Me |
| 4-pyridyl | H | H | H | CF₃ | Me |
| 2-F-Ph | H | H | H | Me | Me |
| 2-F-Ph | H | H | H | Et | Me |
| 2-F-Ph | H | H | H | CF₃ | Me |
| 2-F-Ph | H | H | H | CF₃ | Cl |
| 2-F-Ph | H | H | H | CF₃ | H |
| 2-F-Ph | H | H | B3 | CF₃ | Me |
| 2-F-Ph | H | H | B6 | CF₃ | Me |
| 2-F-Ph | H | H | B7 | CF₃ | Me |
| 3-F-Ph | H | H | H | CF₃ | Me |
| 4-F-Ph | H | H | H | CF₃ | Me |
| 2,3-F₂-Ph | H | H | H | CF₃ | Me |
| 2,4-F₂-Ph | H | H | H | CF₃ | Me |
| 2,5-F₂-Ph | H | H | H | CF₃ | Me |
| Ph | H | H | H | Me | Me |
| Ph | H | H | H | Et | Me |
| Ph | H | H | H | CF₃ | Me |
| Ph | H | H | H | CF₃ | Cl |
| Ph | H | H | H | CF₃ | H |
| Ph | H | H | B3 | CF₃ | Me |
| Ph | H | H | B6 | CF₃ | Me |
| Ph | H | H | B7 | CF₃ | Me |
| 3,4-F₂-Ph | H | H | H | CF₃ | Me |
| 3,5-F₂-Ph | H | H | H | CF₃ | Me |
| 2-Cl-Ph | H | H | H | Me | Me |
| 2-Cl-Ph | H | H | H | Et | Me |
| 2-Cl-Ph | H | H | H | CF₃ | Me |
| 2-Cl-Ph | H | H | H | CF₃ | Cl |
| 2-Cl-Ph | H | H | H | CF₃ | H |
| 2-Cl-Ph | H | H | B3 | CF₃ | Me |
| 2-Cl-Ph | H | H | B6 | CF₃ | Me |
| 2-Cl-Ph | H | H | B7 | CF₃ | Me |
| 3-Cl-Ph | H | H | H | CF₃ | Me |
| 4-Cl-Ph | H | H | H | CF₃ | Me |
| 2,3-Cl₂-Ph | H | H | H | CF₃ | Me |
| 2,4-Cl₂-Ph | H | H | H | CF₃ | Me |
| 2,5-Cl₂-Ph | H | H | H | CF₃ | Me |
| 2,6-Cl₂-Ph | H | H | H | Me | Me |
| 2,6-Cl₂-Ph | H | H | H | Et | Me |
| 2,6-Cl₂-Ph | H | H | H | CF₃ | Me |
| 2,6-Cl₂-Ph | H | H | H | CF₃ | Cl |
| 2,6-Cl₂-Ph | H | H | H | CF₃ | H |
| 2,6-Cl₂-Ph | H | H | B3 | CF₃ | Me |
| 2,6-Cl₂-Ph | H | H | B6 | CF₃ | Me |
| 2,6-Cl₂-Ph | H | H | B7 | CF₃ | Me |
| 3,4-Cl₂-Ph | H | H | H | CF₃ | Me |
| 3,5-Cl₂-Ph | H | H | H | CF₃ | Me |
| 2-Me-Ph | H | H | H | CF₃ | Me |
| 2,6-Me₂-Ph | H | H | H | CF₃ | Me |
| 2-MeO-Ph | H | H | H | CF₃ | Me |
| 2-CF₃O-Ph | H | H | H | CF₃ | Me |
| 2-SMe-Ph | H | H | H | CF₃ | Me |
| 2-SOMe-Ph | H | H | H | CF₃ | Me |
| 2-SO₂Me-Ph | H | H | H | CF₃ | Me |
| 2-CF₃-Ph | H | H | H | CF₃ | Me |
| 2-NO₂-Ph | H | H | H | CF₃ | Me |
| 2-CN-Ph | H | H | H | CF₃ | Me |
| 2-NHMe-Ph | H | H | H | CF₃ | Me |
| 2-NMe₂-Ph | H | H | H | CF₃ | Me |
| 4-benzyl-Ph | H | H | H | Et | Me |
| 4-phenoxy-Ph | H | H | H | CF₃ | Me |
| 2-OH-Ph | H | H | H | CF₃ | Me |
| 2-CO₂Me-Ph | H | H | H | CF₃ | Me |
| 2-CO₂Et-Ph | H | H | H | CF₃ | Me |
| H | CO₂Et | Ph | H | CF₃ | Me |
| Me | Ph | H | H | CF₃ | Me |
| Et | Me | H | H | CF₃ | Me |
| nPr | H | H | H | CF₃ | Me |
| iPr | H | H | H | Et | Me |
| iPr | H | H | H | CF₃ | Me |
| nBu | H | H | H | Et | Me |
| nBu | H | H | H | CF₃ | Me |
| iBu | H | H | H | Et | Me |
| iBu | H | H | H | CF₃ | Me |
| iBu | H | H | B7 | Et | Me |
| iBu | H | H | B7 | CF₃ | Me |
| secBu | H | H | H | Et | Me |
| secBu | H | H | H | CF₃ | Me |
| 2,2-Me₂-propyl | H | H | H | CF₃ | Me |
| nHex | H | H | H | CF₃ | Me |
| ethenyl | H | H | H | CF₃ | Me |
| 1-propenyl | H | H | H | CF₃ | Me |
| ethynyl | H | H | H | CF₃ | Me |
| 1-propynyl | H | H | H | CF₃ | Me |
| CF₃ | H | H | H | CF₃ | Me |
| CHF₂ | H | H | H | CF₃ | Me |
| C₂F₅ | H | H | H | CF₃ | Me |
| 2,2-Cl₂-cPr | H | H | H | Et | Me |
| 2,2-Cl₂-cPr | H | H | H | CF₃ | Me |
| cPr | H | H | H | Et | Me |
| cPr | H | H | H | CF₃ | Me |
| 1-Me-cPr | H | H | H | Et | Me |
| 1-Me-cPr | H | H | H | CF₃ | Me |
| cHex | H | H | H | Et | Me |
| cHex | H | H | H | CF₃ | Me |
| CH₂Ph | H | H | H | CF₃ | Me |
| naphthyl-1 | H | H | H | Et | Me |
| naphthyl-1 | H | H | H | CF₃ | Me |
| naphthyl-2 | H | H | H | CF₃ | Me |
| CO₂Me | H | H | H | CF₃ | Me |
| CO₂Et | H | H | H | CF₃ | Me |
| 2-thienyl | H | H | H | CF₃ | Me |
| CH₂OMe | H | H | H | CF₃ | Me |
| CH₂OEt | H | H | H | CF₃ | Me |
| COCH₃ | H | H | H | CF₃ | Me |
| COtBu | H | H | H | CF₃ | Me |
| COPh | H | H | H | CF₃ | Me |

TABLE 4

TABLE 4-continued
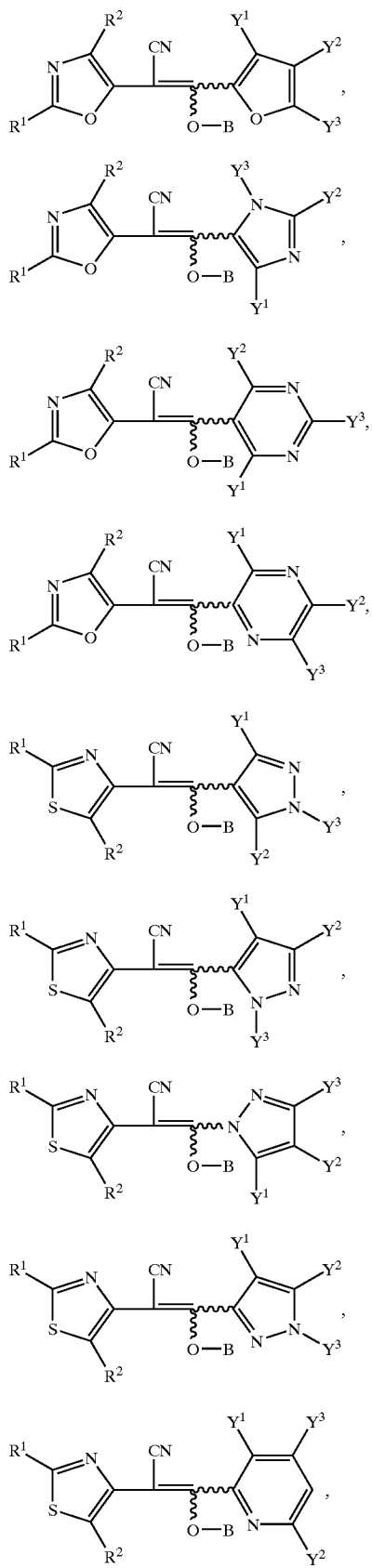
TABLE 4-continued
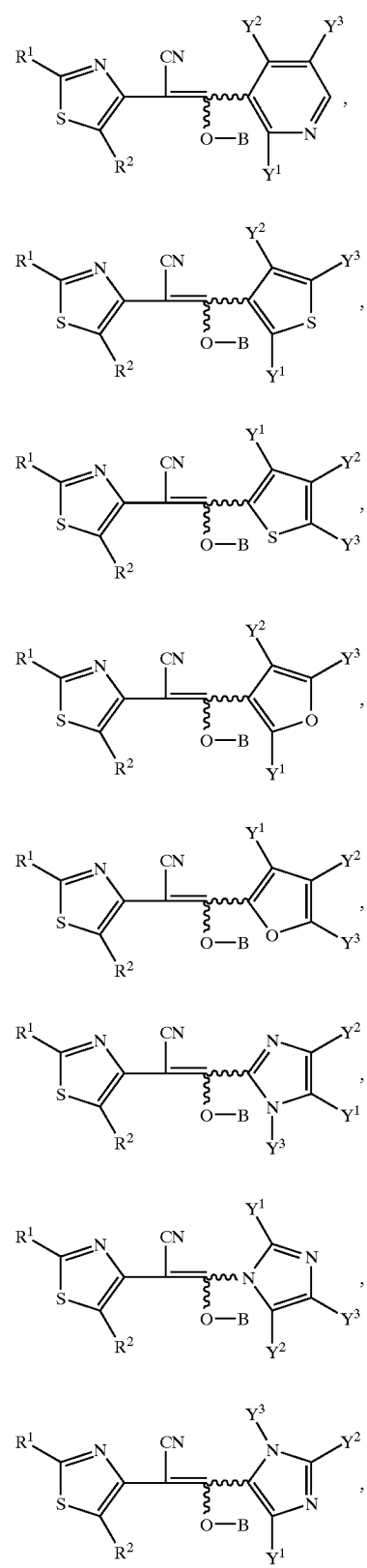

TABLE 4-continued
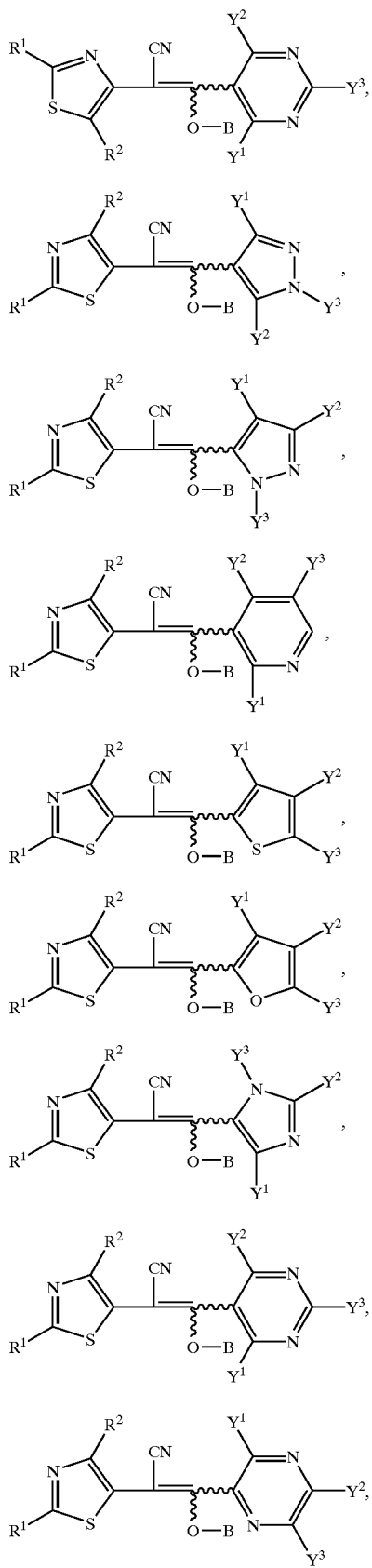
TABLE 4-continued
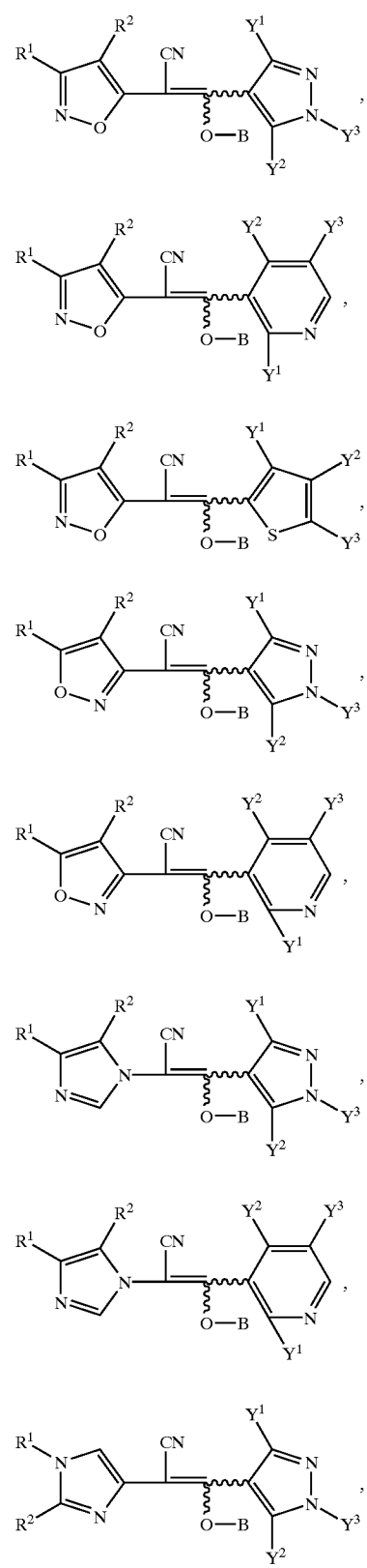

TABLE 4-continued

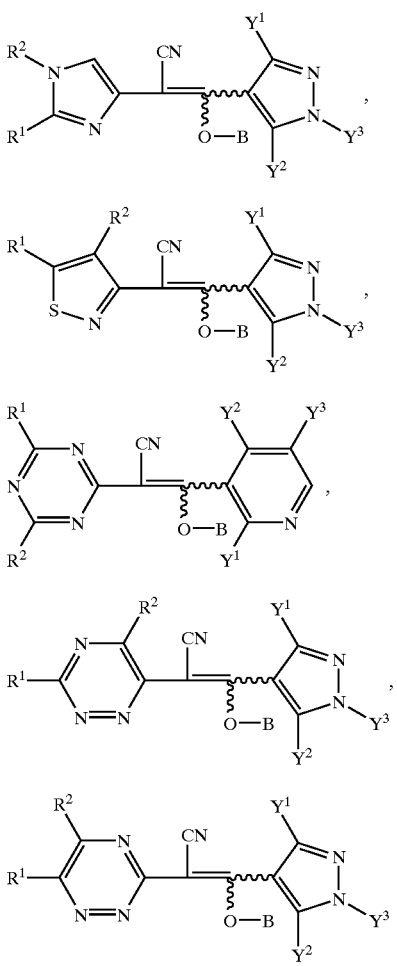

| R¹ | R² | B | Y¹ | Y² | Y³ |
|---|---|---|---|---|---|
| 2,6-F₂—Ph | H | H | H | CF₃ | Me |
| 2,6-F₂—Ph | H | H | Me | H | Me |
| 2,6-F₂—Ph | H | H | Me | H | CF₃ |
| 2,6-F₂—Ph | H | B7 | Me | H | H |
| 2,6-F₂—Ph | H | H | Me | Me | Me |
| 2,6-F₂—Ph | H | H | Me | Cl | Me |
| 2,6-F₂—Ph | H | H | Me | Br | Me |
| 2,6-F₂—Ph | H | H | Et | Me | Me |
| 2,6-F₂—Ph | H | H | Cl | Me | Me |
| 2,6-F₂—Ph | H | H | Cl | H | Me |
| 2,6-F₂—Ph | H | H | Cl | H | CF₃ |
| 2,6-F₂—Ph | H | H | Cl | H | H |
| 2,6-F₂—Ph | H | H | Cl | Cl | Me |
| 2,6-F₂—Ph | H | H | Cl | Cl | CF₃ |
| 2,6-F₂—Ph | H | H | Cl | Cl | CF₂H |
| 2,6-F₂—Ph | H | H | Cl | Cl | CH₂OMe |
| 2,6-F₂—Ph | H | H | Cl | Cl | COMe |
| 2,6-F₂—Ph | H | H | Br | CF₃ | Me |
| 2,6-F₂—Ph | H | H | Br | Me | Me |
| 2,6-F₂—Ph | H | H | Me | OMe | Me |
| 2,6-F₂—Ph | H | B7 | OMe | H | H |
| 2,6-F₂—Ph | H | B7 | OCF₃ | H | H |
| 2,6-F₂—Ph | H | B7 | SMe | H | H |
| 2,6-F₂—Ph | H | H | CF₃ | Me | Me |
| 2,6-F₂—Ph | H | H | CF₃ | Cl | Me |
| 2,6-F₂—Ph | H | H | CF₃ | Cl | CF₃ |
| 2,6-F₂—Ph | H | H | CF₃ | Cl | CF₂H |
| 2,6-F₂—Ph | H | H | CF₃ | Cl | CH₂OMe |
| 2,6-F₂—Ph | H | H | CF₃ | H | Me |
| 2,6-F₂—Ph | H | H | CF₃ | Br | Me |
| 2,6-F₂—Ph | H | H | CF₃ | NO₂ | Me |
| 2,6-F₂—Ph | H | H | CF₃ | CN | Me |
| 2,6-F₂—Ph | H | H | CF₃ | NHMe | Me |
| 2,6-F₂—Ph | H | H | CF₃ | NMe₂ | Me |
| 2,6-F₂—Ph | H | H | CF₃ | CO₂Me | Me |
| 2,6-F₂—Ph | H | H | CF₃ | OMe | Me |
| 2,6-F₂—Ph | H | H | CF₃ | OCF₂H | CF₂H |
| 2,6-F₂—Ph | H | H | Cl | NO₂ | Me |
| 2,6-F₂—Ph | H | H | Cl | CN | Me |
| 2,6-F₂—Ph | H | H | CO₂Me | Me | Me |
| 2,6-F₂—Ph | H | B1 | Cl | Cl | Me |
| 2,6-F₂—Ph | H | B3 | Cl | Cl | Me |
| 2,6-F₂—Ph | H | B6 | Cl | Cl | Me |
| 2,6-F₂—Ph | H | B7 | Cl | Cl | Me |
| 2,6-F₂—Ph | H | B2 | CF₃ | Cl | Me |
| 2,6-F₂—Ph | H | B3 | CF₃ | Cl | Me |
| 2,6-F₂—Ph | H | B4 | CF₃ | Cl | Me |
| 2,6-F₂—Ph | H | B5 | CF₃ | Cl | Me |
| 2,6-F₂—Ph | H | B6 | CF₃ | Cl | Me |
| 2,6-F₂—Ph | H | B7 | CF₃ | Cl | Me |
| 2,6-F₂—Ph | H | B8 | CF₃ | Cl | Me |
| 2,6-F₂—Ph | H | B9 | CF₃ | Cl | Me |
| 2,6-F₂—Ph | H | B10 | CF₃ | Cl | Me |
| 2,6-F₂—Ph | H | B11 | CF₃ | Cl | Me |
| 2,6-F₂—Ph | H | B12 | CF₃ | Cl | Me |
| 2,6-F₂—Ph | H | B13 | CF₃ | Cl | Me |
| 2,6-F₂—Ph | H | B14 | CF₃ | Cl | Me |
| 2,6-F₂—Ph | H | B15 | CF₃ | Cl | Me |
| 2,6-F₂—Ph | H | B16 | CF₃ | Cl | Me |
| 2,6-F₂—Ph | H | B17 | CF₃ | Cl | Me |
| 2,6-F₂—Ph | H | B18 | CF₃ | Cl | Me |
| 2,6-F₂—Ph | H | B19 | CF₃ | Cl | Me |
| 2,6-F₂—Ph | H | B20 | CF₃ | Cl | Me |
| 2,6-F₂—Ph | H | B21 | CF₃ | Cl | Me |
| 2,6-F₂—Ph | H | B22 | CF₃ | Cl | Me |
| 2,6-F₂—Ph | H | B23 | CF₃ | Cl | Me |
| 2,6-F₂—Ph | H | B24 | CF₃ | Cl | Me |
| 2,6-F₂—Ph | H | B25 | CF₃ | Cl | Me |
| 2,6-F₂—Ph | H | B26 | CF₃ | Cl | Me |
| 2,6-F₂—Ph | H | B27 | CF₃ | Cl | Me |
| 2,6-F₂—Ph | H | B28 | CF₃ | Cl | Me |
| 2,6-F₂—Ph | H | B29 | CF₃ | Cl | Me |
| 2,6-F₂—Ph | H | B30 | CF₃ | Cl | Me |
| 2,6-F₂—Ph | H | B31 | CF₃ | Cl | Me |
| 2,6-F₂—Ph | H | B32 | CF₃ | Cl | Me |
| 2,6-F₂—Ph | H | B33 | CF₃ | Cl | Me |
| 2,6-F₂—Ph | H | B34 | CF₃ | Cl | Me |
| 2,6-F₂—Ph | H | Na | CF₃ | Cl | Me |
| 2,6-F₂—Ph | H | K | CF₃ | Cl | Me |
| 2,6-F₂—Ph | H | B7 | Cl | H | H |
| 2,6-F₂—Ph | H | B9 | Cl | H | H |
| 2,6-F₂—Ph | H | B10 | Cl | H | H |
| 2,6-F₂—Ph | H | B11 | Cl | H | H |
| tBu | H | H | H | CF₃ | Me |
| tBu | H | H | Me | H | Me |
| tBu | H | H | Me | H | CF₃ |
| tBu | H | B7 | Me | H | H |
| tBu | H | H | Me | Me | Me |
| tBu | H | H | Me | Cl | Me |
| tBu | H | H | Me | Br | Me |
| tBu | H | H | Et | Me | Me |
| tBu | H | H | Cl | Me | Me |
| tBu | H | H | Cl | H | Me |
| tBu | H | H | Cl | H | CF₃ |
| tBu | H | H | Cl | H | H |
| tBu | Me | H | Cl | H | H |
| tBu | Cl | H | Cl | H | H |
| tBu | H | H | Cl | Cl | Me |

TABLE 4-continued

| | | | | | |
|---|---|---|---|---|---|
| tBu | H | H | Cl | Cl | CF$_3$ |
| tBu | H | H | Cl | Cl | CF$_2$H |
| tBu | H | H | Cl | Cl | CH$_2$OMe |
| tBu | H | H | Cl | Cl | COMe |
| tBu | H | H | Cl | CF$_3$ | Me |
| tBu | H | H | Br | Me | Me |
| tBu | H | Me | OMe | Me | |
| tBu | H | B7 | OMe | H | H |
| tBu | H | B7 | OCF$_3$ | H | H |
| tBu | H | B7 | SMe | H | H |
| tBu | H | H | CF$_3$ | Me | Me |
| tBu | H | H | CF$_3$ | Cl | Me |
| tBu | Br | H | CF$_3$ | Cl | Me |
| tBu | CF$_3$ | H | CF$_3$ | Cl | Me |
| tBu | NO$_2$ | H | CF$_3$ | Cl | Me |
| tBu | CN | H | CF$_3$ | Cl | Me |
| tBu | CO$_2$Me | H | CF$_3$ | Cl | Me |
| tBu | CO$_2$Et | H | CF$_3$ | Cl | Me |
| tBu | H | H | CF$_3$ | Cl | CF$_3$ |
| tBu | H | H | CF$_3$ | Cl | CF$_2$H |
| tBu | H | H | CF$_3$ | Cl | CH$_2$OMe |
| tBu | H | H | CF$_3$ | H | Me |
| tBu | H | H | CF$_3$ | Br | Me |
| tBu | H | H | CF$_3$ | NO$_2$ | Me |
| tBu | H | H | CF$_3$ | CN | Me |
| tBu | H | H | CF$_3$ | NHMe | Me |
| tBu | H | H | CF$_3$ | NMe$_2$ | Me |
| tBu | H | H | CF$_3$ | CO$_2$Me | Me |
| tBu | H | H | CF$_3$ | OMe | Me |
| tBu | H | H | CF$_3$ | OCF$_2$H | CF$_2$H |
| tBu | H | H | Cl | NO$_2$ | Me |
| tBu | H | H | Cl | CN | Me |
| tBu | H | H | CO$_2$Me | Me | Me |
| tBu | H | B1 | Cl | Cl | Me |
| tBu | H | B2 | Cl | Cl | Me |
| tBu | H | B3 | Cl | Cl | Me |
| tBu | H | B4 | Cl | Cl | Me |
| tBu | H | B5 | Cl | Cl | Me |
| tBu | H | B6 | Cl | Cl | Me |
| tBu | H | B7 | Cl | Cl | Me |
| tBu | H | B8 | Cl | Cl | Me |
| tBu | H | B9 | Cl | Cl | Me |
| tBu | H | B10 | Cl | Cl | Me |
| tBu | H | B11 | Cl | Cl | Me |
| tBu | H | B12 | Cl | Cl | Me |
| tBu | H | B13 | Cl | Cl | Me |
| tBu | H | B14 | Cl | Cl | Me |
| tBu | H | B15 | Cl | Cl | Me |
| tBu | H | B16 | Cl | Cl | Me |
| tBu | H | B17 | Cl | Cl | Me |
| tBu | H | B18 | Cl | Cl | Me |
| tBu | H | B19 | Cl | Cl | Me |
| tBu | H | B20 | Cl | Cl | Me |
| tBu | H | B21 | Cl | Cl | Me |
| tBu | H | B22 | Cl | Cl | Me |
| tBu | H | B23 | Cl | Cl | Me |
| tBu | H | B24 | Cl | Cl | Me |
| tBu | H | B25 | Cl | Cl | Me |
| tBu | H | B26 | Cl | Cl | Me |
| tBu | H | B27 | Cl | Cl | Me |
| tBu | H | B28 | Cl | Cl | Me |
| tBu | H | B29 | Cl | Cl | Me |
| tBu | H | B30 | Cl | Cl | Me |
| tBu | H | B31 | Cl | Cl | Me |
| tBu | H | B32 | Cl | Cl | Me |
| tBu | H | B33 | Cl | Cl | Me |
| tBu | H | B34 | Cl | Cl | Me |
| tBu | H | Na | Cl | Cl | Me |
| tBu | H | K | Cl | Cl | Me |
| tBu | H | B2 | CF$_3$ | Cl | Me |
| tBu | H | B3 | CF$_3$ | Cl | Me |
| tBu | H | B4 | CF$_3$ | Cl | Me |
| tBu | H | B5 | CF$_3$ | Cl | Me |
| tBu | H | B6 | CF$_3$ | Cl | Me |
| tBu | H | B7 | CF$_3$ | Cl | Me |
| tBu | H | B8 | CF$_3$ | Cl | Me |
| tBu | H | B9 | CF$_3$ | Cl | Me |
| tBu | H | B10 | CF$_3$ | Cl | Me |
| tBu | H | B11 | CF$_3$ | Cl | Me |
| tBu | H | B12 | CF$_3$ | Cl | Me |
| tBu | H | B13 | CF$_3$ | Cl | Me |
| tBu | H | B14 | CF$_3$ | Cl | Me |
| tBu | H | B15 | CF$_3$ | Cl | Me |
| tBu | H | B16 | CF$_3$ | Cl | Me |
| tBu | H | B17 | CF$_3$ | Cl | Me |
| tBu | H | B18 | CF$_3$ | Cl | Me |
| tBu | H | B19 | CF$_3$ | Cl | Me |
| tBu | H | B20 | CF$_3$ | Cl | Me |
| tBu | H | B21 | CF$_3$ | Cl | Me |
| tBu | H | B22 | CF$_3$ | Cl | Me |
| tBu | H | B23 | CF$_3$ | Cl | Me |
| tBu | H | B24 | CF$_3$ | Cl | Me |
| tBu | H | B25 | CF$_3$ | Cl | Me |
| tBu | H | B26 | CF$_3$ | Cl | Me |
| tBu | H | B27 | CF$_3$ | Cl | Me |
| tBu | H | B28 | CF$_3$ | Cl | Me |
| tBu | H | B29 | CF$_3$ | Cl | Me |
| tBu | H | B30 | CF$_3$ | Cl | Me |
| tBu | H | B31 | CF$_3$ | Cl | Me |
| tBu | H | B32 | CF$_3$ | Cl | Me |
| tBu | H | B33 | CF$_3$ | Cl | Me |
| tBu | H | B34 | CF$_3$ | Cl | Me |
| tBu | H | Na | CF$_3$ | Cl | Me |
| tBu | H | K | CF$_3$ | Cl | Me |
| tBu | H | B7 | Cl | H | H |
| tBu | H | B8 | Cl | H | H |
| tBu | H | B15 | Cl | H | H |
| tBu | H | B34 | Cl | H | H |
| 2-pyridyl | H | H | H | CF$_3$ | Me |
| 2-pyridyl | H | H | Me | H | Me |
| 2-pyridyl | H | H | Me | H | CF$_3$ |
| 2-pyridyl | H | B7 | Me | H | H |
| 2-pyridyl | H | H | Me | Me | Me |
| 2-pyridyl | H | H | Me | Cl | Me |
| 2-pyridyl | H | H | Me | Br | Me |
| 2-pyridyl | H | H | Et | Me | Me |
| 2-pyridyl | H | H | Cl | Me | Me |
| 2-pyridyl | H | H | Cl | H | Me |
| 2-pyridyl | H | H | Cl | H | CF$_3$ |
| 2-pyridyl | H | H | Cl | H | H |
| 2-pyridyl | Me | H | Cl | H | H |
| 2-pyridyl | Cl | H | Cl | H | H |
| 2-pyridyl | H | H | Cl | Cl | Me |
| 2-pyridyl | H | H | Cl | Cl | CF$_3$ |
| 2-pyridyl | H | H | Cl | Cl | CF$_2$H |
| 2-pyridyl | H | H | Cl | Cl | CH$_2$OMe |
| 2-pyridyl | H | H | Cl | Cl | COMe |
| 2-pyridyl | H | H | Cl | CF$_3$ | Me |
| 2-pyridyl | H | H | Br | Me | Me |
| 2-pyridyl | H | H | Me | OMe | Me |
| 2-pyridyl | H | H | Br | H | H |
| 2-pyridyl | H | H | OMe | H | H |
| 2-pyridyl | H | B7 | OCF$_3$ | H | H |
| 2-pyridyl | H | B7 | SMe | H | H |
| 2-pyridyl | H | B7 | NH$_2$ | H | H |
| 2-pyridyl | H | B7 | NHMe | H | H |
| 2-pyridyl | H | B7 | NMe$_2$ | H | H |
| 2-pyridyl | H | B7 | NO$_2$ | H | H |
| 2-pyridyl | H | B7 | CN | H | H |
| 2-pyridyl | H | B7 | CO$_2$Me | H | H |
| 2-pyridyl | H | B7 | CO$_2$Et | H | H |
| 2-pyridyl | H | H | CF$_3$ | Me | Me |
| 2-pyridyl | H | H | CF$_3$ | Cl | Me |
| 2-pyridyl | H | H | CF$_3$ | H | Me |
| 2-pyridyl | H | H | CF$_3$ | Br | Me |
| 2-pyridyl | H | H | CF$_3$ | CO$_2$Me | Me |
| 2-pyridyl | H | H | Cl | NO$_2$ | Me |
| 2-pyridyl | H | H | Cl | CN | Me |
| 2-pyridyl | H | H | CO$_2$Me | Me | Me |
| 2-pyridyl | H | B3 | Cl | Cl | Me |
| 2-pyridyl | H | B6 | Cl | Cl | Me |
| 2-pyridyl | H | B7 | Cl | Cl | Me |
| 2-pyridyl | H | B3 | CF$_3$ | Cl | Me |
| 2-pyridyl | H | B6 | CF$_3$ | Cl | Me |
| 2-pyridyl | H | B7 | CF$_3$ | Cl | Me |
| 2-pyridyl | H | B2 | Cl | H | H |
| 2-pyridyl | H | B3 | Cl | H | H |
| 2-pyridyl | H | B4 | Cl | H | H |

TABLE 4-continued

| | | | | | |
|---|---|---|---|---|---|
| 2-pyridyl | H | B5 | Cl | H | H |
| 2-pyridyl | H | B6 | Cl | H | H |
| 2-pyridyl | H | B7 | Cl | H | H |
| 2-pyridyl | H | B8 | Cl | H | H |
| 2-pyridyl | H | B9 | Cl | H | H |
| 2-pyridyl | H | B10 | Cl | H | H |
| 2-pyridyl | H | B11 | Cl | H | H |
| 2-pyridyl | H | B12 | Cl | H | H |
| 2-pyridyl | H | B13 | Cl | H | H |
| 2-pyridyl | H | B14 | Cl | H | H |
| 2-pyridyl | H | B15 | Cl | H | H |
| 2-pyridyl | H | B16 | Cl | H | H |
| 2-pyridyl | H | B17 | Cl | H | H |
| 2-pyridyl | H | B18 | Cl | H | H |
| 2-pyridyl | H | B19 | Cl | H | H |
| 2-pyridyl | H | B20 | Cl | H | H |
| 2-pyridyl | H | B21 | Cl | H | H |
| 2-pyridyl | H | B22 | Cl | H | H |
| 2-pyridyl | H | B23 | Cl | H | H |
| 2-pyridyl | H | B24 | Cl | H | H |
| 2-pyridyl | H | B25 | Cl | H | H |
| 2-pyridyl | H | B26 | Cl | H | H |
| 2-pyridyl | H | B27 | Cl | H | H |
| 2-pyridyl | H | B28 | Cl | H | H |
| 2-pyridyl | H | B29 | Cl | H | H |
| 2-pyridyl | H | B30 | Cl | H | H |
| 2-pyridyl | H | B31 | Cl | H | H |
| 2-pyridyl | H | B32 | Cl | H | H |
| 2-pyridyl | H | B33 | Cl | H | H |
| 2-pyridyl | H | B34 | Cl | H | H |
| 2-pyridyl | H | Na | Cl | H | H |
| 2-pyridyl | H | K | Cl | H | H |
| 3-pyridyl | H | H | Cl | Cl | Me |
| 3-pyridyl | H | H | $CF_3$ | Cl | Me |
| 3-pyridyl | H | H | Cl | H | H |
| 4-pyridyl | H | H | Cl | Cl | Me |
| 4-pyridyl | H | H | $CF_3$ | Cl | Me |
| 4-pyridyl | H | H | Cl | H | H |
| 2-F—Ph | H | H | Me | Me | Me |
| 2-F—Ph | H | H | Me | Cl | Me |
| 2-F—Ph | H | H | Cl | Me | Me |
| 2-F—Ph | H | H | Cl | H | H |
| 2-F—Ph | H | H | Cl | Cl | Me |
| 2-F—Ph | H | B7 | OMe | H | H |
| 2-F—Ph | H | B7 | SMe | H | H |
| 2-F—Ph | H | B7 | $CF_3$ | Cl | Me |
| 2-F—Ph | H | B7 | $CF_3$ | H | Me |
| 2-F—Ph | H | B1 | Cl | Cl | Me |
| 2-F—Ph | H | B3 | Cl | Cl | Me |
| 2-F—Ph | H | B6 | Cl | Cl | Me |
| 2-F—Ph | H | B7 | Cl | Cl | Me |
| 2-F—Ph | H | B3 | $CF_3$ | Cl | Me |
| 2-F—Ph | H | B6 | $CF_3$ | Cl | Me |
| 2-F—Ph | H | B7 | $CF_3$ | Cl | Me |
| 2-F—Ph | H | B7 | Cl | H | H |
| 3-F—Ph | H | H | Cl | Cl | Me |
| 4-F—Ph | H | H | Cl | Cl | Me |
| 2,3-$F_2$—Ph | H | H | Cl | Cl | Me |
| 2,4-$F_2$—Ph | H | H | Cl | Cl | Me |
| 2,5-$F_2$—Ph | H | H | Cl | Cl | Me |
| Ph | H | H | Me | Me | Me |
| Ph | H | H | Me | Cl | Me |
| Ph | H | H | Cl | Me | Me |
| Ph | H | H | Cl | H | H |
| Ph | H | H | Cl | Cl | Me |
| Ph | H | B7 | OMe | H | H |
| Ph | H | B7 | SMe | H | H |
| Ph | H | H | $CF_3$ | Cl | Me |
| Ph | H | H | $CF_3$ | H | Me |
| Ph | H | B1 | Cl | Cl | Me |
| Ph | H | B3 | Cl | Cl | Me |
| Ph | H | B6 | Cl | Cl | Me |
| Ph | H | B7 | Cl | Cl | Me |
| Ph | H | B3 | $CF_3$ | Cl | Me |
| Ph | H | B6 | $CF_3$ | Cl | Me |
| Ph | H | B7 | $CF_3$ | Cl | Me |
| Ph | Me | B7 | $CF_3$ | Cl | Me |
| Ph | H | B7 | Cl | H | H |
| 3,4-$F_2$—Ph | H | H | Cl | Cl | Me |
| 3,5-$F_2$—Ph | H | H | Cl | Cl | Me |
| 2-Cl—Ph | H | H | Me | Me | Me |
| 2-Cl—Ph | H | H | Me | Cl | Me |
| 2-Cl—Ph | H | H | Cl | Me | Me |
| 2-Cl—Ph | H | H | Cl | H | H |
| 2-Cl—Ph | H | H | Cl | Cl | Me |
| 2-Cl—Ph | H | H | OMe | H | H |
| 2-Cl—Ph | H | H | SMe | H | H |
| 2-Cl—Ph | H | H | $CF_3$ | Cl | Me |
| 2-Cl—Ph | H | H | $CF_3$ | H | Me |
| 2-Cl—Ph | H | B1 | Cl | Cl | Me |
| 2-Cl—Ph | H | B3 | Cl | Cl | Me |
| 2-Cl—Ph | H | B6 | Cl | Cl | Me |
| 2-Cl—Ph | H | B7 | Cl | Cl | Me |
| 2-Cl—Ph | H | B3 | $CF_3$ | Cl | Me |
| 2-Cl—Ph | H | B6 | $CF_3$ | Cl | Me |
| 2-Cl—Ph | H | B7 | $CF_3$ | Cl | Me |
| 2-Cl—Ph | H | B7 | Cl | H | H |
| 3-Cl—Ph | H | H | Cl | Cl | Me |
| 4-Cl—Ph | H | H | Cl | Cl | Me |
| 2,3-$Cl_2$—Ph | H | H | Cl | Cl | Me |
| 2,4-$Cl_2$—Ph | H | H | Cl | Cl | 4Me |
| 2,5-$Cl_2$—Ph | H | H | Cl | Cl | Me |
| 2,6-$Cl_2$—Ph | H | H | Me | Me | Me |
| 2,6-$Cl_2$—Ph | H | H | Me | Cl | Me |
| 2,6-$Cl_2$—Ph | H | H | Cl | Me | Me |
| 2,6-$Cl_2$—Ph | H | H | Cl | H | H |
| 2,6-$Cl_2$—Ph | H | H | Cl | Cl | Me |
| 2,6-$Cl_2$—Ph | H | B7 | OMe | H | H |
| 2,6-$Cl_2$—Ph | H | B7 | SMe | H | H |
| 2,6-$Cl_2$—Ph | H | H | $CF_3$ | Cl | Me |
| 2,6-$Cl_2$—Ph | H | H | $CF_3$ | H | Me |
| 2,6-$Cl_2$—Ph | H | B1 | Cl | Cl | Me |
| 2,6-$Cl_2$—Ph | H | B3 | Cl | Cl | Me |
| 2,6-$Cl_2$—Ph | H | B6 | Cl | Cl | Me |
| 2,6-$Cl_2$—Ph | H | B7 | Cl | Cl | Me |
| 2,6-$Cl_2$—Ph | Cl | B7 | Cl | Cl | Me |
| 2,6-$Cl_2$—Ph | H | B3 | $CF_3$ | Cl | Me |
| 2,6-$Cl_2$—Ph | H | B6 | $CF_3$ | Cl | Me |
| 2,6-$Cl_2$—Ph | H | B7 | $CF_3$ | Cl | Me |
| 2,6-$Cl_2$—Ph | Cl | B7 | $CF_3$ | Cl | Me |
| 2,6-$Cl_2$—Ph | H | B7 | Cl | H | H |
| 3,4-$Cl_2$—Ph | H | H | Cl | Cl | Me |
| 3,5-$Cl_2$—Ph | H | H | Cl | Cl | Me |
| 2-Me—Ph | H | H | Cl | Cl | Me |
| 2-Me—Ph | H | H | $CF_3$ | Cl | Me |
| 2,6-$Me_2$—Ph | H | H | Cl | Cl | Me |
| 2,6-$Me_2$—Ph | H | H | $CF_3$ | Cl | Me |
| 2-MeO—Ph | H | H | Cl | Cl | Me |
| 2-MeO—Ph | H | H | $CF_3$ | Cl | Me |
| 2-$CF_3$O—Ph | H | H | Cl | Cl | Me |
| 2-$CF_3$O—Ph | H | H | $CF_3$ | Cl | Me |
| 2-SMe—Ph | H | H | Cl | Cl | Me |
| 2-SMe—Ph | H | H | $CF_3$ | Cl | Me |
| 2-SOMe—Ph | H | H | Cl | Cl | Me |
| 2-SOMe—Ph | H | H | $CF_3$ | Cl | Me |
| 2-$SO_2$Me—Ph | H | H | Cl | Cl | Me |
| 2-$SO_2$Me—Ph | H | H | $CF_3$ | Cl | Me |
| 2-$CF_3$-Ph | H | H | Cl | Cl | Me |
| 2-$CF_3$-Ph | H | H | $CF_3$ | Cl | Me |
| 2-$NO_2$-Ph | H | H | Cl | Cl | Me |
| 2-$NO_2$-Ph | H | H | $CF_3$ | Cl | Me |
| 2-CN—Ph | H | H | Cl | Cl | Me |
| 2-CN—Ph | H | H | $CF_3$ | Cl | Me |
| 2-NHMe—Ph | H | H | Cl | Cl | Me |
| 2-$NMe_2$—Ph | H | H | Cl | Cl | Me |
| 4-benzyl-Ph | H | H | Cl | Cl | Me |
| 4-phenoxy-Ph | H | H | Cl | Cl | Me |
| 2-OH—Ph | H | H | Cl | Cl | Me |
| 2-$CO_2$Me—Ph | H | H | Cl | Cl | Me |
| 2-$CO_2$Me—Ph | H | H | $CF_3$ | Cl | Me |
| 2-$CO_2$Et—Ph | H | H | Cl | Cl | Me |
| 2-$CO_2$Et—Ph | H | H | $CF_3$ | Cl | Me |
| H | H | H | Cl | Cl | Me |
| Me | H | H | Cl | Cl | Me |
| Et | H | H | Cl | Cl | Me |
| nPr | H | H | Cl | Cl | Me |
| iPr | H | H | Cl | Cl | Me |
| iPr | H | H | $CF_3$ | Cl | Me |

TABLE 4-continued

| | | | | | |
|---|---|---|---|---|---|
| nBu | H | H | Cl | Cl | Me |
| nBu | H | H | CF$_3$ | Cl | Me |
| iBu | H | H | Cl | Cl | Me |
| iBu | H | H | CF$_3$ | Cl | Me |
| iBu | H | B7 | Cl | Cl | Me |
| iBu | H | B7 | CF$_3$ | Cl | Me |
| iBu | H | H | Cl | H | H |
| secBu | H | H | Cl | Cl | Me |
| secBu | H | H | CF$_3$ | Cl | Me |
| 2,2-Me$_2$-propyl | H | H | Cl | Cl | Me |
| nHex | H | H | Cl | Cl | Me |
| ethenyl | H | H | Cl | Cl | Me |
| 1-propenyl | H | H | Cl | Cl | Me |
| 1-propenyl | H | H | CF$_3$ | Cl | Me |
| ethynyl | H | H | Cl | Cl | Me |
| 1-propynyl | H | H | Cl | Cl | Me |
| CF$_3$ | H | H | Cl | Cl | Me |
| CF$_3$ | H | H | CF$_3$ | Cl | Me |
| CHF$_2$ | H | H | Cl | Cl | Me |
| C$_2$F$_5$ | H | H | Cl | Cl | Me |
| 2,2-Cl$_2$-cPr | H | H | Cl | Cl | Me |
| 2,2-Cl$_2$-cPr | H | H | CF$_3$ | Cl | Me |
| cPr | H | H | Cl | Cl | Me |
| cPr | H | H | CF$_3$ | Cl | Me |
| 1-Me-cPr | H | H | Cl | Cl | Me |
| 1-Me-cPr | H | H | CF$_3$ | Cl | Me |
| cHex | H | H | Cl | Cl | Me |
| cHex | H | H | CF$_3$ | Cl | Me |
| CH$_2$Ph | H | H | Cl | Cl | Me |
| naphthyl-1 | H | H | Cl | Cl | Me |
| naphthyl-1 | H | H | CF$_3$ | Cl | Me |
| naphthyl-2 | H | H | Cl | Cl | Me |
| CO$_2$Me | H | H | Cl | Cl | Me |
| CO$_2$Et | H | H | Cl | Cl | Me |
| 2-thienyl | H | H | Cl | Cl | Me |
| 2-thienyl | H | H | CF$_3$ | Cl | Me |
| CH$_2$OMe | H | H | Cl | Cl | Me |
| CH$_2$OEt | H | H | Cl | Cl | Me |
| COCH$_3$ | H | H | Cl | Cl | Me |
| COtBu | H | H | Cl | Cl | Me |
| COPh | H | H | Cl | Cl | Me |

TABLE 5

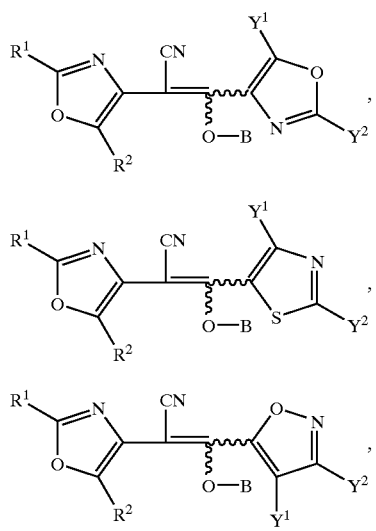

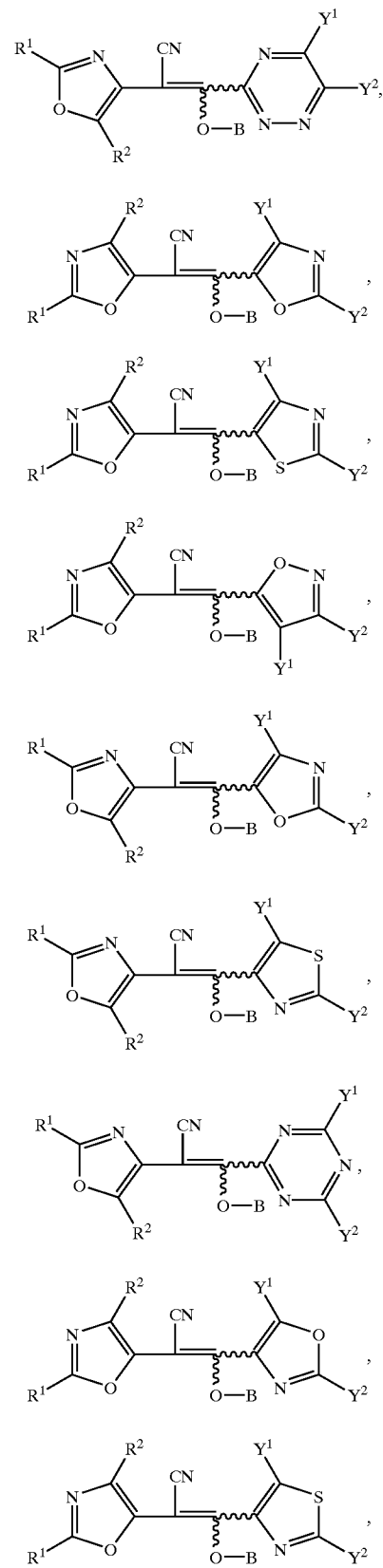

TABLE 5-continued
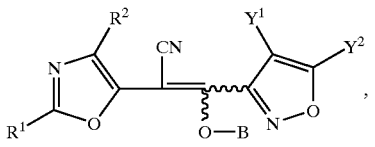
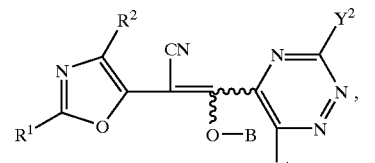
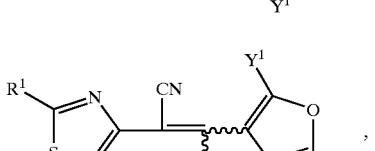
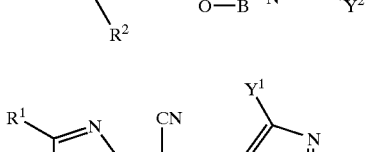
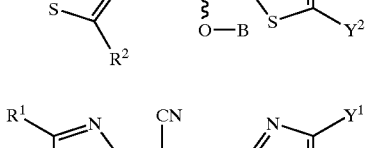
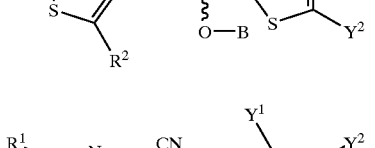
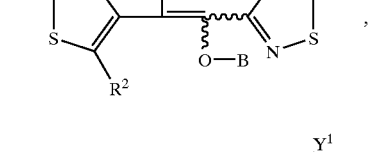
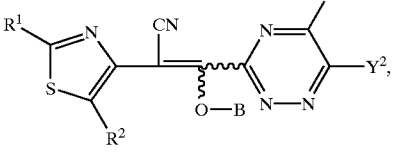
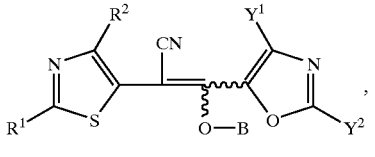
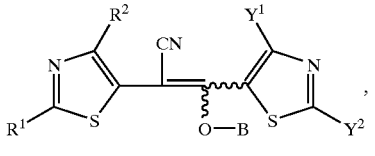
TABLE 5-continued
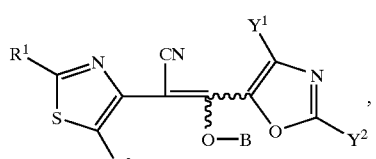
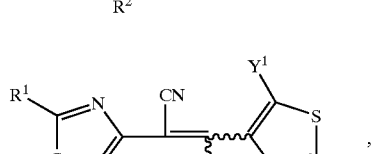
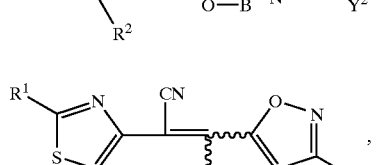
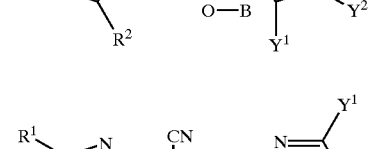
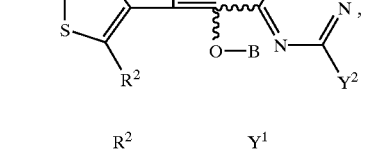
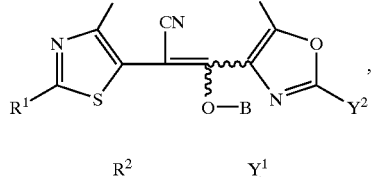
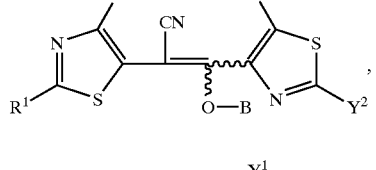
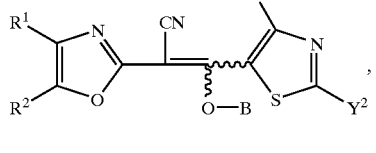
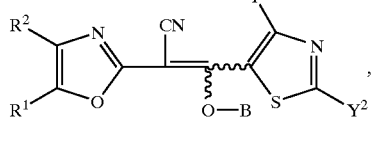
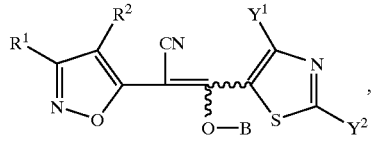

TABLE 5-continued

| R¹ | R² | B | Y¹ | Y² |
|---|---|---|---|---|
| 2,6-F₂-Ph | H | H | Me | H |
| 2,6-F₂-Ph | H | H | Me | Me |
| 2,6-F₂-Ph | H | H | Et | Me |
| 2,6-F₂-Ph | Me | H | Et | Me |
| 2,6-F₂-Ph | H | H | Cl | Cl |
| 2,6-F₂-Ph | H | H | Cl | Me |
| 2,6-F₂-Ph | H | H | Cl | CF₃ |
| 2,6-F₂-Ph | H | H | Me | Cl |
| 2,6-F₂-Ph | H | H | Br | Me |
| 2,6-F₂-Ph | H | H | Me | CF₃ |
| 2,6-F₂-Ph | H | H | OMe | Me |
| 2,6-F₂-Ph | H | H | OCF₃ | Me |
| 2,6-F₂-Ph | H | H | SMe | Me |
| 2,6-F₂-Ph | H | H | CO₂Me | Me |
| 2,6-F₂-Ph | H | H | CO₂Et | Me |
| 2,6-F₂-Ph | H | H | CF₃ | Me |
| 2,6-F₂-Ph | H | H | CF₃ | H |
| 2,6-F₂-Ph | H | H | CF₃ | Br |
| 2,6-F₂-Ph | H | H | CF₃ | NO₂ |
| 2,6-F₂-Ph | H | H | CF₃ | CN |
| 2,6-F₂-Ph | H | H | CF₃ | NHMe |
| 2,6-F₂-Ph | H | H | CF₃ | NMe₂ |
| 2,6-F₂-Ph | H | H | CF₃ | CO₂Me |
| 2,6-F₂-Ph | H | B3 | CF₃ | Me |
| 2,6-F₂-Ph | H | B6 | CF₃ | Me |
| 2,6-F₂-Ph | H | B7 | CF₃ | Me |
| tBu | H | H | Me | Me |
| tBu | H | H | Et | Me |
| tBu | H | H | Cl | Cl |
| tBu | H | H | Cl | Me |
| tBu | H | H | Me | Cl |
| tBu | H | H | Cl | CF₃ |
| tBu | H | H | Br | Me |
| tBu | H | H | Me | Br |
| tBu | H | H | Me | CF₃ |
| tBu | H | H | OMe | Me |
| tBu | H | H | OCF₃ | Me |
| tBu | H | H | SMe | Me |
| tBu | H | H | CO₂Me | Me |
| tBu | H | H | CO₂Et | Me |
| tBu | H | H | CF₃ | Me |
| tBu | H | H | CF₃ | H |
| tBu | H | H | CF₃ | Br |
| tBu | H | H | CF₃ | NO₂ |
| tBu | H | B2 | CF₃ | Me |
| tBu | H | B3 | CF₃ | Me |
| tBu | H | B4 | CF₃ | Me |
| tBu | H | B5 | CF₃ | Me |
| tBu | H | B6 | CF₃ | Me |
| tBu | H | B7 | CF₃ | Me |
| tBu | H | B8 | CF₃ | Me |
| tBu | H | B9 | CF₃ | Me |
| tBu | H | B10 | CF₃ | Me |
| tBu | H | B11 | CF₃ | Me |
| tBu | H | B14 | CF₃ | Me |
| tBu | H | B20 | CF₃ | Me |
| tBu | H | B23 | CF₃ | Me |
| tBu | H | B24 | CF₃ | Me |
| tBu | H | B25 | CF₃ | Me |

TABLE 5-continued

| | | | | |
|---|---|---|---|---|
| tBu | H | B26 | CF$_3$ | Me |
| tBu | H | B28 | CF$_3$ | Me |
| tBu | H | B30 | CF$_3$ | Me |
| tBu | H | B31 | CF$_3$ | Me |
| tBu | H | B32 | CF$_3$ | Me |
| tBu | H | B33 | CF$_3$ | Me |
| tBu | H | B34 | CF$_3$ | Me |
| tBu | H | Na | CF$_3$ | Me |
| tBu | H | K | CF$_3$ | Me |
| 2-pyridyl | H | H | Me | Me |
| 2-pyridyl | H | H | Et | Me |
| 2-pyridyl | H | H | Cl | Cl |
| 2-pyridyl | H | H | Cl | Me |
| 2-pyridyl | H | H | Me | Cl |
| 2-pyridyl | H | H | Br | Me |
| 2-pyridyl | H | H | Me | CF$_3$ |
| 2-pyridyl | H | H | CO$_2$Me | Me |
| 2-pyridyl | H | H | CO$_2$Et | Me |
| 2-pyridyl | H | H | CF$_3$ | Me |
| 2-pyridyl | H | H | CF$_3$ | Br |
| 2-pyridyl | H | H | CF$_3$ | NO$_2$ |
| 2-pyridyl | H | H | CF$_3$ | CN |
| 2-pyridyl | H | H | CF$_3$ | NMe$_2$ |
| 2-pyridyl | H | B3 | CF$_3$ | Me |
| 2-pyridyl | H | B6 | CF$_3$ | Me |
| 2-pyridyl | H | B7 | CF$_3$ | Me |
| 3-pyridyl | H | H | Et | Me |
| 3-pyridyl | H | H | CF$_3$ | Me |
| 4-pyridyl | H | H | Et | Me |
| 4-pyridyl | H | H | CF$_3$ | Me |
| 2-F-Ph | H | H | Me | Me |
| 2-F-Ph | H | H | Et | Me |
| 2-F-Ph | H | H | CF$_3$ | Me |
| 2-F-Ph | H | H | CF$_3$ | Cl |
| 2-F-Ph | H | H | CF$_3$ | H |
| 2-F-Ph | H | B3 | CF$_3$ | Me |
| 2-F-Ph | H | B6 | CF$_3$ | Me |
| 2-F-Ph | H | B7 | CF$_3$ | Me |
| 3-F-Ph | H | H | Et | Me |
| 3-F-Ph | H | H | CF$_3$ | Me |
| 4-F-Ph | H | H | Et | Me |
| 2,3-F$_2$-Ph | H | H | Et | Me |
| 2,4-F$_2$-Ph | H | H | Et | Me |
| 2,5-F$_2$-Ph | H | H | Et | Me |
| Ph | H | H | Me | Me |
| Ph | H | H | Et | Me |
| Ph | H | H | CF$_3$ | Me |
| Ph | H | H | CF$_3$ | Cl |
| Ph | H | H | CF$_3$ | H |
| Ph | H | B3 | CF$_3$ | Me |
| Ph | H | B6 | CF$_3$ | Me |
| Ph | H | B7 | CF$_3$ | Me |
| 3,4-F$_2$-Ph | H | H | Et | Me |
| 3,5-F$_2$-Ph | H | H | Et | Me |
| 2-Cl-Ph | H | H | Me | Me |
| 2-Cl-Ph | H | H | Et | Me |
| 2-Cl-Ph | H | H | CF$_3$ | Me |
| 2-Cl-Ph | H | H | CF$_3$ | Cl |
| 2-Cl-Ph | H | H | CF$_3$ | H |
| 2-Cl-Ph | H | B3 | CF$_3$ | Me |
| 2-Cl-Ph | H | B6 | CF$_3$ | Me |
| 2-Cl-Ph | H | B7 | CF$_3$ | Me |
| 3-Cl-Ph | H | H | CF$_3$ | Me |
| 4-Cl-Ph | H | H | CF$_3$ | Me |
| 2,3-Cl$_2$-Ph | H | H | CF$_3$ | Me |
| 2,4-Cl$_2$-Ph | H | H | CF$_3$ | Me |
| 2,5-Cl$_2$-Ph | H | H | CF$_3$ | Me |
| 2,6-Cl$_2$-Ph | H | H | Me | Me |
| 2,6-Cl$_2$-Ph | H | H | Et | Me |
| 2,6-Cl$_2$-Ph | H | H | CF$_3$ | Me |
| 2,6-Cl$_2$-Ph | H | H | CF$_3$ | Cl |
| 2,6-Cl$_2$-Ph | H | H | CF$_3$ | H |
| 2,6-Cl$_2$-Ph | H | B3 | CF$_3$ | Me |
| 2,6-Cl$_2$-Ph | H | B6 | CF$_3$ | Me |
| 2,6-Cl$_2$-Ph | H | B7 | CF$_3$ | Me |
| 3,4-Cl$_2$-Ph | H | H | CF$_3$ | Me |
| 3,5-Cl$_2$-Ph | H | H | CF$_3$ | Me |
| 2-Me-Ph | H | H | Et | Me |
| 2-Me-Ph | H | H | CF$_3$ | Me |
| 2,6-Me$_2$-Ph | H | H | Et | Me |
| 2,6-Me$_2$-Ph | H | H | CF$_3$ | Me |
| 2-MeO-Ph | H | H | Et | Me |
| 2-MeO-Ph | H | H | CF$_3$ | Me |
| 2-CF$_3$O-Ph | H | H | Et | Me |
| 2-CF$_3$O-Ph | H | H | CF$_3$ | Me |
| 2-SMe-Ph | H | H | Et | Me |
| 2-SMe-Ph | H | H | CF$_3$ | Me |
| 2-SOMe-Ph | H | H | Et | Me |
| 2-SOMe-Ph | H | H | CF$_3$ | Me |
| 2-SO$_2$Me-Ph | H | H | Et | Me |
| 2-SO$_2$Me-Ph | H | H | CF$_3$ | Me |
| 2-CF$_3$-Ph | H | H | Et | Me |
| 2-CF$_3$-Ph | H | H | CF$_3$ | Me |
| 2-NO$_2$-Ph | H | H | Et | Me |
| 2-NO$_2$-Ph | H | H | CF$_3$ | Me |
| 2-CN-Ph | H | H | Et | Me |
| 2-NHMe-Ph | H | H | CF$_3$ | Me |
| 2-NMe$_2$-Ph | H | H | Et | Me |
| 2-NMe$_2$-Ph | H | H | CF$_3$ | Me |
| 4-benzyl-Ph | H | H | CF$_3$ | Me |
| 4-phenoxy-Ph | H | H | CF$_3$ | Me |
| 2-OH-Ph | H | H | CF$_3$ | Me |
| 2-CO$_2$Me-Ph | H | H | Et | Me |
| 2-CO$_2$Me-Ph | H | H | CF$_3$ | Me |
| 2-CO$_2$Et-Ph | H | H | Et | Me |
| 2-CO$_2$Et-Ph | H | H | CF$_3$ | Me |
| H | H | H | CF$_3$ | Me |
| Me | H | H | CF$_3$ | Me |
| Et | H | H | CF$_3$ | Me |
| nPr | H | H | CF$_3$ | Me |
| iPr | H | H | Et | Me |
| iPr | H | H | CF$_3$ | Me |
| nBu | H | H | Et | Me |
| nBu | H | H | CF$_3$ | Me |
| iBu | H | H | Et | Me |
| iBu | H | H | CF$_3$ | Me |
| iBu | H | B7 | Et | Me |
| iBu | H | B7 | CF$_3$ | Me |
| secBu | H | H | Et | Me |
| secBu | H | H | CF$_3$ | Me |
| 2,2-Me$_2$-propyl | H | H | CF$_3$ | Me |
| nHex | H | H | CF$_3$ | Me |
| ethenyl | H | H | CF$_3$ | Me |
| 1-propenyl | H | H | Et | Me |
| 1-propenyl | H | H | CF$_3$ | Me |
| ethynyl | H | H | CF$_3$ | Me |
| 1-propynyl | H | H | CF$_3$ | Me |
| CF$_3$ | H | H | Et | Me |
| CF$_3$ | H | H | CF$_3$ | Me |
| CHF$_2$ | H | H | Et | Me |
| C$_2$F$_5$ | H | H | Et | Me |
| 2,2-Cl$_2$-cPr | H | H | Et | Me |
| 2,2-Cl$_2$-cPr | H | H | CF$_3$ | Me |
| cPr | H | H | Et | Me |
| cPr | H | H | CF$_3$ | Me |
| 1-Me-cPr | H | H | Et | Me |
| 1-Me-cPr | H | H | CF$_3$ | Me |
| cHex | H | H | Et | Me |
| cHex | H | H | CF$_3$ | Me |
| CH$_2$Ph | H | H | CF$_3$ | Me |
| 1-naphthyl | H | H | Et | Me |
| 1-naphthyl | H | H | CF$_3$ | Me |
| 2-naphthyl | H | H | CF$_3$ | Me |
| CO$_2$Me | H | H | CF$_3$ | Me |
| CO$_2$Et | H | H | CF$_3$ | Me |
| 2-thienyl | H | H | CF$_3$ | Me |

TABLE 6

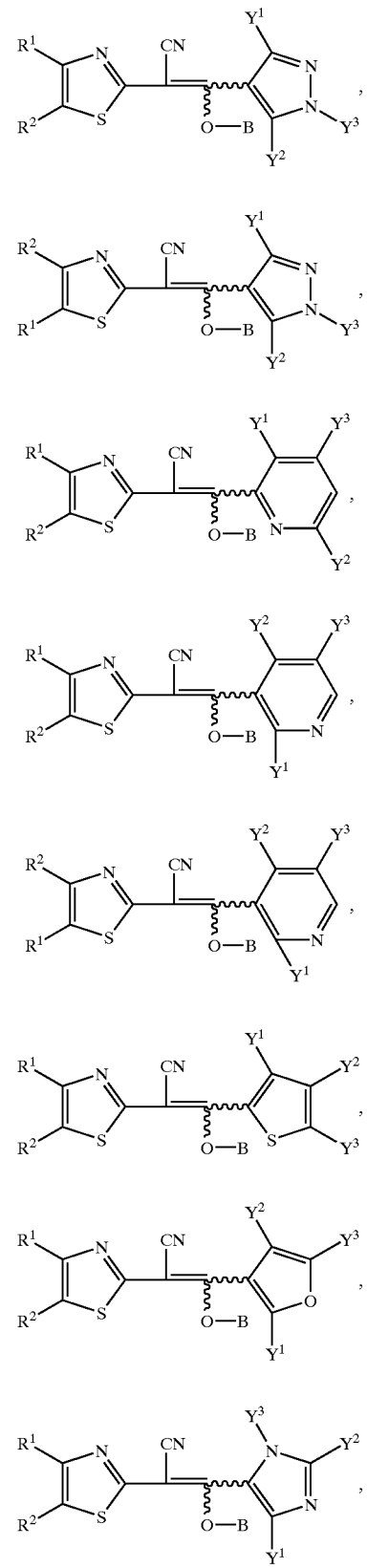

TABLE 6-continued

| R¹ | R² | B | Y¹ | Y² | Y³ |
|---|---|---|---|---|---|
| 2,6-F₂—Ph | H | B7 | H | CF₃ | Me |
| 2,6-F₂—Ph | H | B7 | Me | H | Me |
| 2,6-F₂—Ph | H | B7 | Me | H | CF₃ |
| 2,6-F₂—Ph | H | B7 | Me | H | H |
| 2,6-F₂—Ph | H | B7 | Me | Me | Me |
| 2,6-F₂—Ph | H | B7 | Me | Cl | Me |
| 2,6-F₂—Ph | H | B7 | Me | Br | Me |
| 2,6-F₂—Ph | H | B7 | Et | Me | Me |
| 2,6-F₂—Ph | H | B7 | Cl | Me | Me |
| 2,6-F₂—Ph | H | B7 | Cl | H | Me |
| 2,6-F₂—Ph | H | B7 | Cl | H | CF₃ |
| 2,6-F₂—Ph | H | B7 | Cl | H | H |
| 2,6-F₂—Ph | H | B7 | Cl | Cl | CF₃ |
| 2,6-F₂—Ph | H | B7 | Cl | Cl | CF₂H |
| 2,6-F₂—Ph | H | B7 | Cl | Cl | CH₂OMe |
| 2,6-F₂—Ph | H | B7 | Cl | Cl | COMe |
| 2,6-F₂—Ph | H | B7 | Cl | CF₃ | Me |
| 2,6-F₂—Ph | H | B7 | Br | Me | Me |
| 2,6-F₂—Ph | H | B7 | Me | OMe | Me |
| 2,6-F₂—Ph | H | B7 | OMe | H | H |
| 2,6-F₂—Ph | H | B7 | OCF₃ | H | H |
| 2,6-F₂—Ph | H | B7 | SMe | H | H |
| 2,6-F₂—Ph | H | B7 | CF₃ | Me | Me |
| 2,6-F₂—Ph | H | B7 | CF₃ | Cl | CF₃ |
| 2,6-F₂—Ph | H | B7 | CF₃ | Cl | CF₂H |
| 2,6-F₂—Ph | H | B7 | CF₃ | Cl | CH₂OMe |
| 2,6-F₂—Ph | H | B7 | CF₃ | H | Me |
| 2,6-F₂—Ph | H | B7 | CF₃ | Br | Me |
| 2,6-F₂—Ph | H | B7 | CF₃ | NO₂ | Me |
| 2,6-F₂—Ph | H | B7 | CF₃ | CN | Me |
| 2,6-F₂—Ph | H | B7 | CF₃ | NHMe | Me |
| 2,6-F₂—Ph | H | B7 | CF₃ | NMe₂ | Me |
| 2,6-F₂—Ph | H | B7 | CF₃ | CO₂Me | Me |
| 2,6-F₂—Ph | H | B7 | CF₃ | OMe | Me |
| 2,6-F₂—Ph | H | B7 | CF₃ | OCF₂H | CF₂H |
| 2,6-F₂—Ph | H | B7 | Cl | NO₂ | Me |
| 2,6-F₂—Ph | H | B7 | Cl | CN | Me |
| 2,6-F₂—Ph | H | B7 | CO₂Me | Me | Me |
| 2,6-F₂—Ph | H | B1 | Cl | Cl | Me |
| 2,6-F₂—Ph | Me | B1 | Cl | Cl | Me |
| 2,6-F₂—Ph | H | B3 | Cl | Cl | Me |
| 2,6-F₂—Ph | H | B4 | Cl | Cl | Me |
| 2,6-F₂—Ph | H | B5 | Cl | Cl | Me |
| 2,6-F₂—Ph | H | B6 | Cl | Cl | Me |
| 2,6-F₂—Ph | H | B7 | Cl | Cl | Me |
| 2,6-F₂—Ph | Me | B7 | Cl | Cl | Me |
| 2,6-F₂—Ph | H | B2 | CF₃ | Cl | Me |
| 2,6-F₂—Ph | H | B3 | CF₃ | Cl | Me |
| 2,6-F₂—Ph | H | B4 | CF₃ | Cl | Me |

TABLE 6-continued

| | | | | | |
|---|---|---|---|---|---|
| 2,6-F$_2$—Ph | H | B5 | CF$_3$ | Cl | Me |
| 2,6-F$_2$—Ph | H | B6 | CF$_3$ | Cl | Me |
| 2,6-F$_2$—Ph | H | B7 | CF$_3$ | Cl | Me |
| 2,6-F$_2$—Ph | Me | B7 | CF$_3$ | Cl | Me |
| 2,6-F$_2$—Ph | H | B8 | CF$_3$ | Cl | Me |
| 2,6-F$_2$—Ph | H | B9 | CF$_3$ | Cl | Me |
| 2,6-F$_2$—Ph | H | B10 | CF$_3$ | Cl | Me |
| 2,6-F$_2$—Ph | H | B11 | CF$_3$ | Cl | Me |
| 2,6-F$_2$—Ph | H | B12 | CF$_3$ | Cl | Me |
| 2,6-F$_2$—Ph | H | B13 | CF$_3$ | Cl | Me |
| 2,6-F$_2$—Ph | H | B14 | CF$_3$ | Cl | Me |
| 2,6-F$_2$—Ph | H | B15 | CF$_3$ | Cl | Me |
| 2,6-F$_2$—Ph | H | B16 | CF$_3$ | Cl | Me |
| 2,6-F$_2$—Ph | H | B17 | CF$_3$ | Cl | Me |
| 2,6-F$_2$—Ph | H | B18 | CF$_3$ | Cl | Me |
| 2,6-F$_2$—Ph | H | B19 | CF$_3$ | Cl | Me |
| 2,6-F$_2$—Ph | H | B20 | CF$_3$ | Cl | Me |
| 2,6-F$_2$—Ph | H | B21 | CF$_3$ | Cl | Me |
| 2,6-F$_2$—Ph | H | B22 | CF$_3$ | Cl | Me |
| 2,6-F$_2$—Ph | H | B23 | CF$_3$ | Cl | Me |
| 2,6-F$_2$—Ph | H | B24 | CF$_3$ | Cl | Me |
| 2,6-F$_2$—Ph | H | B25 | CF$_3$ | Cl | Me |
| 2,6-F$_2$—Ph | H | B26 | CF$_3$ | Cl | Me |
| 2,6-F$_2$—Ph | H | B27 | CF$_3$ | Cl | Me |
| 2,6-F$_2$—Ph | H | B28 | CF$_3$ | Cl | Me |
| 2,6-F$_2$—Ph | H | B29 | CF$_3$ | Cl | Me |
| 2,6-F$_2$—Ph | H | B30 | CF$_3$ | Cl | Me |
| 2,6-F$_2$—Ph | H | B31 | CF$_3$ | Cl | Me |
| 2,6-F$_2$—Ph | H | B32 | CF$_3$ | Cl | Me |
| 2,6-F$_2$—Ph | H | B33 | CF$_3$ | Cl | Me |
| 2,6-F$_2$—Ph | H | B34 | CF$_3$ | Cl | Me |
| 2,6-F$_2$—Ph | H | B7 | Cl | H | H |
| 2,6-F$_2$—Ph | H | B9 | Cl | H | H |
| 2,6-F$_2$—Ph | H | B10 | Cl | H | H |
| 2,6-F$_2$—Ph | H | B11 | Cl | H | H |
| 2,6-F$_2$—Ph | H | B45 | CF$_3$ | Cl | Me |
| 2,6-F$_2$—Ph | H | B46 | CF$_3$ | Cl | Me |
| tBu | H | B7 | Me | CF$_3$ | Me |
| tBu | H | B7 | Me | H | Me |
| tBu | H | B7 | Me | H | CF$_3$ |
| tBu | H | B7 | Me | Me | Me |
| tBu | H | B7 | Me | Cl | Me |
| tBu | H | B7 | Me | Br | Me |
| tBu | H | B7 | Et | Me | Me |
| tBu | H | B7 | Cl | Me | Me |
| tBu | H | B7 | Cl | H | Me |
| tBu | H | B7 | Cl | H | CF$_3$ |
| tBu | H | B7 | Cl | Cl | CF$_3$ |
| tBu | H | B7 | Cl | Cl | CF$_2$H |
| tBu | H | B7 | Cl | Cl | CH$_2$OMe |
| tBu | H | B7 | Cl | Cl | COMe |
| tBu | H | B7 | Cl | CF$_3$ | Me |
| tBu | H | B7 | Br | Me | Me |
| tBu | H | B7 | Me | OMe | Me |
| tBu | H | B7 | OMe | H | H |
| tBu | H | B7 | OCF$_3$ | H | H |
| tBu | H | B7 | SMe | H | H |
| tBu | H | B7 | CF$_3$ | Me | Me |
| tBu | Br | B7 | CF$_3$ | Cl | Me |
| tBu | Me | B7 | CF$_3$ | Cl | Me |
| tBu | CF$_3$ | B7 | CF$_3$ | Cl | Me |
| tBu | NO$_2$ | B7 | CF$_3$ | Cl | Me |
| tBu | CN | B7 | CF$_3$ | Cl | Me |
| tBu | CO$_2$Me | B7 | CF$_3$ | Cl | Me |
| tBu | CO$_2$Et | B7 | CF$_3$ | Cl | Me |
| tBu | H | B7 | CF$_3$ | Cl | CF$_3$ |
| tBu | H | B7 | CF$_3$ | Cl | CF$_2$H |
| tBu | H | B7 | CF$_3$ | Cl | CH$_2$OMe |
| tBu | H | B7 | CF$_3$ | H | Me |
| tBu | H | B7 | CF$_3$ | Br | Me |
| tBu | H | B7 | CF$_3$ | NO$_2$ | Me |
| tBu | H | B7 | CF$_3$ | CN | Me |
| tBu | H | B7 | CF$_3$ | NHMe | Me |
| tBu | H | B7 | CF$_3$ | NMe$_2$ | Me |
| tBu | H | B7 | CF$_3$ | CO$_2$Me | Me |
| tBu | H | B7 | CF$_3$ | OMe | Me |
| tBu | H | B7 | CF$_3$ | OCF$_2$H | CF$_2$H |
| tBu | H | B7 | Cl | NO$_2$ | Me |
| tBu | H | B7 | Cl | CN | Me |
| tBu | H | B7 | CO$_2$Me | Me | Me |
| tBu | H | B1 | Cl | Cl | Me |
| tBu | H | B2 | Cl | Cl | Me |
| tBu | H | B3 | Cl | Cl | Me |
| tBu | H | B4 | Cl | Cl | Me |
| tBu | H | B5 | Cl | Cl | Me |
| tBu | H | B6 | Cl | Cl | Me |
| tBu | H | B7 | Cl | Cl | Me |
| tBu | Me | B7 | Cl | Cl | Me |
| tBu | H | B8 | Cl | Cl | Me |
| tBu | H | B9 | Cl | Cl | Me |
| tBu | H | B10 | Cl | Cl | Me |
| tBu | H | B11 | Cl | Cl | Me |
| tBu | H | B12 | Cl | Cl | Me |
| tBu | H | B13 | Cl | Cl | Me |
| tBu | H | B14 | Cl | Cl | Me |
| tBu | H | B15 | Cl | Cl | Me |
| tBu | H | B16 | Cl | Cl | Me |
| tBu | H | B17 | Cl | Cl | Me |
| tBu | H | B18 | Cl | Cl | Me |
| tBu | H | B19 | Cl | Cl | Me |
| tBu | H | B20 | Cl | Cl | Me |
| tBu | H | B21 | Cl | Cl | Me |
| tBu | H | B22 | Cl | Cl | Me |
| tBu | H | B23 | Cl | Cl | Me |
| tBu | H | B24 | Cl | Cl | Me |
| tBu | H | B25 | Cl | Cl | Me |
| tBu | H | B26 | Cl | Cl | Me |
| tBu | H | B27 | Cl | Cl | Me |
| tBu | H | B28 | Cl | Cl | Me |
| tBu | H | B29 | Cl | Cl | Me |
| tBu | H | B30 | Cl | Cl | Me |
| tBu | H | B31 | Cl | Cl | Me |
| tBu | H | B32 | Cl | Cl | Me |
| tBu | H | B33 | Cl | Cl | Me |
| tBu | H | B34 | Cl | Cl | Me |
| tBu | H | B45 | Cl | Cl | Me |
| tBu | H | B46 | Cl | Cl | Me |
| tBu | H | B2 | CF$_3$ | Cl | Me |
| tBu | H | B3 | CF$_3$ | Cl | Me |
| tBu | H | B4 | CF$_3$ | Cl | Me |
| tBu | H | B5 | CF$_3$ | Cl | Me |
| tBu | H | B6 | CF$_3$ | Cl | Me |
| tBu | H | B7 | CF$_3$ | Cl | Me |
| tBu | H | B8 | CF$_3$ | Cl | Me |
| tBu | H | B9 | CF$_3$ | Cl | Me |
| tBu | H | B10 | CF$_3$ | Cl | Me |
| tBu | H | B11 | CF$_3$ | Cl | Me |
| tBu | H | B12 | CF$_3$ | Cl | Me |
| tBu | H | B13 | CF$_3$ | Cl | Me |
| tBu | H | B14 | CF$_3$ | Cl | Me |
| tBu | H | B15 | CF$_3$ | Cl | Me |
| tBu | H | B16 | CF$_3$ | Cl | Me |
| tBu | H | B17 | CF$_3$ | Cl | Me |
| tBu | H | B18 | CF$_3$ | Cl | Me |
| tBu | H | B19 | CF$_3$ | Cl | Me |
| tBu | H | B20 | CF$_3$ | Cl | Me |
| tBu | H | B21 | CF$_3$ | Cl | Me |
| tBu | H | B22 | CF$_3$ | Cl | Me |
| tBu | H | B23 | CF$_3$ | Cl | Me |
| tBu | H | B24 | CF$_3$ | Cl | Me |
| tBu | H | B25 | CF$_3$ | Cl | Me |
| tBu | H | B26 | CF$_3$ | Cl | Me |
| tBu | H | B27 | CF$_3$ | Cl | Me |
| tBu | H | B28 | CF$_3$ | Cl | Me |
| tBu | H | B29 | CF$_3$ | Cl | Me |
| tBu | H | B30 | CF$_3$ | Cl | Me |
| tBu | H | B31 | CF$_3$ | Cl | Me |
| tBu | H | B32 | CF$_3$ | Cl | Me |
| tBu | H | B33 | CF$_3$ | Cl | Me |
| tBu | H | B34 | CF$_3$ | Cl | Me |
| tBu | H | B35 | CF$_3$ | Cl | Me |
| tBu | H | B43 | CF$_3$ | Cl | Me |
| tBu | H | B7 | Cl | H | H |
| tBu | H | B9 | Cl | H | H |
| tBu | H | B10 | Cl | H | H |
| tBu | H | B11 | Cl | H | H |

TABLE 6-continued

| | | | | | |
|---|---|---|---|---|---|
| 2-pyridyl | H | B7 | H | CF$_3$ | Me |
| 2-pyridyl | H | B7 | Me | H | Me |
| 2-pyridyl | H | B7 | Me | H | CF$_3$ |
| 2-pyridyl | H | B7 | Me | H | H |
| 2-pyridyl | H | B7 | Me | Me | Me |
| 2-pyridyl | H | B7 | Me | Cl | Me |
| 2-pyridyl | H | B7 | Cl | H | Me |
| 2-pyridyl | H | B7 | Cl | H | CF$_3$ |
| 2-pyridyl | H | B7 | OMe | H | H |
| 2-pyridyl | H | B7 | OCF$_3$ | H | H |
| 2-pyridyl | H | B7 | SMe | H | H |
| 2-pyridyl | H | B7 | NO$_2$ | H | H |
| 2-pyridyl | H | B7 | CO$_2$Me | H | H |
| 2-pyridyl | H | B7 | CO$_2$Et | H | H |
| 2-pyridyl | H | B7 | CF$_3$ | Me | Me |
| 2-pyridyl | H | B7 | CF$_3$ | H | Me |
| 2-pyridyl | H | B7 | CF$_3$ | Br | Me |
| 2-pyridyl | H | B3 | Cl | Cl | Me |
| 2-pyridyl | H | B7 | Cl | Cl | Me |
| 2-pyridyl | H | B3 | CF$_3$ | Cl | Me |
| 2-pyridyl | H | B7 | CF$_3$ | Cl | Me |
| 2-pyridyl | H | B3 | Cl | H | H |
| 2-pyridyl | H | B4 | Cl | H | H |
| 2-pyridyl | H | B5 | Cl | H | H |
| 2-pyridyl | H | B6 | Cl | H | H |
| 2-pyridyl | H | B7 | Cl | H | H |
| 2-pyridyl | H | B8 | Cl | H | H |
| 2-pyridyl | H | B9 | Cl | H | H |
| 2-pyridyl | H | B10 | Cl | H | H |
| 2-pyridyl | H | B11 | Cl | H | H |
| 2-pyridyl | H | B20 | Cl | H | H |
| 2-pyridyl | H | B24 | Cl | H | H |
| 2-pyridyl | H | B25 | Cl | H | H |
| 2-pyridyl | H | B26 | Cl | H | H |
| 2-pyridyl | H | B28 | Cl | H | H |
| 2-pyridyl | H | B30 | Cl | H | H |
| 2-pyridyl | H | B31 | Cl | H | H |
| 2-pyridyl | H | B32 | Cl | H | H |
| 2-pyridyl | H | B33 | Cl | H | H |
| 2-pyridyl | H | B43 | Cl | H | H |
| 2-pyridyl | H | B46 | Cl | H | H |
| 3-pyridyl | H | B7 | Cl | Cl | Me |
| 3-pyridyl | H | B7 | Cl | H | H |
| 4-pyridyl | H | B7 | Cl | Cl | Me |
| 4-pyridyl | H | B7 | Cl | H | H |
| 2-F—Ph | H | B7 | Me | Me | Me |
| 2-F—Ph | H | B7 | Me | Cl | Me |
| 2-F—Ph | H | B7 | Cl | Me | Me |
| 2-F—Ph | H | B7 | Cl | H | H |
| 2-F—Ph | H | B7 | OMe | H | H |
| 2-F—Ph | H | B7 | SMe | H | H |
| 2-F—Ph | H | B7 | CF$_3$ | H | Me |
| 2-F—Ph | H | B1 | Cl | Cl | Me |
| 2-F—Ph | H | B3 | Cl | Cl | Me |
| 2-F—Ph | H | B6 | Cl | Cl | Me |
| 2-F—Ph | H | B7 | Cl | Cl | Me |
| 2-F—Ph | H | B3 | CF$_3$ | Cl | Me |
| 2-F—Ph | H | B6 | CF$_3$ | Cl | Me |
| 2-F—Ph | H | B7 | CF$_3$ | Cl | Me |
| 2-F—Ph | H | B7 | Cl | H | H |
| 3-F—Ph | H | B7 | Cl | Cl | Me |
| 4-F—Ph | H | B7 | Cl | Cl | Me |
| 2,3-F$_2$—Ph | H | B7 | CF$_3$ | Cl | Me |
| 2,4-F$_2$—Ph | H | B7 | Cl | Cl | Me |
| 2,5-F$_2$—Ph | H | B7 | Cl | Cl | Me |
| Ph | H | B7 | Me | Me | Me |
| Ph | H | B7 | Me | Cl | Me |
| Ph | H | B7 | Cl | Me | Me |
| Ph | H | B7 | Cl | H | H |
| Ph | H | B7 | OMe | H | H |
| Ph | H | B7 | SMe | H | H |
| Ph | H | B7 | CF$_3$ | H | Me |
| Ph | H | B1 | Cl | Cl | Me |
| Ph | H | B3 | Cl | Cl | Me |
| Ph | H | B6 | Cl | Cl | Me |
| Ph | H | B7 | Cl | Cl | Me |
| Ph | H | B3 | CF$_3$ | Cl | Me |
| Ph | H | B6 | CF$_3$ | Cl | Me |
| Ph | H | B7 | CF$_3$ | Cl | Me |
| Ph | Me | B7 | CF$_3$ | Cl | Me |
| Ph | H | B7 | Cl | H | H |
| 3,4-F$_2$—Ph | H | B7 | Cl | Cl | Me |
| 3,5-F$_2$—Ph | H | B7 | Cl | Cl | Me |
| 2-Cl—Ph | H | B7 | Me | Me | Me |
| 2-Cl—Ph | H | B7 | Me | Cl | Me |
| 2-Cl—Ph | H | B7 | Cl | Me | Me |
| 2-Cl—Ph | H | B7 | Cl | H | H |
| 2-Cl—Ph | H | B7 | OMe | H | H |
| 2-Cl—Ph | H | B7 | SMe | H | H |
| 2-Cl—Ph | H | B7 | CF$_3$ | H | Me |
| 2-Cl—Ph | H | B6 | Cl | Cl | Me |
| 2-Cl—Ph | H | B7 | Cl | Cl | Me |
| 2-Cl—Ph | H | B3 | CF$_3$ | Cl | Me |
| 2-Cl—Ph | H | B6 | CF$_3$ | Cl | Me |
| 2-Cl—Ph | H | B7 | CF$_3$ | Cl | Me |
| 2-Cl—Ph | H | B7 | Cl | H | H |
| 3-Cl—Ph | H | B7 | Cl | Cl | Me |
| 4-Cl—Ph | H | B7 | Cl | Cl | Me |
| 2,3-Cl$_2$—Ph | H | B7 | Cl | Cl | Me |
| 2,4-Cl$_2$—Ph | H | B7 | Cl | Cl | Me |
| 2,5-Cl$_2$—Ph | H | B7 | Cl | Cl | Me |
| 2,6-Cl$_2$—Ph | H | B7 | Me | Me | Me |
| 2,6-Cl$_2$—Ph | H | B7 | Me | Cl | Me |
| 2,6-Cl$_2$—Ph | H | B7 | Cl | Me | Me |
| 2,6-Cl$_2$—Ph | H | B7 | Cl | H | H |
| 2,6-Cl$_2$—Ph | H | B7 | OMe | H | H |
| 2,6-Cl$_2$—Ph | H | B7 | SMe | H | H |
| 2,6-Cl$_2$—Ph | H | B7 | CF$_3$ | H | Me |
| 2,6-Cl$_2$—Ph | H | B1 | Cl | Cl | Me |
| 2,6-Cl$_2$—Ph | H | B3 | Cl | Cl | Me |
| 2,6-Cl$_2$—Ph | H | B6 | Cl | Cl | Me |
| 2,6-Cl$_2$—Ph | H | B7 | Cl | Cl | Me |
| 2,6-Cl$_2$—Ph | Me | B7 | Cl | Cl | Me |
| 2,6-Cl$_2$—Ph | H | B3 | CF$_3$ | Cl | Me |
| 2,6-Cl$_2$—Ph | H | B6 | CF$_3$ | Cl | Me |
| 2,6-Cl$_2$—Ph | H | B7 | CF$_3$ | Cl | Me |
| 2,6-Cl$_2$—Ph | Me | B7 | CF$_3$ | Cl | Me |
| 3,4-Cl$_2$—Ph | H | B7 | Cl | Cl | Me |
| 3,5-Cl$_2$—Ph | H | B7 | Cl | Cl | Me |
| 2-Me—Ph | H | B7 | Cl | Cl | Me |
| 2-Me—Ph | H | B7 | CF$_3$ | Cl | Me |
| 2,6-Me$_2$—Ph | H | B7 | Cl | Cl | Me |
| 2,6-Me$_2$—Ph | H | B7 | CF$_3$ | Cl | Me |
| 2-MeO—Ph | H | B7 | Cl | Cl | Me |
| 2-MeO—Ph | H | B7 | CF$_3$ | Cl | Me |
| 2-CF$_3$O | H | B7 | Cl | Cl | Me |
| 2-CF$_3$O | H | B7 | CF$_3$ | Cl | Me |
| 2-SMe—Ph | H | B7 | Cl | Cl | Me |
| 2-SOMe—Ph | H | B7 | Cl | Cl | Me |
| 2-SO$_2$Me—Ph | H | B7 | Cl | Cl | Me |
| 2-CF$_3$—Ph | H | B7 | Cl | Cl | Me |
| 2-NO$_2$—Ph | H | B7 | Cl | Cl | Me |
| 2-NO$_2$—Ph | H | B9 | Cl | Cl | Me |
| 2-CN—Ph | H | B7 | Cl | Cl | Me |
| 2-NHMe—Ph | H | B7 | Cl | Cl | Me |
| 2-NMe$_2$—Ph | H | B7 | Cl | Cl | Me |
| 4-benzyl-Ph | H | B7 | Cl | Cl | Me |
| 4-phenoxy-Ph | H | B7 | Cl | Cl | Me |
| 4-tBu—Ph | H | B1 | Cl | H | Me |
| 2-OH—Ph | H | B7 | Cl | Cl | Me |
| 2-CO$_2$Me—Ph | H | B7 | Cl | Cl | Me |
| 2-CO$_2$Et—Ph | H | B7 | Cl | Cl | Me |
| H | H | B7 | Cl | Cl | Me |
| Me | H | B7 | Cl | Cl | Me |
| Et | H | B7 | Cl | Cl | Me |
| nPr | H | B7 | Cl | Cl | Me |
| iPr | H | B7 | Cl | Cl | Me |
| iPr | H | B7 | CF$_3$ | Cl | Me |
| nBu | H | B7 | Cl | Cl | Me |
| nBu | H | B7 | CF$_3$ | Cl | Me |
| iBu | H | B7 | Cl | Cl | Me |
| iBu | H | B7 | CF$_3$ | Cl | Me |
| iBu | Me | B7 | Cl | Cl | Me |
| iBu | Me | B7 | CF$_3$ | Cl | Me |
| iBu | H | B7 | Cl | H | H |
| secBu | H | B7 | Cl | Cl | Me |
| secBu | H | B7 | CF$_3$ | Cl | Me |
| pentyl-2 | H | B1 | Cl | Cl | Me |

TABLE 6-continued

| | | | | | |
|---|---|---|---|---|---|
| 2,2-Me$_2$-propyl | H | B7 | Cl | Cl | Me |
| nHex | H | B7 | Cl | Cl | Me |
| ethenyl | H | B7 | Cl | Cl | Me |
| 1-propenyl | H | B7 | Cl | Cl | Me |
| 1-propenyl | H | B7 | CF$_3$ | Cl | Me |
| ethynyl | H | B7 | Cl | Cl | Me |
| 1-propynyl | H | B7 | Cl | Cl | Me |
| CF$_3$ | H | B7 | Cl | Cl | Me |
| CHF$_2$ | H | B7 | Cl | Cl | Me |
| C$_2$F$_5$ | H | B7 | Cl | Cl | Me |
| 2,2-Cl$_2$—cPr | H | B7 | Cl | Cl | Me |
| 2,2-Cl$_2$—cPr | H | B7 | CF$_3$ | Cl | Me |
| cPr | H | B7 | Cl | Cl | Me |
| cPr | H | B7 | CF$_3$ | Cl | Me |
| 1-Me—cPr | H | B7 | Cl | Cl | Me |
| 1-Me—cPr | H | B7 | CF$_3$ | Cl | Me |
| cHex | H | B7 | Cl | Cl | Me |
| cHex | H | B7 | CF$_3$ | Cl | Me |
| CH$_2$Ph | H | B7 | Cl | Cl | Me |
| naphthyl-1 | H | B7 | Cl | Cl | Me |
| naphthyl-1 | H | B7 | CF$_3$ | Cl | Me |
| naphthyl-2 | H | B9 | Cl | H | H |
| naphthyl-2 | H | B7 | Cl | Cl | Me |
| CO$_2$Me | H | B7 | Cl | Cl | Me |
| CO$_2$Et | H | B7 | Cl | Cl | Me |
| 2-thienyl | H | B7 | Cl | Cl | Me |
| 2-thienyl | H | B7 | CF$_3$ | Cl | Me |
| CH$_2$OMe | H | B7 | Cl | Cl | Me |
| CH$_2$OEt | H | B7 | Cl | Cl | Me |
| COCH$_3$ | H | B7 | Cl | Cl | Me |
| COtBu | H | B7 | Cl | Cl | Me |
| COPh | H | B7 | Cl | Cl | Me |

TABLE 7

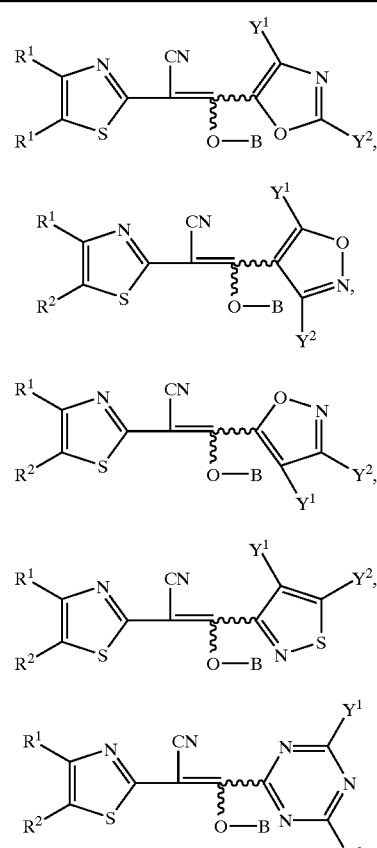

| R$^1$ | R$^2$ | B | Y$^1$ | Y$^2$ |
|---|---|---|---|---|
| Ph | H | B7 | Me | H |
| Ph | H | B7 | Me | Me |
| Ph | H | B7 | Et | Me |
| Ph | Me | B7 | Et | Me |
| Ph | H | B7 | Me | Cl |
| Ph | H | B7 | Cl | Me |
| Ph | H | B7 | Br | Me |
| Ph | H | B7 | Me | Br |
| Ph | H | B7 | Me | CF$_3$ |
| Ph | H | B7 | CF$_3$ | H |
| Ph | H | B7 | CF$_3$ | Br |

TABLE 7-continued

| | | | | |
|---|---|---|---|---|
| Ph | H | B7 | CF$_3$ | NO$_2$ |
| Ph | H | B7 | CF$_3$ | CN |
| Ph | H | B4 | CF$_3$ | Me |
| Ph | H | B7 | CF$_3$ | Me |
| Ph | H | B9 | CF$_3$ | Me |
| tBu | H | B7 | Me | Me |
| tBu | H | B7 | Et | Me |
| tBu | H | B7 | Cl | Cl |
| tBu | H | B7 | Cl | Me |
| tBu | H | B7 | Me | Cl |
| tBu | H | B7 | Cl | CF$_3$ |
| tBu | H | B7 | Br | Me |
| tBu | H | B7 | Me | Br |
| tBu | H | B7 | Me | CF$_3$ |
| tBu | H | B7 | CF$_3$ | Me |
| tBu | H | B7 | CF$_3$ | H |
| tBu | H | B7 | CF$_3$ | Br |
| tBu | H | B7 | CF$_3$ | NO$_2$ |
| tBu | H | B7 | CF$_3$ | CN |
| tBu | H | B4 | CF$_3$ | Me |
| tBu | H | B5 | CF$_3$ | Me |
| tBu | H | B6 | CF$_3$ | Me |
| tBu | H | B7 | CF$_3$ | Me |
| tBu | H | B9 | CF$_3$ | Me |
| tBu | H | B20 | CF$_3$ | Me |
| tBu | H | B24 | CF$_3$ | Me |
| tBu | H | B25 | CF$_3$ | Me |
| tBu | H | B26 | CF$_3$ | Me |
| 2-pyridyl | H | B7 | Me | Me |
| 2-pyridyl | H | B7 | Et | Me |
| 2-pyridyl | H | B7 | Cl | Cl |
| 2-pyridyl | H | B7 | Cl | Me |
| 2-pyridyl | H | B7 | Cl | CF$_3$ |
| 2-pyridyl | H | B7 | Me | Cl |
| 2-pyridyl | H | B7 | Br | Me |
| 2-thienyl | H | B7 | Me | CF$_3$ |
| 2-pyridyl | H | B7 | CF$_3$ | H |
| 2-pyridyl | H | B7 | CF$_3$ | Br |
| 2-pyridyl | H | B7 | CF$_3$ | Me |
| 3-pyridyl | H | B7 | Et | Me |
| 4-pyridyl | H | B7 | CF$_3$ | Me |
| 2-F—Ph | H | B7 | Me | Me |
| 2-F—Ph | H | B7 | Et | Me |
| 2-F—Ph | H | B7 | CF$_3$ | Cl |
| 2-F—Ph | H | B7 | CF$_3$ | H |
| 2-F—Ph | H | B4 | CF$_3$ | Me |
| 2-F—Ph | H | B7 | CF$_3$ | Me |
| 2-F—Ph | H | B9 | CF$_3$ | Me |
| 3-F—Ph | H | B7 | Et | Me |
| 4-F—Ph | H | B7 | Et | Me |
| 2,3-F$_2$—Ph | H | B7 | Et | Me |
| 2,4-F$_2$—Ph | H | B7 | Et | Me |
| 2,5-F$_2$—Ph | H | B7 | Et | Me |
| 2,6-F$_2$—Ph | H | B7 | Me | Me |
| 2,6-F$_2$—Ph | H | B7 | Et | Me |
| 2,6-F$_2$—Ph | H | B7 | CF$_3$ | Cl |
| 2,6-F$_2$—Ph | H | B7 | CF$_3$ | H |
| 2,6-F$_2$—Ph | H | B4 | CF$_3$ | Me |
| 2,6-F$_2$—Ph | H | B7 | CF$_3$ | Me |
| 2,6-F$_2$—Ph | H | B9 | CF$_3$ | Me |
| 3,4-F$_2$—Ph | H | B7 | Et | Me |
| 3,5-F$_2$—Ph | H | B7 | Et | Me |
| 2-Cl—Ph | H | B7 | Me | Me |
| 2-Cl—Ph | H | B7 | Et | Me |
| 2-Cl—Ph | H | B7 | CF$_3$ | Cl |
| 2-Cl—Ph | H | B7 | CF$_3$ | H |
| 2-Cl—Ph | H | B4 | CF$_3$ | Me |
| 2-Cl—Ph | H | B7 | CF$_3$ | Me |
| 2-Cl—Ph | H | B9 | CF$_3$ | Me |
| 3-Cl—Ph | H | B7 | CF$_3$ | Me |
| 4-Cl—Ph | H | B7 | CF$_3$ | Me |
| 2,3-Cl$_2$—Ph | H | B7 | CF$_3$ | Me |
| 2,4-Cl$_2$—Ph | H | B7 | CF$_3$ | Me |
| 2,5-Cl$_2$—Ph | H | B7 | CF$_3$ | Me |
| 2,6-Cl$_2$—Ph | H | B7 | Me | Me |
| 2,6-Cl$_2$—Ph | H | B7 | Et | Me |
| 2,6-Cl$_2$—Ph | H | B7 | CF$_3$ | Cl |
| 2,6-Cl$_2$—Ph | H | B7 | CF$_3$ | H |
| 2,6-Cl$_2$—Ph | H | B4 | CF$_3$ | Me |
| 2,6-Cl$_2$—Ph | H | B7 | CF$_3$ | Me |
| 2,6-Cl$_2$—Ph | H | B9 | CF$_3$ | Me |
| 3,4-Cl$_2$—Ph | H | B7 | CF$_3$ | Me |
| 3,5-Cl$_2$—Ph | H | B7 | CF$_3$ | Me |
| 2-Me—Ph | H | B7 | Et | Me |
| 2-Me—Ph | H | B7 | CF$_3$ | Me |
| 2,6-Me$_2$—Ph | H | B7 | Et | Me |
| 2,6-Me$_2$—Ph | H | B7 | CF$_3$ | Me |
| 2-MeO—Ph | H | B7 | Et | Me |
| 2-MeO—Ph | H | B7 | CF$_3$ | Me |
| 2-CF$_3$O—Ph | H | B7 | CF$_3$ | Me |
| 2-SMe—Ph | H | B7 | CF$_3$ | Me |
| 2-SOMe—Ph | H | B7 | CF$_3$ | Me |
| 2-SO$_2$Me—Ph | H | B7 | CF$_3$ | Me |
| 2-CF$_3$—Ph | H | B7 | CF$_3$ | Me |
| 2-NO$_2$—Ph | H | B7 | CF$_3$ | Me |
| 2-CN—Ph | H | B7 | CF$_3$ | Me |
| 2-NMe$_2$—Ph | H | B7 | CF$_3$ | Me |
| 4-benzyl-Ph | H | B7 | CF$_3$ | Me |
| 4-phenoxy-Ph | H | B7 | CF$_3$ | Me |
| 2-OH—Ph | H | B7 | CF$_3$ | Me |
| 2-CO$_2$Me—Ph | H | B7 | Et | Me |
| 2-CO$_2$Me—Ph | H | B7 | CF$_3$ | Me |
| 2-CO$_2$Et—Ph | H | B7 | Et | Me |
| 2-CO$_2$Et—Ph | H | B7 | CF$_3$ | Me |
| H | H | B7 | CF$_3$ | Me |
| Me | H | B7 | CF$_3$ | Me |
| Et | H | B7 | CF$_3$ | Me |
| nPr | H | B7 | CF$_3$ | Me |
| iPr | H | B7 | Et | Me |
| iPr | H | B7 | CF$_3$ | Me |
| nBu | H | B7 | Et | Me |
| nBu | H | B7 | CF$_3$ | Me |
| iBu | H | B7 | Et | Me |
| iBu | H | B7 | CF$_3$ | Me |
| secBu | H | B7 | Et | Me |
| secBu | H | B7 | CF$_3$ | Me |
| 2,2-Me$_2$-propyl | H | B7 | CF$_3$ | Me |
| nHex | H | B7 | CF$_3$ | Me |
| ethenyl | H | B7 | CF$_3$ | Me |
| 1-propenyl | H | B7 | Et | Me |
| 1-propenyl | H | B7 | CF$_3$ | Me |
| ethynyl | H | B7 | CF$_3$ | Me |
| 1-propynyl | H | B7 | CF$_3$ | Me |
| CF$_3$ | H | B7 | Et | Me |
| CHF$_2$ | H | B7 | CF$_3$ | Me |
| C$_2$F$_5$ | H | B7 | CF$_3$ | Me |
| 2,2-Cl$_2$—cPr | H | B7 | Et | Me |
| 2,2-Cl$_2$—cPr | H | B7 | CF$_3$ | Me |
| cPr | H | B7 | Et | Me |
| cPr | H | B7 | CF$_3$ | Me |
| 1-Me—cPr | H | B7 | Et | Me |
| 1-Me—cPr | H | B7 | CF$_3$ | Me |
| cHex | H | B7 | Et | Me |
| cHex | H | B7 | CF$_3$ | Me |
| CH$_2$Ph | H | B7 | CF$_3$ | Me |
| naphthyl-1 | H | B7 | Et | Me |
| naphthyl-1 | H | B7 | CF$_3$ | Me |
| naphthyl-2 | H | B7 | CF$_3$ | Me |
| CO$_2$Me | H | B7 | CF$_3$ | Me |
| CO$_2$Et | H | B7 | CF$_3$ | Me |
| 2-thienyl | H | B7 | CF$_3$ | Me |

TABLE 8

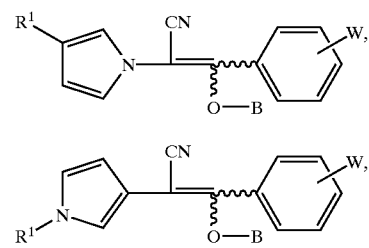

TABLE 8-continued
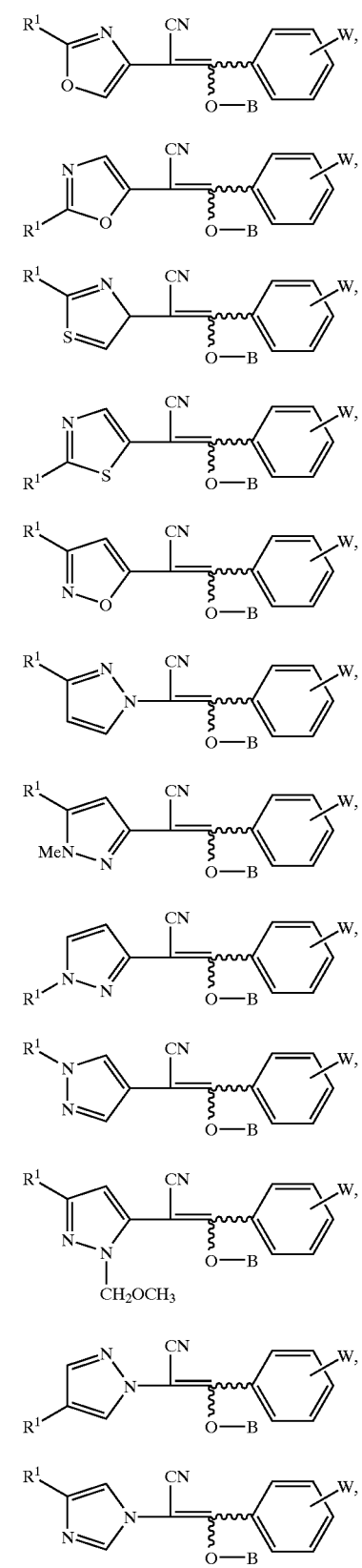
TABLE 8-continued
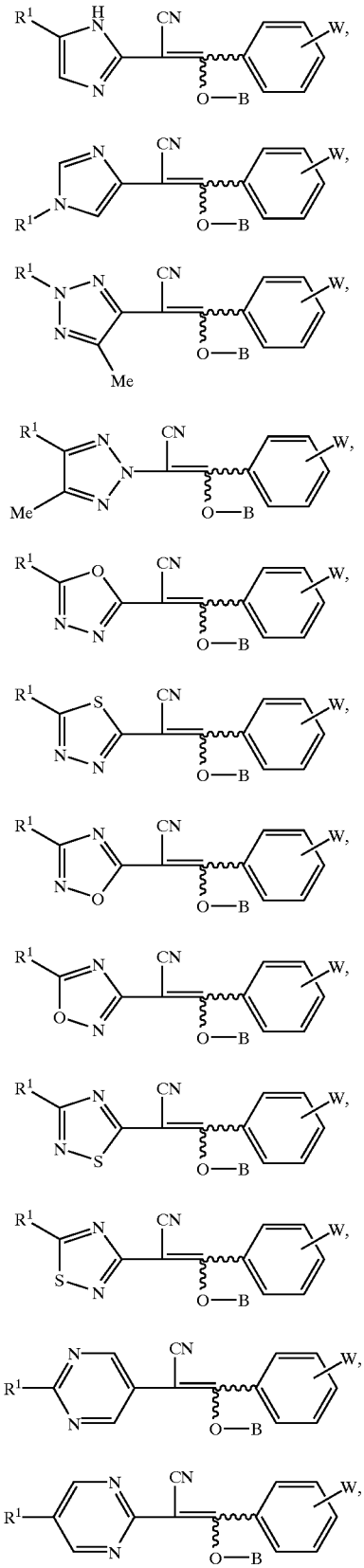

TABLE 8-continued

[Structures shown: three pyridazine/pyrazine compounds with CN and O—B groups attached to phenyl-W]

| R¹ | R² | B | W |
|---|---|---|---|
| 2-F—Ph | H | H | 2-F |
| 2,6,F₂—Ph | H | CO(2,4-Me₂—Ph) | 2-F |
| tBu | H | H | 2-F |
| tBu | H | B7 | 2-F |
| tBuCH₂ | H | B6 | 2-F |
| EtMe₂C | H | B30 | 2-F |
| cHex | H | B31 | 2-Cl |
| 1-Me-cHex | H | B32 | 2-Br |
| Ph | H | B33 | 2-F |
| 2-F—Ph | H | B34 | 2-F |
| 2-Cl | H | H | 2-Me |
| 2-Cl—Ph | H | CO₂iPr | 2-nBu |
| 2,6-F₂—Ph | H | CO(2-MeO—Ph) | 2-OMe |
| 2,6-Cl₂—Ph | H | H | 2-nBeO |
| 1-naphthyl | Cl | CO(4-MeO—Ph) | 2-CF₂ |
| 2-naphthyl | Me | CO(2-Me—Ph) | 2-OCHF₂ |
| tBu | H | Na | 2-CF₃ |
| tBu | H | Ca | 2-OCH₂CH₂CHFCHF₂ |
| 2-pyridyl | H | H | 2-OCF₂CHF₂ |
| 3-pyridyl | H | H | 2-SMe |
| 4-pyridyl | H | B7 | 2-SOMe |
| Me₂C=N— | H | B10 | 2-SO₂Me |
| iPr | H | B13 | 2-SCBrF₂ |
| tBu | H | B19 | 2-SCF₃ |
| tBuCH₂ | H | B22 | 2-SOCBrF₂ |
| EtMe₂C | H | B23 | 2-SO₂CH₂F |
| cHex | H | B7 | 2-SCF₃ |
| Ph | H | B25 | 2-SCBrF₂ |
| 2-F—Ph | H | B26 | 2-SO₂CHF₂ |
| 2-F—Ph | H | B27 | 2-SCBrF₂ |
| 2-CF₃—Ph | H | B28 | 2-CH=CCl₂ |
| 2,6-F₂—Ph | H | CO(2,6-Me₂—Ph) | 2-OCH₂CH=CH₂ |
| 1-naphthyl | H | CO(2,6-(MeO)₂—Ph) | 2-OCH₂CH=CCl₂ |
| PhCH₂ | H | CO(2-Me-6-NO₂—Ph) | 2-OCH₂CH=CHCl |
| 2-thienyl | H | CO(3,4,5-(MeO)₃—Ph) | 2-SCH₂CH=CHMe |
| 4-Cl-2-thienyl | H | SO₂(4-Me—Ph) | 2-SOCH₂CH=CH₂ |
| 3-MeO-2-pyridyl | H | CO(2,6-Cl₂—Ph) | 2-SO₂CHMeCH=CH₂ |
| 2-Cl-3-pyridyl | H | CO(2,5-Me₂—Ph) | 2-SCH₂CMe=CF₂ |
| 2,6-Cl₂-4-pyridyl | H | CO(2,6-F₂—Ph) | 2-SOCH₂CF=CF₂ |
| EtMeC=N— | H | B1 | 2-SO₂CH₂CH=CF₂ |
| Et | H | B2 | 2-CCH |
| tBu | H | B4 | 2-CCl |
| tBuCH₂ | H | H | 2-OCH₂CCH |
| EtMe₂C | H | H | 2-OCH₂CCCl |
| cHex | H | H | 2-SCH₂CCMe |
| Ph | H | H | 2-SOCH₂CCH |
| 2-MeO—Ph | H | B5 | 2-SO₂CH₂CCMe |
| 2-F—Ph | H | B6 | 2-SCH₂CCBr |
| 2,6-F₂—Ph | H | B7 | 2-SOCHMeCCCl |
| 2,6-Me₂—Ph | H | B8 | 2-SO₂CH₂CCl |
| 1-naphthyl | H | Ba | 2-NO₂ |
| PhCH₂ | H | K | 2-CN |
| 2-naphthyl | H | H | 2-CO₂Me |
| 5-Br-3-thienyl | H | B3 | 2-COMe |
| 3-MeO-2-pyridyl | H | B14 | 2-O(CO)Me |
| 2-Cl-3-pyridyl | H | B15 | 2-NHMe |
| 2,6-Cl₂-4-pyridyl | H | B16 | 2-NMe |
| (CH₂)₄C=N— | H | B17 | 3-F |
| tBu | H | H | 3-Cl |
| tBuCH₂ | H | H | 3-nBu |
| EtMe₂C | H | H | 2-OEt |
| 2-Me-cHex | H | H | 3-C₂CH₂CH₂CHF |
| Ph | H | B22 | 3-OCH₂CH₂CHFCHF₂ |
| Ph | H | B27 | 3-S-nBu |
| 2-CF₃—Ph | H | B28 | 3-SOnPr |
| 2,6-F₂—Ph | H | B30 | 3-SO₂iPr |
| 2,6-Me₂—Ph | H | B31 | 3-SCF₃ |
| 1-naphthyl | H | CO(3,4-(MeO)₂—Ph) | 3-SCH₂CH₂CHFCHF₂ |
| PhCH₂ | H | CO(2,4-Cl₂Ph) | 3-SO₂CF₂CHF₂ |
| 2-thienyl | H | CO(3-CF₃—Ph) | 3-SCH₂CMe=CH₂ |
| 3-Me-2-pyridyl | H | CO(2-Me₂N—Ph) | 3-SOCH₂CH=CH₂ |
| 3-NO₂-pyridyl | H | COiPr | 3-SO₂CHMeCH=CH₂ |
| 3,6-Cl₂-2-pyridyl | H | CO₂iPr | 3-SCH₂CMe=CF₂ |
| 2-MeS-3-pyridyl | H | CO₂tBu | 3-SOCH₂CF=CCl₂ |
| (CH₂)₅C=N— | H | CONHMe | 3-SO₂CH₂CH=CH₂Cl |
| sBu | H | CONHEt | 3-OCH₂CCH |
| tBuCH₂ | H | B19 | 3-SCH₂CCMe |
| EtMe₂C | H | B18 | 3-SOCH₂CCH |
| 2-Me-cHex | H | SO₂(2-Me—Ph) | 3-SO₂CH₂CCMe |
| Ph | H | H | 3-NO₂ |
| 2-CF₃O—Ph | H | H | 3-CN |
| 2-MeS—Ph | H | H | 3-CO₂Et |
| 2,6-F₂—Ph | H | Na | 3-CONPr |
| 2,6-Cl₂—Ph | H | K | 3-O(CO)nPr |
| 1-napthyl | H | Mg | 3-NHBu |
| 2-F-2-pyridyl | H | Ca | 3-NEt₂ |
| 6-Me-2-pyridyl | H | Ba | 4-F |
| 4-CF₃-3-pyridyl | H | COCEtMe₂ | 4-Cl |
| 3-NO₂-3-pyridyl | H | CO(3-MeO—Ph) | 4-Br |
| 2,4-Me₂-3-pyridyl | H | CO-2-naphthyl | 4-I |
| iBuMeC=N— | H | CO(4-EtO-3-MeO—Ph) | 4-Me |
| tBu | H | CO(3-Cl-4-MeO—Ph) | 4-tBu |
| tBu | H | CO(3-F-4-nBuO—Ph) | 4-OMe |
| tBu | H | CH₂CO₂Me | 4-CF₃ |
| Ph | H | CH(Me)CO₂Et | 4-OCHF₂ |
| Ph | H | CMe₂CO₂nPr | 4-SMe |
| 2-pyridyl | H | CH₂CN | 4-SOMe |
| sBu | H | CH₂CH₂CH₂CN | 4-SO₂nBu |
| tBuCH₂ | H | CH₂CO₂iPr | 4-SCF₃ |
| EtMe₂C | H | H | 4-SOCBrF₂ |
| 2-Me-cHex | H | H | 4-SO₂CH₂F |
| Ph | H | H | 4-OCH₂CH=CH₂ |
| 2-CF₃—Ph | H | H | 4-OCH₂CH=CCl₂ |
| 2-NO₂—Ph | H | B3 | 4-OCH₂CCH |
| 2,6-F₂—Ph | H | B4 | 4-OCH₂CCCl |
| 2-Cl-6-F—Ph | H | B5 | 4-SCH₂CCMe |
| 1-naphthyl | H | B6 | 4-SO₂CH₂CCMe |
| 2-pyridyl | H | B7 | 4-NO₂ |
| 3-pyridyl | H | B8 | 4-CN |
| PhCH₂ | H | B12 | 4-CO₂nBu |
| 2-thienyl | H | B21 | 4-COiBu |
| 3-thienyl | H | B28 | 4-O(CO)nPr |
| iBuMeC=N— | H | CO(2-MeO—Ph) | 4-NHnBu |
| tBu | H | H | 2,3-Cl₂ |
| tBu | H | H | 2,4-Cl₂ |
| tBu | H | H | 3,4-Cl₂ |
| Ph | H | H | 3,5-Cl₂ |
| Ph | H | H | 2,5-Cl₂ |
| 2-pyridyl | H | B7 | 2,6-Cl₂ |
| sBu | H | B8 | 2,6-Cl₂ |
| tBuCH₂ | H | B12 | 2,6-Cl₂ |
| EtMe₂C | H | B23 | 2,3-F₂ |
| 2-Me-cHex | H | B26 | 2,3-F₂ |
| Ph | H | B28 | 2,3-F₂ |
| 2-Me—Ph | H | CONHiPr | 2,4-F₂ |
| 2-MeO—Ph | H | Ca | 2,4-F₂ |
| 2,6-F₁—Ph | H | Ba | 2,5-F₂ |
| 2,6-Cl₂—Ph | H | H | 2,6-F₂ |
| 1-naphthyl | H | H | 2,6-F₂ |
| 2-pyridyl | H | H | 2,6-F₂ |
| PhCH₂ | H | CO(2,3-Me₂—Ph) | 2,6-F₂ |
| 3-pyridyl | H | CO(3,4-Me₂—Ph) | 2,6-F₂ |
| 4-pyridyl | H | CH₂CO₂Et | 2,6-F₂ |
| 2-thienyl | H | CHMeCO₂Me | 2,6-F₂ |
| iBuMeC=N- | H | CH₂CN | 2,6-F₂ |

TABLE 8-continued

| | | | |
|---|---|---|---|
| tBu | H | H | 2,6-F$_2$ |
| tBu | H | B7 | 2,6-F$_2$ |
| tBu | H | B8 | 2,6-F$_2$ |
| tBu | H | B28 | 2,6-F$_2$ |
| tBu | Me | B31 | 2,6-F$_2$ |
| tBu | H | B34 | 2,6-F$_2$ |
| tBu | H | CO(2-MeO—Ph) | 2,6-F$_2$ |
| tBu | H | CO(2-Cl—Ph) | 2,6-F$_2$ |
| tBu | H | CO(2,6-Me$_2$—Ph) | 2,6-F$_2$ |
| tBuCH$_2$ | H | CO(2,6-(MeO)$_2$—Ph) | 2,6-F$_2$ |
| EtMe$_2$C | H | CO(3,4,5-(MeO)$_3$—Ph) | 2,6-F$_2$ |
| cHex | H | B28 | 2,6-F$_2$ |
| cHex | H | B30 | 2,6-F$_2$ |
| cHex | H | B34 | 2,6-F$_2$ |
| 1-Me-cHex | H | SO$_2$(4-Cl—Ph) | 2,6-F$_2$ |
| Ph | H | H | 2,6-F$_2$ |
| Ph | H | B5 | 2,6-F$_2$ |
| Ph | H | B6 | 2,6-F$_2$ |
| 2-F—Ph | H | B14 | 2,6-F$_2$ |
| 3-F—Ph | H | B19 | 2,6-F$_2$ |
| 4-F—Ph | H | B23 | 2,6-F$_2$ |
| 2-Cl—Ph | H | B24 | 2,6-F$_2$ |
| 2,6-F$_2$—Ph | H | H | 2,6-F$_2$ |
| 2,6-F$_2$—Ph | H | Ca | 2,6-F$_2$ |
| 2,6-F$_2$—Ph | Me | B7 | 2,6-F$_2$ |
| 2,6-F$_2$—Ph | H | B9 | 2,6-F$_2$ |
| 1-naphthyl | H | B10 | 2,6-F$_2$ |
| 2-naphthyl | H | B16 | 2,6-F$_2$ |
| 2-thienyl | H | B22 | 2,6-F$_2$ |
| 3-thienyl | H | B24 | 2,6-F$_2$ |
| 2-pyridyl | Cl | H | 3,4-F$_2$ |
| 3-pyridyl | H | B7 | 3,5-F$_2$ |
| 4-pyridyl | H | B18 | 2,5-(CF$_3$)$_2$ |
| nPr$_2$C=N— | H | B31 | 2,6-(CF$_3$)$_2$ |
| tBu | Et | H | 3,5-(CF$_3$)$_2$ |
| tBu | Br | H | 5-Br-2-Cl |
| tBu | H | SO$_2$(4-Me—Ph) | 3-Br-4-Me |
| tBu | H | COnHex | 2-Cl-4-F |
| tBu | H | CO(2-Cl-6-F—Ph) | 2-Cl-6-F |
| tBuCH$_2$ | H | CO(3,5-Cl$_2$-4-MeO—Ph) | 2-Cl-6-F |
| EtMe$_2$C | H | CO(3-Br-4-Me—Ph) | 2-Cl-6-F |
| cHex | H | H | 2-Cl-6-F |
| cHex | H | B6 | 2-Cl-6-F |
| Ph | H | B7 | 2-Cl-6-F |
| Ph | H | B8 | 2-Cl-6-F |
| 2-F—Ph | H | B34 | 2-Cl-6-F |
| 3-F—Ph | H | CO$_2$tBu | 2-Cl-6-F |
| 2-Cl—Ph | H | CHMeCO$_2$Me | 2-Cl-6-F |
| 2,6-F$_2$—Ph | H | B31 | 3-Cl-4-F |
| 2,6-F$_2$—Ph | H | K | 4-Cl-3-F |
| tBu | H | Ba | 2-F-6-I |
| 2,6-F$_2$—Ph | H | CO(4-nBuO—Ph) | 2-F-6-I |
| 2,6-F$_2$—Ph | H | CO(4-Et$_2$N—Ph) | 2-F-6-I |
| 2,6-F$_2$—Ph | Br | CO(3-Me$_2$N—Ph) | 2-Cl-5-SMe |
| 1-naphthyl | H | CO(4-Et—Ph) | 2-Cl-5-SCBrF$_2$ |
| 2-naphthyl | H | CO(3-F-4-Me—Ph) | 2-Cl-5-SCF$_3$ |
| 2-thienyl | H | CO(3-MeO-4-Me—Ph) | 2-Cl-5-SOMe |
| 3-thienyl | H | CO(2,3,6-F$_3$—Ph) | 2-Cl-5-SO$_2$Me |
| 2-pyridyl | H | CO(2-MeO-5-NO$_2$—Ph) | 2-Cl-4-NO$_2$ |
| 3-pyridyl | H | CO(3,5-Me$_2$—Ph) | 2,4-(OMe)$_2$ |
| 4-pyridyl | H | H | 2,6-(OMe)$_2$ |
| nPr$_2$C=N— | H | H | 2,6-(OMe)$_2$ |
| tBu | H | H | 2,3-Me$_2$ |
| tBu | H | B1 | 2,4-Me$_2$ |
| tBu | H | B2 | 2,5-Me$_2$ |
| tBuCH$_2$ | H | B3 | 2,6-Me$_2$ |
| EtMe$_2$C | H | B4 | 2,6-Me$_2$ |
| cHex | H | B5 | 2,6-Me$_2$ |
| cHex | H | B6 | 3,4-Me$_2$ |
| 1-Me-cHex | H | B7 | 3,5-Me$_2$ |
| Ph | H | B8 | 2-F-4-Me |
| Ph | H | B9 | 2-F-4-Me |
| Ph | H | B10 | 2-F-4-Me |
| 2-F—Ph | H | B11 | 3-F-4-Me |
| 2-F—Ph | H | B12 | 3-I-4-Me |
| 3-F—Ph | H | B13 | 2-OMe-4-NO$_2$ |
| 4-F—Ph | H | B14 | 3-OMe-4-NO$_2$ |
| 2-Cl—Ph | H | CH$_2$CN | 2-Me-4-NO$_2$ |
| 2,6-F$_2$—Ph | H | CMe$_2$CO$_2$Et | 2-Me-6-NO$_2$ |

TABLE 8-continued

| | | | |
|---|---|---|---|
| 2,6-F$_2$—Ph | H | CONHMe | 2,3,6-F$_3$ |
| tBu | H | SO$_2$(4-Cl—Ph) | 2,3,6-F$_3$ |
| cHex | H | CO(2-MeO—Ph) | 2,3,6-F$_3$ |
| 1-naphthyl | H | CO(2-Me—Ph) | 2,3,6-F$_3$ |
| 2-F—Ph | H | CO(2-Cl—Ph) | 2,3,6-F$_3$ |
| 2-pyridyl | H | CO(2,6-(MeO)$_2$—Ph) | 2,4,5-F$_3$ |
| 3-pyridyl | H | CO(3,4-Me$_2$—Ph) | 2,4,5-F$_3$ |
| 4-pyridyl | H | CO(3-MeO-4-EtO—Ph) | 2,4,5-F$_3$ |
| nPr$_2$C=N— | H | B15 | 2,3,5-I$_3$ |
| tBu | H | B16 | 2,3,5-I$_3$ |
| tBu | H | B17 | 2,3,4-(OMe)$_3$ |
| tBu | H | B18 | 2,4,5-(OMe)$_3$ |
| tBu | H | B19 | 3,4,5-(OMe)$_3$ |
| tBu | H | B20 | 2,4,6-Me$_3$ |
| tBuCH$_2$ | H | B21 | 2,3,4,5-F$_4$ |
| EtMe$_2$C | H | B24 | 2,3,4,5-F$_4$ |
| cHex | H | B25 | 2,3,4,5-F$_4$ |
| cHex | H | B27 | 2,3,5,6-F$_4$ |
| cHex | H | B28 | 2,3,5,6-F$_4$ |
| 1-Me-cHex | H | B29 | 2,3,5,6-F$_4$ |
| Ph | H | B30 | 2,3,5,6-F$_4$ |
| Ph | H | B31 | 2,3,4,5,6-F$_5$ |
| Ph | H | B32 | 2,3,4,5,6-F$_5$ |
| 2-F—Ph | H | B33 | 2,3,4,5,6-F$_5$ |
| 3-F—Ph | H | B34 | 2,3,5,6-F$_4$-4-Me |
| 4-F—Ph | H | H | 2,3,5,6-F$_4$-4-Me |
| 2-Cl—Ph | H | H | 2,3,5,6-F$_4$-4-Me |
| 2,6-F$_2$—Ph | H | B27 | 2,3,5,6-F$_4$-4-Me |
| 2,6-F$_2$—Ph | H | Ca | 2,3,5,6-F$_4$-4-Me |

TABLE 9

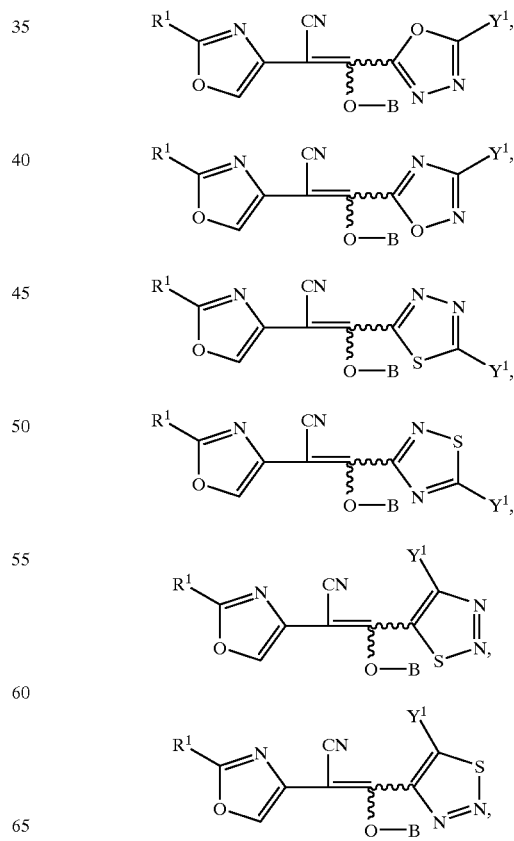

TABLE 9-continued

TABLE 9-continued

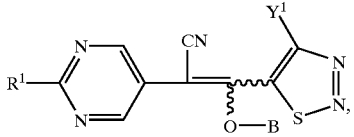

or

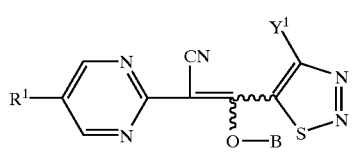

| R¹ | B | Y¹ |
|---|---|---|
| Me | H | H |
| Et | B1 | Me |
| iPr | B2 | Et |
| nBu | B3 | nPr |
| sBu | B4 | iBu |
| tBu | H | nHex |
| tBu | B7 | Me |
| tBu | B8 | MeO |
| tBu | B8 | MeS |
| tBu | B7 | $CF_3$ |
| tBu | B5 | $CF_3$ |
| tBu | B7 | $CClF_2$ |
| tBu | B8 | $CF_3CF_2$ |
| tBu | 4-Cl—$PhCO_2$ | $CF_3CF_2CF_2$ |
| tPen | B6 | MeO |
| nHex | B7 | EtO |
| nHep | B8 | iPrO |
| nOct | B9 | sBuO |
| nNon | B10 | MeS |
| nDec | B11 | EtS |
| $PhCH_2$ | B12 | nPrS |
| Ph(Me)CH | B13 | tBuS |
| $PhMe_2C$ | B14 | Ph |
| $PhMe_2C$ | B7 | Me |
| $PhMe_2C$ | B8 | Me |
| $PhMe_2C$ | B33 | Me |
| $PhMe_2C$ | B34 | Me |
| $PhMe_2C$ | B41 | Me |
| $PhMe_2C$ | B7 | $CF_3$ |
| $PhMe_2C$ | B8 | $CF_3$ |
| $PhMe_2C$ | B34 | $CF_3$ |
| 4-Cl—$PhMe_2C$ | B15 | $Me_2N$ |
| 3-Br—PhEtMeC | B16 | $Et_2N$ |
| 4-Me—$Ph(CH_2)_3$ | B17 | H |
| $CH_2$=CMe | B18 | Me |
| $CF_3CF_2CF_2$ | B19 | Et |
| cPr | B20 | nPr |
| cPen | B21 | iBu |
| cPen | B22 | nHex |
| cPen | B23 | $CF_3$ |
| cHex | B24 | $CClF_2$ |
| cHex | B7 | $CF_3$ |
| cHex | B8 | $CF_3$ |
| cHex | B33 | $CF_3$ |
| cHex | B34 | $CF_3$ |
| cHex | B7 | Me |
| cHex | B8 | Me |
| cHex | B34 | Me |
| 1-Me—cHex | B7 | Me |
| 1-Me—cHex | B8 | $CF_3$ |
| 1-Me—cHex | B7 | $CF_3$ |
| 1-Me—cHex | iBuOC(O) | $CF_3$ |
| 1-Me—cHex | B28 | EtO |
| 1-Me—cHex | B29 | iPrO |
| EtO | B30 | sBuO |
| iPrO | B31 | MeS |
| $CF_3O$ | B32 | EtS |
| tBuOC(O) | B33 | nPrS |
| Ph | B34 | tBuS |
| 2-F—Ph | B35 | Ph |
| 2-F—Ph | B36 | $Me_2N$ |
| 2-Cl—Ph | B37 | $Et_2N$ |
| 2-Cl—Ph | B38 | Cl |
| 2-Br—Ph | B39 | Br |
| 2-I—Ph | B40 | I |
| 2-$CF_3$—Ph | B41 | H |
| 2-MeO—Ph | B42 | $CF_3$ |
| 3,4-$Cl_2$—Ph | $CClF_2C(O)$ | MeO |
| 2,4-$Me_2$—Ph | PhSC(O) | MeS |
| 2,6-$F_2$—Ph | B7 | Me |
| 2,6-$F_2$—Ph | B7 | $CF_3$ |
| 2,6-$F_2$—Ph | B8 | Me |
| 2,6-$F_2$—Ph | B8 | $CF_3$ |
| 2,6-$F_2$—Ph | EtSC(O) | H |
| 2,6-$F_2$—Ph | tBuC(S) | Me |
| 2,6-$F_2$—Ph | cPenOC(O) | Et |
| 2-pyridyl | cHexOC(O) | nPr |
| 2-pyridyl | B7 | Me |
| 2-pyridyl | B8 | Me |
| 2-pyridyl | B7 | $CF_3$ |
| 2-pyridyl | B8 | $CF_3$ |
| 2-pyridyl | iBuOC(O) | $CF_3$ |
| 2-pyridyl | B33 | $CF_3$ |
| 2-pyridyl | B34 | $CF_3$ |
| 2-pyridyl | B34 | Me |
| 2-pyridyl | 2-pyridyl-C(O) | $CClF_2$ |
| 2-pyridyl | 2-pyridyl-C(O) | $CF_3CF_2$ |
| 2-thienyl | 3-pyridyl-C(O) | $CF_3CF_2CF_2$ |
| 1-naphthyl | 4-pyridyl-C(O) | MeO |
| 2-naphthyl | H | EtO |
| tBu | $CClF_2C(O)$ | H |
| tBu | PhSC(O) | Me |
| tBu | EtSC(O) | Et |
| tBu | tBuC(S) | nPr |
| cPr | cPenOC(O) | iBu |
| cPen | cHexOC(O) | nHex |
| cHex | B7 | $CF_3$ |
| 1-Et—cPr | B8 | $CClF_2$ |
| 1-Me—cPen | iBuOC(O) | $CF_3CF_2$ |
| 1-Me—cPen | 2-pyridyl-C(O) | $CF_3CF_2CF_2$ |
| 2,6-$F_2$—Ph | 2-pyridyl-C(O) | MeO |
| 2,6-$F_2$—Ph | 2-pyridyl-C(O) | MeO |
| 2,6-$F_2$—Ph | 4-pyridyl-C(O) | Me |
| 2,6-$F_2$—Ph | 2-pyridyl-C(O) | $CF_3$ |

TABLE 10

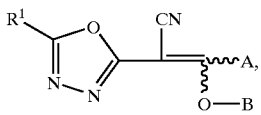

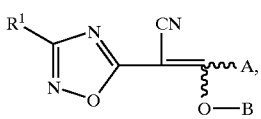

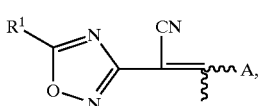

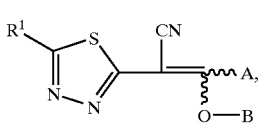

TABLE 10-continued

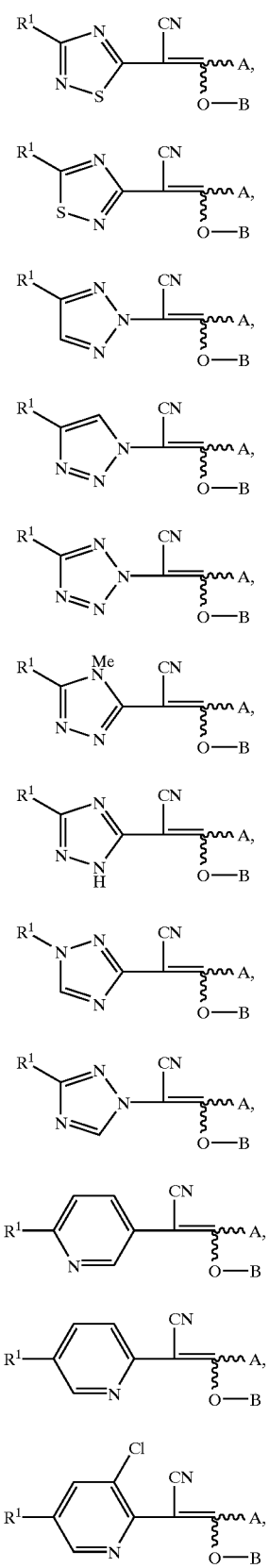

TABLE 10-continued

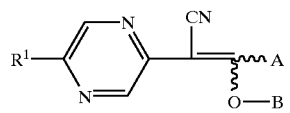

or

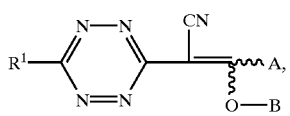

| R¹ | B | A |
|---|---|---|
| Et | H | A1 |
| iPr | B7 | A2 |
| iBu | B7 | A1 |
| sBu | B7 | A2 |
| tBu | B7 | A1 |
| tBu | B8 | A1 |
| tBu | B15 | A1 |
| tBu | B34 | A1 |
| tBu | B7 | A2 |
| tBu | B8 | A2 |
| tBu | B15 | A2 |
| tBu | B34 | A2 |
| tBu | $CO_2$—iBu | A2 |
| tBu | B7 | A3 |
| tBu | B7 | A4 |
| tBu | B7 | A5 |
| tBu | B7 | A6 |
| tBu | H | A7 |
| tBu | B7 | A7 |
| tBu | B8 | A7 |
| tBu | B15 | A7 |
| tBu | B34 | A7 |
| tBu | H | A8 |
| tBu | B7 | A8 |
| tBu | B8 | A8 |
| tBu | B7 | A13 |
| tBu | B8 | A13 |
| tBu | B15 | A13 |
| tBu | B34 | A13 |
| tBu | $CO_2$—iBu | A13 |
| tBu | H | A14 |
| tBu | B7 | A14 |
| tBu | B16 | A14 |
| tBu | B17 | A14 |
| tBu | B7 | A15 |
| tBu | B8 | A16 |
| tBu | B9 | A17 |
| tBu | B10 | A18 |
| tBu | B11 | A19 |
| tBu | B12 | A20 |
| tBu | B13 | A21 |
| tBu | B7 | A22 |
| tBu | B8 | A22 |
| tBu | B7 | A23 |
| tBu | B8 | A23 |
| tBu | B15 | A23 |
| tBu | B34 | A23 |
| tBu | B14 | A24 |
| tBu | B15 | A25 |
| tBu | B16 | A26 |
| nHex | B7 | A1 |
| nHep | B7 | A2 |
| nOct | B7 | A1 |
| nNon | B7 | A2 |
| nDec | B7 | A7 |
| cPr | B7 | A8 |
| 1-Me—cPr | B7 | A1 |
| 1-Me—cPr | B7 | A2 |
| 1-Me—cPr | B8 | A2 |
| 1-Me—cPr | B34 | A2 |
| 1-Me—cPr | H | A2 |
| cPen | B7 | A2 |

TABLE 10-continued

| | | |
|---|---|---|
| cHex | B7 | A1 |
| cHex | B7 | A2 |
| cHex | B8 | A2 |
| cHex | B15 | A2 |
| cHex | B34 | A2 |
| cHex | B35 | A2 |
| cHex | B36 | A1 |
| cHex | B37 | A2 |
| Ph | H | A2 |
| Ph | B7 | A2 |
| Ph | B7 | A7 |
| Ph | B7 | A8 |
| Ph | B7 | A9 |
| 2-Me—Ph | B7 | A1 |
| 2-Me—Ph | B7 | A2 |
| 2-MeO—Ph | B2 | A7 |
| 2-CF$_2$—Ph | B3 | A8 |
| 2-NO$_2$—Ph | B4 | A9 |
| 2-CN—Ph | B5 | A10 |
| 2-CBrF$_2$O—Ph | B6 | A11 |
| 2-CF$_3$O—Ph | B7 | A12 |
| 2-MeS—Ph | B8 | A13 |
| 2-nBuS—Ph | B9 | A14 |
| 2-MeSO—Ph | B10 | A15 |
| 2-MeSO$_2$—Ph | B11 | A16 |
| 2-CH$_2$=CHCH$_2$S—Ph | B12 | A17 |
| 2-CH$_2$=CHCH$_2$SO—Ph | B13 | A18 |
| 2-CH$_2$=CHCH$_2$SO$_2$—Ph | B14 | A19 |
| 2-CF$_3$S—Ph | B15 | A20 |
| 2-CHF$_2$S—Ph | B16 | A21 |
| 2-CBrF$_2$SO—Ph | B17 | A22 |
| 2-CF$_3$SO$_2$—Ph | B18 | A23 |
| 2-CHO—Ph | B19 | A24 |
| 2-OH—Ph | B20 | A25 |
| 2-Me$_2$N—Ph | B21 | A26 |
| 3-Ph—Ph | B22 | A27 |
| 4-PhO—Ph | B23 | A28 |
| 2-MeOC(O)—Ph | B24 | A29 |
| Cl | B7 | A1 |
| PhCH$_2$ | B7 | A1 |
| PhCH$_2$ | B7 | A2 |
| PhCH$_2$ | B8 | A2 |
| PhCH$_2$ | B34 | A2 |
| (4-Cl—Ph)CH$_2$ | B7 | A30 |
| (4-Me—Ph)CH$_2$ | B7 | A31 |
| (3,4-Cl$_2$—Ph)CH$_2$ | B7 | A32 |
| (2,4-Me$_2$—Ph)CH$_2$ | B7 | A33 |
| PhMeCH | B7 | A34 |
| Ph(Me)$_2$C | B3 | A1 |
| Ph(Me)$_2$C | B7 | A1 |
| Ph(Me)$_2$C | B3 | A2 |
| Ph(Me)$_2$C | B7 | A2 |
| Ph(Me)$_2$C | B8 | A2 |
| Ph(Me)$_2$C | B33 | A2 |
| Ph(Me)$_2$C | B34 | A2 |
| Ph(Me)$_2$C | B35 | A2 |
| Ph(Me)$_2$C | B7 | A13 |
| Ph(Me)$_2$C | B8 | A13 |
| Ph(Me)$_2$C | B34 | A13 |
| CF$_3$ | B15 | A35 |
| CF$_3$CH$_2$ | B6 | A36 |
| CH$_2$=CMe | B6 | A1 |
| Cl$_2$C=CH | B29 | A2 |
| BrCCCH$_2$SO | B28 | A1 |
| ClCCH$_2$SO$_2$ | B29 | A2 |
| 1-naphthyl | B30 | A2 |
| 2-naphthyl | B31 | A13 |
| MeC(O) | B32 | A13 |
| MeC(O)O | B33 | A1 |
| CF$_3$C(O)O | B34 | A1 |
| 2-thienyl | B35 | A2 |
| 3-thienyl | B36 | A2 |
| Me$_2$C=N | B37 | A1 |
| EtMeC=N | B38 | A1 |
| PhCH=N | B39 | A2 |
| PhMeC=N | B40 | A2 |
| 2-pyridyl | B7 | A1 |
| 2-pyridyl | B8 | A1 |
| 2-pyridyl | B15 | A1 |
| 2-pyridyl | B34 | A1 |
| 2-pyridyl | B7 | A2 |
| 2-pyridyl | B8 | A2 |
| 2-pyridyl | B15 | A2 |
| 2-pyridyl | B34 | A2 |
| 2-pyridyl | CO$_2$—iBu | A2 |
| 2-pyridyl | B7 | A3 |
| 2-pyridyl | B7 | A4 |
| 2-pyridyl | B7 | A5 |
| 2-pyridyl | B7 | A6 |
| 2-pyridyl | H | A12 |
| 2-pyridyl | B7 | A12 |
| 2-pyridyl | B8 | A12 |
| 2-pyridyl | B15 | A12 |
| 2-pyridyl | B34 | A12 |
| 2-pyridyl | CO$_2$—iBu | A12 |
| 2-pyridyl | H | A13 |
| 2-pyridyl | B7 | A13 |
| 2-pyridyl | B8 | A13 |
| 2-pyridyl | B15 | A13 |
| 2-pyridyl | B34 | A13 |
| 2-pyridyl | CO$_2$—iBu | A13 |
| 2-pyridyl | H | A14 |
| 2-pyridyl | B7 | A14 |
| 2-pyridyl | B16 | A14 |
| 2-pyridyl | B17 | A14 |
| 2-pyridyl | B7 | A15 |
| 2-pyridyl | B8 | A16 |
| 2-pyridyl | B9 | A17 |
| 2-pyridyl | B10 | A18 |
| 2-pyridyl | B11 | A19 |
| 2-pyridyl | B12 | A20 |
| 2-pyridyl | B13 | A21 |
| 2-pyridyl | B7 | A22 |
| 2-pyridyl | B8 | A22 |
| tBu | B15 | A8 |
| tBu | B34 | A8 |
| tBu | H | A9 |
| tBu | B7 | A9 |
| tBu | B8 | A9 |
| tBu | B15 | A9 |
| tBu | B34 | A9 |
| tBu | CO$_2$—iBu | A9 |
| tBu | H | A10 |
| tBu | B7 | A10 |
| tBu | B8 | A10 |
| tBu | B15 | A10 |
| tBu | B34 | A10 |
| tBu | CO$_2$—iBu | A10 |
| tBu | H | A11 |
| tBu | B7 | A11 |
| tBu | B8 | A11 |
| tBu | B15 | A11 |
| tBu | H | A12 |
| tBu | B7 | A12 |
| tBu | B8 | A12 |
| tBu | B15 | A12 |
| tBu | B34 | A12 |
| tBu | CO$_2$—iBu | A12 |
| tBu | H | A13 |
| tBu | B17 | A27 |
| tBu | B18 | A28 |
| tBu | B19 | A29 |
| tBu | B7 | A30 |
| tBu | B8 | A30 |
| tBu | B15 | A30 |
| tBu | B20 | A31 |
| tBu | H | A32 |
| tBu | B7 | A32 |
| tBu | B8 | A32 |
| tBu | B15 | A32 |
| tBu | B34 | A32 |
| tBu | CO$_2$—iBu | A32 |
| tBu | B21 | A33 |
| tBu | B22 | A34 |
| tBu | B23 | A35 |
| tBu | B24 | A36 |
| tBuCH$_2$ | B3 | A1 |
| tBuCH$_2$ | B7 | A2 |

TABLE 10-continued

| | | |
|---|---|---|
| tBuCH$_2$ | B8 | A2 |
| Et(Me)$_2$C | B15 | A2 |
| Et(Me)$_2$C | B16 | A2 |
| Et(Me)$_2$C | B34 | A2 |
| Et(Me)$_2$C | H | A2 |
| Et(Me)$_2$C | B7 | A2 |
| Ph | B7 | A10 |
| Ph | B7 | A13 |
| Ph | B7 | A32 |
| 2-F—Ph | B7 | A1 |
| 2-F—Ph | B7 | A2 |
| 2-F—Ph | B7 | A7 |
| 2-F—Ph | B7 | A8 |
| 2-F—Ph | B7 | A9 |
| 2-F—Ph | B7 | A10 |
| 2-F—Ph | B7 | A13 |
| 2-F—Ph | B8 | A32 |
| 2-Cl—Ph | B7 | A1 |
| 2-Cl—Ph | B7 | A2 |
| 2-Cl—Ph | B7 | A7 |
| 2-Cl—Ph | B7 | A8 |
| 2-Cl—Ph | B7 | A9 |
| 2-Cl—Ph | B7 | A10 |
| 2-Cl—Ph | B7 | A13 |
| 2-Cl—Ph | B8 | A30 |
| 2-Cl—Ph | B34 | A32 |
| 2-Br—Ph | B7 | A1 |
| 2-I—Ph | B7 | A2 |
| 2-Me—Ph | B7 | A7 |
| 2-Me—Ph | B7 | A8 |
| 2-Me—Ph | B7 | A9 |
| 2,6-Cl$_2$-Ph | B7 | A1 |
| 2,6-Cl$_2$-Ph | B7 | A2 |
| 2,6-Cl$_2$-Ph | B7 | A7 |
| 2,6-F$_2$—Ph | B7 | A1 |
| 2,6-F$_2$—Ph | B7 | A2 |
| 2,6-F$_2$—Ph | B7 | A7 |
| 2,6-F$_2$—Ph | B7 | A8 |
| 2,6-F$_2$—Ph | B7 | A9 |
| 2,6-F$_2$—Ph | B7 | A10 |
| 2,6-F$_2$—Ph | B7 | A13 |
| 2,6-F$_2$—Ph | B7 | A21 |
| 2,6-F$_2$—Ph | B7 | A32 |
| 2,6-F$_2$—Ph | B3 | A2 |
| 2,6-F$_2$—Ph | B4 | A2 |
| 2,6-F$_2$—Ph | B5 | A2 |
| 2,6-F$_2$—Ph | B8 | A2 |
| 2,6-F$_2$—Ph | B15 | A2 |
| 2,6-F$_2$—Ph | B19 | A2 |
| 2,6-F$_2$—Ph | B32 | A2 |
| 2,6-F$_2$—Ph | B33 | A2 |
| 2,6-F$_2$—Ph | B34 | A2 |
| 2,6-F$_2$—Ph | B35 | A2 |
| 2,6-F$_2$—Ph | B37 | A2 |
| 2,6-F$_2$—Ph | B40 | A2 |
| 2,6-F$_2$—Ph | B43 | A2 |
| ClCC | B3 | A23 |
| 2,2-Cl$_2$—cPr | B4 | A23 |
| 2,2-F$_2$—cBu | B5 | A23 |
| MeO | B6 | A24 |
| nHexO | B7 | A25 |
| CH$_2$=CHCH$_2$O | B8 | A26 |
| CHCCH$_2$O | B9 | A27 |
| CF$_3$O | B10 | A28 |
| ClCH=CHCH$_2$O | B11 | A29 |
| MeS | B12 | A30 |
| MeSO | B13 | A30 |
| MeSO$_2$ | B14 | A30 |
| Me$_2$C=CHCH$_2$S | B15 | A31 |
| Me$_2$C=CHCH$_2$SO | B16 | A32 |
| Me$_2$C=CHCH$_2$SO$_2$ | B17 | A32 |
| CHCCH$_2$S | B18 | A32 |
| CHCCH$_2$SO | B19 | A1 |
| CHCCH$_2$SO$_2$ | B20 | A2 |
| CF$_3$S | B21 | A2 |
| CF$_3$SO | B22 | A13 |
| CF$_3$SO$_2$ | B23 | A13 |
| ClCH=CHCH$_2$S | B24 | A1 |
| ClCH=CHCH$_2$SO | B25 | A1 |
| ClCH=CHCH$_2$SO$_2$ | B26 | A2 |
| ClCCCH$_2$S | B27 | A2 |
| 2-pyridyl | H | A7 |
| 2-pyridyl | B7 | A7 |
| 2-pyridyl | B8 | A7 |
| 2-pyridyl | B15 | A7 |
| 2-pyridyl | B34 | A7 |
| 2-pyridyl | H | A8 |
| 2-pyridyl | B7 | A8 |
| 2-pyridyl | B8 | A8 |
| 2-pyridyl | B15 | A8 |
| 2-pyridyl | B34 | A8 |
| 2-pyridyl | H | A9 |
| 2-pyridyl | B7 | A9 |
| 2-pyridyl | B8 | A9 |
| 2-pyridyl | B15 | A9 |
| 2-pyridyl | B34 | A9 |
| 2-pyridyl | CO$_2$—iBu | A9 |
| 2-pyridyl | H | A10 |
| 2-pyridyl | B7 | A10 |
| 2-pyridyl | B8 | A10 |
| 2-pyridyl | B15 | A10 |
| 2-pyridyl | B34 | A10 |
| 2-pyridyl | CO$_2$—iBu | A10 |
| 2-pyridyl | H | A11 |
| 2-pyridyl | B7 | A11 |
| 2-pyridyl | B8 | A11 |
| 2-pyridyl | B15 | A11 |
| 2-pyridyl | B8 | A23 |
| 2-pyridyl | B15 | A23 |
| 2-pyridyl | B34 | A23 |
| 2-pyridyl | B14 | A24 |
| 2-pyridyl | B15 | A25 |
| 2-pyridyl | B16 | A26 |
| 2-pyridyl | B17 | A27 |
| 2-pyridyl | B18 | A28 |
| 2-pyridyl | B19 | A29 |
| 2-pyridyl | B7 | A30 |
| 2-pyridyl | B8 | A30 |
| 2-pyridyl | B15 | A30 |
| 2-pyridyl | B20 | A31 |
| 2-pyridyl | H | A32 |
| 2-pyridyl | B7 | A32 |
| 2-pyridyl | B8 | A32 |
| 3-pyridyl | B7 | A1 |
| 3-pyridyl | B34 | A2 |
| 3-pyridyl | CO$_2$—iBu | A2 |
| 3-pyridyl | B7 | A13 |
| 3-pyridyl | B8 | A13 |
| 4-pyridyl | B7 | A1 |
| 4-pyridyl | B8 | A1 |
| 4-pyridyl | B15 | A2 |
| 4-pyridyl | B34 | A2 |

TABLE 11

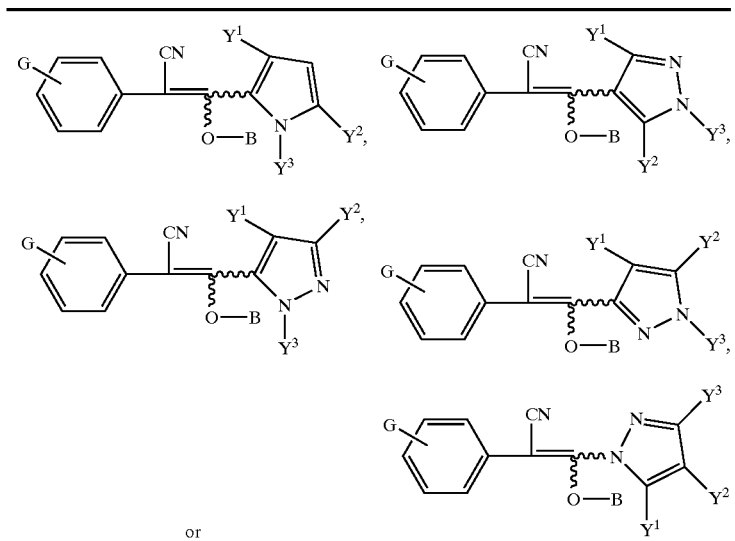

or

| G | B | Y¹ | Y² | Y³ |
|---|---|----|----|----|
| 2-Cl | H | Me | Me | Me |
| 3-Cl | B1 | Me | Cl | Me |
| 4-Cl | B2 | Cl | Me | Me |
| 4-Br | B3 | Cl | Cl | Me |
| 4-I | B4 | $CF_3$ | Cl | Me |
| 4-F | B5 | $CF_3$ | H | Me |
| 4-Me | B6 | H | $CF_3$ | Me |
| 4-Et | B7 | H | Cl | Me |
| 4-iPr | B8 | Cl | H | Me |
| 4-nBu | B9 | H | H | Me |
| 4-iBu | B10 | OMe | Cl | Me |
| 4-sBu | B11 | SMe | Cl | Me |
| 4-sBu | H | Me | Me | Me |
| 4-sBu | B16 | Me | Me | Me |
| 4-sBu | B17 | Me | Me | Me |
| 4-sBu | B7 | Me | Cl | Me |
| 4-sBu | B8 | Me | Cl | Me |
| 4-sBu | B16 | Me | Cl | Me |
| 4-sBu | B17 | Me | Cl | Me |
| 4-sBu | B34 | Me | Cl | Me |
| 4-sBu | B3 | $CF_3$ | Cl | Me |
| 4-sBu | B7 | $CF_3$ | Cl | Me |
| 4-sBu | B8 | $CF_3$ | Cl | Me |
| 4-sBu | B34 | $CF_3$ | Cl | Me |
| 4-sBu | B7 | Cl | Cl | Me |
| 4-sBu | B17 | Cl | Cl | Me |
| 4-tBu | B12 | $SCF_3$ | Cl | Me |
| 4-tBu | H | Me | Me | Me |
| 4-tBu | B3 | Me | Cl | Me |
| 4-tBu | B7 | Cl | Me | Me |
| 4-tBu | B8 | Cl | Cl | Me |
| 4-tBu | B15 | Cl | Cl | Me |
| 4-tBu | B16 | Cl | Cl | Me |
| 4-tBu | B28 | Cl | Cl | Me |
| 4-tBu | B30 | Cl | Cl | Me |
| 4-tBu | B34 | Cl | Cl | Me |
| 4-tBu | CO-n$C_8H_{17}$ | Cl | Cl | Me |
| 4-tBu | CO-n$C_{15}H_{31}$ | Cl | Cl | Me |
| 4-tBu | $CO_2$-nHex | Cl | Cl | Me |
| 4-tBu | $CO_2$-n$C_{10}H_{21}$ | Cl | Cl | Me |
| 4-tBu | H | CN | Cl | Me |
| 4-tBu | H | $CF_3$ | Cl | Me |
| 4-tBu | B3 | $CF_3$ | Cl | Me |
| 4-tBu | B7 | $CF_3$ | Cl | Me |
| 4-tBu | B8 | $CF_3$ | Cl | Me |
| 4-tBu | B15 | $CF_3$ | Cl | Me |
| 4-tBu | B16 | $CF_3$ | Cl | Me |
| 4-tBu | B28 | $CF_3$ | Cl | Me |
| 4-tBu | B30 | $CF_3$ | Cl | Me |
| 4-tBu | B16 | Cl | Cl | Me |
| 4-tBu | B16 | $CF_3$ | Cl | Me |

TABLE 11-continued

| G | B | Y¹ | Y² | Y³ |
|---|---|---|---|---|
| 4-tBu | B17 | $CF_3$ | Cl | Me |
| 4-tBu | B17 | Cl | Cl | Me |
| 4-tBu | $CO_2$-$nC_{10}H_{21}$ | $CF_3$ | Cl | Me |
| 4-tBu | $CH_2OEt$ | $CF_3$ | Cl | Me |
| 4-tBu | B7 | Me | Cl | Me |
| 4-tBu | B7 | Me | Me | Me |
| 4-tBu | B7 | CN | Cl | Me |
| 4-tBu | B16 | CN | Cl | Me |
| 4-tBu | B3 | CN | Cl | Me |
| 4-tBu | 2-(4-tBu-Ph)-3,3-$Me_2$-cPrC(O) | $CF_3$ | Cl | Me |
| 4-tBu | B45 | $CF_3$ | Cl | Me |
| 4-$tBuCH_2$ | B3 | $CF_3$ | Cl | Me |
| 4-$tBuCH_2$ | B7 | Me | Me | Me |
| 4-$tBuCH_2$ | B16 | Me | Cl | Me |
| 4-$tBuCH_2$ | B7 | $CF_3$ | Cl | Me |
| 4-$tBuCH_2$ | B8 | $CF_3$ | Cl | Me |
| 4-$tBuCH_2$ | B7 | Cl | Cl | Me |
| 4-Et$(Me)_2$C | H | $CF_3$ | Cl | Me |
| 4-Et$(Me)_2$C | B3 | $CF_3$ | Cl | Me |
| 4-Et$(Me)_2$C | B7 | $CF_3$ | Cl | Me |
| 4-Et$(Me)_2$C | B8 | $CF_3$ | Cl | Me |
| 4-Et$(Me)_2$C | B34 | $CF_3$ | Cl | Me |
| 4-Et$(Me)_2$C | B42 | $CF_3$ | Cl | Me |
| 4-Et$(Me)_2$C | B16 | Me | Me | Me |
| 4-Et$(Me)_2$C | B17 | Me | Me | Me |
| 4-Et$(Me)_2$C | H | Cl | Me | Me |
| 4-Et$(Me)_2$C | B7 | Cl | Cl | Me |
| 4-Et$(Me)_2$C | B8 | Cl | Cl | Me |
| 4-Et$(Me)_2$C | B7 | $CF_3$ | Me | Me |
| 4-Et$(Me)_2$C | B7 | CN | Cl | Me |
| 4-Et$(Me)_2$C | B4 | H | Cl | Me |
| 4-Et$(Me)_2$C | B5 | Cl | H | Me |
| 4-Et$(Me)_2$C | B6 | H | H | Me |
| 4-Et$(Me)_2$C | B3 | Cl | Cl | Me |
| 4-Et$(Me)_2$C | B16 | Cl | Cl | Me |
| 4-Et$(Me)_2$C | B17 | Cl | Cl | Me |
| 4-Et$(Me)_2$C | B24 | Cl | Cl | Me |
| 4-nHex | B34 | $CF_3$ | Cl | Me |
| 4-nHep | B42 | $CF_3$ | Cl | Me |
| 4-nOct | B43 | Me | Me | Me |
| 4-nNon | B43 | Me | Cl | Me |
| 4-nDec | H | Cl | Me | Me |
| 4-$(Me)_2$(CN)C | B7 | Cl | Cl | Me |
| 4-$PhCH_2$ | B7 | $CF_3$ | Cl | Me |
| 4-Ph$(Me)_2$C | B7 | $CF_3$ | Me | Me |
| 4-(4-F-Ph)$(Me)_2$C | B7 | CN | Cl | Me |
| 4-MeCH=CH | B4 | H | Cl | Me |
| 4-MeCC | B5 | Cl | H | Me |
| 3-$CF_3$ | B6 | H | H | Me |
| 4-$CF_3$ | B7 | OMe | Cl | Me |
| 4-$CF_3$ | B8 | SMe | Cl | Me |

TABLE 11-continued

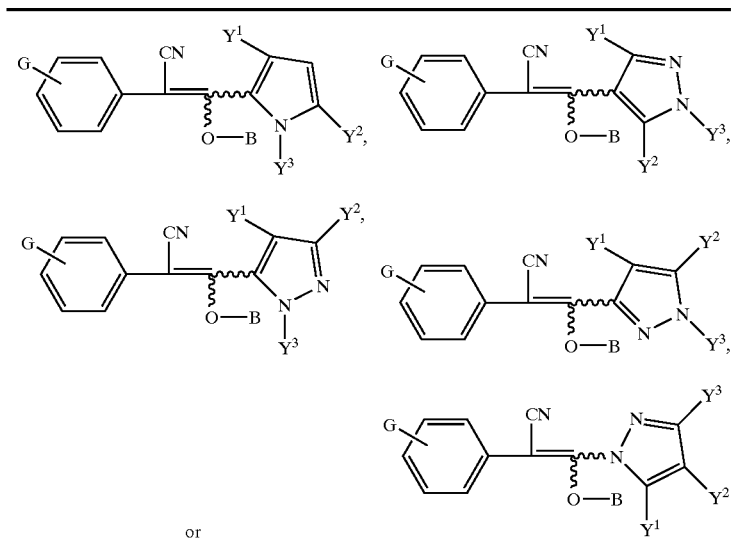

or

| G | B | Y¹ | Y² | Y³ |
|---|---|----|----|----|
| 4-CF₃ | B9 | SCF₃ | Cl | Me |
| 4-CF₃ | B16 | Me | Me | Me |
| 4-CF₃ | B17 | Me | Me | Me |
| 4-CF₃ | B16 | Me | Cl | Me |
| 4-CF₃ | B17 | Cl | Me | Me |
| 4-CF₃ | B7 | Cl | Cl | Me |
| 4-CF₃ | B7 | CF₃ | Cl | Me |
| 4-CF₃ | B7 | CN | Cl | Me |
| 4-CF₃ | B3 | Cl | Cl | Me |
| 4-CF₃CH₂ | B7 | Me | Cl | Me |
| 4-Cl₂C=CHCH₂ | B8 | Cl | Me | Me |
| 4-BrCC | B7 | Cl | Cl | Me |
| 4-(2,2-F₂)cBuCH₂ | B7 | CF₃ | Cl | Me |
| 4-(1-Me)cPr | B16 | CN | Cl | Me |
| 4-cHex | B7 | Cl | Cl | Me |
| 4-(1-Me)cHex | B8 | CF₃ | Cl | Me |
| 4-MeO | B7 | Cl | H | Me |
| 4-iPrO | B7 | Cl | Cl | Me |
| 4-iPrO | B7 | CF₃ | Cl | Me |
| 4-iPrO | B15 | CF₃ | Cl | Me |
| 4-iPrO | B7 | Me | Me | Me |
| 4-iPrO | B16 | Me | Me | Me |
| 4-iPrO | B17 | Me | Me | Me |
| 4-iPrO | B23 | SCF₃ | Cl | Me |
| 4-tBuO | B7 | Cl | Cl | Me |
| 4-tBuO | B8 | Cl | Cl | Me |
| 4-tBuO | B7 | CF₃ | Cl | Me |
| 4-nHexO | B8 | CF₃ | Cl | Me |
| 4-nOctO | B34 | CF₃ | Cl | Me |
| 4-nDecO | H | CF₃ | Cl | Me |
| 4-CH₂=CHCH₂O | B7 | CF₃ | Cl | Me |
| 4-CHCCH₂O | B8 | CF₃ | Cl₃ | Me |
| 4-CHF₂O | B34 | CF₃ | Cl | Me |
| 4-CHF₂O | B7 | Me | Me | Me |
| 4-CHF₂O | B35 | Me | Cl | Me |
| 4-CHF₂O | B36 | Cl | Cl | Me |
| 4-CHF₂O | B7 | Cl | Cl | Me |
| 4-CBrF₂O | B8 | Cl | Cl | Me |
| 4-CBrF₂O | B34 | Cl | Cl | Me |
| 4-CBrF₂O | B40 | Me | Me | Me |
| 4-CBrF₂O | B41 | Me | Cl | Me |
| 4-CBrF₂O | B42 | Cl | Me | Me |
| 4-CBrF₂O | B43 | Cl | Cl | Me |
| 4-CBrF₂O | B44 | CF₃ | Cl | Me |
| 4-CBrF₂O | COCO₂Me | CF₃ | H | Me |
| 4-CBrF₂O | H | H | CF₃ | Me |
| 4-CBrF₂O | B1 | H | Cl | Me |
| 4-CF₃O | B2 | Cl | H | Me |
| 4-CF₃O | B3 | H | H | Me |
| 4-CF₃O | B4 | OMe | Cl | Me |
| 4-CF₃O | B5 | SMe | Cl | Me |

TABLE 11-continued

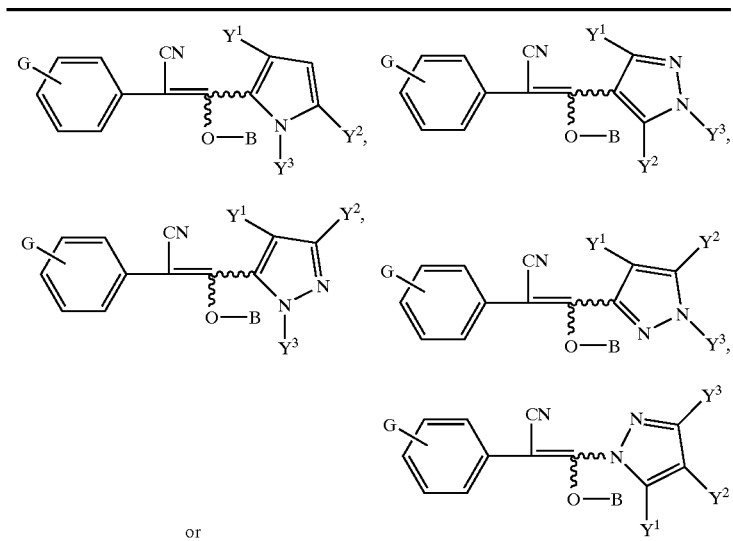

or

| G | B | Y$^1$ | Y$^2$ | Y$^3$ |
|---|---|---|---|---|
| 4-CF$_3$O | B6 | SCF$_3$ | Cl | Me |
| 4-CF$_3$O | B7 | Me | Me | Me |
| 4-CF$_3$CH$_2$O | B8 | Me | Me | Me |
| 4-CF$_2$=CHCH$_2$CH$_2$O | B9 | Me | Cl | Me |
| 4-CCl$_2$=CHCH$_2$O | B10 | Cl | Me | Me |
| 4-ClCCCH$_2$O | B11 | Cl | Cl | Me |
| 4-MeS | B12 | CF$_3$ | Cl | Me |
| 4-sBuS | H | CF$_3$ | H | Me |
| 4-EtSO | B3 | H | CF$_3$ | Me |
| 4-MeSO$_2$ | H | CF$_3$ | Cl | Me |
| 4-MeSO$_2$ | B3 | CF$_3$ | Cl | Me |
| 4-MeSO$_2$ | B32 | CF$_3$ | Cl | Me |
| 4-MeSO$_2$ | B33 | CF$_3$ | Cl | Me |
| 4-EtSO$_2$ | H | CF$_3$ | Cl | Me |
| 4-EtSO$_2$ | B3 | Cl | Cl | Me |
| 4-iPrSO$_2$ | B32 | Cl | Cl | Me |
| 4-iPrSO$_2$ | B33 | Cl | Cl | Me |
| 4-tBuSO$_2$ | B7 | Cl | Cl | Me |
| 4-tBuSO$_2$ | B33 | CF$_3$ | Cl | Me |
| 4-MeCH=CHCH$_2$S | B15 | H | H | Me |
| 4-CH$_2$=CHCH$_2$SO | B16 | OMe | Cl | Me |
| 4-CH$_2$=CHCH$_2$SO$_2$ | B28 | SMe | Cl | Me |
| 4-CHCCH$_2$S | B30 | SCF$_3$ | Cl | Me |
| 4-CHCCH$_2$SO | B34 | Me | Me | Me |
| 4-CHCCH$_2$SO$_2$ | CO-nC$_8$H$_{17}$ | Me | Me | Me |
| 4-CHF$_2$S | H | CF$_3$ | Cl | Me |
| 4-CHF$_2$S | B7 | CF$_3$ | Cl | Me |
| 4-CHF$_2$S | B8 | CF$_3$ | Cl | Me |
| 4-CHF$_2$S | B15 | CF$_3$ | Cl | Me |
| 4-CHF$_2$S | B29 | CF$_3$ | Cl | Me |
| 4-CHF$_2$S | H | Cl | Cl | Me |
| 4-CHF$_2$S | B7 | Cl | Cl | Me |
| 4-CHF$_2$S | B15 | Cl | Cl | Me |
| 4-CBrF$_2$S | B7 | Cl | Cl | Me |
| 4-CBrF$_2$S | B15 | Cl | Cl | Me |
| 4-CBrF$_2$S | B30 | Cl | Cl | Me |
| 4-CBrF$_2$S | B43 | Cl | Cl | Me |
| 4-CBrF$_2$S | CO-nC$_{15}$H$_{31}$ | Me | Cl | Me |
| 4-CBrF$_2$S | CO$_2$-nHex | CF$_3$ | Cl | Me |
| 4-CBrF$_2$S | H | CF$_3$ | Cl | Me |
| 4-CBrF$_2$S | B7 | CF$_3$ | Cl | Me |
| 4-CBrF$_2$S | B8 | CF$_3$ | Cl | Me |
| 4-CBrF$_2$S | B15 | CF$_3$ | Cl | Me |
| 4-CBrF$_2$S | B28 | CF$_3$ | Cl | Me |
| 4-CBrF$_2$S | B34 | CF$_3$ | Cl | Me |
| 4-CBrF$_2$S | B7 | Me | Cl | Me |
| 4-CF$_3$S | CO$_2$-nC$_{10}$H$_{21}$ | Cl | Cl | Me |
| 4-CF$_3$S | H | Cl | Cl | Me |
| 4-CF$_3$S | B3 | Cl | Cl | Me |
| 4-CF$_3$S | B7 | Cl | Cl | Me |
| 4-CF$_3$S | B8 | Cl | Cl | Me |

TABLE 11-continued

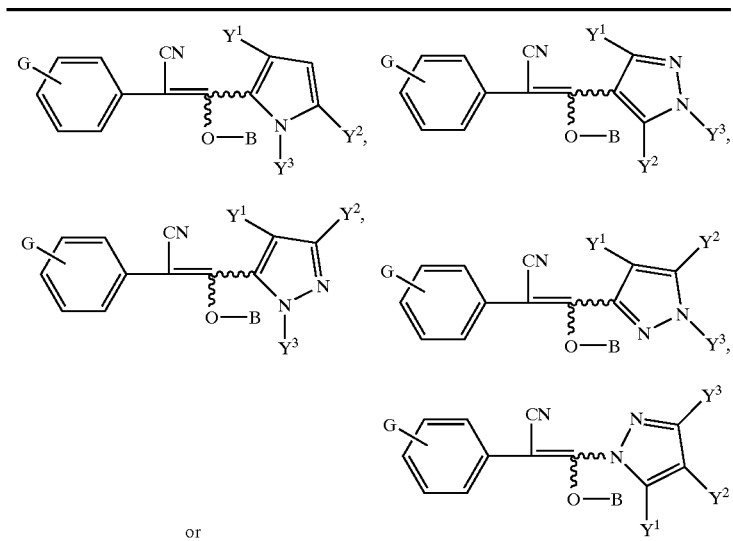

or

| G | B | Y¹ | Y² | Y³ |
|---|---|----|----|----|
| 4-CF₃S | B15 | Cl | Cl | Me |
| 4-CF₃S | H | CF₃ | Cl | Me |
| 4-CF₃S | B7 | CF₃ | Cl | Me |
| 4-CF₃S | B8 | CF₃ | Cl | Me |
| 4-CF₃S | B15 | CF₃ | Cl | Me |
| 4-CF₃S | B34 | CF₃ | Cl | Me |
| 4-CF₃S | CO₂-nC₁₂H₂₅ | CF₃ | Cl | Me |
| 4-CF₃S | CO-nC₁₅H₃₁ | CF₃ | Cl | Me |
| 4-CF₃S | CO-nC₁₆H₃₃ | Me | Me | Me |
| 4-CF₃S | CO-nC₁₇H₃₅ | Me | Cl | Me |
| 4-CF₃CH₂S | CO-nC₁₈H₃₇ | CF₃ | Cl | Me |
| 4-CHF₂CF₂S | CO-nC₁₉H₃₉ | CF₃ | H | Me |
| 4-CHF₂SO | CO-nC₂₀H₄₁ | H | CF₃ | Me |
| 4-CBrF₂SO | H | H | Cl | Me |
| 4-CBrF₂SO | B3 | CF₃ | Cl | Me |
| 4-CBrF₂SO | B7 | CF₃ | Cl | Me |
| 4-CBrF₂SO | B24 | CF₃ | Cl | Me |
| 4-CBrF₂SO | B32 | CF₃ | Cl | Me |
| 4-CBrF₂SO | B33 | CF₃ | Cl | Me |
| 4-CF₃SO | H | Cl | Cl | Me |
| 4-CF₃SO | B3 | Cl | Cl | Me |
| 4-CF₃SO | B7 | Cl | Cl | Me |
| 4-CF₃SO | B33 | Cl | H | Me |
| 4-CF₃CH₂SO₂ | B15 | H | H | Me |
| 4-CHF₂CF₂SO₂ | B16 | OMe | Cl | Me |
| 4-CHF₂SO₂ | B28 | SMe | Cl | Me |
| 4-CHF₂SO₂ | B7 | CF₃ | Cl | Me |
| 4-CHF₂SO₂ | B24 | CF₃ | Cl | Me |
| 4-CHF₂SO₂ | B32 | CF₃ | Cl | Me |
| 4-CHF₂SO₂ | B33 | CF₃ | Cl | Me |
| 4-CHF₂SO₂ | H | Cl | Cl | Me |
| 4-CHF₂SO₂ | B3 | Cl | Cl | Me |
| 4-CHF₂SO₂ | B7 | Cl | Cl | Me |
| 4-CHF₂SO₂ | B33 | Cl | H | Me |
| 4-CBrF₂SO₂ | H | SCF₃ | Cl | Me |
| 4-CBrF₂SO₂ | B2 | Cl | Cl | Me |
| 4-CBrF₂SO₂ | B3 | Cl | Cl | Me |
| 4-CBrF₂SO₂ | B18 | Cl | Cl | Me |
| 4-CBrF₂SO₂ | B19 | Cl | Cl | Me |
| 4-CBrF₂SO₂ | B33 | Cl | Cl | Me |
| 4-CBrF₂SO₂ | H | CF₃ | Cl | Me |
| 4-CBrF₂SO₂ | B3 | CF₃ | Cl | Me |
| 4-CBrF₂SO₂ | B7 | CF₃ | Cl | Me |
| 4-CBrF₂SO₂ | B20 | CF₃ | Cl | Me |
| 4-CBrF₂SO₂ | B32 | CF₃ | Cl | Me |
| 4-CBrF₂SO₂ | B33 | CF₃ | Cl | Me |
| 4-CBrF₂SO₂ | B37 | CF₃ | Cl | Me |
| 4-CBrF₂SO₂ | B7 | Me | Me | Me |
| 4-CBrF₂SO₂ | B15 | Me | Me | Me |
| 4-CBrF₂SO₂ | B17 | Me | Me | Me |
| 4-CBrF₂SO₂ | B7 | Me | Cl | Me |

TABLE 11-continued

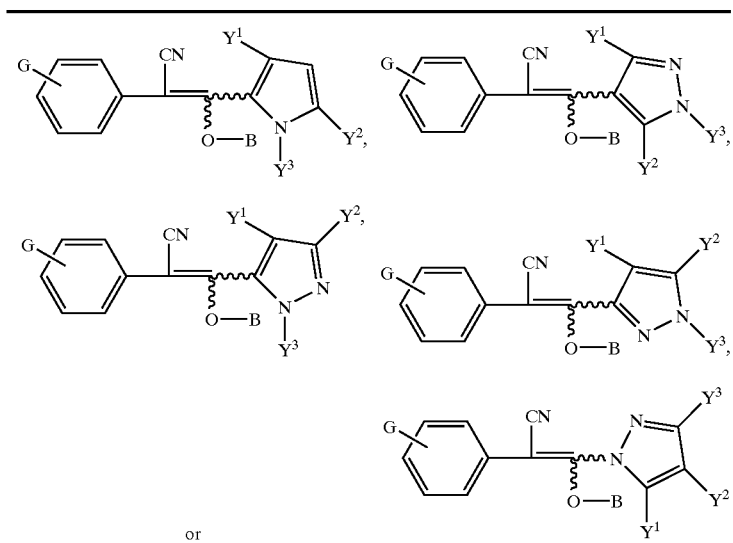

or

| G | B | Y¹ | Y² | Y³ |
|---|---|---|---|---|
| 4-CBrF$_2$SO$_2$ | B16 | Me | Cl | Me |
| 4-CF$_3$SO$_2$ | B16 | Me | Me | Me |
| 4-CF$_3$SO$_2$ | B7 | Cl | Cl | Me |
| 4-CF$_3$SO$_2$ | B15 | Cl | Cl | Me |
| 4-CF$_3$SO$_2$ | B3 | CF$_3$ | Cl | Me |
| 4-CF$_3$SO$_2$ | B7 | CF$_3$ | Cl | Me |
| 4-CF$_3$SO$_2$ | B15 | Me | Me | Me |
| 4-CF$_3$SO$_2$ | B7 | Me | Cl | Me |
| 4-CF$_3$SO$_2$ | B8 | Me | Cl | Me |
| 4-Cl$_2$C=CHCH$_2$S | B16 | Me | Me | Me |
| 4-Cl$_2$C=CHCH$_2$SO | B17 | Me | Cl | Me |
| 4-Cl$_2$C=CHCH$_2$SO$_2$ | B17 | Cl | Me | Me |
| 4-CBrCCH$_2$S | CO$_2$-nC$_{10}$H$_{21}$ | Cl | Cl | Me |
| 4-CBrCCH$_2$SO | B33 | CF$_3$ | Cl | Me |
| 4-CBrCCH$_2$SO$_2$ | B7 | CF$_3$ | H | Me |
| 4-CHO | B7 | H | CF$_3$ | Me |
| 4-NO$_2$ | B8 | H | Cl | Me |
| 4-CN | B16 | Cl | H | Me |
| 4-(Me)$_2$N | B3 | H | H | Me |
| 4-Me(MeCO)N | B7 | OMe | Cl | Me |
| 4-PhMeN | B8 | SMe | Cl | Me |
| 4-PhCH$_2$(MeCO)N | B15 | SCF$_3$ | Cl | Me |
| 4-(1-naphthyl) | B16 | Me | Me | Me |
| 4-(2-naphthyl) | B28 | Me | Me | Me |
| 4-(2-Cl-Ph)CH$_2$O | B30 | Me | Cl | Me |
| 4-(3-Cl-Ph)CH$_2$O | B34 | Cl | Me | Me |
| 4-(4-Cl-Ph)CH$_2$O | B7 | CF$_3$ | Cl | Me |
| 4-(4-Cl-Ph)CH$_2$O | B7 | Cl | Cl | Me |
| 4-(4-Cl-Ph)CH$_2$O | B37 | Cl | Cl | Me |
| 4-(4-F-Ph)CH$_2$O | B42 | CF$_3$ | Cl | Me |
| 4-(2-Me-Ph)CH$_2$O | B43 | CF$_3$ | H | Me |
| 4-(4-Me-Ph)CH$_2$O | B43 | H | CF$_3$ | Me |
| 4-(4-Et-Ph)CH$_2$O | H | H | Cl | Me |
| 3-(2,4-Cl$_2$-Ph)CH$_2$O | B7 | Cl | H | Me |
| 4-(3,4-Cl$_2$-Ph)CH$_2$O | B7 | H | H | Me |
| 4-(2,5-Me$_2$-Ph)CH$_2$O | B7 | OMe | Cl | Me |
| 4-(2,3,4,5,6-F$_5$-Ph)CH$_2$O | B7 | SMe | Cl | Me |
| 4-MeOC(O) | B4 | SCF$_3$ | Cl | Me |
| 4-EtOC(O) | B5 | Me | Me | Me |
| 4-nPrOC(O) | B6 | Me | Me | Me |
| 4-iPrOC(O) | B7 | Me | Cl | Me |
| 4-iBuOC(O) | B8 | Cl | Me | Me |
| 4-tBuOC(O) | B9 | Cl | Cl | Me |
| 4-tBuCH$_2$OC(O) | B7 | Cl | Cl | Me |
| 4-tBuCH$_2$OC(O) | B15 | Cl | Cl | Me |
| 4-tBuCH$_2$OC(O) | B34 | Cl | Cl | Me |
| 4-tBuCH$_2$OC(O) | B7 | CF$_3$ | Cl | Me |
| 4-tBuCH$_2$OC(O) | B15 | CF$_3$ | Cl | Me |
| 4-tBuCH$_2$OC(O) | B34 | CF$_3$ | Cl | Me |
| 4-tBuCH$_2$OC(O) | B10 | CF$_3$ | Cl | Me |
| 4-Et(Me)$_2$COC(O) | B11 | CF$_3$ | H | Me |

TABLE 11-continued

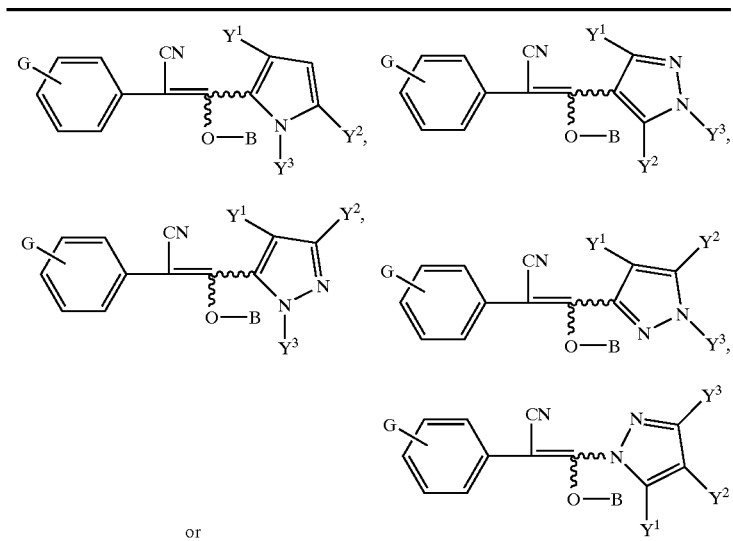

or

| G | B | Y¹ | Y² | Y³ |
|---|---|----|----|----|
| 4-nHexOC(O) | B7 | H | CF₃ | Me |
| 4-MeOCH₂ | B8 | H | Cl | Me |
| 4-EtOCH₂ | B7 | Cl | H | Me |
| 4-iPrOCH₂ | B7 | H | H | Me |
| 4-MeC(O) | B16 | OMe | Cl | Me |
| 4-EtC(O) | B7 | SMe | Cl | Me |
| 4-iPrC(O) | B8 | SCF₃ | Cl | Me |
| 4-tBuC(O) | H | Cl | Cl | Me |
| 4-tBuC(O) | B3 | Cl | Cl | Me |
| 4-tBuC(O) | B7 | Cl | Cl | Me |
| 4-tBuC(O) | B3 | CF₃ | Cl | Me |
| 4-tBuC(O) | B7 | CF₃ | Cl | Me |
| 4-tBuC(O) | B15 | CF₃ | Cl | Me |
| 4-tBuC(O) | B7 | Me | Me | Me |
| 4-tBuC(O) | B17 | Me | Me | Me |
| 4-tBuC(O) | B16 | Me | Cl | Me |
| 4-CF₃C(O) | B7 | Me | Me | Me |
| 4-CF₃CF₂C(O) | B8 | Me | Cl | Me |
| 4-CF₂CF₂CF₂C(O) | B22 | Cl | Me | Me |
| 4-MeC(O)O | B23 | Cl | Cl | Me |
| 4-iPrC(O)O | B7 | CF₃ | Cl | Me |
| 4-tBuC(O)O | B8 | CF₃ | H | Me |
| 4-CF₃C(O)O | B7 | H | CF₃ | Me |
| 4-CF₂CF₂CF₂C(O)O | B8 | H | Cl | Me |
| 4-Me₂NC(O)O | B34 | Cl | H | Me |
| 4-Et₂NC(O)O | H | H | H | Me |
| 4-(nPr)₂NC(O)O | B7 | OMe | Cl | Me |
| 3-Ph | B8 | SMe | Cl | Me |
| 4-Ph | B34 | SCF₃ | Cl | Me |
| 4-(4-F-Ph) | B7 | Cl | Cl | Me |
| 4-(4-F-Ph) | B7 | CF₃ | Cl | Me |
| 3-PhO | B7 | Cl | Cl | Me |
| 3-PhO | B15 | CF₃ | Cl | Me |
| 4-PhO | B7 | Me | Me | Me |
| 4-(4-F-Ph)O | B35 | Me | Cl | Me |
| 4-(4-Cl-Ph)O | B36 | Cl | Me | Me |
| 4-(4-Br-Ph)O | B7 | Cl | Cl | Me |
| 4-(4-Me-Ph)O | B8 | CF₃ | Cl | Me |
| 4-(2-Cl-Ph)O | B34 | CF₃ | H | Me |
| 4-(2-F-Ph)O | B40 | H | CF₃ | Me |
| 4-(3-Cl-Ph)O | B41 | H | Cl | Me |
| 4-(4-Cl-Ph)O | B42 | Cl | H | Me |
| 4-(2,4-Cl₂-Ph)O | B43 | H | H | Me |
| 4-(3,4-Cl₂-Ph)O | B44 | OMe | Cl | Me |
| 4-(3,4,5-Cl₃-Ph)O | COCO₂Me | SMe | Cl | Me |
| 4-(2-Me-Ph)O | H | SCF₃ | Cl | Me |
| 4-(4-Me-Ph)O | B1 | Me | Me | Me |
| 4-(3-Cl-4-Me-Ph)O | B2 | H | CF₃ | Me |
| 4-(2-pyridyl) | B3 | H | Cl | Me |
| 4-(5-CF₃-pyridin-2-yl) | B4 | Cl | H | Me |
| 4-(2-pyridyl)O | B7 | Cl | Cl | Me |

TABLE 11-continued

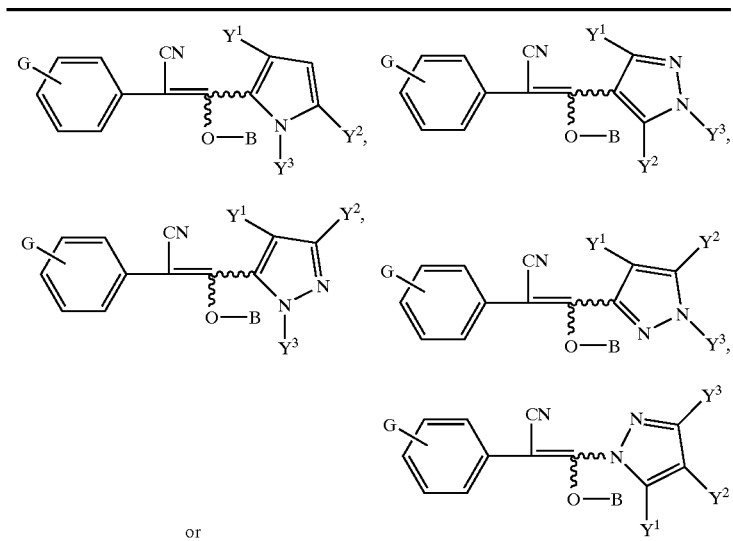

or

| G | B | Y¹ | Y² | Y³ |
|---|---|---|---|---|
| 4-(2-pyridyl)O | B15 | Cl | Cl | Me |
| 4-(2-pyridyl)O | B7 | $CF_3$ | Cl | Me |
| 4-(2-pyridyl)O | B8 | $CF_3$ | Cl | Me |
| 4-(2-pyridyl)O | B34 | $CF_3$ | Cl | Me |
| 4-(2-pyridyl)O | B5 | Cl | Cl | Me |
| 4-(5-$CF_3$-pyridin-2-yl)O | B7 | Cl | Cl | Me |
| 4-(5-$CF_3$-pyridin-2-yl)O | B8 | Cl | Cl | Me |
| 4-(5-$CF_3$-pyridin-2-yl)O | B15 | $CF_3$ | Cl | Me |
| 4-(5-$CF_3$-pyridin-2-yl)O | B7 | $CF_3$ | Cl | Me |
| 4-(5-$CF_3$-pyridin-2-yl)O | B15 | $CF_3$ | Cl | Me |
| 4-(5-$CF_3$-pyridin-2-yl)O | B34 | Me | Cl | Me |
| 4-(3-Cl-5-$CF_3$-pyridin-2-yl) | B7 | Cl | Cl | Me |
| 4-(3-Cl-5-$CF_3$-pyridin-2-yl) | B15 | Cl | Cl | Me |
| 4-(3-Cl-5-$CF_3$-pyridin-2-yl) | B34 | Cl | Cl | Me |
| 4-(3-Cl-5-$CF_3$-pyridin-2-yl) | B7 | $CF_3$ | Cl | Me |
| 4-(3-Cl-5-$CF_3$-pyridin-2-yl) | B15 | $CF_3$ | Cl | Me |
| 4-(3-Cl-5-$CF_3$-pyridin-2-yl) | B17 | $CF_3$ | Cl | Me |
| 4-(3-Cl-5-$CF_3$-pyridin-2-yl) | H | Cl | Cl | Me |
| 4-(5-Cl-thiophen-2-yl) | B8 | Cl | Cl | Me |
| 3-$OCH_2O$-4 | B9 | Cl | Cl | Me |
| 3-$OCF_2O$-4 | B10 | $CF_3$ | Cl | Me |
| 4-MeCH=N | B11 | $CF_3$ | Cl | Me |
| 4-$Me_2$C=N | B12 | $CF_3$ | Cl | Me |
| 4-MeEtC=N | H | Cl | Cl | Me |
| 4-PhCH=N | B3 | Cl | Cl | Me |
| 4-PhMeC=N | B7 | Cl | Cl | Me |
| 4-$PhCH_2$CH=N | B8 | $CF_3$ | Cl | Me |
| 4-$cC_6H_{10}$=N | B15 | $CF_3$ | Cl | Me |
| 3-$CH_2CH_2CH_2$-4 | B16 | $CF_3$ | Cl | Me |
| 3-$CH_2CH_2CH_2CH_2$-4 | B28 | Cl | Cl | Me |
| 4-PhC(O) | H | Cl | Cl | Me |
| 4-PhC(O) | B7 | Cl | Cl | Me |
| 4-PhC(O) | B7 | Cl | Cl | Me |
| 4-PhC(O) | B33 | $CF_3$ | Cl | Me |
| 4-(2-Cl-Ph)C(O) | B7 | $CF_3$ | Cl | Me |
| 4-(4-F-Ph)C(O) | H | $CF_3$ | Cl | Me |
| 4-(4-Cl-Ph)C(O) | B7 | Cl | Cl | Me |
| 4-(4-Cl-Ph)C(O) | B15 | Cl | Cl | Me |
| 4-(4-Cl-Ph)C(O) | B34 | Cl | Cl | Me |
| 4-(4-Me-Ph)C(O) | B3 | $CF_3$ | Cl | Me |
| 4-(4-Me-Ph)C(O) | B16 | $CF_3$ | Cl | Me |
| 4-(3,4-$Cl_2$-Ph)C(O) | B45 | $CF_3$ | Cl | Me |
| 3,4-$Cl_2$ | B15 | Cl | Cl | Me |
| 3-Cl-4-F | B7 | Cl | Cl | Me |
| 2,6-$F_2$ | B15 | $CF_3$ | Cl | Me |
| 3-Cl-4-$CF_3$ | B7 | $CF_3$ | Cl | Me |
| 4-tBu-3-Cl | B7 | Cl | Cl | Me |
| 4-tBu-3-Cl | B15 | $CF_3$ | Cl | Me |
| 4-$tBuCH_2$-3-Cl | B7 | Cl | Cl | Me |
| 4-nHep-3-Cl | B15 | $CF_3$ | Cl | Me |
| 3-Cl-4-iPrO | B7 | Cl | Cl | Me |

TABLE 11-continued

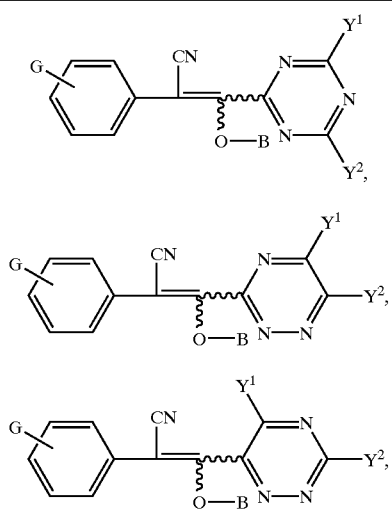

| G | B | Y$^1$ | Y$^2$ | Y$^3$ |
|---|---|---|---|---|
| 3-Cl-4-iPrO | B7 | CF$_3$ | Cl | Me |
| 3-Cl-4-nHepO | B15 | CF$_3$ | Cl | Me |
| 3-Cl-4-(3,4-Cl$_2$-PhCH$_2$)O | H | CF$_3$ | Cl | Me |
| 3-Cl-4-PhCH$_2$O | B7 | CF$_3$ | Cl | Me |
| 3,4-(MeO)$_2$ | B16 | CF$_3$ | Cl | Me |
| 4-MeO-3-Me | B17 | CF$_3$ | Cl | Me |
| 4-OH-3,5-(tBu)$_2$ | B3 | CF$_3$ | Cl | Me |
| 3,4,5-Cl$_3$ | B15 | CF$_3$ | Cl | Me |
| 2,6-Cl$_2$-4-CF$_3$ | B7 | CF$_3$ | Cl | Me |
| 2,6-F$_2$-4-CF$_3$ | B15 | Cl | Cl | Me |
| 2,6-F$_2$-4-CF$_3$O | B7 | CF$_3$ | Cl | Me |
| 3,5-Cl$_2$-4-tBu | B7 | Cl | Cl | Me |
| 3,5-Cl$_2$-4-tBuCH$_2$ | B15 | CF$_3$ | Cl | Me |
| 3,5-Cl$_2$-4-nDec | B7 | Cl | Cl | Me |
| 3,5-Cl$_2$-4-PhCH$_2$O | B15 | CF$_3$ | Cl | Me |
| 2,3,5,6-F$_4$-4-Me | B3 | CF$_3$ | Cl | Me |
| 2,3,4,5,6-F$_5$ | B33 | CF$_3$ | Cl | Me |

TABLE 12

TABLE 12-continued
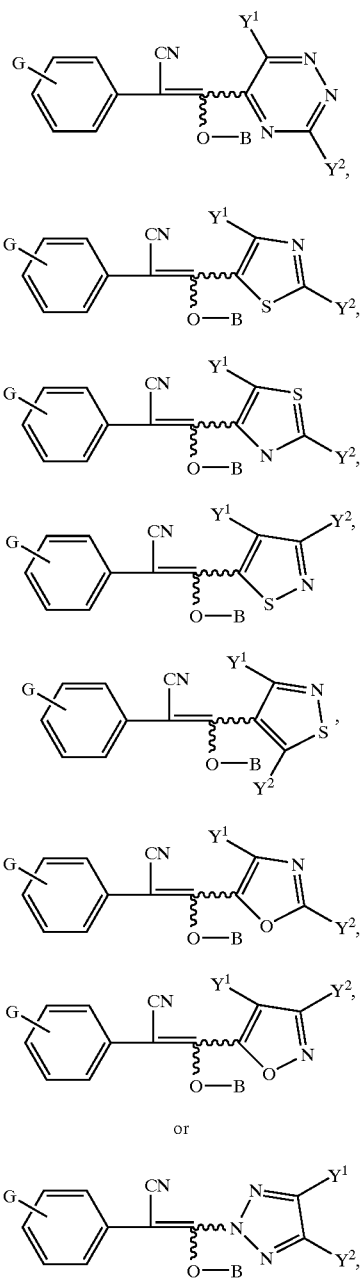
| G | B | Y¹ | Y² |
|---|---|---|---|
| 2-Cl | H | Me | Me |
| 3-Cl | B1 | H | H |
| 4-Cl | B2 | Me | H |
| 4-Br | B3 | H | Me |
| 4-I | B4 | Me | Me |
| 4-F | B5 | CF$_3$ | Me |
| 4-Me | B6 | Cl | Me |
| 4-Et | B7 | H | Me |
| 4-iPr | B8 | Cl | Me |
| 4-nBu | B9 | H | Me |
| 4-iBu | B10 | OMe | Me |
| 4-sBu | B11 | SMe | Me |
| 4-sBu | H | Me | Me |
| 4-sBu | B16 | Et | Me |
| 4-sBu | B17 | Cl | Me |
| 4-sBu | B7 | Cl | Cl |

TABLE 12-continued

| | | | |
|---|---|---|---|
| 4-sBu | B8 | $CF_3$ | Me |
| 4-sBu | B16 | Me | $CF_3$ |
| 4-sBu | B17 | Me | Me |
| 4-sBu | B34 | $CF_3$ | Me |
| 4-sBu | B3 | $CF_3$ | Me |
| 4-sBu | B7 | $CF_3$ | Me |
| 4-sBu | B8 | Cl | Me |
| 4-sBu | B34 | Me | Cl |
| 4-sBu | B7 | H | H |
| 4-sBu | B17 | $CF_3$ | Me |
| 4-tBu | B12 | $SCF_3$ | Me |
| 4-tBu | H | Me | Me |
| 4-tBu | B3 | Me | Me |
| 4-tBu | B7 | Me | Me |
| 4-tBu | B8 | Et | Me |
| 4-tBu | B15 | Me | nPr |
| 4-tBu | B16 | OMe | OMe |
| 4-tBu | B28 | Cl | Cl |
| 4-tBu | B30 | $OCHF_2$ | Me |
| 4-tBu | B34 | $CF_3$ | $CF_3$ |
| 4-tBu | $CO-nC_8H_{17}$ | H | H |
| 4-tBu | $CO-nC_{15}H_{31}$ | Cl | Cl |
| 4-tBu | $CO_2$-nHex | Me | Me |
| 4-tBu | $CO_2-nC_{10}H_{21}$ | Me | Me |
| 4-tBu | H | CN | Me |
| 4-tBu | H | $CF_3$ | Me |
| 4-tBu | B3 | $CF_3$ | Me |
| 4-tBu | B7 | $CF_3$ | Me |
| 4-tBu | B8 | $CF_3$ | Me |
| 4-tBu | B15 | $CF_3$ | Me |
| 4-tBu | B16 | $CF_3$ | Me |
| 4-tBu | B28 | $CF_3$ | Me |
| 4-tBu | B30 | $CF_3$ | Me |
| 4-tBu | B16 | Cl | Cl |
| 4-tBu | B16 | $CF_3$ | Me |
| 4-tBu | B17 | $CF_3$ | Me |
| 4-tBu | B17 | Me | Me |
| 4-tBu | $CO_2-nC_{10}H_{21}$ | $CF_3$ | Me |
| 4-tBu | $CH_2OEt$ | $CF_3$ | Me |
| 4-tBu | B7 | Me | $CF_3$ |
| 4-tBu | B7 | Cl | Cl |
| 4-tBu | B7 | CN | Me |
| 4-tBu | B16 | CN | Me |
| 4-tBu | B3 | CN | Me |
| 4-tBu | 2-(4-tBu-Ph)-3,3-$Me_2$-cPrC(O) | $CF_3$ | Me |
| 4-tBu | B45 | $CF_3$ | Me |
| 4-tBuCH$_2$ | B3 | $CF_3$ | Me |
| 4-tBuCH$_2$ | B7 | Me | Me |
| 4-tBuCH$_2$ | B16 | Me | Me |
| 4-tBuCH$_2$ | B7 | $CF_3$ | Me |
| 4-tBuCH$_2$ | B8 | $CF_3$ | Me |
| 4-tBuCH$_2$ | B7 | Cl | Me |
| 4-Et(Me)$_2$C | H | $CF_3$ | Me |
| 4-Et(Me)$_2$C | B3 | $CF_3$ | Me |
| 4-Et(Me)$_2$C | B7 | $CF_3$ | Me |
| 4-Et(Me)$_2$C | B8 | $CF_3$ | Me |
| 4-Et(Me)$_2$C | B34 | $CF_3$ | Me |
| 4-Et(Me)$_2$C | B42 | $CF_3$ | Me |
| 4-Et(Me)$_2$C | B16 | $CF_3$ | Me |
| 4-Et(Me)$_2$C | B17 | $CF_3$ | Me |
| 4-Et(Me)$_2$C | H | Cl | Me |
| 4-Et(Me)$_2$C | B7 | Cl | Me |
| 4-Et(Me)$_2$C | B8 | Cl | Me |
| 4-Et(Me)$_2$C | B7 | Me | $CF_3$ |
| 4-Et(Me)$_2$C | B7 | CN | Me |
| 4-Et(Me)$_2$C | B4 | H | Me |
| 4-Et(Me)$_2$C | B5 | Me | Me |
| 4-Et(Me)$_2$C | B6 | Me | Me |
| 4-Et(Me)$_2$C | B3 | Me | Cl |
| 4-Et(Me)$_2$C | B16 | Me | Cl |
| 4-Et(Me)$_2$C | B17 | Me | Cl |
| 4-Et(Me)$_2$C | B24 | Me | Cl |
| 4-nHex | B34 | $CF_3$ | Me |
| 4-nHep | B42 | $CF_3$ | Me |
| 4-nOct | B43 | Me | Me |
| 4-nNon | B43 | Me | Me |
| 4-nDec | H | Cl | Me |
| 4-(Me)$_2$(CN)C | B7 | Cl | Me |
| 4-PhCH$_2$ | B7 | $CF_3$ | Me |

TABLE 12-continued

| | | | |
|---|---|---|---|
| 4-Ph(Me)$_2$C | B7 | CF$_3$ | Me |
| 4-(4-F-Ph)(Me)$_2$C | B7 | CN | Me |
| 4-MeCH=CH | B4 | H | Me |
| 4-MeCC | B5 | Cl | Me |
| 3-CF$_3$ | B6 | H | Me |
| 4-CF$_3$ | B7 | OMe | Me |
| 4-CF$_3$ | B8 | SMe | Me |
| 4-CF$_3$ | B9 | SCF$_3$ | Me |
| 4-CF$_3$ | B16 | Me | Me |
| 4-CF$_3$ | B17 | Me | Me |
| 4-CF$_3$ | B16 | Me | Me |
| 4-CF$_3$ | B17 | Cl | Me |
| 4-CF$_3$ | B7 | Cl | Me |
| 4-CF$_3$ | B7 | CF$_3$ | Me |
| 4-CF$_3$ | B7 | Me | Me |
| 4-CF$_3$ | B3 | Cl | Me |
| 4-CF$_3$CH$_2$ | B7 | Me | Me |
| 4-Cl$_2$C=CHCH$_2$ | B8 | Cl | Me |
| 4-BrCC | B7 | Cl | Me |
| 4-(2,2-F$_2$)cBuCH$_2$ | B7 | CF$_3$ | Me |
| 4-(1-Me)cPr | B16 | CN | Me |
| 4-cHex | B7 | CF$_3$ | Me |
| 4-(1-Me)cHex | B8 | CF$_3$ | Me |
| 4-MeO | B7 | CF$_3$ | Me |
| 4-iPrO | B7 | Cl | Me |
| 4-iPrO | B7 | CF$_3$ | Me |
| 4-iPrO | B15 | CF$_3$ | Me |
| 4-iPrO | B7 | Me | Me |
| 4-iPrO | B16 | Me | Me |
| 4-iPrO | B17 | Me | Me |
| 4-iPrO | B23 | SCF$_3$ | Me |
| 4-tBuO | B7 | Me | Me |
| 4-tBuO | B8 | CF$_3$ | Me |
| 4-tBuO | B7 | CF$_3$ | Me |
| 4-n-HexO | B8 | CF$_3$ | Me |
| 4-nOctO | B34 | CF$_3$ | Me |
| 4-nDecO | H | CF$_3$ | Me |
| 4-CH$_2$=CHCH$_2$O | B7 | CF$_3$ | Me |
| 4-CHCCH$_2$O | B8 | CF$_3$ | Me |
| 4-CHF$_2$O | B34 | CF$_3$ | Me |
| 4-CHF$_2$O | B7 | Et | Me |
| 4-CHF$_2$O | B35 | Me | Me |
| 4-CHF$_2$O | B36 | Cl | Me |
| 4-CHF$_2$O | B7 | CF$_3$ | Me |
| 4-CBrF$_2$O | B8 | Cl | Me |
| 4-CBrF$_2$O | B34 | Cl | Me |
| 4-CBrF$_2$O | B40 | Me | Me |
| 4-CBrF$_2$O | B41 | Me | Me |
| 4-CBrF$_2$O | B42 | Cl | Me |
| 4-CBrF$_2$O | B7 | CF$_3$ | Me |
| 4-CBrF$_2$O | B8 | CF$_3$ | Me |
| 4-CBrF$_2$O | COCO$_2$Me | CF$_3$ | Me |
| 4-CBrF$_2$O | H | H | Me |
| 4-CBrF$_2$O | B1 | CF$_3$ | Me |
| 4-CF$_3$O | B2 | Cl | Me |
| 4-CF$_3$O | B3 | H | Me |
| 4-CF$_3$O | B4 | OMe | Me |
| 4-CF$_3$O | B5 | SMe | Me |
| 4-CF$_3$O | B6 | SCF$_3$ | Me |
| 4-CF$_3$O | B7 | CF$_3$ | Me |
| 4-CF$_3$CH$_2$O | B8 | Me | Me |
| 4-CF$_2$=CHCH$_2$CH$_2$O | B9 | Me | Me |
| 4-CCl$_2$=CHCH$_2$O | B10 | Cl | Me |
| 4-ClCCCH$_2$O | B11 | Cl | Me |
| 4-MeS | B12 | CF$_3$ | Me |
| 4-sBuS | H | CF$_3$ | Me |
| 4-EtSO | B3 | H | Me |
| 4-MeSO$_2$ | H | CF$_3$ | Me |
| 4-MeSO$_2$ | B3 | CF$_3$ | Me |
| 4-MeSO$_2$ | B32 | CF$_3$ | Me |
| 4-MeSO$_2$ | B33 | CF$_3$ | Me |
| 4-EtSO$_2$ | H | CF$_3$ | Me |
| 4-EtSO$_2$ | B3 | Et | Me |
| 4-iPrSO$_2$ | B32 | CF$_3$ | Me |
| 4-iPrSO$_2$ | B33 | CF$_3$ | Me |
| 4-tBuSO$_2$ | B7 | CF$_3$ | Me |
| 4-tBuSO$_2$ | B33 | CF$_3$ | Me |
| 4-MeCH=CHCH$_2$S | B15 | H | Me |
| 4-CH$_2$=CHCH$_2$SO | B16 | OMe | Me |

TABLE 12-continued

| | | | |
|---|---|---|---|
| 4-CH$_2$=CHCH$_2$SO$_2$ | B28 | SMe | Me |
| 4-CHCCH$_2$S | B30 | SCF$_3$ | Me |
| 4-CHCCH$_2$SO | B34 | Me | Me |
| 4-CHCCH$_2$SO$_2$ | CO-nC$_8$H$_{17}$ | Me | Me |
| 4-CHF$_2$S | H | CF$_3$ | Me |
| 4-CHF$_2$S | B7 | CF$_3$ | Me |
| 4-CHF$_2$S | B8 | CF$_3$ | Me |
| 4-CHF$_2$S | B15 | CF$_3$ | Me |
| 4-CHF$_2$S | B29 | CF$_3$ | Me |
| 4-CHF$_2$S | H | Me | Me |
| 4-CHF$_2$S | B7 | Me | Me |
| 4-CHF$_2$S | B15 | Me | Me |
| 4-CBrF$_2$S | B7 | Me | CF$_3$ |
| 4-CBrF$_2$S | B15 | Me | CF$_3$ |
| 4-CBrF$_2$S | B30 | Me | CF$_3$ |
| 4-CBrF$_2$S | B43 | Me | CF$_3$ |
| 4-CBrF$_2$S | CO-nC$_{15}$H$_{31}$ | nPr | Me |
| 4-CBrF$_2$S | CO$_2$-nHex | CF$_3$ | Me |
| 4-CBrF$_2$S | H | CF$_3$ | Me |
| 4-CBrF$_2$S | B7 | CF$_3$ | Me |
| 4-CBrF$_2$S | B8 | CF$_3$ | Me |
| 4-CBrF$_2$S | B15 | CF$_3$ | Me |
| 4-CBrF$_2$S | B28 | CF$_3$ | Me |
| 4-CBrF$_2$S | B34 | CF$_3$ | Me |
| 4-CBrF$_2$S | B7 | Me | Me |
| 4-CF$_3$S | CO$_2$-nC$_{10}$H$_{21}$ | Cl | Me |
| 4-CF$_3$S | H | Me | Me |
| 4-CF$_3$S | B3 | Me | Me |
| 4-CF$_3$S | B7 | Me | Me |
| 4-CF$_3$S | B8 | Me | Me |
| 4-CF$_3$S | B15 | Me | Me |
| 4-CF$_3$S | H | CF$_3$ | Me |
| 4-CF$_3$S | B7 | CF$_3$ | Me |
| 4-CF$_3$S | B8 | CF$_3$ | Me |
| 4-CF$_3$S | B15 | CF$_3$ | Me |
| 4-CF$_3$S | B34 | CF$_3$ | Me |
| 4-CF$_3$S | CO$_2$-nC$_{12}$H$_{25}$ | CF$_3$ | Me |
| 4-CF$_3$S | CO-nC$_{15}$H$_{31}$ | CF$_3$ | Me |
| 4-CF$_3$S | CO-nC$_{16}$H$_{33}$ | Me | Me |
| 4-CF$_3$S | CO-nC$_{17}$H$_{35}$ | Me | Me |
| 4-CF$_3$CH$_2$S | CO-nC$_{18}$H$_{37}$ | CF$_3$ | Me |
| 4-CHF$_2$CF$_2$S | CO-nC$_{19}$H$_{39}$ | CF$_3$ | Me |
| 4-CHF$_2$SO | CO-nC$_{20}$H$_{41}$ | Cl | Cl |
| 4-CBrF$_2$SO | H | H | Me |
| 4-CBrF$_2$SO | B3 | CF$_3$ | Me |
| 4-CBrF$_2$SO | B7 | CF$_3$ | Me |
| 4-CBrF$_2$SO | B24 | CF$_3$ | Me |
| 4-CBrF$_2$SO | B32 | CF$_3$ | Me |
| 4-CBrF$_2$SO | B33 | CF$_3$ | Me |
| 4-CF$_3$SO | H | Me | Me |
| 4-CF$_3$SO | B3 | Me | Me |
| 4-CF$_3$SO | B7 | Me | Me |
| 4-CF$_3$SO | B33 | Me | Me |
| 4-CF$_3$CH$_2$SO$_2$ | B15 | H | Me |
| 4-CHF$_2$CF$_2$SO$_2$ | B16 | OMe | Me |
| 4-CHF$_2$SO$_2$ | B28 | SMe | Me |
| 4-CHF$_2$SO$_2$ | B7 | CF$_3$ | Me |
| 4-CHF$_2$SO$_2$ | B24 | CF$_3$ | Me |
| 4-CHF$_2$SO$_2$ | B32 | CF$_3$ | Me |
| 4-CHF$_2$SO$_2$ | B33 | CF$_3$ | Me |
| 4-CHF$_2$SO$_2$ | H | Me | Me |
| 4-CHF$_2$SO$_2$ | B3 | Me | Me |
| 4-CHF$_2$SO$_2$ | B7 | Me | Me |
| 4-CHF$_2$SO$_2$ | B33 | Me | Me |
| 4-CBrF$_2$SO$_2$ | H | SCF$_3$ | Me |
| 4-CBrF$_2$SO$_2$ | B2 | Me | Me |
| 4-CBrF$_2$SO$_2$ | B3 | Me | Me |
| 4-CBrF$_2$SO$_2$ | B18 | Me | Me |
| 4-CBrF$_2$SO$_2$ | B19 | Me | Me |
| 4-CBrF$_2$SO$_2$ | B33 | Me | Me |
| 4-CBrF$_2$SO$_2$ | H | CF$_3$ | Me |
| 4-CBrF$_2$SO$_2$ | B3 | CF$_3$ | Me |
| 4-CBrF$_2$SO$_2$ | B7 | CF$_3$ | Me |
| 4-CBrF$_2$SO$_2$ | B20 | CF$_3$ | Me |
| 4-CBrF$_2$SO$_2$ | B32 | CF$_3$ | Me |
| 4-CBrF$_2$SO$_2$ | B33 | CF$_3$ | Me |
| 4-CBrF$_2$SO$_2$ | B37 | CF$_3$ | Me |
| 4-CBrF$_2$SO$_2$ | B7 | Me | CF$_3$ |
| 4-CBrF$_2$SO$_2$ | B15 | Me | CF$_3$ |

TABLE 12-continued

| | | | |
|---|---|---|---|
| 4-CBrF$_2$SO$_2$ | B17 | Me | CF$_3$ |
| 4-CBrF$_2$SO$_2$ | B7 | Me | CF$_3$ |
| 4-CBrF$_2$SO$_2$ | B16 | Me | CF$_3$ |
| 4-CF$_3$SO$_2$ | B16 | Me | Me |
| 4-CF$_3$SO$_2$ | B7 | Cl | Me |
| 4-CF$_3$SO$_2$ | B15 | Cl | Cl |
| 4-CF$_3$SO$_2$ | B3 | CF$_3$ | Me |
| 4-CF$_3$SO$_2$ | B7 | CF$_3$ | Me |
| 4-CF$_3$SO$_2$ | B15 | Me | Me |
| 4-CF$_3$SO$_2$ | B7 | Me | Me |
| 4-CF$_3$SO$_2$ | B8 | Me | Me |
| 4-Cl$_2$C=CHCH$_2$S | B16 | Me | Me |
| 4-Cl$_2$C=CHCH$_2$SO | B17 | Me | Me |
| 4-Cl$_2$C=CHCH$_2$SO$_2$ | B17 | Cl | Me |
| 4-CBrCCH$_2$S | CO$_2$-nC$_{10}$H$_{21}$ | Cl | Me |
| 4-CBrCCH$_2$SO | B33 | CF$_3$ | Me |
| 4-CBrCCH$_2$SO$_2$ | B7 | CF$_3$ | Me |
| 4-CHO | B7 | H | Me |
| 4-NO$_2$ | B8 | H | Me |
| 4-CN | B16 | Cl | Me |
| 4-(Me)$_2$N | B3 | H | Me |
| 4-Me(MeCO)N | B7 | OMe | Me |
| 4-PhMeN | B8 | SMe | Me |
| 4-PhCH$_2$(MeCO)N | B15 | SCF$_3$ | Me |
| 4-(1-naphthyl) | B16 | Me | Me |
| 4-(2-naphthyl) | B28 | Me | Me |
| 4-(2-Cl-Ph)CH$_2$O | B30 | Me | Me |
| 4-(3-Cl-Ph)CH$_2$O | B34 | Cl | Me |
| 4-(4-Cl-Ph)CH$_2$O | B7 | CF$_3$ | Me |
| 4-(4-Cl-Ph)CH$_2$O | B7 | Cl | Me |
| 4-(4-Cl-Ph)CH$_2$O | B37 | Cl | Me |
| 4-(4-F-Ph)CH$_2$O | B42 | CF$_3$ | Me |
| 4-(2-Me-Ph)CH$_2$O | B43 | CF$_3$ | Me |
| 4-(4-Me-Ph)CH$_2$O | B43 | CF$_3$ | Me |
| 4-(4-Et-Ph)CH$_2$O | H | CF$_3$ | Me |
| 3-(2,4-Cl$_2$-Ph)CH$_2$O | B7 | CF$_3$ | Me |
| 4-(3,4-Cl$_2$-Ph)CH$_2$O | B7 | H | Me |
| 4-(2,5-Me$_2$-Ph)CH$_2$O | B7 | OMe | Me |
| 4-(2,3,4,5,6-F$_5$-Ph)CH$_2$O | B7 | SMe | Me |
| 4-MeOC(O) | B4 | SCF$_3$ | Me |
| 4-EtOC(O) | B5 | Me | Me |
| 4-nPrOC(O) | B6 | Me | Me |
| 4-iPrOC(O) | B7 | Me | Me |
| 4-tBuOC(O) | B7 | Me | Me |
| 4-tBuOC(O) | B3 | CF$_3$ | Me |
| 4-tBuOC(O) | B5 | CF$_3$ | Me |
| 4-tBuOC(O) | B33 | CF$_3$ | Me |
| 4-tBuOC(O) | H | CF$_3$ | Me |
| 4-tBuOC(O) | B7 | CF$_3$ | Me |
| 4-tBuOC(O) | B8 | CF$_3$ | Me |
| 4-tBuOC(O) | B34 | CF$_3$ | Me |
| 4-tBuCH$_2$OC(O) | B10 | CF$_3$ | Me |
| 4-Et(Me)$_2$COC(O) | B11 | CF$_3$ | Me |
| 4-nHexOC(O) | B7 | H | Me |
| 4-MeOCH$_2$ | B8 | H | Me |
| 4-EtOCH$_2$ | B7 | Cl | Me |
| 4-iPrOCH$_2$ | B7 | H | Me |
| 4-MeC(O) | B16 | OMe | Me |
| 4-EtC(O) | B7 | SMe | Me |
| 4-iPrC(O) | B8 | SCF$_3$ | Me |
| 4-tBuC(O) | H | Cl | Cl |
| 4-tBuC(O) | B3 | Cl | Cl |
| 4-tBuC(O) | B7 | Cl | Cl |
| 4-tBuC(O) | B3 | CF$_3$ | Me |
| 4-tBuC(O) | B7 | CF$_3$ | Me |
| 4-tBuC(O) | B15 | CF$_3$ | Me |
| 4-tBuC(O) | B7 | Me | Me |
| 4-tBuC(O) | B17 | Me | Me |
| 4-tBuC(O) | B16 | Me | Me |
| 4-CF$_3$C(O) | B33 | Me | Me |
| 4-CF$_3$CF$_2$C(O) | B8 | Me | Me |
| 4-CF$_2$CF$_2$CF$_2$C(O) | B22 | Cl | Me |
| 4-MeC(O)O | B23 | Cl | Me |
| 4-iPrC(O)O | B7 | CF$_3$ | Me |
| 4-tBuC(O)O | B8 | CF$_3$ | Me |
| 4-CF$_3$C(O)O | B7 | H | Me |
| 4-CF$_2$CF$_2$CF$_2$C(O)O | B8 | H | Me |
| 4-Me$_2$NC(O)O | B34 | Cl | Me |
| 4-Et$_2$NC(O)O | H | H | Me |

TABLE 12-continued

| | | | |
|---|---|---|---|
| 4-(nPr)$_2$NC(O)O | B7 | OMe | Me |
| 3-Ph | B8 | SMe | Me |
| 4-Ph | B34 | SCF$_3$ | Me |
| 4-(4-F-Ph) | B7 | Et | Me |
| 4-(4-F-Ph) | B7 | CF$_3$ | Me |
| 3-PhO | B7 | Me | Me |
| 3-PhO | B15 | CF$_3$ | Me |
| 4-PhO | B7 | Me | Me |
| 4-(4-F-Ph)O | B35 | Me | Me |
| 4-(4-Cl-Ph)O | B36 | Et | Me |
| 4-(4-Br-Ph)O | B7 | CF$_3$ | Me |
| 4-(4-Me-Ph)O | B8 | CF$_3$ | Me |
| 4-(2-Cl-Ph)O | B34 | CF$_3$ | Me |
| 4-(2-F-Ph)O | B40 | H | Me |
| 4-(3-Cl-Ph)O | B41 | H | Me |
| 4-(4-Cl-Ph)O | B42 | Cl | Me |
| 4-(2,4-Cl$_2$-Ph)O | B43 | H | Me |
| 4-(3,4-Cl$_2$-Ph)O | B44 | OMe | Me |
| 4-(3,4,5-Cl$_3$-Ph)O | COCO$_2$Me | SMe | Me |
| 4-(2-Me-Ph)O | H | SCF$_3$ | Me |
| 4-(4-Me-Ph)O | B1 | Me | Me |
| 4-(3-Cl-4-Me-Ph)O | B2 | H | Me |
| 4-(2-pyridyl) | B3 | H | Me |
| 4-(5-CF$_3$-pyridin-2-yl) | B4 | Cl | Me |
| 4-(2-pyridyl)O | B7 | Me | Me |
| 4-(2-pyridyl)O | B15 | Me | Me |
| 4-(2-pyridyl)O | B7 | CF$_3$ | Me |
| 4-(2-pyridyl)O | B8 | CF$_3$ | Me |
| 4-(2-pyridyl)O | B34 | CF$_3$ | Me |
| 4-(2-pyridyl)O | B5 | CF$_3$ | Me |
| 4-(5-CF$_3$-pyridin-2-yl)O | B7 | Me | Me |
| 4-(5-CF$_3$-pyridin-2-yl)O | B8 | Me | Me |
| 4-(5-CF$_3$-pyridin-2-yl)O | B15 | CF$_3$ | Me |
| 4-(5-CF$_3$-pyridin-2-yl)O | B7 | CF$_3$ | Me |
| 4-(5-CF$_3$-pyridin-2-yl)O | B15 | CF$_3$ | Me |
| 4-(5-CF$_3$-pyridin-2-yl)O | B34 | CF$_3$ | Me |
| 4-(3-Cl-5-CF$_3$-pyridin-2-yl) | B7 | Me | Me |
| 4-(3-Cl-5-CF$_3$-pyridin-2-yl) | B15 | Me | Me |
| 4-(3-Cl-5-CF$_3$-pyridin-2-yl) | B34 | Me | Me |
| 4-(3-Cl-5-CF$_3$-pyridin-2-yl) | B7 | CF$_3$ | Me |
| 4-(3-Cl-5-CF$_3$-pyridin-2-yl) | B15 | CF$_3$ | Me |
| 4-(3-Cl-5-CF$_3$-pyridin-2-yl) | B17 | CF$_3$ | Me |
| 4-(3-Cl-5-CF$_3$-pyridin-2-yl) | H | CF$_3$ | Me |
| 4-(5-Cl-thiophen-2-yl) | B8 | Cl | Me |
| 3-OCH$_2$O-4 | B9 | Cl | Me |
| 4-OCH$_2$O-4 | B10 | CF$_3$ | Me |
| 4-MeCH=N | B11 | CF$_3$ | Me |
| 4-Me$_2$C=N | B12 | CF$_3$ | Me |
| 4-MeEtC=N | H | Cl | Me |
| 4-PhCH=N | B3 | Cl | Me |
| 4-PhMeC=N | B7 | Cl | Me |
| 4-PhCH$_2$CH=N | B8 | CF$_3$ | Me |
| 4-cC$_6$H$_{10}$=N | B15 | CF$_3$ | Me |
| 3-CH$_2$CH$_2$CH$_2$-4 | B16 | CF$_3$ | Me |
| 3-CH$_2$CH$_2$CH$_2$CH$_2$-4 | B28 | Cl | Me |
| 4-PhC(O) | H | CF$_3$ | Me |
| 4-PhC(O) | B7 | Et | Me |
| 4-PhC(O) | B7 | CF$_3$ | Me |
| 4-PhC(O) | B33 | CF$_3$ | Me |
| 4-(2-Cl-Ph)C(O) | B7 | CF$_3$ | Me |
| 4-(4-F-Ph)C(O) | H | CF$_3$ | Me |
| 4-(4-Cl-Ph)C(O) | B7 | CF$_3$ | Me |
| 4-(4-Cl-Ph)C(O) | B15 | CF$_3$ | Me |
| 4-(4-Cl-Ph)C(O) | B34 | CF$_3$ | Me |
| 4-(4-Me-Ph)C(O) | B3 | CF$_3$ | Me |
| 4-(4-Me-Ph)C(O) | B16 | CF$_3$ | Me |
| 4-(3,4-Cl$_2$-Ph)C(O) | B45 | CF$_3$ | Me |
| 2,4-Cl$_2$ | B7 | CF$_3$ | Me |
| 3,4-Cl$_2$ | B7 | CF$_3$ | Me |
| 4-Cl-2-F | B7 | CF$_3$ | Me |
| 3-Cl-4-nHex | B7 | CF$_3$ | Me |
| 4-tBu-3-Cl | B7 | CF$_3$ | Me |
| 4-tBu-3-Cl | B15 | CF$_3$ | Me |
| 3-Cl-4-iPrO | B7 | Me | Me |
| 3-Cl-4-iPrO | B7 | CF$_3$ | Me |
| 3-Cl-4-nHepO | B15 | CF$_3$ | Me |
| 3-Cl-4-(3,4-Cl$_2$-PhCH$_2$)O | H | CF$_3$ | Me |
| 3-Cl-4-PhCH$_2$O | B7 | CF$_3$ | Me |
| 3-Cl-4-Me$_3$CCH$_2$ | B7 | CF$_3$ | Me |

TABLE 12-continued
| | | | |
|---|---|---|---|
| 3,4-(MeO)$_2$ | B7 | CF$_3$ | Me |
| 4-MeO-3-Me | B17 | CF$_3$ | Me |
| 4-OH-3,5-(tBu)$_2$ | B3 | CF$_3$ | Me |
| 3,4,5-Cl$_3$ | B15 | CF$_3$ | Me |
| 3,5-Cl$_2$-4-F | B7 | CF$_3$ | Me |
| 4-Cl-2,6-F$_2$ | B7 | CF$_3$ | Me |
| 2,6-F$_2$-4-CF$_3$ | B7 | CF$_3$ | Me |
| 2,6-F$_2$-4-CF$_3$O | B7 | CF$_3$ | Me |
| 3,5-Cl$_2$-4-nOct | B7 | CF$_3$ | Me |
| 3,5-Cl$_2$-4-PhCH$_2$O | B15 | CF$_3$ | Me |
| 2,3,5,6-F$_4$-4-Me | B3 | CF$_3$ | Me |
| 2,3,4,5,6-F$_5$ | B33 | CF$_3$ | Me |
TABLE 13
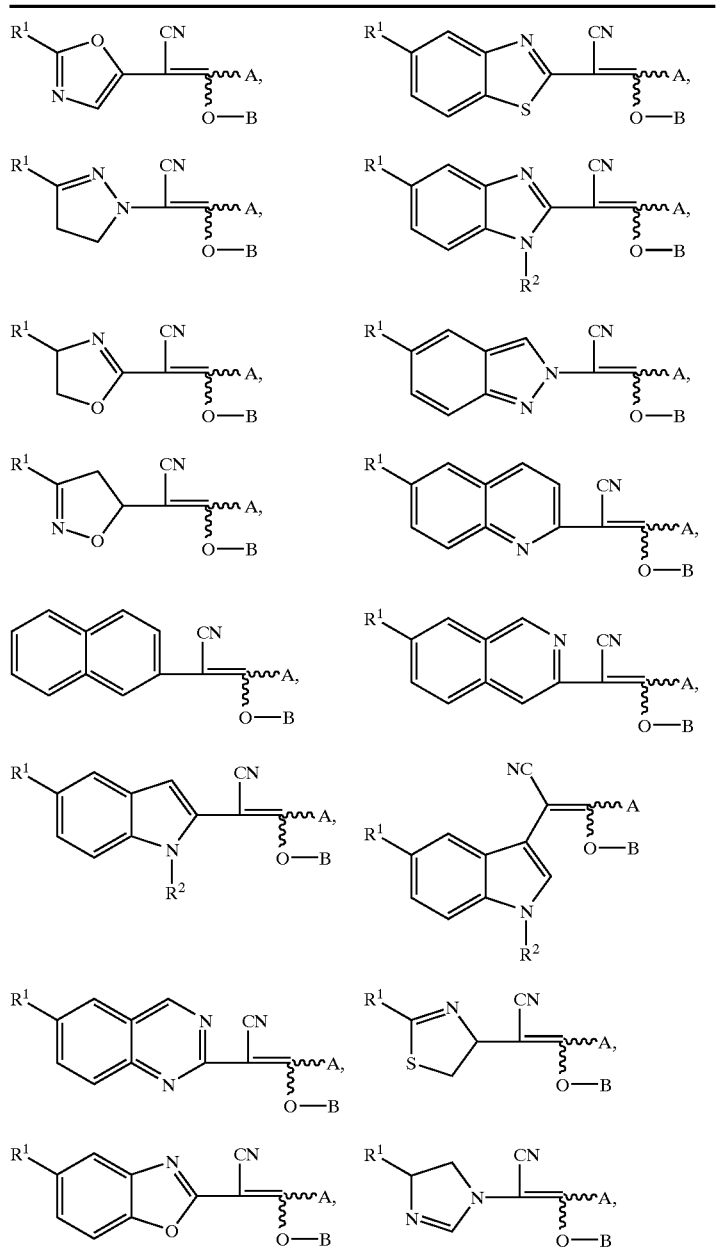

TABLE 13-continued

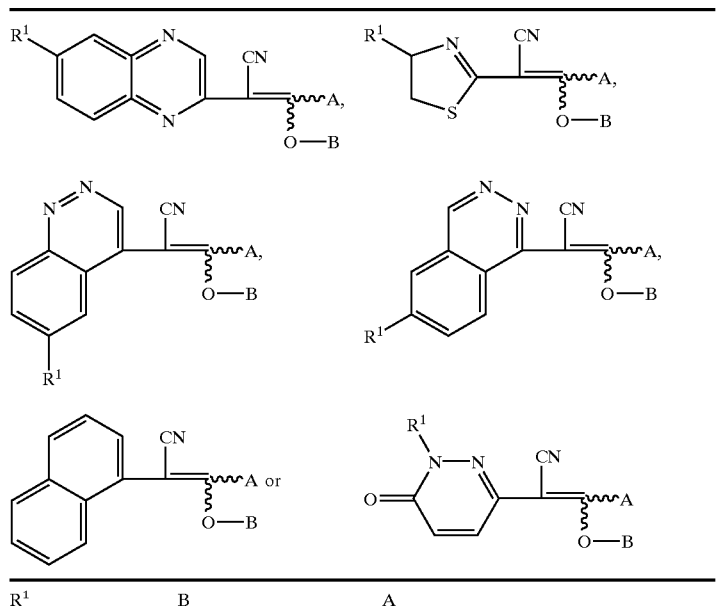

| R¹ | B | A |
|---|---|---|
| iPr | H | 2,5-Me₂-1-pyrrolyl |
| iPr | B3 | 1-Me-2-pyrrolyl |
| tBu | B5 | 3,5-Me₂-2-pyrrolyl |
| tBu | B6 | 3,4-Me₂-2-pyrrolyl |
| tBu | B7 | 3,4,5-Me₃-2-pyrrolyl |
| 1-Me-cPr | B8 | 3,5-Me₂-4-MeO-2-pyrrolyl |
| 1-Me-cPr | B15 | 4-MeC(O)-3,5-Me₂-2-pyrrolyl |
| 1-Me-cPr | B16 | 4-NO₂-2-pyrrolyl |
| 1-Me-cPr | B17 | 2-Me-3-pyrrolyl |
| 1-Me-cHex | B22 | 4-Me-3-pyrrolyl |
| 1-Me-cHex | B31 | 2,4,5-Me₃3-pyrrolyl |
| 1-Me-cHex | B32 | 2,4-Me₂-5-EtO₂C-3-pyrrolyl |
| 1-Me-cHex | B33 | 1,2,3-triazol-4-yl |
| PhCH₂ | B34 | 1-Me-1,2,3-triazol-4-yl |
| PhCH₂ | B35 | 2-Me-1,2,3-triazol-4-yl |
| PhCH₂ | B36 | 3-Me-1,2,3-triazol-4-yl |
| PhMe₂C | B40 | 2-EtO₂C-1,2,3-triazol-4-yl |
| PhMe₂C | B41 | 5-Me-2-Ph-1,2,3-triazol-4-yl |
| PhMe₂C | pyridin-2-yl-C(O) | 5-CF₃-2-Me-1,2,3-triazol-4-yl |
| PhMe₂C | pyridin-2-yl-C(O) | 2,5-Me₂-1,2,3-triazol-4-yl |
| Ph | pyridin-2-yl-C(O) | 1-PhCH₂-5-Me-1,2,3-trizol-4-yl |
| 2-F—Ph | H | 1-PhCH₂-5-CF₃-1,2,3-trizol-4-yl |
| 2-F—Ph | B3 | 1-PhCH₂-5-Cl-1,2,3-trizol-4-yl |
| 2-F—Ph | B5 | 4-Me-1,2,3-triazol-1-yl |
| 2-F—Ph | B6 | 5-Me-1,2,3-triazol-2-yl |
| 2-Cl—Ph | B7 | 4-MeO₂C-1,2,3-triazol-1-yl |
| 2-Cl—Ph | B8 | 4,5-EtO₂C-1,2,3-triazol-2-yl |
| 2-Cl—Ph | B15 | 4,5-Me₂-1,2,3-triazol-1-yl |
| 2-Me—Ph | B16 | 4-5-(MeO₂C)₂-1,2,3-triazol-2-yl |
| 2-Me—Ph | B17 | 4-5-Me₂-1,2,4-triazol-3-yl |
| 2-Me—Ph | B22 | 2,4-Me₂-1,2,4-triazol-3-yl |
| 4-NO₂—Ph | B31 | 1,5-Me₂-1,2,4-trizol-3-yl |
| 2,6-F₂—Ph | B32 | 5-Me-3-CF₃-1,2,4-triazol-2-yl |
| 2,6-F₂—Ph | B33 | 3-Cl-5-CF₃-1,2,4-triazol-2-yl |
| 2,6-F₂—Ph | B34 | 5-Cl-3-CF₃-1,2-4-triazol-2-yl |
| 2,6-F₂—Ph | B35 | 3,5-Me₃1,2-4-triazol-4-yl |
| 2,6-F₂—Ph | B36 | 3,5-Cl₂-1,2-4-triazol-4-yl |
| 2,6-Cl₂—Ph | B40 | 3,5-(CF₃)₂-1,2-4-triazol-4-yl |
| 2,6-Cl₂—Ph | B41 | 5-tetrazolyl |
| 2,6-Cl₂—Ph | pyridin-2-yl-C(O) | 5-Ph-1-tetrazolyl |
| 2,6-Cl₂—Ph | pyridin-2-yl-C(O) | 5-Ph-2-tetrazolyl |
| 2-pyridyl | pyridin-2-yl-C(O) | 3,4,4,5-Me₄-2-pyrazolin-1-yl |
| 2-pyridyl | B8 | 3-Me-5-CF₃-2-pyrazolin-1-yl |
| 2-pyridyl | B15 | 1,5-Me₂-3-CF₃-2-pyrazolin-4-yl |
| 2-pyridyl | B16 | 1,4-Me₂-3-Ph-2-pyrazolin-4-yl |
| 2-pyridyl | B17 | 1,4-Me₂-5-Ph-2-pyrazolin-4-yl |
| 2-pyridyl | B22 | 1,3-Me₂-2-pyrazolin-5-yl |
| 1-naphthyl | B31 | 1,5-Me₂-2-pyrazolin-3-yl |
| 1-naphthyl | B32 | 2-Me-2-imizolin-1-yl |
| 1-naphthyl | B33 | 2-CF₃-2-imizolin-1-yl |

TABLE 13-continued

| | | |
|---|---|---|
| iPr | B34 | 2-MeS-2-imizolin-1-yl |
| iPr | B35 | 2-MeO-2-imizolin-1-yl |
| tBu | B36 | 5-Me-2-Ph-2-oxazolin-4-yl |
| 1-Me-cPr | B40 | 2,5-Me$_2$-2-oxazolin-4-yl |
| cHex | B41 | 5-Me-2-CF$_3$-2-oxazolin-4-yl |
| 1-Me-cHex | pyridin-2-yl-C(O) | 2-thiazolin-2-yl |
| PhCH$_2$ | pyridin-2-yl-C(O) | 2-Me$_2$N-2-thiazolin-4-yl |
| PhMe$_2$C | pyridin-2-yl-C(O) | 2,4-Me$_2$-2-thiazolin-5-yl |
| Ph | B8 | 2-Me-4-CF$_3$-2-thiazolin-5-yl |
| 2-F—Ph | B15 | 5-Me-2-isoxazolin-3-yl |
| 2-Cl—Ph | B16 | 3-Cl-5-Me-2-isoxazolin-4-yl |
| 2-Me—Ph | B17 | 3,5-(MeS)$_2$-2-isothiazolin-4-yl |
| 4-NO$_2$—Ph | B22 | 5-Cl-2-Me-3(2H)-pyridazinon-4-yl |
| 2,6-F$_2$—Ph | B31 | 5,6-Cl$_2$-2-Me-pyridazinon-4-yl |
| 2,6-Cl$_2$—Ph | B32 | 4-Cl-2-Me-pyridazinon-4-yl |
| 2-pyridyl | B33 | 4,6-Cl$_2$-2-Me-pyridazinon-4-yl |
| 1-naphthyl | B34 | 4,5-Cl$_2$-2-Me-pyridazinon-4-yl |

TABLE 14

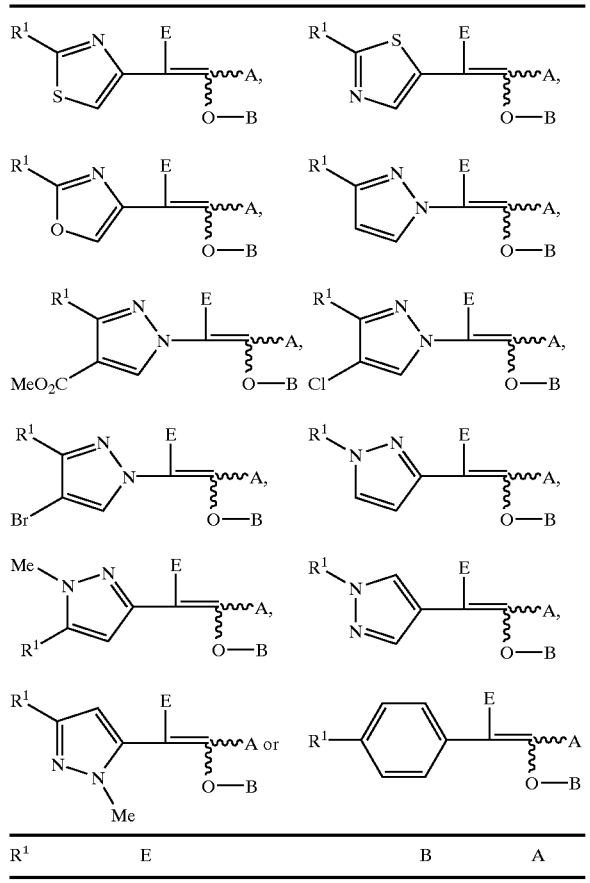

| R$^1$ | E | B | A |
|---|---|---|---|
| tBu | oxazol-2-yl | H | A1 |
| tBu | thiazol-2-yl | B3 | A2 |
| tBu | imidazol-2-yl | B7 | A3 |
| tBu | 1,5-Me$_2$-1,2,4-triazol-3-yl | B8 | A4 |
| tBu | 5-Me-1,2,4-oxadiazol-3-yl | B15 | A5 |
| tBu | 5-CF$_3$-1,2,4-thiadiazol-3-yl | B16 | A6 |
| tBu | 5-Me-1,3,4-oxadiazol-2-yl | B17 | A7 |
| tBu | tetrazol-5-yl | B18 | A8 |
| tBu | 2-oxazolin-2-yl | B32 | A9 |
| tBu | 1,2,4,5-tetrazin-3-yl | B33 | A10 |
| tBu | F | B34 | A11 |
| tBu | Cl | H | A12 |
| tBu | Br | B7 | A13 |
| tBu | I | B8 | A14 |
| tBu | CHC | H | A15 |
| tBu | CHC | B7 | A2 |
| 2,6-F$_2$—Ph | CHC | B7 | A2 |
| tBu | MeCC | B7 | A16 |
| tBu | EtCC | B7 | A17 |
| tBu | PhCC | B7 | A2 |
| tBu | PhCC | B8 | A13 |
| 2,6-F$_2$—Ph | PhCC | H | A2 |
| 2,6-F$_2$—Ph | PhCC | B7 | A2 |
| pyridin-2-yl | PhCC | B7 | A2 |
| tBu | (2-Cl—Ph) CC | B15 | A19 |
| tBu | (3-Cl—Ph) CC | B15 | A20 |
| 2,6-F$_2$—Ph | (4-Cl—Ph) CC | B16 | A21 |
| 2,6-F$_2$—Ph | (4-F—Ph) CC | B17 | A22 |
| 2,6-F$_2$—Ph | (4-Me—Ph) CC | B18 | A23 |
| 2,6-F$_2$—Ph | (4-nHex-Ph) CC | B34 | A24 |
| 2,6-F$_2$—Ph | (2,6-Cl$_2$—Ph) CC | H | A25 |
| 2,6-F$_2$—Ph | (2,4-Cl$_2$—Ph) CC | (EtO)$_2$P(S) | A26 |
| 2,6-F$_2$—Ph | (3,4-Cl$_2$—Ph) CC | B3 | A27 |
| 2,6-F$_2$—Ph | (2,4,6-Me$_3$—Ph) CC | B7 | A28 |
| 2,6-F$_2$—Ph | (4-CF$_3$—Ph) CC | B15 | A29 |
| 2,6-F$_2$—Ph | CF$_3$ | B7 | A2 |
| 2,6-F$_2$—Ph | CF$_3$CF$_2$ | H | A31 |
| 2,6-F$_2$—Ph | NO$_2$ | B3 | A32 |
| 2,6-F$_2$—Ph | N$_3$ | B7 | A33 |
| 2,6-F$_2$—Ph | N$_3$ | H | A2 |
| 2,6-F$_2$—Ph | N$_3$ | B7 | A1 |
| tBu | N$_3$ | B7 | A2 |
| tBu | N$_3$ | H | A2 |
| pyridin-2-yl | N$_3$ | B7 | A2 |
| 2,6-F$_2$—Ph | CHO | B8 | A34 |
| 2,6-F$_2$—Ph | C(O)Me | B15 | A35 |
| 2,6-F$_2$—Ph | C(O)Et | B16 | A36 |
| 2,6-F$_2$—Ph | C(O)iPr | B17 | A1 |
| 2,6-F$_2$—Ph | C(O)nBu | B18 | A2 |
| 2,6-F$_2$—Ph | C(O)sBu | B32 | A3 |
| 2,6-F$_2$—Ph | C(O)tBu | H | A2 |
| 2,6-F$_2$—Ph | C(O)tBu | H | A1 |
| 2,6-F$_2$—Ph | C(O)tBu | B7 | A1 |
| tBu | C(O)tBu | H | A2 |
| tBu | C(O)tBu | B7 | A2 |
| tBu | CO$_2$Me | H | A2 |
| tBu | CO$_2$Me | B7 | A2 |
| tBu | CO$_2$Me | B8 | A2 |
| 2,6-F$_2$—Ph | CO$_2$Me | H | A2 |
| 2,6-F$_2$—Ph | CO$_2$Me | B7 | A2 |
| 2,6-F$_2$—Ph | CO$_2$Me | B8 | A2 |
| pyridin-2-yl | CO$_2$Me | H | A2 |
| pyridin-2-yl | CO$_2$Me | B7 | A2 |
| pyridin-2-yl | CO$_2$Me | B8 | A2 |
| tBu | CO$_2$Me | B34 | A5 |
| tBu | CO$_2$Et | H | A2 |
| tBu | CO$_2$Et | B7 | A2 |
| tBu | CO$_2$Et | B8 | A2 |
| 2,6-F$_2$—Ph | CO$_2$Et | H | A2 |

TABLE 14-continued

| | | | |
|---|---|---|---|
| 2,6-F$_2$—Ph | CO$_2$Et | B7 | A2 |
| 2,6-F$_2$—Ph | CO$_2$Et | B8 | A2 |
| pyridin-2-yl | CO$_2$Et | H | A2 |
| pyridin-2-yl | CO$_2$Et | B7 | A2 |
| pyridin-2-yl | CO$_2$Et | B8 | A2 |
| pyridin-2-yl | CO$_2$Et | H | A6 |
| pyridin-2-yl | CO$_2$nPr | B7 | A7 |
| pyridin-2-yl | CO$_2$iPr | B8 | A8 |
| pyridin-2-yl | CO$_2$nBu | H | A9 |
| pyridin-2-yl | CO$_2$iBu | B7 | A10 |
| pyridin-2-yl | CO$_2$sBu | B7 | A11 |
| pyridin-2-yl | CO$_2$tBu | B8 | A12 |
| pyridin-2-yl | CO$_2$CH$_2$CH=CH$_2$ | B15 | A13 |
| pyridin-2-yl | CO$_2$CH$_2$CH=CH$_2$ | B7 | A2 |
| tBu | CO$_2$CH$_2$CH=CH$_2$ | B8 | A2 |
| tBu | CO$_2$CH$_2$CH=CH$_2$ | H | A2 |
| tBu | CO$_2$CH$_2$CH=CH$_2$ | B7 | A2 |
| 2,6-F$_2$—Ph | CO$_2$CH$_2$CH=CH$_2$ | B8 | A2 |
| 2,6-F$_2$—Ph | CO$_2$CH$_2$CH=CH$_2$ | H | A2 |
| 2,6-F$_2$—Ph | CO$_2$CH$_2$CH=CH$_2$ | B7 | A2 |
| pyridin-2-yl | C(O)NHMe | B8 | A2 |
| 2,6-F$_2$—Ph | C(O)NHMe | H | A2 |
| tBu | C(O)NHMe | H | A2 |
| pyridin-2-yl | C(O)NHEt | B16 | A15 |
| pyridin-2-yl | C(O)NHnPr | B17 | A16 |
| tBu | C(O)NHiPr | B18 | A17 |
| tBu | C(O)NHiBu | B34 | A18 |
| tBu | C(O)NHtBu | H | A19 |
| tBu | C(O)NMe$_2$ | (EtO)$_2$P(S) | A20 |
| tBu | C(O)NMe$_2$ | H | A2 |
| tBu | C(O)NMe$_2$ | B7 | A2 |
| 2,6-F$_2$—Ph | C(O)NMe$_2$ | B7 | A2 |
| pyridin-4-yl | C(O)NMeEt | B3 | A21 |
| 2,6-F$_2$—Ph | C(O)NEt$_2$ | B7 | A22 |
| tBu | C(O)N(nPr)$_2$ | B15 | A23 |
| tBu | PhC(O) | H | A24 |
| tBu | PhC(O) | H | A2 |
| tBu | PhC(O) | B7 | A2 |
| tBu | PhC(O) | B8 | A2 |
| 2,6-F$_2$—Ph | PhC(O) | H | A2 |
| 2,6-F$_2$—Ph | PhC(O) | B7 | A2 |
| 2,6-F$_2$—Ph | PhC(O) | B8 | A2 |
| pyridin-2-yl | PhC(O) | H | A2 |
| pyridin-2-yl | PhC(O) | B7 | A2 |
| 2,6-F$_2$—Ph | (4-F—Ph)C(O) | B8 | A2 |
| 2,6-F$_2$—Ph | (3,4-Cl$_2$—Ph)C(O) | H | A6 |
| pyridin-3-yl | (3-Cl-4-F—Ph)C(O) | B8 | A27 |
| pyridin-3-yl | (4-Me—Ph)C(O) | B15 | A28 |
| tBu | C(S)NH$_2$ | B16 | A29 |
| tBu | C(S)NH$_2$ | H | A2 |
| tBu | C(S)NH$_2$ | B7 | A2 |
| 2,6-F$_2$—Ph | C(S)NH$_2$ | B8 | A2 |
| 2,6-F$_2$—Ph | C(S)NH$_2$ | H | A2 |
| 2,6-F$_2$—Ph | C(S)NH$_2$ | B7 | A2 |
| pyridin-2-yl | C(S)NH$_2$ | B8 | A2 |
| pyridin-2-yl | C(S)NH$_2$ | H | A2 |
| 2,6-F$_2$—Ph | MeS | B7 | A2 |
| 2,6-F$_2$—Ph | EtS | B18 | A31 |
| pyridin-2-yl | nPrS | B32 | A32 |
| pyridin-2-yl | tBuS | B33 | A33 |
| tBu | MeSO | B34 | A34 |
| tBu | EtSO | H | A35 |
| tBu | nPrSO | B7 | A36 |
| 2,6-F$_2$—Ph | tBuSO | B8 | A1 |
| 2,6-F$_2$—Ph | MeSO$_2$ | H | A2 |
| 2,6-F$_2$—Ph | EtSO$_2$ | B7 | A3 |
| pyridin-2-yl | iPrSO$_2$ | B7 | A4 |
| pyridin-2-yl | nBuSO$_2$ | B8 | A5 |
| tBu | PhS | B15 | A6 |
| tBu | PhS | H | A2 |
| tBu | PhS | B7 | A2 |
| 2,6-F$_2$—Ph | PhS | B8 | A2 |
| 2,6-F$_2$—Ph | PhS | H | A2 |
| 2,6-F$_2$—Ph | PhS | B7 | A2 |
| pyridin-2-yl | PhS | B8 | A2 |
| pyridin-2-yl | PhS | H | A2 |
| pyridin-2-yl | PhS | B7 | A2 |
| tBu | (4-Me—Ph)S | B8 | A2 |
| tBu | (4-Cl—Ph)SO | H | A6 |
| tBu | (2-F—Ph)SO$_2$ | B17 | A9 |
| 2,6-F$_2$—Ph | (MeO)$_2$P(O) | B18 | A10 |
| 2,6-F$_2$—Ph | (EtO)$_2$P(O) | B34 | A11 |
| 2,6-F$_2$—Ph | (nPrO)$_2$P(O) | H | A12 |
| pyridin-2-yl | (PhO)(MeO)P(O) | (EtO)$_2$P(S) | A13 |
| pyridin-2-yl | (MeO)$_2$P(S) | B3 | A14 |
| tBu | (EtO)$_2$P(S) | B7 | A15 |
| tBu | (nPrO)$_2$P(S) | B15 | A16 |
| tBu | (PhO)(MeO)P(S) | B7 | A17 |

Where the compounds of the present invention are used as pesticides, in general, they can be mixed with a suitable carrier, for example a solid carrier, such as clay, talc, bentonite, diatomaceous earth or white carbon, or a liquid carrier such as water, alcohols (e.g., isopropanol, butanol, benzyl alcohol, furfuryl alcohol), aromatic hydrocarbons (e.g., toluene, xylene), ethers (e.g., anisole), ketones (e.g., cyclohexanone, isophorone), esters (e.g., butyl acetate), acid amides (e.g., N-methylpyrrolidone) or halogenated hydrocarbons (e.g., chlorobenzene), optionally along with other additives such as surfactant, emulsifier, dispersing agent , penetrating agent, spreading agent, thickener, anti-freezing agent, anti-caking agent and stabilizer, and can be formulated into any desired forms for practical use, such as liquid preparations, emulsions, wettable powders, dry flowables, flowables, dusts and granules.

Where the compounds of the present invention are used as agricultural chemicals, they can be combined with any other herbicides, various insecticides, acaricides, nematecides, fungicides, plant growth regulators, synergists, fertilizer and soil improvers, when they are formulated into preparations for practical use or while they are actually used through spraying or the like.

In particular, the combination of the compounds of the invention and other agricultural chemicals or plant hormones will be advantageous in that the amount of the chemicals to be used can be reduced thereby resulting in the reduction of the costs for the treatment, and that the mixed chemicals exhibit synergistic effects to broaden the insecticidal spectrum while displaying higher pesticidal activities. If desired, the compounds of the invention can be combined with a plurality of known agricultural chemicals. For the agricultural chemicals capable of being combined with the compounds of the invention, for example, the compounds described in Farm Chemicals Handbook, 1994 are referred.

Their concrete general names are raised below. However, the present invention is not necessarily limited by them.
Fungicide: acibenzolar, ampropyfos, anilazine, azaconazole, azoxystrobin, benalaxyl, benodanil, benomyl, benzamacril, binapacryl, biphenyl, bitertanol, bethoxazine, bordeaux mixture, blasticidin-S, bromoconazole, bupirimate, buthiobate, calcium polysulfide, captafol, captan, copper oxychloride, carpropamid, carbendazim, carboxin, chinomethionat, chlobenthiazone, chlorfenazol, chloroneb, chlorothalonil, chlozolinate, cufraneb, cymoxanil, cyproconazol, cyprodinil, cyprofuram, debacarb, dichlorophen, diclobutrazol, dichlofluanid, diclomezine, dicloran, diethofencarb, diclocymet, difenoconazole, diflumetorim, dimethirimol, dimethomorph, diniconazole, diniconazole-M, dinocap, diphenylamine, dipyrithione, ditalimfos, dithianon, dodemorph, dodine, drazoxolon, edifenphos, epoxiconazole, etaconazole, ethirimol, etridiazole, famoxadone, fenarimol, febuconazole, fenfuram, fenpiclonil, fenpropidin, fenpropimorph, fentin, ferbam, ferimzone, fluazinam, fludioxonil, fluoroimide, fluquinconazole, flusilazole, flusulfamide, flutolanil, flutriafol, folpet, fosetyl-aluminium, fuberidazole, furalaxyl, fenamidone, fenhexamid, guazatine, hexachlorobenzene, hexaconazole, hymexazol, imazalil, imibenconazole, iminoctadine, ipconazole, iprobenfos, iprodione, isoprothiolane, iprovalicarb, kasugamycin, kresoxim-methyl, mancopper, mancozeb, maneb, mepanipyrim, mepronil, metalaxyl, metconazole, metiram, metominostrobin, myclobutanil, nabam, nickel bis (dimethyldithiocarbamate), nitrothal-isopropyl, nuarimol, octhilinone, ofurace, oxadixyl, oxycarboxin, oxpoconazole fumarate, pefurzoate, penconazole, pencycuron, phthalide, piperalin, polyoxins, probenazole, prochloraz, procymidone, propamocarb hydrochloride, propiconazole, propineb, pyrazophos, pyrifenox, pyrimethanil, pyroquilon, quinoxyfen, quintozene, sulfur, spiroxamine, tebuconazole, tecnazene, tetraconazole, thiabendazole, thifluzamide, thiophanate-methyl, thiram, tolclofos-methyl, tolylfluanid, triadimefon, toriadimenol, triazoxide, tricyclazole, tridemorph, triflumizole, triforine, triticonazole, validamycin, vinclozolin, zineb, ziram.

Bacteriazide: streptomycin, oxyterracycline, oxolinic acid.

Nematicide: aldoxycarb, cadusafos, fosthiazate, fosthietan, oxamyl, fenamiphos.

Acaricide: acequinocyl, acrinathrin, amitraz, bifenazate, bromopropylate, chinomethionat, chlorobezilate, clofentezine, cyhexatine, dicofol, dienochlor, etoxazole, fenazaquin, fenbutatin oxide, fenpropathrin, fenproximate, halfenprox, hexythiazox, milbemectin, phenisobromolate, polynactins, propargite, pyridaben, pyrimidifen, tebufenpyrad, tetradifon.

Insecticide: abamectin, acephate, acetamipirid, alanycarb, azinphos-methyl, bendiocarb, benfuracarb, bensultap, bifenthrin, Batillus thuringiensis, buprofezin, butocarboxim, carbaryl, carbofuran, carbosulfan, cartap, chlorfenapyr, chlorpyrifos, chlorfenvinphos, chlorfluazuron, clothianidin, chromafenozide, chlorpyrifos-methyl, cyanox, cycloprothrin, cyfluthrin, beta-cyfluthrin, cypermethrin, cyromazine, cyhalothrin, lambda-cyhalothrin, deltamethrin, diafenthiuron, diazinon, diacloden, dichlorvos, diflubenzuron, dimethylvinphos, diofenolan, disulfoton, dimethoate, emamectin-benzoate, EPN, esfenvalerate, ethiofencarb, endosulfan, ethiprole, ethylthiometone, etofenprox, etrimfos, fenitrothion, fenobucarb, fenothiocarb, fenthion, fenoxycarb, fenpropathrin, fenvalerate, fipronil, flucythrinate, flufenoxuron, flufenprox, tau-fluvalinate, fonophos, formetanate, formothion, furathiocarb, halofenozide, hexaflumuron, hydramethylnon, imidacloprid, isofenphos, indoxacarb, isoprocarb, isoxathion, lufenuron, malathion, metaldehyde, methamidophos, methidathion, methacrifos, metalcarb, methomyl, methoprene, methoxychlor, methoxyfenbzide, monocrotophos, muscalure, nicotin-sulfate, nitenpyram, omethoate, oxydemeton-methyl, oxamyl, parathion, parathion-methyl, permethrin, phenthoate, phoxim, phorate, phosalone, phosmet, phosphamidon, pirimicarb, pirimiphos-methyl, profenofos, propafos, prothiofos, pymetrozine, pyraclofos, pyridafenthion, pyriproxyfen, rotenone, sulprofos, silafluofen, spinosad, sulfotep, tebfenozide, teflubenzuron, tefluthorin, terbufos, tetrachlorvinphos, thiodicarb, thiamethoxam, thiocyclam, thiofanox, thiometon, tolfenpyrad, tralomethrin, trichlorfon, triazuron, triflumuron, vamidothion.

The dose of the compounds of the present invention varies depending on an application place, an application time, an application method, cultivation crops, etc. In general, it may be between approximately 0.005 kg and 50 kg per hectare (ha) in terms of the amount of the active ingredient.

Now, formulation examples comprising the compounds of the invention are mentioned below, which, however, are not intended to restrict the scope of the invention. In the following formulation examples, "part" or "parts" are by weight.

| [Wettable Powders] | |
|---|---|
| Compound of the invention | 5 to 80 parts |
| Solid carrier | 10 to 85 parts |
| Surfactant | 1 to 10 parts |
| Others | 1 to 5 parts |

The others include, for example, anti-caking agent, etc.

| [Emulsions] | |
|---|---|
| Compound of the invention | 1 to 30 parts |
| Liquid carrier | 30 to 95 parts |
| Surfactant | 5 to 15 parts |
| [Flowables] | |
| Compound of the invention | 5 to 70 parts |
| Liquid carrier | 15 to 65 parts |
| Surfactant | 5 to 12 parts |
| Others | 5 to 30 parts |

The others include, for example, anti-freezing agent, thickener, etc.

| [Dry Flowables (wettable granules)] | |
|---|---|
| Compound of the invention | 20 to 90 parts |
| Solid carrier | 10 to 60 parts |
| Surfactant | 1 to 20 parts |
| [Granules] | |
| Compound of the invention | 0.1 to 10 parts |
| Solid carrier | 90 to 99.99 parts |
| Others | 1 to 5 parts |
| [Dusts] | |
| Compound of the invention | 0.01 to 30 parts |
| Solid carrier | 67 to 99.5 parts |
| Others | 0 to 3 parts |

Where the compounds of the present invention are used as an agent for preventing the attachment of aquatic organisms, they may be formulated into various preparations of, for example, coating paints, solutions, emulsions, pellets or flakes to be applicable to various objects. Depending on the application place, the object and the form, the preparations can be used in any ordinary manners of, for example, coating, spraying, dipping, adding to water or installing in water. To prepare such coating paints, solutions, emulsions and others, employable are any ordinary methods. Apart from the above-mentioned preparations and modes of using the compounds of the present invention, the compounds may also be used, for example, by incorporating them into ropes or fiber materials for fishingnets in the stage of preparing the ropes or fiber materials to thereby making them have the ability to prevent the attachment of aquatic organisms thereto. The agents for preveting the attachment of aquatic organisms according to the present invention can be used either singly or as combined with any other agents for preventing the attachment of aquatic organisms.

Where the aquatic adhesion inhibitors of the invention are used in the form of antifouling coatings, for example, the compounds of the invention may be mixed with film-forming agents to prepare coatings. The film-forming agents include oil varnishes, synthetic resins, artificial rubbers, etc. If desired, solvents, pigments and others can be added to the coatings. To prepare the paints, the uppermost limit of the concentration of the compounds of the invention to be therein is not specifically limited, provided that the resulting coatings can form film, but may be from 1 to 50% by weight, preferably from 5 to 20% by weight, relative to the weight of the antifouling coatings.

Where the agents for preventing the attachment of aquatic organisms of the present invention are used in the form of solutions, for example, the compounds of the invention may be dissolved in solvents along with film-forming agents to prepare solutions. The film-forming agents include synthetic resins, artificial rubbers, natural resins, etc. The solvents include xylene, toluene, cumene, methyl ethyl ketone, methyl isobutyl ketone, acetone, etc. If desired, additives such as plasticizer may be added to the solutions. To prepare the solutions, the uppermost limit of the concentration of the compounds of the invention to be therein is not specifically limited, provided that the compounds are dissolved to give solutions, but may be from 1 to 50% by weight, preferably from 5 to 30% by weight, relative to the weight of the solutions.

Where the agents for, preventing the attachment of aquatic organisms of the present invention are used in the form of emulsions, surfactants areadded to the compounds of the invention to prepare the intended emulsions according to ordinary methods of preparing general emulsions. In this, the type of the surfactants to be used is not specifically limited. To prepare the emulsions, the uppermost limit of the concentration of the compounds of the invention to be therein is not specifically limited, provided that the compounds are emulsified to give emulsions, but may be from 1 to 50% by weight, preferably from 5 to 30% by weight, relative to the weight of the emulsions.

Where the agents for preventing the attachment of aquatic organisms of the present invention are used in the form of pellets or flakes, for example, the constitutive components of the compounds of the invention and optionally plasticizers, surfactants and others are added to the base of hydrophilic resins which are solid at room temperature, such as polyethylene glycol in a solid form, and the resulting mixtures are shaped into pellets or flakes through meltting molding, compression molding or the like. To prepare the pellets or flakes, the uppermost limit of the concentration of the compounds to be therein is not specifically limited, provided that the compounds can be shaped into pellets or flakes, but may be from 20 to 95% by weight, preferably from 30 to 90% by weight, relative to the weight of the pellets or flakes.

EXAMPLES

The present invention is illustrated specifically by referring to the following Synthesis Examples, Formulation Examples and Test Examples, which, however, are not intended to restrict the scope of the invention.

Synthesis Example 1

Synthesis of 2-{3-(2,6-Difluorophenyl)pyrazol-1-yl}-3-(1-methyl-3,5-dichloropyrazol-4-yl )-3-hydroxyacrylonitrile (Compound No. I-40)

1) 3.0 g of 3-(2,6-difluorophenyl)pyrazole was dissolved in 20 ml of acetonitrile, and 2.52 g of chloroacetonitrile and 4.61 g of potassium carbonate were added thereto at room temperature, and heated under reflux for 5 hours. After acetonitrile was distilled off under reduced pressure, ethyl acetate was added to the residue, which was then washed with a small amount of water. The organic layer was dried over sodium sulfate, and the solvent was distilled off under reduced pressure. The residual product was recrystallized from a mixed solvent of isopropylether and diethyl ether to obtain 1.74 g of 1-cyanomethyl-3-(2,6-difluorophenyl) pyrazole. 2) A solution of 0.5 g of 1-cyanomethyl-3-(2,6-difluorophenyl)pyrazole dissolved in 10 ml of THF was dropwise added to a suspension of 0.15 g of 55% sodium hydride in 10 ml of THF, at; 50° C. After the resulting product was stirred for 30 minutes, a solution of 0.67 g of 1-(1-methyl-3,5-dichloropyrazole-4-carbonyl)pyrazole dissolved in 10 ml of THF was dropwise added thereto at 50° C. and then stirred overnight at room temperature. The reaction mixture was poured into water, then extracted with ethyl acetate and washed with a small amount of water. The resulting product was dried over sodium sulfate, and the solvent was distilled off under reduced pressure. The residual product was recrystallized from a mixed solvent of isopropyl ether/ethyl acetate=3/1 to obtain 0.52 g of 2-(3-(2,6-difluorophenyl)pyrazol-1-yl)-3-(1-methyl-3,5-dichloropyrazol-4-yl)-3-hydroxyacrylonitrile.

Synthesis Example 2

Synthesis of 3-(1-Methyl-3,5-dichloropyrazol-4-yl)-2-(2-phenylthiazol-4-yl)-3-hydroxyacrylonitrile (Compound No. II-1)

1) 2.33 g of thiobenzamide was dissolved in 20 ml of dry methanol, and 2.16 g of 1,3-dichloroacetone was added thereto at room temperature and then heated under reflux for 1 hour. The solvent was distilled off under reduced pressure, and ice water was added to the remaining product, which was then neutralized with an aqueous solution of sodium hydrogen carbonate. The resulting product was extracted with ethyl acetate, washed with saturated saline, and dried over sodium sulfate, and the solvent was distilled off under reduced pressure. The residual product was purified through silica gel column chromatography to obtain 2.03 g of 4-chloromethyl-2-phenylthiazole, was obtained from the fraction eluted with chloroform/n-hexane=1/2.

2) 1.39 g of 4-chloromethyl-2-phenylthiazole was dissolved in 10 ml of acetonitrile, and 0.65 g of potassium cyanide and 0.05 g of dibenzo-18-crown-6-ether were added thereto at room temperature, and then heated under reflux for 10 hours. After the temperature was returned to room temperature, ethyl acetate was added the resulting mixture, and the insoluble solid was removed through filtration. The resulting ethyl acetate solution was washed with saturated saline and water, and dried over sodium sulfate, and the solvent was distilled off under reduced pressure. The residual product was purified through silica gel column chromatography to obtain 0.98 g of 4-cyanomethyl-2-phenylthiazole from the fraction eluted with chloroform.

3) 0.72 g of 4-cyanomethyl-2-phenylthiazole was dissolved in 10 ml of dry THF, and 4.6 ml of n-butyl lithium (1.56 M hexane solution) was dropwise added thereto at −60° C. or lower in an argon atmosphere. After the resulting product was stirred at −60° C. or lower for 20 minutes, 0.84 g of 1-methyl-3,5-dichloropyrazole-4-carbonyl chloride as dissolved in 3 ml of dry THF was dropwise added thereto at −60° C. or lower. Then, the resulting product was gradually heated, and stirred for 4 hours at room temperature. The reaction mixture was poured into ice water, acidified with diluted hydrochloric acid, extracted with ethyl acetate, and washed with saturated saline. The resulting product was dried over sodium sulfate, and the solvent was distilled off under reduced pressure. The residual product was purified through silica gel column chromatography to obtain the intended product from the fraction eluted with chloroform. The resulting product was crystallized and washed with diethyl ether to obtain 0.86 g of 3-(1-methyl-3,5-dichloropyrazol-4-yl)-2-(2-phenylthiazol-4-yl)-3-hydroxyacrylonitrile.

Synthesis Example 3

Synthesis of 3-(1-Methyl-3-trifluoromethyl-5-chloropyrazol-4-yl)-2-(4-tert-butylthiazol-2-yl)-3-pivaloyloxyacrylonitrile (Compound No. III-6, III-15)

0.5 g of 3-(1-methyl-3-trifluoromethyl-5-chloropyrazol-4-yl)-2-(4-tert-butylthiazol-2-yl)-3-hydroxyacrylonitrile and 0.14 g of triethylamine were added to 15 ml of THF at room temperature and stirred to give a uniform solution. 0.16 g of pivaloyl chloride was dropwise added to the solution with cooling with ice, then gradually heated, and stirred at room temperature for 8 hours. The reaction mixture was poured into ice water, extracted with ethyl acetate, and washed thrice with saturated saline. After having been dried over sodium sulfate, the resulting product was passed through a short column filled with silica gel. The solvent was distilled off under reduced pressure, and the residual product was applied to silica gel thin-layer chromatography (developer solvent: chloroform) to obtain 0.16 g of 3-(1-methyl-3-trifluoromethyl-5-chloropyrazol-4-yl)-2-(4-tert-butylthiazol-2-yl)-3-pivaloyloxyacrylonitrile (III-6) and 0.35 g of its geometric isomer (III-15).
Compound No. III-6:
$^1$H-NMR (CDCl$_3$, δ ppm); 1.18 (9H, s), 1.32 (9H, s), 3.85 (3H, s), 6.88 (1H, s).
Compound No. III-15:
$^1$H-NMR (CDCl$_3$, δ ppm); 1.33 (9H, s), 1.39 (9H, s), 3.94 (3H, s), 7.03 (1H, s).

Reference Example

Synthesis of 1-Methyl-3-trifluoromethyl-5-chloropyrazole-4-carboxylic Acid 1) 21.35 g of phosphorus oxychloride was dropwise added to 4.72 g of DMF at 10° C. or lower. After the temperature of the reaction solutio was returned to room temperature, the reaction mixture was stirred for 1 hour, and 10.71 g of 1-methyl-3-trifluoromethyl-5-pyrazolone was added thereto. The resulting mixture was heated up to 110° C., and stirred for 7 hours. After having been left to be at 70° C. the reaction mixture was poured into ice water. After pH of the mixture was made to be about 4 with an aqueous solution of sodium hydroxide added thereto, and precipitated crystals were taken out through filtration and dried to obtain 10.55 g of 1-methyl-3-trifluoromethyl-5-chloropyrazole-4-carbaldehyde.

2) 8.88 g of 1-methyl-3-2-(tert-trifluoromethyl-5-chloropyrazole-4-carbaldehyde and 7.24 g of potassium permanganate were added to an aqueous solution of 0.23 g of potassium hydroxide in 85 ml of water, at room temperature. After having been heated upto 60° C., the resulting mixture was stirred for 2 hours. Next, the temperature of the mixture was return to room temperature, and the solid was removed through filtration. The resulting filtrate was acidified with an aqueous solution of hydrochloric acid, and precipitated crystals were taken out through filtration, washed with water, and dried. The thus-obtained crystals were added to 150 ml of chloroform, and heated under reflux, and the insoluble solid was removed through filtration at a heating time. Chloroform was distilled off under reduced pressure, and 6.24 g of 1-methyl-3-trifluoromethyl-5-chloropyrazole-4-carboxylic acid was obtained.

Synthesis Example 4

Synthesis of 2-(2-tert-Butylthiazol-4-yl)-3-(2-methyl-4-trifluoromethylthiazol-5-yl)-3-benzoyloxyacrylonitrile (Compound No. II-75)

In the same manner as above, the above-mentioned compound was synthesized (viscous liquid, E-Z mixture).
$^1$H-NMR (CDCl$_3$, δ ppm); 1.09 (9H, s), 2.75 (3H, s), 7.3–7.6 (4H, m), 8.05–8.25 (2H, m): major; 1.19 (9H, s), 2.70 (3H, s), 7.3–7.6 (4H, m), 8.05–8.25 (2H, m): minor.

Synthesis Example 5

Synthesis of 2-(4-Trifluoromethylphenyl)-3-(1-methyl-3,5-dichloropyrazol-4-yl)-3-(1-methyl-3,5-dichloropyrazole-4-carbonyloxy)acrylonitrile (Compound No. IV-5)

1.0 g of 4-(trifluoromethyl)phenylacetonitrile and 2.31 g of 1-methyl-3,5-dichloropyrazole-4-carbonyl chloride were dissolved in 30 ml of dry THF, and 0.61 g of potassium t-butoxide was added thereto at room temperature. After having been heated, the resulting product was kept heated under reflux for 3 hours. 0.61 g of potassium t-butoxide was again added thereto and further heated under reflux for 2 hours. THF was distilled off under reduced pressure, and water was added to the residual product, which was then extracted with ethyl acetate. The resulting organic layer was washed with a dilute aqueous solution of sodium hydroxide and then with water. This was dried with sodium sulfate, and the solvent was distilled off under reduced pressure. The residue was purified through silica gel column chromatography to obtain 1.92 g of 3-(1-methyl-3,5-dichloropyrazol-4-yl)-2-(4-trifluoromethylphenyl)-3-(1-methyl-3,5-dichloropyrazole-4-carbonyloxy)acrylonitrile from the fraction eluted with n-hexane:ethyl acetate=2:1.

Synthesis Example 6

Synthesis of 2-(4-tert-Butylphenyl)-3-(1-methyl-3,5-dichloropyrazol-4-yl)-3-hydroxyacrylonitrile (Compound No. IV-18)

0.22 g of dibenzo-18-crown-6-ether and 1.57 g of sodium cyanide were suspended in 20 ml of DMSO, and 5.00 g of 4-tert-butylbenzyl bromide was dropwise added thereto with cooling with water. After having been stirred overnight at room temperature, the resulting mixture was further stirred at 50° C. for 5 hours. After this was left to be at room temperature, water was added thereto and extracted with ether. The organic layer was washed with water, and dried over sodium sulfate, and the solvent was distilled off under reduced pressure. The residual product was purified through silica gel column chromatography to obtain 1.19 g of 4-tert-butylphenylacetonitrile was obtained from the fraction eluted with n-hexane:ethyl acetate=5:1.

1.00 g of 4-tert-butylphenylacetonitrile and 1.23 g of 1-methyl-3,5-dichloropyrazole-4-carbonyl chloride were dissolved in 20 ml of THF, and 1.01 g of potassium t-butoxide was added thereto with cooling with ice. After the resulting mixture was stirred overnight at room temperature, water was added thereto, acidified with diluted hydrochloric acid, and extracted with ethyl acetate. The organic layer was washed with water, and dried with sodium sulfate, and the solvent was distilled off under reduced pressure. The residual product was dissolved in a mixed solvent of 10 ml of water and 10 ml of dioxane, and 0.38 g of potassium hydroxide was added thereto and heated under reflux for 4 hours. After having been left to be at room temperature, this was acidified with diluted hydrochloric acid, and extracted with ethyl acetate. The organic layer was washed with water, and dried over sodium sulfate, and the solvent was distilled off under reduced pressure. The residual product was purified through silica gel column chromatography to obtain 0.64 g of 2-(4-tert-butylphenyl)-3-(1-methyl-3,5-dichloropyrazol-4-yl)-3-hydroxyacrylonitrile from the fraction eluted with n-hexane:ethyl acetate=2:1.

Synthesis Example 7

Synthesis of 2-(4-tert-Butylphenyl)-3-(1-methyl-3-trifluoromethyl-5-chloropyrazol-4-yl)-3-pivaloyloxyacrylonitrile (Compound No.(IV-24)

In the same manner as above, the above-mentioned compound was synthesized (viscous liquid).

$^1$H-NMR (CDCl$_3$, δ ppm); 1.13 (9H, s), 1.33 (9H, s), 3.98 (3H, s), 7.48 (4H, brs).

Synthesis Example 8

Synthesis of 2-(4-tert-Butylphenyl)-3-(3,5-dichloro-1-methylpyrazol-4-yl)-3-methoxycarbonyloxyacrylonitrile (Compound No. IV-36)

In the same manner as above, the above-mentioned compound was synthesized (vitreous, E-Z mixture).

$^1$H-NMR (CDCl$_3$, δ ppm); 1.32 (9H, s), 3.75 (3H, s), 3.87 (3H, s), 7.49 (2H, d, J=8Hz), 7.58 (2H, d, J=8 Hz): 75%; 1.27 (9H, s), 3.88 (3H, s), 3.96 (3H, s), 7.49 (2H, d, J=8 Hz), 7.58 (2H, d, J=8 Hz): 25%.

Synthesis Example 9

Synthesis of 2-{2-tert-Butyloxazol-4-yl}-3-(3,5-dichloro-1-methyl-pyrazol-4-yl)-3-hydroxyacrylonitrile (Compound No. V-40)

1) 25 g of pivalic acid amide and 25 g of 1,3-dichloro-2-propanone were mixed and heated on an oil bath at 135° C. for 2.5 hours. After having been cooled with ice, the mixture was made alkaline with an aqueous solution of sodium hydroxide added thereto. Then, the resulting product was extracted with ethyl acetate, washed with water, and dried over anhydrous sodium sulfate, and the solvent was distilled off under reduced pressure. The residual product was purified through column chromatography (silica gel; ethyl acetate:n-hexane=1:8) to obtain 17.5 g of 2-tert-butyl-4-chloromethyloxazole.

2) 6.2 g of sodium cyanide was weighed, 50 ml of dimethylsulfoxide was added thereto, and a dimethylsulfoxide solution of 16.9 g of 2-tert-butyl-4-chloromethyloxazole was dropwise added thereto, and heated on an oil bath at 65° C. for 1 hour with stirring. After the resulting product was cooled to room temperature, 150 ml of a dilute aqueous solution of sodium hydroxide was added thereto, and extracted with toluene. The organic layer was fully washed with water, and dried over anhydrous sodium sulfate, and the solvent was distilled off under reduced pressure to obtain 14.8 g of 2-tert-butyl-4-cyanomethyloxazole.

3) 2.87 g of potassium tert-butoxide was suspended in 20 ml of THF, and a solution of 2.00 g of 2-tert-butyl-4-cyanomethyloxazole and 2.37 g of 3,5-dichloro-1-methylpyrazole-4-carbonyl chloride as dissolved in 10 ml of THF was dropwise added thereto with cooling with ice, and then stirred overnight at room temperature. The reaction mixture was poured into ice water, extracted with ethyl acetate, and washed with a small amount of water. After the resulting product was dried with anhydrous sodium sulfate, the solvent was evaporated out under reduced pressure. The residual product was purified through column chromatography (silica gel; n-hexane:ethyl acetate=4:1) to obtain 3.26 g of the intended compound.

Synthesis Example 10

Synthesis of 2-(2-tert-Butyloxazol-4-yl)-3-(5-chloro-1-methyl-3-trifluoromethylpyrazol-4-yl)-3-ethoxymethoxyacrylonitrile (Compound No. V-44)

0.6 g of 2-{2-tert-butyloxazol-4-yl}-3-(5-chloro-3-trifluoromethyl-1-methyl-pyrazol-4-yl)-3-hydroxyacrylonitrile was dissolved in 5 ml of THF, and 0.07 g of 60% sodium hydride was added thereto with cooling with ice, and then stirred for 15 minutes at room temperature. 0.17 g of ethoxymethyl chloride was added thereto and stirred for 6 days at room temperature. The reaction mixture was poured into ice water, extracted with ethyl acetate, and washed with saturated saline. The resulting product was dried over anhydrous sodium sulfate, and the solvent was distilled off under reduced pressure. The resulting residual product was purified through silica gel thin-layer chromatography (ethyl acetate:n-hexane=1:4) to obtain 0.1 g of the intended compound in vitreous state.

$^1$H-NMR-(CDCl$_3$, δ ppm); 1.17 (3H, t), 1.41 (9H, s), 3.98 (3H, s), 5.03 (2H, s), 8.00 (1H, s).

Synthesis Example 11

Synthesis of Ethyl 2-Phenyl-3-(3,5-dichloro-1-methylpyrazol-4-yl)-3-hydroxyacrylate (Compound No. IV-91)

8.2 g (50 mmols) of ethyl phenylacetate and 10.7 g (50 mmols) of 3,5-dichloro-1-methylpyrazole-4-carboxylic acid chloride were dissolved in 100 ml of dry tetrahydrofuran, and 14 g (125 mmols) of potassium tert-butoxide at room temperature. The reaction mixture was stirred at room temperature for 1 hour, and 300 ml of water was added thereto, and extracted with ethyl acetate. The organic layer was washed with water and saturated saline, and dried over anhydrous magnesium sulfate, and the solvent was distilled off under reduced pressure to obtain 17 g of the intended ethyl 2-phenyl-3-(3,5-dichloro-1-methylpyrazol-4-yl)-3-hydroxyacrylate.

$^1$H-NMR (CDCl$_3$, δ ppm); 1.1–1.5 (3H, m), 3.59 (1.5H, s), 3.73 (1.5H, s), 3.95–4.45 (2H, m), 5.58 (0.5H, s), 7.0–7.35 (5H, m), 13.21 (0.5H, s).

Synthesis Example 12

Synthesis of 1-(3,5-Dichloro-1-methylpyrazol-4-yl)-2-phenyl-2-bromoethanone (Compound No. IV-90)

1) 17 g (50 mmols) of ethyl 2-phenyl-3-(3,5-dichloro-1-methylpyrazol-4-yl)-3-hydroxyacrylate was dissolved in 50 ml of 6 N HCl and 250 ml of 1,4-dioxane, and heated under reflux for 15 hours. The reaction mixture was poured into 500 ml of ice water, and precipitated crystals were taken out through filtration to obtain 8 g of the intended 1-(3,5-dichloro-1-methylpyrazol-4-yl)-2-phenylethanone as white crystals. m.p.: 94–96° C.

2) 5.38 g (20 mmols) of 1-(3,5-dichloro-1-methylpyrazol-4-yl)-2-phenylethane was dissolved in 50 ml of chloroform, and stirred at room temperature for 1 hour, and the solvent was distilled off under reduced pressure to obtain the intended 1-(3,5-dichloro-1-methylpyrazol-4-yl)-2-phenyl-2-bromoethanone as white crystals. m.p.: 74.5–75.5° C.

Synthesis Example 13

Synthesis of 1-(3,5-Dichloro-1-methylpyrazol-4-yl)-1-pivaloyloxy-2-phenyl-2-bromoethylene (Compound No. IV-92)

0.55 g (1.58 mmols) of 1-(3,5-dichloro-1-methylpyrazol-4-yl)-2-phenyl-bromoethane and 0.18 g (1.74 mmols) of triethylamine were dissolved in 4 ml of dry tetrahydrofuran, and 0.19 g (1.58 mmols) of pivalic acid chloride was added thereto at room temperature. After the reaction mixture was stirred for 16 hours at room temperature, 10 ml of water was added thereto, and extracted with ethyl acetate. The organic layer was washed with water and saturated saline, and dried over anhydrous magnesium sulfate, and the solvent was distilled off under reduced pressure. The obtained residue was purified through silica gel column chromatography to obtain 0.23 g of the intended 1-(3,5-dichloro-1-methylpyrazol-4-yl)-1-pivaloyloxy-2-phenyl-2-bromoethylene as a colorless liquid (E-Z mixture).

$^1$H-NMR (CDCl$_3$, δ ppm); 1.05 (9H, s), 3.81 (3H, s), 7.37 (5H, m): major; 1.32 (9H, s), 3.62 (3H, s), 7.24 (5H, m): minor.

Synthesis Example 14

Synthesis of 1-(3,5-Dichloro-1-methylpyrazol-4-yl)-2-{2-(1-methylcyclohexan-1-yl)-thiazol-4-yl}-2-diethylphosphonoethanone (Compound No. II-156)

1) 4.15 g (18.1 mmols) of 2-(1-methyl-cyclohexan-1-yl)-4-chloromethylthiazole and 3.32 g (20 mmols) of trimethyl phosphite were mixed and heated under reflux for 16 hours. The reaction mixture was cooled to room temperature, and purified through silica gel column chromatography to obtain 4.63 g of the intended diethyl {2-(1-methylcyclohexan-1-yl)-thiazol-4-yl}methylphosphonate as a colorless liquid.

$^1$H-NMR (CDCl$_1$, δ ppm); 1.25 (3H, t, J=7.2 Hz), 1.31 (3H, s), 1.1–2.3 (10H, m), 3.33 (2H,. d, J=20.4 Hz), 4.04 (4H, dd, J=7.2, 7.2 Hz), 7.01 (1H, m).

2) 0.85 g (4 mmols) of 3,5-dichloro-1-methylpyrazole-4-carboxylic acid chloride and 1.32 g (4 mmols) of diethyl {2-(1-methylcyclohexan-1-yl)-thiazol-4-yl}methylphosphonate were dissolved in 15 ml of dry tetrahydrofuran, and 1.12 g (10 mmols) of potassium t-butoxide was added thereto at room temperature. The reaction mixture was stirred for 1 hour at room temperature, and 20 ml of water was added thereto, and extracted with ethyl acetate. The organic layer was washed with water and saturated saline, and dried over anhydrous magnesium sulfate, and the solvent was distilled off under reduced pressure. The obtained residue was purified through silica gel column chromatography to obtain 0.4 g of the intended 1-(3,5-dichloro-1-methylpyrazol-4-yl)-2-{2-(1-methylcyclohexan-1-yl)-thiazol-4-yl}-2-diethylphosphonoethanone.

$^1$H-NMR (CDCl$_3$, δ ppm); 1.23 (3H, t, J=7.2 Hz), 1.23 (3H, s), 1.1–2.3 (10H, m), 3.79 (3H, s), 4.09 (2H, dd, J=7.2, 7.2 Hz), 5.90 (1H, d, J=22.8 Hz), 7.43 (1H, m).

Synthesis Example 15

Synthesis of allyl 2-{3-(2,6-difluorophenyl)pyrazol-1-yl}-3-(5-chloro-1-methyl-3-trifluoromethylpyrazol-4-yl)-3-hydroxyacrylate (Compound No. I-133)

1) Potassium carbonate (1.53 g) was added to an acetonitrile (10 mL) solution of 3-(2,6-difluorophenyl)pyrazole (1 g) and allyl 2-bromoacetate (1.49 g), and refluxed for 3 hours. The resulting product was extracted with acetate and diluted hydrochloric acid added thereto at room temperature. The organic layer was dried over anhydrous magnesium sulfate and concentrated, and the resulting concentrate was purified through silica gel column chromatography (chloroform) to obtain allyl 2-{3-(2,6-difluorophenyl)pyrazol-1-yl}acetate (1.5 g).

$^1$H-NMR (CDCl$_3$, δ ppm); 4.70 (2H, d, J=6.0 Hz), 5.10 (2H, s), 5.30–5.60 (2H, m), 5.70–6.40 (1H, m), 6.50–7.80 (5H, m).

2) Potassium butoxide (0.5 g) was added to a THF (10 mL) solution of allyl 2-{3-(2,6-difluorophenyl)pyrazol-1-yl}acetate (0.5 g) and 5-chloro-1-methyl-3-trifluoromethylpyrazole-4-carbonyl chloride (0.44 g) at 0° C. and stirred for 5 minutes. Water (5 ml) was added thereto, and then extracted with diluted hydrochloric acid and ethyl acetate. After the organic layer was dried over anhydrous magnesium sulfate, and then concentrated, and the resulting concentrate was purified through silica gel column chromatography (chloroform) to obtain the intended product, Compound No. I-133 (0.89 g).

$^1$H-NMR (CDCl$_3$, δ ppm): 3.95 (3H, s), 4.80 (2H, d, J=6.0 Hz), 5.20–5.60 (2H, m), 5.60–6.40 (1H, m), 6.45–7.90 (6H, m).

Synthesis Example 16

Synthesis of 2-Bromo-2-{3-(2,6-difluorophenyl) pyrazol-1-yl}-1-(5-chloro-1-methyl-3-trifluoromethylpyrazol-4-yl}-1-hydroxyethylene (Compound No. I-134)

1) Formic acid (60 mg) was added to a THF (1 mL) solution of palladium acetate (7 mg) and triphenylphosphine (17 mg) and stirred for 5 minutes at room temperature in a nitrogen atmosphere. A THF (5 mL) solution of Compound I-133 (0.32 g) was added thereto and refluxed for 1 hour. The reaction mixture was left to be at room temperature, and concentrated, and the resulting concentrate was purified through silica gel column chromatography (chloroform) and recrystallization (chloroform-diisopropyl ether) to obtain 2-{3-(2,6-difluorophenyl)pyrazol-1-yl}-3-(5-chloro-1-methyl-3-trifluoromethylpyrazol-4-yl)ethan-1-one (0.1 g). m.p.: 152–154° C.

2) A THF solution (0.27 mL) of 1M lithium hexamethyldisilazide was added to a THF solution of 2-{3-(2,6-difluorophenyl)pyrazol-1-yl}-3-(5-chloro-1-methyl-3-trifluoromethylpyrazol-4-yl)ethan-1-one (0.1 g) at −78° C. and stirred at the same temperature in a nitrogen atmosphere. To the resulting solution was added a THF (2 mL) solution of carbon tetrabromide (0.098 g), and then gradually heated up to room temperature. Water (1 mL) was added thereto, and then extracted with diluted hydrochloric acid and ethyl acetate. The organic layer was dried over anhydrous magnesium sulfate, concentrated, and recrystallized from chloroform-diethyl ether) to obtain the intended product, Compound No. I-134 (0.062 g). m.p.: 123–125° C.

Synthesis Example 17

Synthesis of 2-Bromo-2-{3-(2,6-difluorophenyl) pyrazol-1-yl}-1-(5-chloro-1-methyl-3-trifluoromethylpyrazol-4-yl}-1-pivaloyloxyethylene (Compound No. I-135)

Triethylamine (0.3 g) and pivalic acid chloride (0.23 g) were added in that order to a chloroform (25 mL) solution of Compound No. I-134 (0.47 g) at 0° C., and stirred at room temperature for 1 hour. The resulting product was extracted with water and chloroform. The organic layer was dried with anhydrous magnesium sulfate, concentrated, and purified through silica gel column chromatography (chloroform) to obtain the intended product, Compound No. I-135 (0.4 g).

$^1$H-NMR (CDCl$_3$, δ ppm); 1.25 (9H, s), 3.90 (3H, s), 6.55–7.80 (5H, m).

In accordance with the above-mentioned reaction schemes or Examples, various compounds of the present invention were produced, of which the structure and the melting point are shown in Table 15 to Table 19 below. Unless otherwise specifically indicated, the compounds shown in these are in the form of a mixture of E-form and Z-form. The abbreviations in these have the same meanings as those mentioned above.

TABLE 15

| No. | R$^1$ | R$^2$ | R$^3$ | E | B | A | m.p. (° C.) |
|---|---|---|---|---|---|---|---|
| I-1 | Ph | H | H | CN | H | A1 | 144–145 |
| I-2 | Ph | Cl | H | CN | H | A1 | 300< |
| I-3 | Ph | H | Me | CN | H | A1 | 300< |
| I-4 | Ph | Me | H | CN | H | A1 | 141–143 |
| I-5 | Ph | H | H | CN | B1 | A1 | 75–77* |
| I-6 | Ph | H | H | CN | B2 | A1 | viscous oil |
| I-7 | Ph | CO$_2$Et | H | CN | H | A1 | 202–203 |
| I-8 | Ph | H | H | CN | H | A2 | 300< |
| I-9 | Ph | H | H | CN | H | A7 | 124–125 |
| I-10 | Ph | H | H | CN | H | A8 | 265–267 |
| I-11 | 2-pyridyl | H | H | CN | H | A1 | 290< |
| I-12 | 2-pyridyl | H | H | CN | H | A2 | 300< |
| I-13 | 2-pyridyl | H | H | CN | H | A3 | 260–267 |
| I-14 | 2-pyridyl | H | H | CN | H | A4 | 300< |
| I-15 | 2-pyridyl | H | H | CN | H | A6 | 297–298 |
| I-16 | 2-pyridyl | H | H | CN | H | A7 | 163–165 |
| I-17 | 2-pyridyl | H | H | CN | H | A8 | 300< |
| I-18 | 2-pyridyl | H | H | CN | H | A9 | 240–245 |
| I-19 | 2-pyridyl | H | H | CN | H | A10 | 261–266 |
| I-20 | 2-pyridyl | H | H | CN | H | A11 | 232–234 |
| I-21 | 2-pyridyl | H | H | CN | H | A12 | 284–287 |
| I-22 | 2-pyridyl | H | H | CN | H | A13 | 300< |
| I-23 | 2-pyridyl | H | H | CN | B7 | A7 | 103–110* |
| I-24 | 2-pyridyl | H | H | CN | B8 | A1 | viscous oil |
| I-25 | 3-pyridyl | H | H | CN | H | A1 | 298–300 |
| I-26 | 3-pyridyl | H | H | CN | H | A2 | 158–160 |
| I-27 | 3-pyridyl | H | H | CN | H | A7 | 168–169 |
| I-28 | 4-pyridyl | H | H | CN | H | A1 | 251–253 |
| I-29 | 2-F—Ph | H | H | CN | H | A1 | 125–126 |
| I-30 | 2-F—Ph | H | H | CN | H | A2 | 281–282 |
| I-31 | 2-F—Ph | Cl | H | CN | H | A1 | 281–287 |
| I-32 | 3-F—Ph | H | H | CN | H | A2 | 300< |
| I-33 | 4-F—Ph | H | H | CN | H | A2 | 169–173 |
| I-34 | 2-Cl—Ph | H | H | CN | H | A1 | viscous oil |
| I-35 | 2-Cl—Ph | H | H | CN | H | A2 | viscous oil |
| I-36 | 3-Cl—Ph | H | H | CN | H | A1 | 141–149 |
| I-37 | 3-Cl—Ph | H | H | CN | H | A7 | 291–293 |
| I-38 | 4-Cl—Ph | H | H | CN | H | A1 | 186–188 |
| I-39 | 4-Cl—Ph | H | H | CN | H | A7 | 300< |
| I-40 | 2,6-F$_2$—Ph | H | H | CN | H | A1 | 267–269 |
| I-41 | 2,6-F$_2$—Ph | H | H | CN | H | A2 | 300< |
| I-42 | 2,6-F$_2$—Ph | H | H | CN | H | A7 | 242–243 |
| I-43 | 2,6-Cl$_2$—Ph | H | H | CN | H | A1 | 147–148 |
| I-44 | 2,6-Cl$_2$—Ph | H | H | CN | H | A2 | 100–102 |
| I-45 | tBu | H | H | CN | H | A1 | viscous oil |
| I-46 | tBu | H | H | CN | H | A2 | 65–67 |
| I-47 | 2-MeO—Ph | H | H | CN | H | A1 | 300< |
| I-48 | 2-MeO—Ph | H | H | CN | H | A2 | 300< |
| I-49 | H | CO$_2$Et | Ph | CN | H | A1 | 236–237 |
| I-50 | Me | Ph | H | CN | H | A1 | viscous oil |
| I-51 | cHex | H | H | CN | H | A1 | 204–205 |
| I-52 | 1-naphthyl | H | H | CN | H | A1 | 225–227 |
| I-53 | 2-thienyl | H | H | CN | H | A1 | 146–147 |
| I-54 | 2-thienyl | H | H | CN | H | A7 | 271–273 |
| I-55 | Ph | H | H | CN | H | A34 | 173.3–174.1 |
| I-56 | Ph | H | H | CN | B1 | A34 | viscous oil* |
| I-57 | Ph | H | H | CN | B7 | A1 | 140–141* |
| I-58 | Ph | H | H | CN | B8 | A1 | 50–51* |

TABLE 15-continued

| No. | R¹ | R² | R³ | E | B | A | m.p. (° C.) |
|---|---|---|---|---|---|---|---|
| I-59 | Ph | H | H | CN | CO$_2$$^t$Bu | A1 | viscous oil |
| I-60 | tBu | CO$_2$Me | H | CN | H | A1 | 105–106 |
| I-61 | tBu | CO$_2$Me | H | CN | B7 | A1 | 125–126 |
| I-62 | Ph | H | H | CN | B7 | A2 | viscous oil |
| I-63 | 2,6-F$_2$—Ph | H | H | CN | B7 | A2 | 200–201 |
| I-64 | Ph | H | H | CN | B6 | A2 | viscous oil |
| I-65 | 2,6-F$_2$—Ph | H | H | CN | Na | 2,6-(MeO)$_2$—Ph | 300< |
| I-66 | 2,6-F$_2$—Ph | H | H | CN | Na | 2-CF$_3$O—Ph | 282.8–287.2 |
| I-67 | 2,6-F$_2$—Ph | H | H | CN | Na | 2-MeO—Ph | 300< |
| I-68 | 2,6-F$_2$—Ph | H | H | CN | H | 2-CF$_3$O—Ph | 157.9–160.1 |
| I-69 | 2-pyridyl | H | H | CN | B8 | A7 | 118–119* |
| I-70 | 2,6-F$_2$—Ph | H | H | CN | B7 | A2 | viscous oil |
| I-71 | Ph | H | H | CN | H | 2-Cl—Ph | 108–109 |
| I-72 | Ph | H | H | CN | H | 2,6-F$_2$—Ph | 167–168 |
| I-73 | Ph | H | H | CN | H | 2,6-Cl$_2$—Ph | 170–171 |
| I-74 | Ph | H | H | CN | H | 2-CF$_3$—Ph | viscous oil |
| I-75 | Ph | H | H | CN | H | 1-naphthyl | 137–138 |
| I-76 | Ph | Ph | H | CN | H | A2 | 145–147 |
| I-77 | Ph | H | H | CN | H | 2-Cl-4-F—Ph | 94–95 |
| I-78 | Ph | H | H | CN | B35 | A2 | 164–165 |
| I-79 | 2,6-F$_2$—Ph | H | H | CN | H | 2-Me—Ph | 113.1–119.8 |
| I-80 | 2,6-F$_2$—Ph | H | H | CN | H | 2-Cl-6-F—Ph | 144–146 |
| I-81 | 2,6-F$_2$—Ph | H | H | CN | H | 2-NO$_2$—Ph | 176–179 |
| I-82 | 2,6-F$_2$—Ph | H | H | CN | H | 2-AcO—Ph | vitreous state |
| I-83 | 2,6-F$_2$—Ph | H | H | CN | H | 2,6-Me—Ph | vitreous state |
| I-84 | 2-pyridyl | H | H | CN | H | 2,6-F$_2$—Ph | 188–189 |
| I-85 | 2-pyridyl | H | H | CN | H | 2,6-Cl$_2$—Ph | 278–280 |
| I-86 | 2-pyridyl | H | H | CN | H | 2-NO$_2$—Ph | 285–287 |
| I-87 | 2-pyridyl | H | H | CN | H | 2-MeO—Ph | 275–276 |
| I-88 | 2-pyridyl | H | H | CN | H | 2-CO$_2$Me—Ph | 248–249 |
| I-89 | 2-pyridyl | H | H | CN | B7 | 2-Cl—Ph | 124–125 |
| I-90 | 2-pyridyl | H | H | CN | Na | 2-Cl—Ph | 278–280 |
| I-91 | 2-pyridyl | H | H | CN | H | pyridin-2-yl | 216–217 |
| I-92 | 2-pyridyl | H | H | CN | CO$^a$C$_{17}$H$_{35}$ | A7 | 58–59 |
| I-93 | t-Bu | CO$_2$Me | H | CN | H | 2-Cl-4-F—Ph | 114–115 |
| I-94 | t-Bu | CO$_2$Me | H | CN | B7 | A2 | 105–106 |
| I-95 | t-Bu | CO$_2$Me | H | CN | H | A2 | 102–103 |
| I-96 | t-Bu | H | H | CN | B7 | A2 | viscous oil |
| I-97 | t-Bu | H | H | CN | B7 | A2 | viscous oil$^{\#1}$ |
| I-98 | t-Bu | NO$_2$ | H | CN | B7 | A2 | viscous oil |
| I-99 | t-Bu | Br | H | CN | B7 | A2 | viscous oil |
| I-100 | t-Bu | CN | H | CN | H | A2 | 178–180 |
| I-101 | t-Bu | CN | H | CN | CO$_2$$^t$Bu | A2 | vitreous state |
| I-102 | t-Bu | CN | H | CN | CO$_2$$^t$Bu | A2 | 201–202.5$^{\#2}$ |
| I-103 | t-Bu | CN | H | CN | CO$_2$Ph | A2 | vitreous state |
| I-104 | t-Bu | Cl | H | CN | B7 | A2 | viscous oil |
| I-105 | t-Bu | CO$_2$Me | H | CN | CO$_2$$^i$Bu | A2 | 155.8–156.9 |
| I-106 | t-Bu | Cl | H | CN | H | A2 | viscous oil |
| I-107 | t-Bu | NO$_2$ | H | CN | H | A2 | 87–88 |
| I-108 | t-Bu | CO$_2$$^a$Hex | H | CN | H | A2 | vitreous state |
| I-109 | t-Bu | CO$_2$Me | H | CN | B8 | A2 | 152.1–153.5 |
| I-110 | t-Bu | Me | H | CN | H | A2 | vitreous state |
| I-111 | t-Bu | CO$_2$Me | H | CN | CO$^a$C$_{17}$H$_{35}$ | A14 | viscous oil |
| I-112 | t-Bu | CO$_2$Me | H | CN | B7 | A14 | viscous oil |
| I-113 | t-Bu | CO$_2$Me | H | CN | H | A14 | 101–102 |
| I-114 | t-Bu | Me | H | CN | B7 | A2 | vitreous state |
| I-115 | t-Bu | CO$_2$Me | H | CN | B7 | A3 | 131–132 |
| I-116 | t-Bu | CO$_2$Me | H | CN | Me | A2 | 166–167* |
| I-117 | t-Bu | CO$_2$Me | H | CN | B3 | A14 | viscous oil |
| I-118 | t-Bu | CO$_2$Me | H | CN | H | A21 | 152.6–154 |
| I-119 | t-Bu | CO$_2$Me | H | CN | CO$^a$C$_9$H$_{19}$ | A3 | viscous oil |
| I-120 | t-Bu | CO$_2$Me | H | CN | B7 | A15 | 125–127* |
| I-121 | t-Bu | CO$_2$Me | H | CN | H | A15 | 138–139 |
| I-122 | t-Bu | CO$_2$Me | H | CN | B7 | A21 | viscous oil |
| I-123 | t-Bu | CO$_2$Me | H | CN | CO$^a$C$_5$H$_{11}$ | A21 | viscous oil |
| I-124 | t-Bu | CO$_2$Me | H | CN | CO$^a$C$_5$H$_{11}$ | A21 | viscous oil$^{\#3}$ |
| I-125 | H | H | 2,6-F$_2$—Ph | CN | H | A2 | 157.4–162.4 |
| I-126 | H | Ph | H | CN | H | A1 | vitreous state |

TABLE 15-continued

| No. | R¹ | R² | R³ | E | B | A | m.p. (° C.) |
|---|---|---|---|---|---|---|---|
| I-127 | H | t-Bu | H | CN | B7 | A2 | vitreous state |
| I-128 | H | t-Bu | H | CN | H | A2 | vitreous state |
| I-129 | Ph | H | H | $CO_2Me$ | H | A1 | 158–160 |
| I-130 | Ph | H | H | $CO_2Me$ | B7 | A2 | viscous oil |
| I-131 | 2,6-$F_2$—Ph | H | H | $CO_2Me$ | H | A2 | 248–250 |
| I-132 | 2,6-$F_2$—Ph | H | H | COMe | H | A2 | vitreous state |
| I-133 | 2,6-$F_2$—Ph | H | H | $CO_2CH_2CH=CH_2$ | H | A2 | vitreous state |
| I-134 | 2,6-$F_2$—Ph | H | H | Br | H | A2 | 123–125 |
| I-135 | 2,6-$F_2$—Ph | H | H | Br | B7 | A2 | vitreous state |
| I-136 | 2-pyridyl | H | H | CN | B7 | A37 | 86–94[#4] |
| I-137 | 2-pyridyl | H | H | CN | B7 | A10 | 92–93 |
| I-138 | 2-pyridyl | Cl | H | CN | B7 | A7 | viscous oil* |

*E-form or Z-form
[#1] geometric isomer of I-96
[#2] geometric isomer of I-101
[#3] geometric isomer of I-123
[#4] mixture of E/Z = 2/1

TABLE 16

| No. | R | E | B | A | m.p. (° C.) |
|---|---|---|---|---|---|
| II-1 | Ph | CN | H | A1 | 200–205 |
| II-2 | 2-Cl—Ph | CN | H | A2 | 137–138 |
| II-3 | t-Bu | CN | H | A2 | 151–153 |
| II-4 | t-Bu | CN | B3 | A2 | 147–150* |
| II-5 | t-Bu | CN | B7 | A2 | 89.5–92* |
| II-6 | t-Bu | CN | H | A1 | viscous oil* |
| II-7 | t-Bu | CN | B7 | A1 | viscous oil* |
| II-8 | t-Bu | CN | H | 2,6-$F_2$—Ph | 90–92.5 |
| II-9 | t-Bu | CN | H | 2-Cl—Ph | 96.2–98.6 |
| II-10 | t-Bu | CN | B6 | A2 | vitreous state* |
| II-11 | t-Bu | CN | B5 | A2 | viscous oil |
| II-12 | t-Bu | CN | B8 | A2 | viscous oil |
| II-13 | t-Bu | CN | $SO_2$(4-Cl—Ph) | A2 | vitreous state* |
| II-14 | t-Bu | CN | H | 2,6-$Cl_2$—Ph | 150.3–151.7 |
| II-15 | t-Bu | CN | H | 2-$CF_3$—Ph | 71.9–79.6 |
| II-16 | t-Bu | CN | H | A3 | viscous oil |
| II-17 | t-Bu | CN | B7 | A3 | viscous oil* |
| II-18 | t-Bu | CN | $CO_2Et$ | A2 | viscous oil |
| II-19 | t-Bu | CN | $CO_2CH_2Ph$ | A2 | viscous oil |
| II-20 | t-Bu | CN | $CONMe_2$ | A2 | 136.7–138.2 |
| II-21 | t-Bu | CN | $CH_2CO_2Me$ | A2 | viscous oil |
| II-22 | t-Bu | CN | $PO(OEt)_2$ | A2 | viscous oil |
| II-23 | 2-pyridyl | CN | H | A2 | 184.5–188.5 |
| II-24 | 2-pyridyl | CN | H | A7 | 210.3–218.8 |
| II-25 | 2-pyridyl | CN | B7 | A7 | 162.7–167* |
| II-26 | 2-pyridyl | CN | B7 | A2 | vitreous state* |
| II-27 | 2-pyridyl | CN | H | A3 | 148–151 |
| II-28 | 2-pyridyl | CN | B7 | A3 | vitreous state* |
| II-29 | 2-pyridyl | CN | H | A35 | 188–193 |
| II-30 | 2-pyridyl | CN | B7 | A35 | 200.5–202.5* |
| II-31 | 2-pyridyl | CN | H | A36 | viscous oil |
| II-32 | 2-pyridyl | CN | B7 | A36 | viscous oil |
| II-33 | c-Hex | CN | H | A2 | 126.5–128.1 |
| II-34 | c-Hex | CN | H | 2,6-$F_2$—Ph | 110.9–112.7 |
| II-35 | c-Hex | CN | B7 | 2,6-$F_2$—Ph | 111.2–117.4* |
| II-36 | c-Hex | CN | B7 | A2 | viscous oil* |
| II-37 | 2,6-$F_2$—Ph | CN | H | A2 | 176.8–178.2 |
| II-38 | 2,6-$F_2$—Ph | CN | B7 | A2 | 95.9–98.0* |
| II-39 | 2-Cl—Ph | CN | H | A2 | 172.9–175.2 |

TABLE 16-continued

| No. | R | E | B | A | m.p. (° C.) |
|---|---|---|---|---|---|
| II-40 | t-Bu | CN | B35 | A2 | vitreous state |
| II-41 | t-Bu | CN | B35 | A2 | vitreous state[#4] |
| II-42 | t-Bu | CN | B36 | A2 | vitreous state |
| II-43 | t-Bu | CN | H | A13 | 168–173 |
| II-44 | t-Bu | CN | B28 | A2 | vitreous state |
| II-45 | t-Bu | CN | B30 | A2 | vitreous state |
| II-46 | t-Bu | CN | B30 | A2 | vitreous state[#5] |
| II-47 | t-Bu | CN | CO(2-Me—Ph) | A2 | vitreous state |
| II-48 | t-Bu | CN | B38 | A2 | vitreous state |
| II-49 | t-Bu | CN | B37 | A2 | vitreous state |
| II-50 | t-Bu | CN | nicotinoyl | A2 | vitreous state |
| II-51 | t-Bu | CN | B40 | A2 | vitreous state |
| II-52 | t-Bu | CN | $CO_2^iBu$ | A2 | viscous oil |
| II-53 | t-Bu | CN | $CO_2Ph$ | A2 | viscous oil |
| II-54 | t-Bu | CN | B41 | A2 | viscous oil |
| II-55 | t-Bu | CN | $CO_2^aHex$ | A2 | viscous oil |
| II-56 | t-Bu | CN | H | 3-Cl—Ph | 89.7–91.1 |
| II-57 | t-Bu | CN | H | 3-F—Ph | 63.7–64.4 |
| II-58 | t-Bu | CN | H | 2-Br—Ph | 86–87 |
| II-59 | t-Bu | CN | H | 2-I—Ph | vitreous state |
| II-60 | t-Bu | CN | H | 2-Cl-6-F—Ph | 109.6–110.6 |
| II-61 | t-Bu | CN | CO(2-MeS—Ph) | A2 | vitreous state |
| II-62 | t-Bu | CN | H | 2-MeS—Ph | 120.6–122.1 |
| II-63 | t-Bu | CN | H | A22 | 113–118 |
| II-64 | t-Bu | CN | B7 | A22 | 98–99.5* |
| II-65 | t-Bu | CN | B15 | A22 | viscous oil |
| II-66 | t-Bu | CN | B38 | A13 | viscous oil |
| II-67 | t-Bu | CN | B39 | A2 | vitreous state |
| II-68 | t-Bu | CN | CO(4-Cl—Ph) | A2 | vitreous state |
| II-69 | t-Bu | CN | CO(3-Cl—Ph) | A2 | vitreous state |
| II-70 | t-Bu | CN | B7 | 2,6-$F_2$—Ph | viscous oil |
| II-71 | t-Bu | CN | B8 | 2,6-$F_2$—Ph | viscous oil |
| II-72 | t-Bu | CN | B6 | 2,6-$F_2$—Ph | 150.2–151.3 |
| II-73 | t-Bu | CN | $CO_2^nPr$ | A2 | viscous oil |
| II-74 | t-Bu | CN | $CO_2^nBu$ | A2 | viscous oil |
| II-75 | t-Bu | CN | B6 | A13 | viscous oil |
| II-76 | t-Bu | CN | $CO_2CH_2CCl_3$ | A2 | viscous oil |
| II-77 | t-Bu | CN | CO(2-Cl—Ph) | A2 | vitreous state |
| II-78 | t-Bu | CN | CO(3-$CF_3$—Ph) | A2 | vitreous state |
| II-79 | t-Bu | CN | CO(4-$CF_3$—Ph) | A2 | vitreous state |
| II-80 | t-Bu | CN | CO(3-$NO_2$—Ph) | A2 | vitreous state |
| II-81 | t-Bu | CN | CO(2-Cl-6-F—Ph) | A2 | vitreous state |
| II-82 | t-Bu | CN | $CO_2^cPen$ | 2,6-$F_2$—Ph | vitreous state |
| II-83 | t-Bu | CN | 3-Cl-pivaloyl | A2 | viscous oil* |
| II-84 | t-Bu | CN | $CO_2^iPr$ | A2 | viscous oil |
| II-85 | t-Bu | CN | $CO_2CH_2CH_2Cl$ | A2 | viscous oil |
| II-86 | t-Bu | CN | $CO_2CHClCH_3$ | A2 | viscous oil |
| II-87 | t-Bu | CN | $CO^iPr$ | A2 | viscous oil |
| II-88 | t-Bu | CN | isonicotinoyl | A2 | viscous oil |
| II-89 | t-Bu | CN | picolinoyl | A2 | viscous oil |
| II-90 | t-Bu | CN | CO(4-Me—Ph) | A2 | viscous oil |
| II-91 | t-Bu | CN | CO(4-$NO_2$—Ph) | A2 | viscous oil |
| II-92 | t-Bu | CN | methacryloyl | A2 | viscous oil |
| II-93 | t-Bu | CN | B15 | A2 | vitreous state |
| II-94 | t-Bu | CN | $PhCH_2$ | A2 | viscous oil |
| II-95 | t-Bu | CN | Me | A2 | 136.5–138 |
| II-96 | t-Bu | CN | $CBrF_2$ | A2 | 84–86.5 |
| II-97 | t-Bu | CN | $CO^nPr$ | A2 | viscous oil |
| II-98 | t-Bu | CN | $CO^iBr$ | A2 | viscous oil |
| II-99 | t-Bu | CN | B43 | A2 | vitreous state |
| II-100 | t-Bu | CN | $PhCOCH_2$ | A2 | 148–152* |
| II-101 | t-Bu | CN | B42 | A2 | 128–129.5* |
| II-102 | t-Bu | CN | H | A14 | 98–99 |
| II-103 | t-Bu | CN | H | A16 | viscous oil |
| II-104 | t-Bu | CN | B7 | A16 | viscous oil* |
| II-105 | t-Bu | CN | cinnamoyl | A2 | vitreous state |
| II-106 | t-Bu | CN | H | A23 | 109–112 |
| II-107 | t-Bu | CN | B7 | A23 | 120–122.5 |
| II-108 | t-Bu | CN | B7 | A14 | viscous oil |
| II-109 | t-Bu | CN | B7 | A14 | viscous oil[#6] |
| II-110 | t-Bu | CN | $CO^aC_{17}H_{35}$ | A14 | viscous oil |

TABLE 16-continued

| No. | R | E | B | A | m.p. (° C.) |
|---|---|---|---|---|---|
| II-111 | t-Bu | CN | PhCH$_2$CO | A2 | viscous oil |
| II-112 | t-Bu | CN | B7 | A17 | viscous oil |
| II-113 | t-Bu | CN | H | A17 | 140–143 |
| II-114 | t-Bu | CN | H | A24 | 115–117 |
| II-115 | t-Bu | CN | CO$_2^i$Bu | A24 | vitreous state |
| II-116 | t-Bu | CN | B7 | A2 | 69.5–73.5$^{\#7}$ |
| II-117 | t-Bu | CN | H | A25 | 107–109 |
| II-118 | t-Bu | CN | B7 | A25 | viscous oil |
| II-119 | t-Bu | CN | H | A31 | 116–117 |
| II-120 | t-Bu | CN | CO$_2$(4-Me—Ph) | A31 | 92–93 |
| II-121 | t-Bu | CN | H | A26 | 133.2–135.4 |
| II-122 | t-Bu | CN | B7 | A26 | 133.9–145 |
| II-123 | t-Bu | CN | H | A27 | 46–47 |
| II-124 | t-Bu | CN | H | A28 | 168–169 |
| II-125 | t-Bu | CN | H | A29 | 94.7–95.4 |
| II-126 | t-Bu | CN | B8 | A29 | viscous oil |
| II-127 | t-Bu | CN | B8 | A29 | viscous oil$^{\#8}$ |
| II-128 | t-Bu | CN | H | A32 | 133.9–134.4 |
| II-129 | t-Bu | CN | H | A33 | 220–230 |
| II-130 | 2,6-F$_2$—Ph | CN | H | 2,6-F$_2$—Ph | 138–143 |
| II-131 | 2-pyridyl | CN | B7 | A18 | 115–145 |
| II-132 | 2-pyridyl | CN | H | A18 | 176–178 |
| II-133 | 2-pyridyl | CN | H | A9 | 191.5–195 |
| II-134 | 2-pyridyl | CN | B7 | A9 | 101–103 |
| II-135 | 2-pyridyl | CN | H | A8 | 211–216 |
| II-136 | 2-pyridyl | CN | H | A10 | 189–193 |
| II-137 | 2-pyridyl | CN | CO$_2$(4-F—Ph) | A10 | 137–142 |
| II-138 | 2-pyridyl | CN | H | A24 | 188–191.5 |
| II-139 | 2-pyridyl | CN | B7 | A24 | 160–163.5 |
| II-140 | 2-pyridyl | CN | B7 | A30 | 123–125 |
| II-141 | 2-pyridyl | CN | H | A30 | 165–166 |
| II-142 | 2-pyridyl | CN | H | A13 | 149.5–151 |
| II-143 | NMePh | CN | H | A7 | 161.5–164 |
| II-144 | NMePh | CN | B7 | A7 | 120–123 |
| II-145 | NMePh | CN | H | A2 | vitreous state |
| II-146 | NMePh | CN | B7 | A2 | vitreous state |
| II-147 | 1-piperidyl | CN | B3 | A2 | 165.5–169 |
| II-148 | 1-piperidyl | CN | H | A2 | 151–153 |
| II-149 | 1-piperidyl | CN | H | A7 | 187–190 |
| II-150 | 1-piperidyl | CN | B8 | A7 | viscous oil |
| II-151 | 1-piperidyl | CN | B8 | A2 | 120–121.5 |
| II-152 | 1-piperidyl | CN | B6 | A2 | viscous oil |
| II-153 | 1-naphthyl | CN | H | A2 | 161–163 |
| II-154 | 1-naphthyl | CN | B7 | A2 | vitreous state |
| II-155 | t-Bu | CO$_2$Me | H | A2 | viscous oil |
| II-156 | 1-Me-1-$^c$Hex | PO(OEt)$_2$ | H | A1 | vitreous state |
| II-157 | t-Bu | CO$_2$Et | H | A1 | viscous oil |
| II-158 | t-Bu | CO$_2$Et | B7 | A1 | viscous oil |
| II-159 | 1-Me-1-$^c$Hex | CN | H | A2 | vitreous state |
| II-160 | n-Pen | CN | H | A2 | 73–75 |
| II-161 | t-Bu | CN | B8 | A32 | 108–112 |
| II-162 | t-Bu | CN | H | A1 | viscous oil |
| II-163 | t-Bu | CO$_2$Me | H | A1 | 89–92 |
| II-164 | t-Bu | SO$_2$Ph | H | A1 | 145–148 |
| II-165 | t-Bu | SO$_2$Ph | B7 | A1 | 122–123 |
| II-166 | t-Bu | SO$_2$Ph | B7 | A1 | 152–153$^{\#14}$ |
| II-167 | t-Bu | CO$_2$Me | B7 | A1 | viscous oil |
| II-168 | t-Bu | CO$_2$Me | B7 | A2 | 76–78 |
| II-169 | t-Bu | CO$_2$CH$_2$CH=CH$_2$ | H | A2 | viscous oil |
| II-170 | t-Bu | CO$_2$CH$_2$CH=CH$_2$ | B7 | A2 | viscous oil |
| II-171 | 1-Me-1-$^c$Hex | CN | B7 | A2 | vitreous state |
| II-172 | n-Pen | CN | B7 | A2 | vitreous state |
| II-173 | 1-Me-1-$^c$Hex | CN | CH$_2$O(CH$_2$)$_2$OCH$_3$ | A2 | 97–98* |
| II-174 | t-Bu | 5-Me-1,3,4-oxadiazol-2-yl | H | A1 | vitreous state |
| II-175 | t-Bu | 5-Me-1,3,4-oxadiazol-2-yl | H | A1 | vitreous state |
| II-176 | t-Bu | Bu | H | A2 | viscous oil |
| II-177 | t-Bu | CN | B6 | A13 | 104–107* |

TABLE 16-continued

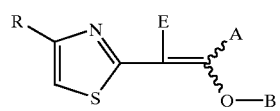

| No. | R | E | B | A | m.p. (° C.) |
|---|---|---|---|---|---|
| II-178 | t-Bu | 5-Me-1,3,4-oxadiazol-2-yl | B7 | A1 | 134–137 |
| II-179 | t-Bu | 5-Me-1,3,4-oxadiazol-2-yl | B7 | A1 | 114–116[#15] |
| II-180 | t-Bu | 5-Me-1,3,4-thiadiazol-2-yl | B7 | A1 | 86–90* |

*E-form or Z-form.
[#4]geometric isomer of II-40
[#5]geometric isomer of II-45
[#6]geometric isomer of II-108
[#7]geometric isomer of II-5
[#8]geometric isomer of II-126
[#14]geometric isomer of II-165
[#15]geometric isomer of II-178

TABLE 17

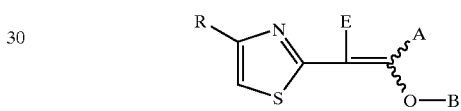

| No. | R | E | B | A | m.p. (° C.) |
|---|---|---|---|---|---|
| III-1 | Ph | CN | B4 | A1 | viscous oil* |
| III-2 | Ph | CN | B5 | A1 | 40–41* |
| III-3 | t-Bu | CN | B1 | A1 | 151–152* |
| III-4 | t-Bu | CN | B4 | A1 | 77–79* |
| III-5 | t-Bu | CN | B6 | A2 | 55–61* |
| III-6 | t-Bu | CN | B7 | A2 | viscous oil* |
| III-7 | 2-pentyl | CN | B1 | A1 | viscous oil |
| III-8 | 4-tBu—Ph | CN | B1 | A5 | viscous oil |
| III-9 | t-Bu | CN | Na | A2 | 165–174 |
| III-10 | t-Bu | CN | B9 | A2 | viscous oil |
| III-11 | t-Bu | CN | B10 | A2 | 185–186* |
| III-12 | t-Bu | CN | B11 | A2 | viscous oil |
| III-13 | 2-NO$_2$—Ph | CN | B9 | A1 | 168–171* |
| III-14 | 1-naphthyl | CN | B9 | A7 | 136–138* |
| III-15 | t-Bu | CN | B7 | A2 | viscous oil[#9] |
| III-16 | Ph | CN | B4 | A1 | solid[#10] |
| III-17 | t-Bu | CN | B4 | A1 | viscous oil[#11] |
| III-18 | 2-Cl-6-F—Ph | CN | B7 | A2 | 152–153 |
| III-19 | 2,6-F$_2$—Ph | CN | B7 | A2 | vitreous state* |
| III-20 | Ph | CN | B5 | A1 | 105–107[#12] |
| III-21 | Ph | CN | B7 | A2 | viscous oil |

*E-form or Z-form,
[#9]geometric isomer of III-6,
[#10]geometric isomer of III-1,
[#11]geometric isomer of III-4,
[#12]geometric isomer of III-2

TABLE 18

| No. | G | E | B | A | m.p. (° C.) |
|---|---|---|---|---|---|
| IV-1 | 2-CF$_3$ | CN | H | A1 | viscous oil |
| IV-2 | 3-CF$_3$ | CN | H | A1 | 159–163 |
| IV-3 | 3-CF$_3$ | CN | B1 | A1 | 174–175 |

TABLE 18-continued

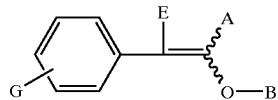

| No. | G | E | B | A | m.p. (° C.) |
|---|---|---|---|---|---|
| IV-4 | 4-CF$_3$ | CN | H | A1 | 176–179 |
| IV-5 | 4-CF$_3$ | CN | B1 | A1 | viscous oil |
| IV-6 | 2-CF$_3$ | CN | CSNMe$_2$ | A1 | viscous oil |
| IV-7 | 3(1-CN-1-Me)-Et | CN | H | A1 | viscous oil |
| IV-8 | 3(1-CN-1-Me)-Et | CN | B1 | A1 | 148–155 |
| IV-9 | 3-OPh | CN | H | A1 | 103–110 |
| IV-10 | 3-OPh | CN | B7 | A1 | viscous oil |
| IV-11 | 4-OPh | CN | H | A1 | 148–150 |
| IV-12 | 4-OPh | CN | B7 | A1 | viscous oil |
| IV-13 | 4-Et | CN | H | A1 | 148–149 |
| IV-14 | 4-Et | CN | B7 | A1 | 81–82 |
| IV-15 | 4-Et | CN | B5 | A1 | viscous oil |
| IV-16 | 4-i-Pr | CN | H | A1 | 126–127 |
| IV-17 | 4-i-Pr | CN | B7 | A1 | 105–106 |
| IV-18 | 4-t-Bu | CN | H | A1 | 117–118 |
| IV-19 | 4-t-Bu | CN | B1 | A1 | viscous oil |
| IV-20 | 4-OCF$_3$ | CN | H | A1 | 128–129 |
| IV-21 | 4-OCF$_3$ | CN | B7 | A1 | 96–99 |
| IV-22 | 3,4-methylene-dioxy | CN | H | A1 | 129–131 |
| IV-23 | 3,4-methylene-dioxy | CN | B7 | A1 | viscous oil |
| IV-24 | 4-t-Bu | CN | B7 | A2 | viscous oil |
| IV-25 | 4-t-Bu | CN | B15 | A2 | viscous oil |
| IV-26 | 4-t-Bu | CN | H | A2 | 139–140 |
| IV-27 | 4-t-Bu | CN | B7 | A13 | 87–88 |
| IV-28 | 4-t-Bu | CN | H | A13 | 141–142 |
| IV-29 | 4-t-Bu | CN | B8 | A2 | vitreous state |
| IV-30 | 4-t-Bu | CN | H | A19 | 169.5–173 |
| IV-31 | 4-t-Bu | CN | H | A20 | vitreous state |
| IV-32 | 4-t-Bu | CN | B7 | A20 | 146–148 |
| IV-33 | 4-t-Bu | CN | B15 | A14 | viscous oil |
| IV-34 | 4-t-Bu | CN | B7 | A19 | vitreous state |
| IV-35 | 4-t-Bu | CN | B7 | A1 | viscous oil* |
| IV-36 | 4-t-Bu | CN | B8 | A1 | viscous oil |
| IV-37 | 4-t-Bu | CN | H | A24 | vitreous state |
| IV-38 | 4-t-Bu | CN | B8 | A24 | vitreous state |
| IV-39 | 4-t-Bu | CN | CO$_2$Et | A1 | viscous oil |
| IV-40 | 4-t-Bu | CN | CO$_2{}^i$Bu | A1 | viscous oil |
| IV-41 | 4-t-Bu | CN | COCO$_2$CH$_3$ | A1 | viscous oil |
| IV-42 | 4-s-Bu | CN | H | A2 | 107–108 |
| IV-43 | 4-s-Bu | CN | B15 | A2 | 77–85 |
| IV-44 | 4-i-Bu | CN | B15 | A1 | 100–101 |
| IV-45 | 4-i-Bu | CN | B15 | A2 | viscous oil |
| IV-46 | 4-i-Bu | CN | H | A2 | 98–99 |
| IV-47 | 4-i-Pr | CN | B8 | A2 | viscous oil |
| IV-48 | 4-i-Pr | CN | CO(4-NO$_2$-Ph) | A2 | vitreous state |
| IV-49 | 4-Et | CN | B15 | A1 | viscous oil |
| IV-50 | 4-Ph | CN | H | A1 | vitreous state |
| IV-51 | 4-Ph | CN | H | A2 | vitreous state |
| IV-52 | 4-Ph | CN | H | A12 | vitreous state |
| IV-53 | 4-Ph | CN | H | A13 | 167–169 |
| IV-54 | 3,4-Cl$_2$ | CN | H | A1 | vitreous state |
| IV-55 | 4-Cl | CN | H | A1 | vitreous state |
| IV-56 | 2-F-4-CF$_3$ | CN | H | A2 | vitreous state |
| IV-57 | 2-F-4-CF$_3$ | CN | B7 | A2 | vitreous state |
| IV-58 | 2-F-4-CF$_3$ | CN | B15 | A2 | vitreous state |
| IV-59 | 4-NO$_2$ | CN | H | A1 | 186–188 |
| IV-60 | 4-MeO | CN | H | A1 | 108–110 |
| IV-61 | 4-MeO | CN | B15 | A1 | viscous oil* |
| IV-62 | 4-i-Pro | CN | H | A1 | 127–131 |
| IV-63 | 4-i-Pro | CN | H | A2 | 141.4–148.3 |
| IV-64 | 4-i-Pro | CN | B15 | A1 | viscous oil |
| IV-65 | 4-i-Pro | CN | B15 | A2 | viscous oil |
| IV-66 | 4-i-Pro | CN | B6 | A2 | viscous oil |
| IV-67 | 4-n-BuO | CN | H | A1 | 101–104 |
| IV-68 | 4-n-BuO | CN | B15 | A1 | 75–70 |
| IV-69 | 4-n-BuO | CN | H | A2 | 104.6–105.4 |
| IV-70 | 4-n-BuO | CN | B8 | A1 | 77.1–80.7 |
| IV-71 | 4-n-BuO | CN | B15 | A2 | viscous oil |
| IV-72 | 4-t-amyl | CN | B15 | A2 | viscous oil |

TABLE 18-continued

| No. | G | E | B | A | m.p. (° C.) |
|---|---|---|---|---|---|
| IV-73 | 4-allyloxy | CN | H | A1 | vitreous state |
| IV-74 | 4-allyloxy | CN | B15 | A1 | vitreous state |
| IV-75 | 4-(Cl$_2$C=CHCH$_2$O) | CN | H | A1 | vitreous state |
| IV-76 | 4-(Cl$_2$C=CHCH$_2$O) | CN | B15 | A1 | vitreous state |
| IV-77 | 4-(ClCCCH$_2$O) | CN | H | A1 | vitreous state |
| IV-78 | 4-PhCH$_2$O | CN | H | A1 | 152.9–154.7 |
| IV-79 | 4-PhCH$_2$O | CN | H | A2 | 189–190.5 |
| IV-80 | 4-PhCH$_2$O | CN | B15 | A2 | 123–129 |
| IV-81 | 4-MeOCH$_2$O | CN | H | A1 | 130.4–131.7 |
| IV-82 | 4-CF$_3$CH$_2$O | CN | H | A1 | 100–103 |
| IV-83 | 4-pivaloyl | CN | B15 | A2 | vitreous state |
| IV-84 | 4-pivaloyl | CN | H | A2 | vitreous state |
| IV-85 | 4-Me$_2$NCO$_2$ | CN | H | A2 | vitreous state |
| IV-86 | 4-Me$_2$NCO$_2$ | CN | B15 | A2 | vitreous state |
| IV-87 | 4-Me$_2$NCO$_2$ | CN | B7 | A2 | vitreous state |
| IV-88 | 4-t-Bu | PO(OEt)$_2$ | H | A1 | 87–88 |
| IV-89 | 4-t-Bu | PO(OEt)$_2$ | B1 | A1 | 121–124 |
| IV-90 | H | Br | H | A1 | 74.5–75.5 |
| IV-91 | H | CO$_2$Et | H | A1 | viscous oil |
| IV-92 | H | Br | B7 | A1 | viscous oil |
| IV-93 | 4-t-Bu | PO(OEt)$_2$ | H | A2 | viscous oil |
| IV-94 | 4-t-Bu | CN | COCO$_2$Et | A1 | viscous oil |
| IV-95 | 4-t-Bu | CN | CO$_2^i$Bu | A2 | viscous oil |
| IV-96 | 4-t-Bu | CN | CO$_2^i$Bu | A13 | 104–105 |
| IV-97 | 4-t-Bu | SO$_2$Ph | H | A1 | 143–145 |
| IV-98 | H | CO$_2$Et | B7 | A1 | viscous oil |
| IV-99 | 4-t-Bu | CN | B3 | A1 | viscous oil |
| IV-100 | 4-t-Bu | CN | B19 | A1 | vitreous state |
| IV-101 | 4-t-Bu | CN | CO(4-CO$_2$Me-Ph) | A2 | vitreous state |
| IV-102 | 4-t-Bu | CN | CO(4-CO$_2$Me-Ph) | A13 | vitreous state |
| IV-103 | 4-t-Bu | CO$_2$Me | H | A2 | 88–89 |
| IV-104 | 4-t-Bu | CO$_2$Me | H | A1 | 123–124 |
| IV-105 | 4-t-Bu | CO$_2$Me | B7 | A1 | 77–78 |
| IV-106 | 4-t-Bu | CO$_2$Me | B7 | A2 | viscous oil |
| IV-107 | 4-t-Bu | SO$_2$Ph | B7 | A1 | 98–99 |
| IV-108 | 4-t-Bu | SO$_2$Ph | B7 | A1 | 130–131[#13] |
| IV-109 | 4-t-Bu | CN | B3 | A2 | 71–72* |
| IV-110 | 4-CHF$_2$O | CN | H | A2 | vitreous state |
| IV-111 | 4-CHF$_2$O | CN | B15 | A2 | vitreous state |
| IV-112 | 4-CHF$_2$O | CN | B7 | A2 | vitreous state |
| IV-113 | 4-CH$_3$CONH | CN | H | A2 | 247.9–251.9 |
| IV-114 | 4-CH$_3$CONH | CN | B7 | A2 | 82.1–84.3 |
| IV-115 | 4-CO$_2$Me | CN | H | A2 | 151–152 |
| IV-116 | 4-CO$_2$Me | CN | B7 | A2 | viscous oil* |
| IV-117 | 4-vinyl | CN | H | A2 | vitreous state |
| IV-118 | 4-t-Bu | CN | B15 | A1 | 78–82 |
| IV-119 | 4-t-Bu | CN | methacryloyl | A1 | viscous oil* |
| IV-120 | 4-t-Bu | CN | COCH=(CH$_3$)$_2$ | A1 | viscous oil |
| IV-121 | 4-t-Bu | CN | B33 | A1 | viscous oil |
| IV-122 | 4-t-Bu | CN | CH$_2$OCH$_2$Ph | A1 | viscous oil |
| IV-123 | 4-t-Bu | CN | B24 | A1 | viscous oil |
| IV-124 | H | Cl | H | A1 | 48–49 |
| IV-125 | 4-t-Bu | 5-Me-1,3,4-oxadiazol-2-yl | H | A1 | 149–151 |
| IV-126 | 4-SMe | CN | H | A2 | 154–156 |
| IV-127 | 4-SMe | CN | B7 | A2 | viscous oil* |
| IV-128 | 4-SOMe | CN | H | A2 | vitreous state |
| IV-129 | 4-t-Bu | CN | B33 | A2 | viscous oil |
| IV-130 | 4-t-Bu | CN | B3 | A13 | 111–112* |
| IV-131 | 4-t-Bu | CN | B7 | A3 | viscous oil |
| IV-132 | 4-t-Bu | CN | B3 | A3 | viscous oil |
| IV-133 | 4-t-Bu | CN | COCH$_2$(4-OMe-Ph) | A1 | 117–121 |
| IV-134 | 4-SO$_2$Me | CN | B7 | A2 | vitreous state* |
| IV-135 | 4-SOMe | CN | B7 | A2 | vitreous state* |
| IV-136 | 4-OCH$_2$Ph-3-Cl | CN | H | A2 | vitreous state |
| IV-137 | 4-OPr$^i$-3-Cl | CN | H | A2 | vitreous state |
| IV-138 | 4-OBu$^i$-3-Cl | CN | H | A2 | vitreous state |

TABLE 18-continued

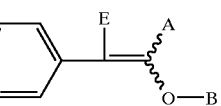

| No. | G | E | B | A | m.p. (° C.) |
|---|---|---|---|---|---|
| IV-139 | 4-t-Bu | CN | B8 | A3 | viscous oil |
| IV-140 | 4-t-Bu | CN | B7 | 2-Cl-4-CF$_3$-thiazol-5-yl | 90–91 |

*E-form or Z-form
[#13]geometric isomer of IV-107

TABLE 19

| No. | Q | R | E | B | A | m.p. (° C.) |
|---|---|---|---|---|---|---|
| V-1 | Q9 | 1-Ph | CN | H | A1 | 148.7–151.3 |
| V-2 | Q9 | 1-Ph | CN | H | A2 | 156–157 |
| V-3 | Q9 | 5-Me-1-$^i$Pr | CN | H | A2 | 78–80 |
| V-4 | Q9 | 5-Me-1-$^i$Bu | CN | B7 | A2 | 84–89* |
| V-5 | Q9 | 5-Me-1-$^s$Bu | CN | B7 | A2 | 99–105 |
| V-6 | Q9 | 5-Me-1-$^i$Bu | CN | H | A2 | 113–114 |
| V-7 | Q9 | 5-Me-1-$^s$Bu | CN | H | A2 | 75–80 |
| V-8 | Q9 | 1-t-Bu | CN | B7 | A2 | vitreous state* |
| V-9 | Q9 | 1-t-Bu | CN | H | 2,6-F$_2$-Ph | 111–113 |
| V-10 | Q9 | 1-t-Bu | CN | H | A2 | 127–129 |
| V-11 | Q9 | 1-pyridin-2-yl | CN | H | A2 | 156.4–158.1 |
| V-12 | Q9 | 1-pyridin-2-yl | CN | B15 | A2 | vitreous state* |
| V-13 | Q9 | 1-pyridin-2-yl | CN | B7 | A2 | vitreous state* |
| V-14 | Q10 | 1-Ph | CN | B7 | A2 | 130–131 |
| V-15 | Q10 | 1-Ph | CN | H | A2 | 207–208 |
| V-16 | Q10 | 1-t-Bu | CN | B7 | A2 | viscous oil |
| V-17 | Q10 | 1-t-Bu | CN | H | A2 | viscous oil |
| V-18 | Q11 | 1-Me-3-$^t$Bu | CN | H | A2 | vitreous state |
| V-19 | Q11 | 1-Me-3-$^t$Bu | CN | B7 | A2 | 119–124 |
| V-20 | Q12 | Ph | CN | H | A2 | 247–253 |
| V-21 | Q12 | Ph | CN | B7 | A2 | 147.5–148.5* |
| V-22 | Q12 | Ph | CN | SO$_2$(4-$^t$Bu-Ph) | A2 | 174–176.5 |
| V-23 | 2-naphthyl | — | CN | B1 | A1 | viscous oil |
| V-24 | 2-naphthyl | — | CN | H | A1 | 140.1–141.1 |
| V-25 | 2-naphthyl | — | CN | B7 | A1 | viscous oil |
| V-26 | Q13 | — | CN | H | A2 | 121–122 |
| V-27 | Q1 | 5-Cl | CN | H | A2 | 160 (decomposition) |
| V-28 | Q1 | 5-Cl | CN | B7 | A2 | 79.5–81 |
| V-29 | Q2 | 4-Ph | CN | H | A1 | 231–232 |
| V-30 | Q2 | 4-t-Bu | CN | H | A1 | 218–219 |
| V-31 | Q3 | 3-Ph | CN | H | A1 | 243–245 |
| V-32 | Q4 | Ph | CN | H | A1 | 255.8–256.8 |
| V-33 | Q4 | Ph | Cn | B1 | A1 | 187–190 |
| V-34 | Q5 | t-Bu | CN | H | A2 | 158–160 |
| V-35 | Q6 | t-Bu | CN | H | A2 | 215–216 |
| V-36 | Q7 | 5-CF$_3$ | CN | H | A1 | 184–185 |
| V-37 | Q7 | 5-CF$_3$ | CN | H | A2 | 211–212 |
| V-38 | Q7 | 5-PhCH$_2$O | CN | H | A1 | 220–221 |
| V-39 | Q8 | 4,6-(MeO)$_2$ | CN | H | A1 | 149–155 |
| V-40 | Q14 | t-Bu | CN | H | A1 | 137.9–143.7 |
| V-41 | Q14 | t-Bu | CN | B7 | A1 | vitreous state |
| V-42 | Q14 | t-Bu | CN | H | A2 | 127.5–128.9 |
| V-43 | Q14 | t-Bu | CN | B7 | A2 | vitreous state |
| V-44 | Q14 | t-Bu | CN | B33 | A2 | vitreous state |
| V-45 | Q14 | t-Bu | CN | H | 2,6-F$_2$-Ph | 105.6–108.1 |
| V-46 | Q14 | t-Bu | CN | B7 | 2,6-F$_2$-Ph | viscous oil |
| V-47 | Q14 | Ph | CN | H | A2 | 113.0–114.9 |
| V-48 | Q14 | Ph | CN | B7 | A2 | vitreous state |
| V-49 | Q14 | Ph | CN | B15 | A2 | vitreous state |

TABLE 19-continued

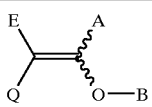

| No. | Q | R | E | B | A | m.p. (° C.) |
|---|---|---|---|---|---|---|
| V-50 | Q14 | 2-Cl-Ph | CN | H | A1 | 125.5–127.5 |
| V-51 | Q14 | 2-Cl-Ph | CN | B7 | A1 | 104.0–107.5 |
| V-52 | Q14 | 2-Cl-Ph | CN | H | A2 | 142.4–143.6 |
| V-53 | Q14 | 2-Cl-Ph | CN | B15 | A2 | vitreous state |
| V-54 | Q14 | 2-Cl-Ph | CN | B7 | A2 | vitreous state |
| V-55 | Q14 | 2,6-F$_2$-Ph | CN | H | A2 | 136.3–164.7 |
| V-56 | Q14 | 2,6-F$_2$-Ph | CN | B15 | A2 | vitreous state |
| V-57 | Q14 | 2,6-F$_2$-Ph | CN | B7 | A2 | vitreous state |
| V-58 | Q14 | PhCH$_2$ | CN | H | A2 | 113.2–114.3 |
| V-59 | Q14 | PhCH$_2$ | CN | B15 | A2 | vitreous state |
| V-60 | Q14 | PhCH$_2$ | CN | B7 | A2 | vitreous state |
| V-61 | Q14 | 2-Cl-Ph | CN | H | 2-MeO-Ph | 131.4–132.8 |
| V-62 | Q14 | 2-Cl-Ph | CN | CO$_2$-2-Oct | 2-MeO-Ph | viscous oil |
| V-63 | Q14 | 2-Cl-Ph | CN | B44 | 2-MeO-Ph | vitreous state |
| V-64 | Q14 | 2-Cl-Ph | CN | H | 2,6-F$_2$-Ph | 155.1–157.9 |
| V-65 | Q14 | 2-Cl-Ph | CN | B45 | 2,6-F$_2$-Ph | 159.3–160.3 |
| V-66 | Q14 | 2-Cl-Ph | CN | H | A7 | 150–152 |
| V-67 | Q14 | 2-Cl-Ph | CN | SO$_2$(3-Cl-Ph) | A7 | 132–133 |
| V-68 | Q14 | PhMe$_2$C | CN | H | A2 | vitreous state |
| V-69 | Q14 | PhMe$_2$C | CN | B7 | A2 | vitreous state |
| V-70 | Q14 | PhMe$_2$C | CN | COCH$_2$OMe | A2 | vitreous state |
| V-71 | Q15 | Ph | CN | H | A1 | 151–153 |
| V-72 | Q16 | 2-CN-Ph | CN | H | A1 | 174–175 |
| V-73 | Q17 | 5-CO$_2$Et | CN | B7 | A2 | viscous oil |
| V-74 | Q18 | 3-pyridin-2-yl | CN | H | A2 | 219 (decomposition) |
| V-75 | Q19 | 5-Me-2-Ph | CN | H | A2 | 181–182 |
| V-76 | Q19 | 5-Me-2-Ph | CN | B7 | A2 | viscous oil |
| V-77 | Q18 | 3-pyridin-2-yl | CN | B7 | A2 | vitreous state |
| V-78 | Q18 | 3-pyridin-2-yl | CN | B46 | A2 | vitreous state |
| V-79 | Q18 | t-Bu | CN | H | A2 | 110.4–110.8 |
| V-80 | Q20 | 6-I | CN | H | A2 | 205–208 |
| V-81 | Q20 | 6-I | CN | B7 | A2 | 137–142 |
| V-82 | 4-Ph-oxazol-2-yl | — | CN | H | A2 | 165.9–166.7 |
| V-83 | 4-Ph-oxazol-2-yl | — | CN | B15 | A2 | vitreous state |
| V-84 | 4-Ph-oxazol-2-yl | — | CN | B7 | A2 | vitreous state |
| V-85 | Q19 | 5-Me-2-Ph | CN | H | A7 | 117–118 |
| V-86 | 3-(2-Cl-Ph)-imidazolin-2-on-1-yl | — | CN | H | A2 | 155–156 |

*E-form or Z-form

TABLE 20

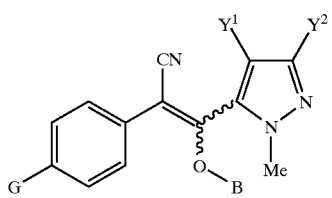

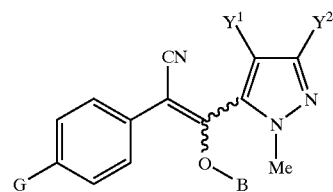

| No. | G | B | Y$^1$ | Y$^2$ | melting point (° C.) |
|---|---|---|---|---|---|
| VI-4 | tBu | B33 | H | Me | 93.7–96.6 |
| VI-5 | tBu | Et | Me | H | resinous |
| VI-6 | tBu | B33 | Me | H | resinous |
| VI-7 | tBu | Me | Me | Me | resinous |
| VI-8 | tBu | Et | Me | Me | resinous |
| VI-9 | tBu | B3 | Me | Me | resinous |
| VI-10 | tBu | B3 | Me | Me | resinous (Isomer of VI-9) |
| VI-11 | tBu | CH$_2$OCH$_2$Ph | Me | Me | resinous |
| VI-12 | tBu | CH$_2$OCH$_2$Ph | Me | Me | resinous (isomer of VI-11) |
| VI-13 | tBu | B24 | Me | Me | resinous |
| VI-14 | tBu | B32 | Me | Me | resinous |
| VI-15 | tBu | B32 | Me | Me | resinous |

TABLE 20-continued

| No. | G | B | Y$^1$ | Y$^2$ | melting point (° C.) |
|---|---|---|---|---|---|
| | | | | | (Isomer of VI-14) |
| VI-16 | tBu | B33 | Cl | Me | 66.5–67.45 |
| VI-17 | tBu | B33 | Me | Br | 94.0–95.0 |
| VI-18 | tBu | Et | H | Me | 133.0–135.5 |
| VI-19 | tBu | B33 | Me | Me | resinous |
| | | | | | (Z-form) |
| VI-20 | tBu | B33 | Me | Me | resinous |
| VI-21 | tBu | H | Me | H | resinous |
| VI-22 | tBu | H | H | Me | resinous |
| VI-23 | tBu | H | Me | Me | resinous |
| VI-24 | tBu | H | Cl | Me | 68.0–69.0 |
| VI-25 | tBu | H | Me | Br | resinous |
| VI-26 | sBu | H | Me | Me | resinous |
| VI-27 | EtMe$_2$C | H | Me | Me | resinous |
| VI-28 | EtMe$_2$C | H | Cl | Me | resinous |
| VI-29 | tBu | B7 | Me | Me | 102.2–103.8 |
| VI-30 | tBu | B6 | Me | Me | resinous |
| VI-31 | tBu | CO(2-MeO-Ph) | Me | Me | resinous |
| VI-32 | tBu | B26 | Me | Me | resinous |
| VI-33 | tBu | B7 | Cl | Me | resinous |
| VI-34 | tBu | COOiBu | Me | Me | resinous |
| VI-35 | EtMe$_2$C | B7 | Me | Me | resinous |
| VI-36 | sBu | B7 | Me | Me | resinous |
| VI-37 | tBu | CO(2-MeO-Ph) | Cl | Me | 181.5–182.5 |
| VI-38 | tBu | B7 | —(CH$_2$)$_3$— | | 105.3–106.8 |
| VI-39 | tBu | B7 | MeO | Me | 68.1–70.6 |
| VI-40 | tBu | B7 | Me | H | resinous |
| VI-41 | tBu | CO(2-Me-Ph) | Cl | Me | 128.0–130.0 |
| VI-42 | tBu | CO(3-pyridyl) | Me | Me | resinous |
| VI-43 | tBu | CO(2-Cl-Ph) | Me | Me | 133.0–134.0 |
| VI-44 | tBu | CO(2-Cl-Ph) | Me | Me | 150.0–151.0 |
| | | | | | (Isomer of I-43) |
| VI-45 | tBu | B7 | Me | Br | 118.0–119.0 |
| VI-46 | tBu | CO(3-Cl-Ph) | Me | Me | 143.0–145.0 |
| VI-47 | tBu | CO(4-Cl-Ph) | Me | Me | 169.0–170.0 |
| VI-48 | tBu | B5 | Me | Me | resinous |
| VI-49 | tBu | B2 | Me | Me | 110.6–111.8 |
| VI-50 | tBu | CO(2-Me-Ph) | Me | Me | 127.0–128.0 |
| VI-51 | tBu | CO(3-Me-Ph) | Me | Me | 111.0–112.0 |
| VI-52 | tBu | CO(4-Me-Ph) | Me | Me | 134.5–136.0 |

TABLE 21

| No. | B | Y$^1$ | Y$^2$ | melting point ° C. (ratio of isomer) |
|---|---|---|---|---|
| VII-1 | H | H | H | pale brown solid |
| VII-2 | H | H | Me | >200 (hydrochloride) |
| VII-3 | H | Me | H | 86.2–88.1 |
| VII-4 | H | Cl | Me | resinous |
| VII-5 | H | H | Cl | resinous |
| VII-6 | H | Cl | Et | resinous |
| VII-7 | H | Me | Me | 207–210 |
| VII-8 | H | —(CH$_2$)$_3$— | | resinous |
| VII-9 | Me | Me | Me | resinous |
| VII-10 | CH$_2$Ph | Me | Me | resinous |
| VII-11 | B7 | Me | Me | 133.7–134.5 |
| | | | | (Z-form) |
| VII-12 | B7 | Me | Me | resinous |
| | | | | (E-form) |
| VII-13 | B7 | H | Me | resinous (3/2) |
| VII-14 | B7 | H | Cl | resinous (20/1) |
| VII-15 | B7 | Me | H | resinous |
| VII-16 | B7 | Cl | Me | resinous (20/1) |
| VII-17 | B7 | Cl | Et | resinous (10/1) |
| VII-18 | B6 | Cl | Me | resinous (=3/1) |
| VII-19 | B36 | Cl | Me | resinous (5/1) |
| VII-20 | B7 | —(CH$_2$)$_3$— | | resinous (5/1) |
| VII-21 | B15 | Me | Me | resinous (10/1) |
| VII-22 | CO-cPen | Me | Me | resinous (10/1) |
| VII-23 | B8 | Me | Me | resinous (10/1) |
| VII-24 | B6 | Me | Me | resinous (10/1) |
| VII-25 | CO(4-Me—Ph) | Me | Me | resinous (10/1) |
| VII-26 | B40 | Me | Me | resinous (10/1) |
| VII-27 | CO(2-MeO—Ph) | Me | Me | resinous (10/1) |
| VII-29 | B38 | Me | Me | resinous (10/1) |
| VII-30 | B36 | Me | Me | resinous (10/1) |
| VII-31 | B35 | Me | Me | resinous (10/1) |
| VII-32 | B37 | Me | Me | resinous (10/1) |
| VII-33 | B5 | Me | Me | resinous (10/1) |
| VII-34 | SO$_2$Ph | Me | Me | resinous (10/1) |
| VII-35 | SO$_2$(4-Me—Ph) | Me | Me | resinous (10/1) |
| VII-36 | SO$_2$(4-CF3—Ph) | Me | Me | resinous (10/1) |
| VII-37 | SO$_2$(2,4,6-Me$_3$—Ph) | Me | Me | resinous (10/1) |
| VII-38 | B23 | Me | Me | resinous (10/1) |
| VII-39 | Et | Me | Me | resinous (7/1) |
| VII-40 | B7 | H | CF$_3$ | resinous |
| VII-41 | B7 | H | H | resinous (2/1) |
| VII-42 | H | Cl | MeO | 149.6–151.2 |
| VII-43 | B7 | Cl | MeO | resinous |
| VII-44 | H | MeO | Me | resinous |
| VII-45 | H | MeO | Me | resinous |

TABLE 22

Structure: NC-C(Q)=C(A)-O-B (with R substituent)

| No. | Q | R | B | A | melting point °C. |
|---|---|---|---|---|---|
| VIII-1 | Q21 | Ph | H | A2 | 165.9–166.7 |
| VIII-2 | Q21 | Ph | B15 | A2 | resinous |
| VIII-3 | 4-tBu—Ph | — | CH$_2$O(4-Cl—Ph) | A1 | resinous |
| VIII-4 | Q19 | 5-Me-2-Ph | H | A7 | 117.0–118.0 |
| VIII-5 | Q7 | 5-CF$_3$ | H | A38 | 74.0–77.0 |
| VIII-6 | 4-tBu—Ph | — | B7 | A48 | 145.0–146.0 |
| VIII-7 | Q19 | 5-Me-2-Ph | B3 | A7 | 117.0–122.0 |
| VIII-8 | Q23 | cHex | H | A13 | resinous |
| VIII-9 | Q23 | tBu | SO2(3-Cl—Ph) | A13 | resinous |
| VIII-10 | Q23 | 1-naphtyl | H | A13 | 145.0–146.0 |
| VIII-11 | Q8 | 4-Cl—Ph | H | A2 | 212.0–214.0 |
| VIII-12 | Q24 | 2-pyridyl | B7 | A2 | 182.0–183.0 |
| VIII-13 | 3-Cl-4-CHF$_2$O—Ph | — | B7 | A2 | resinous |
| VIII-14 | Q22 | tBu | CONMe$_2$ | A13 | 98.0–100.0 |
| VIII-15 | Q24 | tBu | B7 | A2 | 80.0–92.0 |
| VIII-16 | Q22 | 2-pyridyl | B7 | A2 | 133.0–134.0 |
| VIII-17 | Q19 | 5-Me-2-Ph | B7 | A7 | 85.0–102.0 |
| VIII-18 | Q10 | 5-Me-1-(2-pyridyl) | H | A2 | 139.0–142.0 |
| VIII-19 | Q22 | 1-Me-cHex | H | A13 | 98.0–99.0 |
| VIII-20 | Q14 | PhMe$_2$C | B6 | A13 | resinous |
| VIII-21 | Q22 | tBu | B2 | A13 | resinous |
| VIII-22 | Q22 | nPen | H | A13 | resinous |
| VIII-23 | Q25 | 4-I | H | A13 | 177.5–178.2 |
| VIII-24 | Q25 | 4-I | B7 | A2 | resinous |
| VIII-25 | Q22 | tBu | B7 | A39 | resinous |
| VIII-26 | Q22 | nNon | H | A13 | resinous |
| VIII-27 | Q22 | C$_{17}$H$_{35}$ | H | A13 | resinous |
| VIII-28 | Q22 | cPr | H | A13 | 88.8–89.7 |
| VIII-29 | Q22 | cPen | B6 | A13 | resinous |
| VIII-30 | Q22 | PhMeCH | H | A13 | resinous |
| VIII-31 | Q22 | nPrMe$_2$C | H | A13 | resinous |
| VIII-32 | Q25 | 2-pyridyl | H | A41 | 261.0–262.0 |
| VIII-33 | Q25 | 4-COOMe | B7 | A2 | 97.0–98.0 |
| VIII-34 | Q22 | CH$_2$=CHCH$_2$CHMe | H | A13 | resinous |
| VIII-35 | Q22 | 3-Me-cHex | H | A13 | resinous |
| VIII-36 | Q22 | 4-Me-CHex | H | A13 | resinous |
| VIII-37 | Q22 | 2-Me-cPr | H | A13 | resinous |
| VIII-38 | Q22 | sBu | H | A13 | resinous |
| VIII-39 | Q26 | tBu | H | A13 | 134.3–135.7 |
| VIII-40 | Q22 | Et$_2$CH | H | A13 | 74.0–75.0 |
| VIII-41 | Q22 | nPr$_2$CH | H | A13 | resinous |
| VIII-42 | Q22 | 2-Me-cHex | B6 | A13 | resinous |
| VIII-43 | Q22 | cHep | H | A13 | resinous |
| VIII-44 | Q25 | 2-pyridyl | H | A42 | 270.0–272.0 |
| VIII-45 | Q22 | 2,3-(MeO)$_2$—Ph | B7 | A13 | resinous |
| VIII-46 | Q22 | 2-EtO—Ph | B7 | A13 | 131.3–132.6 |
| VIII-47 | Q25 | 3-(2-pyridyl) | H | A21 | resinous |
| VIII-48 | Q25 | 3-(2-pyridyl) | B7 | A14 | 84.0–85.0 |
| VIII-49 | Q25 | 3-(2-pyridyl) | H | A43 | 186.9–188.3 |
| VIII-50 | Q25 | 3-COOEt | B7 | A2 | resinous |
| VIII-51 | Q22 | 2,4-Cl$_2$—Ph | H | A13 | 137.5–138.5 |
| VIII-52 | Q22 | 2-Ph—Ph | H | A13 | 112.0–113.0 |
| VIII-53 | Q19 | 2-Ph | H | A10 | 232.5–235.6 |
| VIII-54 | Q19 | 2-Ph | B7 | A10 | resinous |
| VIII-55 | Q25 | 5-(2-pyridyl) | B7 | A10 | resinous |
| VIII-56 | Q25 | 3-COOiPr | H | A2 | 130.0–131.0 |
| VIII-57 | Q25 | 3-(2-pyridyl) | H | 4-NH$_2$-2-F—Ph HCl | 114.3–117.5 |
| VIII-58 | Q25 | 3-(2-pyridyl) | B7 | A22 | resinous |
| VIII-59 | Q25 | 3-(2-pyridyl) | B7 | A44 | resinous |
| VIII-60 | Q25 | 3-(2-pyridyl) | H | A18 | resinous |
| VIII-61 | Q25 | 3-(2-pyridyl) | B7 | A7 | resinous |
| VIII-62 | Q25 | 3-CN | B7 | A45 | resinous |
| VIII-63 | Q25 | 3-(2-pyridyl) | B7 | A49 | resinous |
| VIII-64 | Q25 | 3-(2-pyridyl) | H | A50 | 143.2–147.6 |
| VIII-65 | Q25 | 3-(2-pyridyl) | B7 | A30 | 116.0–117.0 |
| VIII-66 | Q25 | 3-COOiPr | B7 | A45 | resinous |
| VIII-67 | Q25 | 3-(4-pyridyl) | H | A45 | resinous |
| VIII-68 | Q25 | 3-(2-pyridyl) | B7 | A46 | 140.7–144.5 |
| VIII-69 | 4-tBu—Ph | — | B7 | A42 | resinous |

TABLE 22-continued

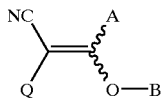

| No. | Q | R | B | A | melting point ° C. |
|---|---|---|---|---|---|
| VIII-70 | Q25 | 3-(2-thienyl) | H | A47 | resinous |
| VIII-71 | Q22 | cHep | H | A47 | resinous |
| VIII-72 | Q22 | cHep | B7 | A47 | resinous |
| VIII-73 | 4-tBu—Ph | — | B6 | A42 | resinous |
| VIII-74 | 4-tBu—Ph | — | B33 | A42 | 62.0–63.0 |
| VIII-75 | Q22 | tBu | B33 | A47 | resinous |
| VIII-76 | Q27 | 2-pyridyl | B7 | A45 | 144.0–145.0 |
| VIII-77 | Q27 | 2-pyridyl | H | A45 | 170.0–171.0 |
| VIII-78 | Q27 | 2-pyridyl | B7 | A42 | 180.0–181.0 |
| VIII-79 | Q28 | 2-pyridyl | H | A45 | resinous |
| VIII-80 | Q28 | 2-pyridyl | B7 | A45 | resinous |
| VIII-81 | Q19 | 5-Me-2-Ph | H | A47 | resinous |
| VIII-82 | Q19 | 5-Me-2-Ph | B7 | A47 | 139.2–141.6 |
| VIII-83 | Q25 | 3-tBu-4-COOMe | B7 | A47 | 115.0–116.0 |
| VIII-84 | Q22 | EtMe$_2$C | B7 | A47 | resinous |
| VIII-85 | Q27 | 2-pyridyl | H | A3 | 139.0–140.0 |
| VIII-86 | 4-tBu—Ph | — | B7 | A49 | 93.6–95.2 |
| VIII-87 | Q9 | 1-(2-pyridyl) | H | A47 | resinous |
| VIII-88 | Q9 | 5-MeO-1-(2-pyridyl) | H | A47 | resinous |
| VIII-89 | 4-tBu—Ph | — | H | A21 | 123.0–124.0 |
| VIII-90 | Q29 | tBu | B7 | A47 | resinous |
| VIII-91 | Q22 | iBu | B7 | A2 | 73.0–74.0 |
| VIII-92 | Q22 | iBu | H | A2 | 62.0–63.0 |
| VIII-93 | 4-tBu—Ph | — | B7 | A14 | 98.0–99.0 |
| VIII-94 | Q22 | tBu | B33 | A52 | 92.0–93.0 |

FORMULATION EXAMPLES

Now, Formulation Examples of pesticides comprising the compounds of the present invention as the active ingredient are shown below, which, however, are not intended to restrict the scope of the invention. In the following Formulation Examples, "part" or "parts" are by weight.

| [Formulation Example 1] Wettable Powder: | |
|---|---|
| Compound No. I-1 of the invention | 50 parts |
| Zeeklite PFP (trade name, kaolin-type clay manufactured by Zeeklite Mining Industries, Co., Ltd.) | 43 parts |
| Solpol 5050 (trade name, anionic surfactant manufactured by Toho Chemical Co., Ltd.) | 2 parts |
| Runox 100C (trade name, anionic surfactant manufactured by Toho Chemical Co., Ltd.) | 3 parts |
| Carplex #80 (anti-caking agent, trade name, white carbon manufactured by Shinogi Pharmaceutical Co., Ltd.) | 2 parts |

The above-mentioned components were homogeneously mixed and ground to form a wettable powder.

| [Formulation Example 2] Emuslion: | |
|---|---|
| Compound No. I-1 of the invention | 3 parts |
| Methylnaphthalene | 76 parts |
| Isophorone | 15 parts |
| Solpol 3005X (trade name, mixture of nonionic surfactant and anionic surfactant manufactured by Toho Chemical Co., Ltd.) | 6 parts |

The above-mentioned components were homogeneously mixed to form an emulsion.

| [Formulation Example 3] Flowable: | |
|---|---|
| Compound No. I-1 of the invention | 35 parts |
| Agrisol S-711 (trade name, nonionic surfactant manufactured by Kao Corp.) | 8 parts |
| Runox 1000C (trade name, anionic surfactant manufactured by Toho Chemical Co., Ltd.) | 0.5 part |
| Aqueous solution of 1% Rhodopol (trade name, thickener manufactrued by Rhone-Poulenc) | 20 parts |
| Ethylene glycol (freezing inhibitor) | 8 parts |
| Water | 28.5 parts |

The above-mentioned components were homogeneously mixed to prepare a flowable.

| [Formulation Example 4] Granular wettable powder (Dry flowable): | |
|---|---|
| Compound No. I-1 of the invention | 75 parts |
| Isoban No. 1 (trade name, anionic surfactant manufactured bu Kuraray Isoprene Chemical Co., Ltd.) | 10 parts |
| Vanilex N (trade name, anionic surfactant manufactured by Sanyo Kokusaku Pulp Co., Ltd.) | 5 parts |
| Carplex #80 (trade name, white carbon manufactured by Shionogi Pharmaceutical Co., Ltd.) | 10 parts |

The above-mentioned components were homogeneously mixed and finely ground to form a dry flowable.

[Formulation Example 5] Granules:

| | |
|---|---|
| Compound No. I-1 of the invention | 0.1 part |
| Bentonite | 55.0 parts |
| Talc | 44.9 parts |

The above-mentioned components were homogeneously mixed and ground, to which was added a small amount of water, stirred, mixed and kneaded. The resulting mixture was granulated and dried into granules, using an extrusion granulator.

[Formulation Example 6] Dust:

| | |
|---|---|
| Compound No. I-1 of the invention | 3.0 parts |
| Carplex #80 (trade name, white carbon manufactured by Shionogi Pharmaceutical Co., Ltd.) | 0.5 part |
| Clay | 95 parts |
| Diisopropyl phosphate | 1.5 parts |

The above-mentioned components were homogeneously mixed and ground to form a dust.

Upon use, the wettable powder, emulsion, flowable and dry flowable are diluted from 50 to 20000 times with water, and applied in an amount of from 0.005 to 50 kg/ha in terms of the active ingredient.

Now, Formulation Examples of agents for preventing the attachment of aquatic organisms of the present invention are shown below, which, however, are not intended to restrict the scope of the invention.

[Formulation Example 7]

| | |
|---|---|
| Compound No. II-2 of the invention | 8 parts |
| VYHH (vinyl-type synthetic resin manufactrued by UCC Co., Ltd.) | 7 parts |
| Rosin | 7 parts |
| Tricresyl phosphate | 3 parts |
| Talc | 20 parts |
| Barium sulfate | 15 parts |
| Red iron oxide | 10 parts |
| Xylene | 20 parts |
| Methyl isobutyl ketone | 10 parts |

The above-mentioned components were homogeneously mixed to form an agent for preventing the attachment of aquatic organisms of the invention. This agent can be used as a coating paint.

[Formulation Example 8]

| | |
|---|---|
| Compound No. II-2 of the invention | 5 parts |
| CR-10 (chlorine rubber resin manufactured by Asahi Denka KK) | 13 parts |
| Zinc flower | 20 parts |
| Talc | 20 parts |
| Plasticizer | 2 parts |
| Red iron oxide | 10 parts |
| Xylene | 30 parts |

The above-mentioned components were homogeneously mixed to form an agent for preventing the attachment of aquatic organisms of the invention. This agent can be used as a coating paint.

[Formulation Example 9]

| | |
|---|---|
| Compound No. II-2 of the invention | 8 parts |
| VYHH (vinyl-type synthetic resin manufactured by UCC Co., Ltd.) | 7 parts |
| Rosin | 7 parts |
| Tricresyl phosphate | 3 parts |
| Talc | 20 parts |
| Barium sulfate | 15 parts |
| Red iron oxide | 10 parts |
| Xylene | 20 parts |
| Methyl isobutyl ketone | 10 parts |

The above-mentioned components were homogeneously mixed to form an agent for preventing the attachment of aquatic organisms the invention. This agent can be used as a coating paint.

[Formulation Example 10]

| | |
|---|---|
| Compound No. II-2 of the invention | 5 parts |
| CR-10 (chlorine rubber resin manufactured by Asahi Denka KK) | 13 parts |
| Zinc flower | 20 parts |
| Talc | 20 parts |
| Plasticizer | 2 parts |
| Red iron oxide | 10 parts |
| Xylene | 30 parts |

The above-mentioned components were homogeneously mixed to form an agent for preventing the attachment of aquatic organisms of the invention. This agent can be used as a coating paint.

TEST EXAMPLES

Now, the following Test Examples are to demonstrate the usefulness of the compounds of the present invention as pesticides.

Test Example 1

Insecticidal Test for Brown Rice Planthopper (*Nilaparvata lugens Stal*)

A 5% emulsion (or 25% wettable powder) of a compound of the present invention was diluted with water containing a spreading agent to give a 500 ppm solution of the compound.

The stems and leaves of rice-plants in 1/20,000 are pot were sufficiently applied with the resulting solution. After the thus-applied chemical solution was dried in air, each pot was covered with a cylindrical cover. Ten (10) second instar nymphae of brown rice planthoppers (*Nilaparvata lugens*) were released in each pot. After having been thus covered, the pots were stored in a thermostatic chamber. After 6 days passed, the insects in each pot were observed, and the mortality thereof was determined according to the following equation. Each compound was tested in that manner for two groups of pots.

Mortality (%)=[number of insect killed/(number of insect killed+number of living insect)]×100

In this test, the following compounds exhibited mortality of 80% or more.

Compounds of the invention: Nos. I-2, I-18, I-19, I-23, I-30, I-31, I-32, I-35, I-39, I-42, I-44, I-58, I-59, I-62, I-63, I-70, I-72, I-80, I-106, I-114, I-123, I-137, II-1, II-2, II-3, II-5, II-6, II-12, II-15, II-23, II-25, II-26, II-28, II-33, II-34, II-36, II-37, II-38, II-39, II-43, II-44, II-46, II-53, II-54, II-55, II-61, II-66, II-73, II-74, II-75, II-76, II-80, II-83, II-84, II-85, II-86, II-87, II-88, II-89, II-91, II-92, II-93, II-97, II-98, II-111, II-114, II-116, II-134, II-136, II-137, II-154, II-155, II-159, III-1, III-2, III-4, III-6, III-15, III-16, III-17, III-18, III-19, III-21, IV-48, IV-58, V-2, V-12, V-13, V-28, V-48, V-49, V-51, V-53, V-54, V-55, V-56, V-57, V-59, V-60

Test Example 2

Insecticidal Test for Green Rice Leafhoppers
(*Nephotettix cincticeps* Uhler)

The stems and leaves of plants was dipped in a 500 ppm emulsion of a compound of the invention for about 10 seconds. The thus-treated stems and leaves were put into glass cylinders, into which were released adults of green rice leafhoppers (*Nephotettix cincticeps*) that were resistant to organic phosphorous insecticides. Each glass cylinder was covered with a perforated cover, and stored in a thermostatic chamber at 25° C. After 6 days passed, the insects in each cylinder were observed, and the mortality of the insects was determined according to the same equation as in Test Example 1. Each compound was tested in that manner for two groups of cylinders. In this test, the following compounds exhibited morality of 80% or more.

Compounds of the invention: Nos. I-1, I-2, I-4, I-5, I-8, I-9, I-10, I-19, I-24, I-29, I-30, I-31, I-32, I-33, I-34, I-35, I-36, I-39, I-40, I-41, I-42, I-43, I-44, I-47, I-53, I-54, I-55, I-56, I-57, I-58, I-59, I-62, I-63, 1-69, I-70, I-71, I-72, I-74, I-79, I-80, I-81, I-115, I-121, I-125, I-127, I-137, II-1, II-2, II-3, II-5, II-6, II-7, II-9, II-10, II-11, II-12, II-13, II-15, II-23, II-26, II-28, II-33, II-34, II-36, II-38, II-37, II-43, II-46, II-49, II-52, II-54, II-55, II-63, II-64, II-65, II-66, II-67, II-68, II-69, II-73, II-74, II-75, II-76, II-77, II-78, II-79, II-80, II-81, II-83, II-84, II-85, II-86, II-87, II-88, II-89, II-91, II-92, II-93, II-97, II-98, II-99, II-107, II-111, II-116, II-117, II-130, II-131, II-132, II-134, II-136, II-137, II-142, II-145, II-153, II-154, III-1, III-2, III-3, III-4, III-5, III-6, III-13, III-15, III-16, III-17, III-18, III-19, III-20, III-21, IV-32, IV-58, V-2, V-12, V-13, V-14, V-38, V-41, V-43, V-48, V-49, V-51, V-53, V-54, V-55, V-56, V-57, V-59, V-60, V-75

Test Example 3

Insecticidal Test for Green Peach Aphids (*Myzus persicae* Sulzer)

Moistured filter paper was placed in each laboratory glass dish having an inner diameter of 3 cm, and a leaf cabbage having the same diameter as that of the dish was put on the filter paper. Four female, apterous adults of green peach aphids (*Myzus persicae*) were put on the cabbage leaf. Fllowing day, a chemical sample (2.5 mg/cm$^2$) was sprayed over the dishes, using a rotary sprinkler. The chemical solution herein was prepared by diluting a 5% emulsion (or 25% wetttable powder) of a compound of the invention to 500 ppm with water containing a spreading agent. After 6 days passed, the insects in each cylinder were observed, and mortality of the insects (larvae and adults) was determined according to the following equation. Each compound was tested in that manner for two groups of dishes.

Mortality (%)=[number of insect killed/(number of insect killed+number of living insect)]×100

In this test, the following compounds exhibited mortality of 80% or more.

Compounds of the invention: Nos. I-1, I-2, I-3, I-4, I-5, I-7, I-8, I-9, I-10, I-11, I-12, I-13, I-14, I-16, I-17, I-18, I-19, I-21, I-22, I-23, 1-24, I-25, I-26, I-27, I-28, I-29, I-30, I-31I-32, I-33, I-34, I-35, I-36, I-37, I-38, I-40, I-41[, ]I-42, I-43, I-44, I-45, I-46, I-47, I-48, I-51, I-52, I-53, I-54, I-55, I-56, I-57, I-58, I-59, I-62, I-63, I-69, I-70, I-71, I-72, I-73, I-74, I-76, I-77, I-78, I-79, I-80, I-81, I-84, I-85, I-86, I-89, I-90, I-92, I-96, I-97, I-104, I-108, I-125, I-136, I-137, I-138, II-2, II-3, II-5, II-6, II-7, II-8, II-9, II-10, II-11, II-12, II-15, II-16, II-17, II-23, II-24, II-25, II-26, II-27, II-28, II-33, II-34, II-35, II-36, II-37, II-38, II-39, II-43, II-44, II-50, II-52, II-53, II-54, II-55, II-58, II-60, II-63, II-64, II-65, II-66, II-68, II-69, II-70, II-71, II-73, II-74, II-75, II-76, II-78, II-79, II-83, II-84, II-85, II-86, II-87, II-88, II-89, II-90, II-91, II-92, II-93, II-97, II-98, II-99, II-101, II-102, II-105, II-107, II-111, II-116, II-117, II-118, II-121, II-130, II-131, II-132, II-133, II-134, II-136, II-137, II-138, II-140, II-141, II-142, II-151, II-153, II-154, II-159, II-160, III-1, III-2, III-3, III-4, III-5, III-6, III-15, III-16, III-17, III-18, III-19, III-20, III-21, IV-7, IV-10, IV-11, IV-21, IV-23, IV-45, V-1, V-2, V-10, V-11, V-12, V-13, V-14, V-28, V-31, V-32, V-41, V-45, V-48, V-49, V-50, V-51, V-52, V-53, V-54, V-55, V-56, V-57, V-59, V-60, V-73, V-75, VII-1, VII-2, VII-3, VII-4, VII-5, VII-6, VII-7, VII-8, VII-9, VII-10, VII-11, VII-12, VII-13, VII-14, VII-15, VII-16, VII-17, VII-18, VII-19, VII-20, VII-21, VII-22, VII-23, VII-24, VII-25, VII-26, VII-27, VII-28, VII-29, VII-30, VII-31, VII-32, VII-33, VII-34, VII-35, VII-36, VII-37, VII-38, VII-39, VII-40, VII-41, VII-42, VII-43, VII-44, VII-45, VIII-12, VIII-32, VIII-42, VIII-47, VIII-49, VIII-55, VIII-57, VIII-58, VIII-61, VIII-64, VIII-65, VIII-67, VIII-85.

Test Example 4

Insecticidal Test for Diamond Back Moth (*Plutella xylostella* Linne)

The leaves of cabbage were dipped in a 500 ppm aqueous emulsion of a compound of the invention for about 10 seconds. After having been dried in air, the thus-treated leaves were put into laboratory dishes. Ten (10) second larvae of diamond back moth (*Plutella xylostella*) were released in each dish. Each dish was covered with a perforated cover, and stored in a thermostatic chamber at 25° C. After 6 days passed, the insects in each dish were observed, and mortality of the insects was obtained according to the same equation as in Test Example 1. Each compound was tested in that manner for two groups of dishes. In this test, the following compounds exhibited mortality of 80% or more. Compounds of the invention: Nos. I-1, I-2, I-4I-5, I-6, I-8, I-9, I-10, I-13, I-18, I-19, I-29, I-30, I-31, I-33, 1-34, I-35, I-36, I-38, I-39, I-40, I-41, I-43, I-44, I-45, I-46, I-47, I-51, I-52, I-53, I-56, I-57, I-58, I-59, I-62, I-63, I-70, I-71, I-72, I-73, I-74, I-76, I-77, I-78, I-79, I-80, I-81, I-84, I-86, I-89, I-96, I-97, I-99, I-104, I-106, I-114, I-125, I-137, II-1, II-2, II-5, II-6, II-7, II-8, II-9, II-10, II-11, II-12, II-13, II-15, II-17, II-23, II-24-, II-25, II-26, II-27, II-28, II-33, II-34, II-35, II-36, II-37, II-38, II-39, II-40, II-41, II-42, II-43, II-54, II-55, II-58, II-60, II-61, II-62, II-63, II-64, II-65, II-66, II-67, II-68, II-69, II-70, II-71, II-72, II-73, II-74, II-75, II-76, II-77, II-78, II-79, II-80, II-81, II-83, II-84, II-85, II-86, II-87, II-88, II-89, II-90, II-91, II-92, II-93, II-94, II-97, II-98, II-99, II-100, II-101, II-105, II-106, II-107, II-108, II-109, II-110, II-111, II-116, II-117, II-118, II-121, II-122, II-155, II-159, II-161, III-1, III-2, III-3, III-4, III-5, III-6, III-7, III-9, III-10, III-11, III-13, III-14, III-15, III-16, III-17, III-18, III-19, III-20, III-21, IV-7, IV-8, IV-29, IV-47, IV-53, IV-58, V-1, V-2, V-11, V-12, V-13, V-29, V-37, V-41, V-43, V-46, V-48, V-50, V-51, V-52, V-53, V-54, V-55, V-56, V-57, V-58, V-59, V-60, V-64, V-75

Test Example 5

Insecticidal Test for Cucurbit Leaf Beetles
(*Aulacophora femoralis* Motschulsky)

A 5% emulsion (or 25% wettable powder) of a compound of the present invention was diluted with water containing a spreading agent to give a 500 ppm solution of the compound. The leaves of cucumbers were dipped in this chemical solution for about 10 seconds, dried in air, and put into a laboratory dish. Ten (10) second instar nymphae of cucurbit leaf beetles (Aulacophora femoralis) were released in each dish. Each dish was covered with a cover, and stored in a thermostatic chamber at 25° C. After 6 days passed, the insects in each dish were observed, and mortality of the insects was determined according to the same equation as in Test Example 1. Each compound was tested in that manner for two groups of dishes.

In this test, the following compounds exhibited mortality of 100%.

Compounds of the invention: Nos. I-1, I-2, I-4, I-6, I-8, I-9, I-10, I-11, I-12, I-13, I-29, I-30, I-31, I-32, I-33, I-34, I-35, I-39, I-40, I-41, I-43, I-44, I-46, I-53, I-54, I-55, I-56, I-57-, I-58, I-59, I-61, I-62, I-63, 1-69, I-70, I-71, I-72, I-74, I-76, I-77, I-78, I-79, I-80, I-81, I-82, I-83, I-92, I-101, I-103, I-104, I-108, I-109, I-124, I-127, I-128, II-1, II-6, II-7, II-8, II-9, II-10, II-11, II-12, II-13, II-14, II-15, II-16, II-17, II-23, II-24, II-25, II-26, II-27, II-28, II-33, II-34, II-35, II-36, II-37, II-38, II-39, II-41, II-42, II-43, II-47, II-50, II-53, II-54, II-55, II-57, II-58, II-61, II-62, II-63, II-65, II-66, II-99, II-101, II-102, II-104, II-105, II-106, II-107, II-108, II-109, II-110, II-114, II-122, II-124, II-125, II-131, II-132, II-133, II-134, II-136, II-137, II-139, II-140, II-141, II-142, II-153, II-154, III-1, III-2, III-3, III-4, III-5, III-6, III-9, III-10, III-11, III-12, III-14, III-15, III-16, III-17, III-20, IV-6, IV-13, IV-33, IV-39, IV-56, IV-60, IV-61, IV-72, IV-82, V-1, V-2, V-11, V-12, V-13, V-17, V-22, V-26, V-27, V-29, V-37, V-40, V-42, V-48, V-49, V-50, V-51, V-52, V-54, V-55, V-57, V-59, V-60, V-61, V-64, V-75

Test Example 6

Acaricidal Test for Two-spotted Spider Mites
(*Tetranychus urticae* Koch)

The leaves of kidney bean plants were punched into 3 cm-diameter discs, using a leaf punch, and put onto moistured filter paper in a 7 cm-diameter styrol cup. Ten (10) larvae of two-spotted spider mites (*Tetranychus urticae*) were put to each leaf. A 5% emulsion (or 25% wettable powder) of a compound of the invention was diluted with water containing a spreading agent to give a 500 ppm solution of the compound. The solution was sprayed over each cup in an amount of 2 ml/cup, using a rotary sprinkler, and the cups were stored in a thermostatic chamber at 25° C. After 96 hours passed, the mites in each cup were observed, and mortality of the mites was determined according to the same equation as in Test Example 1. Each compound was tested in that manner for two groups of cups.

In this test, the following compounds exhibited the mites at a percentage of 80% or more.

Compounds of the invention: Nos. I-1, I-2, I-3, I-4, I-5, I-7, I-8, I-9, I-10, I-12, I-13, I-19, I-24, I-25, I-26, I-27, I-28, I-29, I-30, I-31, I-32, I-33, I-34, I-35, I-36, I-38, I-40, I-41, I-42, I-43, I-44, I-45, I-46, I-47, I-48, I-50, I-51, I-52, I-55, I-56, I-57, I-58, I-59, I-60, I-61, I-62, I-63, I-70, I-71, I-72, I-74, I-76, I-80, I-94, I-95, I-96, I-97, I-99, I-101, I-102, I-103, I-104, I-105, I-106, I-108, I-109, I-110, I-111, I-112, I-113, I-114, I-115, I-117, I-118, I-119, I-122, I-123, I-124, I-125, I-126, I-127, I-128, I-137, II-2, II-3, II-5, II-6, II-7, II-8, II-9, II-10, II-11, II-12, II-13, II-15, II-16, II-17, II-23, II-25, II-26, II-27, II-28, II-33, II-34, II-35, II-36, II-37, II-38, II-39, II-40, II-41, II-42, II-43, II-45, II-46, II-47, II-48, II-50, II-52, II-53, II-54, II-55, II-58, II-59, II-60, II-61, II-63, II-64, II-65, II-66, II-67, II-68, II-69, II-70, II-71, II-72, II-73, II-74, II-75, II-76, II-77, II-78, II-79, II-80, II-81, II-83, II-84, II-85, II-86, II-87, II-88, II-89, II-90, II-91, II-92, II-93, II-95, II-97, II-98, II-99, II-101, II-102, II-103, II-105, II-106, II-107, II-108, II-109, II-110, II-111, II-116, II-117, II-118, II-133, II-134, II-136, II-137, II-151, II-153, II-154, II-155, II-159, II-160, II-161, II-173, III-3, III-4, III-5, III-6, III-7, III-9, III-10, III-11, III-12, III-15, III-17, III-18, III-19, III-21, IV-1, IV-2, IV-3, IV-4, IV-5, IV-7, IV-10, IV-11, IV-12, IV-13, IV-14, IV-16, IV-17, IV-18, IV-19, IV-20, IV-21, IV-22, IV-24, IV-25, IV-26, IV-28, IV-29, IV-33, IV-35, IV-36, IV-39, IV-40, IV-41, IV-42, IV-43, IV-44, IV-45, IV-46, IV-47, IV-48, IV-49, IV-50, IV-51, IV-54, IV-55, IV-56, IV-58, IV-59, IV-60, IV-61, IV-62, IV-63, IV-64, IV-65, IV-66, IV-67, IV-68, IV-69, IV-70, IV-71, IV-72, IV-74, IV-75, IV-76, IV-79, IV-80, IV-82, IV-94, IV-95, IV-96, IV-99, IV-100, IV-101, IV-102, IV-109, IV-110, IV-111, IV-112, V-1, V-2, V-3, V-4, V-5, V-6, V-7, V-8, V-10, V-11, V-12, V-13, V-14, V-15, V-16, V-17, V-19, V-23, V-24, V-25, V-26, V-28, V-31, V-36, V-37, V-38, V-40, V-41, V-42, V-43, V-44, V-46, V-47, V-48, V-49, V-50, V-51, V-52, V-53, V-54, V-55, V-56, V-57, V-58, V-59, V-60, V-73, V-75, VI-1, VI-2, VI-3, VI-4, VI-5, VI-6, VI-7, VI-8, VI-9, VI-10, VI-11, VI-12, VI-13, VI-14, VI-15, VI-16, VI-17, VI-18, VI-19, VI-20, VI-21, VI-22, VI-23, VI-24, VI-25, VI-29, VI-30, VI-31, VI-32, VI-33, VI-34, VI-35, VI-36, VI-37, VI-38, VI-39, VI-40, VI-41, VI-42, VI-43, VI-44, VI-45, VI-46, VI-47, VI-48, VI-49, VI-50, VI-51, VI-52, VIII-1, VIII-2, VIII-4, VIII-6, VIII-7, VIII-8, VIII-9, VIII-10, VIII-13, VIII-14, VIII-15, VIII-16, VIII-17, VIII-18, VIII-19, VIII-20, VIII-21, VIII-22, VIII-23, VIII-24, VIII-26, VIII-27, VIII-28, VIII-29, VIII-30, VIII-31, VIII-33, VIII-34, VIII-35, VIII-36, VIII-37, VIII-38, VIII-39, VIII-40, VIII-41, VIII-43, VIII-44, VIII-45, VIII-46, VIII-48, VIII-50, VIII-51, VIII-52, VIII-53, VIII-54, VIII-56, VIII-59, VIII-60, VIII-63, VIII-66, VIII-69, VIII-70, VIII-71, VIII-72, VIII-73, VIII-74, VIII-75, VIII-76, VIII-77, VIII-78, VIII-81, VIII-82, VIII-83, VIII-84, VIII-86, VIII-87, VIII-89, VIII-90, VIII-91, VIII-92, VIII-93.

Test Example 7

Test for Preventing Leaf Rust, Brown Rust
(*Puccinia recondita* ex Desmaziere)

A chemical solution obtained by diluting an emulsion of a compound of the invention to 500 ppm with water was sprayed on wheat plants (Norin No. 61) grown to 1.5- to 2.0-leaf in a pot having a diameter of 5.5 cm-diameter at a dose of 20 ml/pot using a spraygun.

The following day, a spore suspension ($2 \times 10^5$ spore/ml) of leaft rust (brown rust) (*Puccinia recondita*) was sprayed over the plant-pots were placed overnight in an inoculation box having a temperature of 25° C. and a humidity of 95% or more. Then, the pots were put in a green house. After 7 days of the inoculation, a ratio of an infected and spored area formed to the leaf inoculated was measured, and a preventive vlaue was calculated according to the following equation.

Preventive value=[1−(infected and spotted area ratio in treated region/infected and spotted area ratio in untreated region)]×100

In this test, the following compounds had an protective value of from 70 to 100.

Compounds of the invention: Nos. I-9, I-108, I-127, I-128, II-14, II-15, IV-2, IV-7, V-15, V-10.

With the long-term use of insecticides and microbicides, recently, some pests have become resistant to chemicals and are often difficult to exterminate with conventional insecticides and microbicides. In addition, some insecticides are highly toxic and are prone to remain long, without being decomposed, to destroy the ecosystem. Accordingly, the present invention provides novel, non-toxic and non-persistent insecticides and fungicides, and provides agents for preventing the attachment of aquatic organisms having few influences on the ecosystem and causing little secondary pollution.

What is claimed is:
1. A compound of a formula:

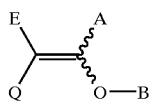

wherein:

Q represents a thiazolyl group optionally substituted by R;

A represents a phenyl group optionally substituted by W, a naphthyl group optionally substituted by W, or a heterocyclic group optionally substituted by Y, wherein said heterocyclic group is selected from the group consisting of a thienyl, furyl, pyrrolyl, oxazolyl, isoxazolyl, thiazolyl, isothiazolyl, pyrazolyl, imidazolyl, 1,3,4-oxadiazolyl, 1,2,4-oxadiazolyl, 1,3,4-thiadiazolyl, 1,2,4-thiadiazolyl, 1,2,3-thiadiazolyl, 1,2,4-triazolyl, 1,2,3-triazolyl, 1,2,3,4-tetrazolyl, pyridinyl, pyrimidinyl, pyrazinyl, pyridazinyl, 1,3,5-triazinyl, 1,2,4-triazinyl, pyrazolinyl, imidazolinyl, oxazolinyl, isoxazolinyl, thiazolinyl, 3(2H)-pyridazinone, benzothiazolyl, benzimidazolyl, indazolyl, benzoxazolyl, quinolyl, isoquinolyl, quinoxalinyl, phthalazinyl, cinnolinyl, and quinazolinyl groups;

provided that when Q is a 2-thiazolyl group optionally substituted by R, then A is a naphthyl group optionally substituted by W, or a heterocyclic group optionally substituted by Y (said heterocyclic group being a thienyl, furyl, pyrrolyl, oxazolyl, isoxazolyl, thiazolyl, isothiazolyl, pyrazolyl, imidazolyl, 1,3,4-oxadiazolyl, 1,2,4-oxadiazolyl, 1,3,4-thiadiazolyl, 1,2,4-thiadiazolyl, 1,2,4-triazolyl, 1,2,3-thiadiazolyl, 1,2,3-triazolyl, 1,2,3,4-tetrazolyl, pyridinyl, pyrimidinyl, pyrazinyl, pyridazinyl, 1,3,5-triazinyl, 1,2,4-triazinyl, pyrazolinyl, imidazolinyl, oxazolinyl, isoxazolinyl, thiazolinyl, 3(2H)-pyridazinone, benzothiazolyl, benzimidazolyl, indazolyl, benzoxazolyl, quinolyl, isoquinolyl, quinoxalinyl, phthalazinyl, cinnolinyl, or quinazolinyl group);

B represents H, a $C_1$–$C_4$ alkyl group, a $C_1$–$C_4$ haloalkyl group, a $C_2$–$C_4$ alkoxyalkyl group, $CH_3SCH_2$, $CH_3OC_2H_4OCH_2$, a $C_1$–$C_4$ alkyl group substituted by a phenyl group optionally substituted by a halogen or a $C_1$–$C_4$ alkyl group, a $C_1$–$C_4$ alkyl group substituted by a benzoyl group optionally substituted by a halogen or a $C_1$–$C_4$ alkyl group, a tetrahydropyranyl group, $(CH_3)_3Si$, a $C_1$–$C_4$ alkylsulfonyl group, a phenylsulfonyl group optionally substituted by a halogen or a $C_1$–$C_4$ alkyl group, —$SO_2CF_3$, a $C_1$–$C_4$ monoalkylaminosulfonyl group, a $C_2$–$C_8$ dialkylaminosulfonyl group, a phenylaminosulfonyl group, a $C_2$–$C_5$ monoalkylaminothiocarbonyl group, a $C_3$–$C_9$ dialkylaminothiocarbonyl group, a $C_2$–$C_5$ cyanoalkyl group, a $C_3$–$C_9$ alkoxycarbonylalkyl group, —$C(=O)T^1$, —$P(=O)T^2T^3$, —$P(=S)T^2T^3$, an alkali metal atom, an alkaline earth metal atom, or $NHT^4T^5T^6$;

provided that, when Q is a 2-thiazolyl group, then B is a $C_1$–$C_4$ alkyl group, $C_1$–$C_4$ haloalkyl group, a $C_2$–$C_4$ alkoxyalkyl group, $CH_3SCH_2$, $CH_3OC_2H_4OCH_2$, a $C_1$–$C_4$ alkyl group substituted by a phenyl group optionally substituted by a halogen or a $C_1$–$C_4$ alkyl group, a $C_1$–$C_4$ alkyl group substituted by a benzoyl group optionally substituted by a halogen or a $C_1$–$C_4$ alkyl group, a tetrahydropyranyl group, $(CH_3)_3Si$, a $C_1$–$C_4$ alkylsulfonyl group, a phenylsulfonyl group optionally substituted by a halogen or a $C_1$–$C_4$ alkyl group, —$SO_2CF_3$, a $C_1$–$C_4$ monoalkylaminosulfonyl group, a $C_2$–$C_8$ dialkylaminosulfonyl group, a phenylaminosulfonyl group, a $C_2$–$C_5$ monoalkylaminothiocarbonyl group, a $C_3$–$C_9$ dialkylaminothiocarbonyl group, a $C_2$–$C_5$ cyanoalkyl group, a $C_3$–$C_9$ alkoxycarbonylalkyl group, —$C(=O)T^1$, —$P(=O)T^2T^3$, or —$P(=S)T^2T^3$;

E represents CN;

R is a substituent selected from the group consisting of a halogen atom, a $C_1$–$C_{10}$ alkyl group, a $C_1$–$C_4$ alkyl group substituted by a phenyl group optionally substituted by a halogen or a $C_1$–$C_4$ alkyl group, a $C_2$–$C_6$ alkenyl group, a $C_2$–$C_6$ alkynyl group, a $C_1$–$C_6$ haloalkyl group, a $C_2$–$C_6$ haloalkenyl group, a $C_2$–$C_6$ haloalkynyl group, a $C_3$–$C_6$ halocycloalkyl group, a $C_3$–$C_6$ cycloalkyl group optionally substituted by a $C_1$–$C_3$ alkyl group, a $C_1$–$C_6$ alkoxy group, a $C_2$–$C_6$ alkenyloxy group, a $C_2$–$C_6$ alkynyloxy group, a $C_1$–$C_4$ haloalkoxy group, a $C_2$–$C_6$ haloalkenyloxy group, a $C_2$–$C_6$ haloalkynyloxy group, a $C_1$–$C_4$ alkylsulfenyl group, a $C_1$–$C_4$ alkylsulfinyl group, a $C_1$–$C_4$ alkylsulfonyl group, a $C_2$–$C_6$ alkenylsulfenyl group, a $C_2$–$C_6$ alkenylsulfinyl group, a $C_2$–$C_6$ alkenylsulfonyl group, a $C_2$–$C_6$ alkynylsulfenyl group, a $C_2$–$C_6$ alkynylsulfinyl group, a $C_2$–$C_6$ alkynylsulfonyl group, a $C_1$–$C_4$ haloalkylsulfenyl group, a $C_1$–$C_4$ haloalkylsulfinyl group, a $C_1$–$C_4$ haloalkylsulfonyl group, a $C_2$–$C_6$ haloalkenylsulfenyl group, a $C_2$–$C_6$ haloalkenylsulfinyl group, a $C_2$–$C_6$ haloalkenylsulfonyl group, a $C_2$–$C_6$ haloalkynylsulfenyl group, a $C_2$–$C_6$ haloalkynylsulfinyl group, a $C_2$–$C_6$ haloallynylsulfonyl group, $NO_2$, CN, —$NU^1U^2$, a phenoxy group, OH, a naphthyl group, a $C_2$–$C_7$ alkoxycarbonyl group, a $C_2$–$C_4$ alkoxyalkyl group, a $C_2$–$C_4$ alkylcarbonyl group, a $C_2$–$C_5$ alkylcarbonyloxy group, a $C_2$–$C_5$ haloalkylcarbonyloxy group, a benzoyl group optionally substituted by X, a phenyl group optionally substituted by X, a pyridyl group optionally substituted by X, a thienyl group optionally substituted by X, and —$N=CT^7T^8$, provided that when the substituent is two or more, then said substituents may be the same or different, and the number of the substituient, R, is 1, 2, 3 or 4, or R is an alkylene group as bonded to the adjacent substituting positions to form a 5-, 6-, 7- or 8-membered ring;

Y is a substituent selected from the group consisting of a halogen atom, a $C_1$–$C_{10}$ alkyl group, a $C_1$–$C_6$ haloalkyl group, a $C_1$–$C_6$ alkoxy group, a $C_2$–$C_6$ alkenyloxy group, a $C_2$–$C_6$ alkynyloxy group, a $C_1$–$C_4$ haloalkoxy group, a $C_2$–$C_6$ haloalkenyloxy group, a $C_2$–$C_6$ haloalkynyloxy group, a $C_1$–$C_4$ alkylsulfenyl group, a $C_1$–$C_4$ alkylsulfinyl group, a $C_1$–$C_4$ alkylsulfonyl group, a $C_2$–$C_6$ alkenylsulfenyl group, a $C_2$–$C_6$ alkenylsulfinyl group, a $C_2$–$C_6$ alkenylsulfonyl group, a $C_2$–$C_6$ alkynylsulfenyl group, a $C_2$–$C_6$ alkynylsulfinyl group, a $C_2$–$C_6$ alkynylsulfonyl group, a $C_1$–$C_4$ haloalkylsulfenyl group, a $C_1$–$C_4$ haloalkylsulfinyl group, a $C_1$–$C_4$ haloalkylsulfonyl group, a $C_2$–$C_6$ haloalkenylsulfenyl group, a $C_2$–$C_6$ haloalkenylsulfinyl group, a $C_2$–$C_6$ haloalkenylsulfonyl group, a $C_2$–$C_6$ haloalkynylsulfenyl group, a $C_2$–$C_6$ haloalkynylsulfinyl group, a $C_2$–$C_6$ haloalkynylsulfonyl group, $NO_2$, CN, —$NU^1U^2$, OH, a $C_2$–$C_7$ alkoxycarbonyl group, a $C_2$–$C_4$ alkoxyalkyl group, a $C_2$–$C_5$ alkylcarbonyloxy group, a $C_2$–$C_5$ haloalkylcarbonyloxy group, a $C_3$–$C_7$ dialkylaminocarbonyloxy group, a phenyl group optionally substituted by X, and —N=$CT^7T^8$, provided that when the substituent is two or more, then said substituents may be the same or different, and the number of the substituent, Y, is 1, 2, 3 or 4, or Y is an alkylene group as bonded to the adjacent substituting positions to form a 5-, 6-, 7- or 8-membered ring;

W is a substituent selected from the group consisting of a halogen atom, a $C_1$–$C_6$ alkyl group, a $C_1$–$C_4$ haloalkyl group, a $C_1$–$C_4$ alkoxy group, a $C_1$–$C_4$ haloalkoxy group, a $C_1$–$C_4$ alkylsulfenyl group, a $C_1$–$C_4$ alkylsulfinyl group, a $C_1$–$C_4$ alkylsulfonyl group, a $C_1$–$C_4$ haloalkylsulfenyl group, a $C_1$–$C_4$ haloalkylsulfinyl group, a $C_1$–$C_4$ haloalkylsulfonyl group, a $C_2$–$C_4$ alkenyl group, a $C_2$–$C_4$ haloalkenyl group, a $C_2$–$C_4$ alkenyloxy group, a $C_2$–$C_4$ haloalkenyloxy group, a $C_2$–$C_4$ alkenylsulfenyl group, a $C_2$–$C_4$ alkenylsulfinyl group, a $C_2$–$C_4$ alkenylsulfonyl group, a $C_2$–$C_4$ haloalkenylsulfenyl group, a $C_2$–$C_4$ haloalkenylsulfinyl group, a $C_2$–$C_4$ haloalkenylsulfonyl group, a $C_2$–$C_4$ alkynyl group, a $C_2$–$C_4$ haloalkynyl group, a $C_2$–$C_4$ alkynyloxy group, a $C_2$–$C_4$ haloalkynyloxy group, a $C_2$–$C_4$ alkynylsulfenyl group, a $C_2$–$C_4$ alkynylsulfinyl group, a $C_2$–$C_4$ alkynylsulfonyl group, a $C_2$–$C_4$ haloalkynylsulfenyl group, a $C_2$–$C_4$ haloalkynylsulfinyl group, a $C_2$–$C_4$ haloalkynylsulfonyl group, $NO_2$, CN, a formyl group, a $C_2$–$C_6$ alkoxycarbonyl group, a $C_2$–$C_6$ alkylcarbonyl group, a $C_2$–$C_6$ haloalkylcarbonyl group, a $C_2$–$C_6$ alkylcarbonyloxy group, and —$NU^1U^2$, provided that when the substituent is two or more, then said substituents may be the same or different, and the number of the substituent, W, is 1, 2, 3 or 4;

$T^1$ represents a $C_1$–$C_{20}$ alkyl group, a $C_2$–$C_6$ alkenyl group, a $C_1$–$C_6$ haloalkyl group, a $C_1$–$C_4$ alkoxy-$C_1$–$C_4$ alkyl group, a $C_3$–$C_6$ halocycloalkyl group, a $C_1$–$C_4$ alkyl group substituted by a phenyl group optionally substituted by a halogen or a $C_1$–$C_4$ alkyl group, a $C_3$–$C_6$ cycloalkyl group optionally substituted by a $C_1$–$C_3$ alkyl group, a cycloalkyl group substituted by a phenyl group optionally substituted by a halogen or a $C_1$–$C_4$ alkyl group, a cyclopropyl group substituted by both a phenyl group optionally substituted by a halogen or a $C_1$–$C_4$ alkyl group and a $C_1$–$C_4$ alkyl group, a $C_3$–$C_4$ cycloalkyl group substituted by both a phenyl group optionally substituted by a halogen or a $C_1$–$C_4$ alkoxy group and a halogen, a cyclopropyl group substituted by both a $C_2$–$C_4$ alkenyl group optionally substituted by a halogen and a $C_1$–$C_4$ alkyl group, a $C_2$–$C_4$ alkenyl group substituted by a phenyl group optionally substituted by a halogen or a $C_1$–$C_4$ alkyl group, a $C_1$–$C_{12}$ alkoxy group, a $C_1$–$C_4$ haloalkoxy group, a $C_2$–$C_5$ alkenyloxy group, a $C_3$–$C_6$ cycloalkoxy group optionally substituted by a $C_1$–$C_3$ alkyl group, a benzyloxy group, a $C_2$–$C_5$ alkoxycarbonyl group, —$NU^1U^2$, a phenylamino group, a phenyl group optionally substituted by Z, a phenoxy group optionally substituted by Z, a phenylthio group optionally substituted by Z, a naphthyl group optionally substituted by Z, or a 5-membered or 6-membered heterocyclic group optionally substituted by Z wherein said heterocyclic group is selected from the group consisting of a thienyl, furyl, pyrrolyl, oxazolyl, isoxazolyl, thiazolyl, isothiazolyl, pyrazolyl, imidazolyl, 1,3,4-oxadiazolyl, 1,2,4-oxadiazolyl, 1,3,4-thiadiazolyl, 1,2,4-thiadiazolyl, 1,2,3-thiadiazolyl, 1,2,4-triazolyl, 1,2,3-triazolyl, 1,2,3,4-tetrazolyl, pyridinyl, pyrimidinyl, pyrazinyl, pyridazinyl, 1,3,5-triazinyl, 1,2,4-triazinyl, pyrazolinyl, imidazolinyl, oxazolinyl, isoxazolinyl, thiazolinyl, and 3(2H)-pyridazinone groups;

$T^2$ and $T^3$ each independently represent OH, a phenyl, a $C_1$–$C_6$ alkyl group, a $C_1$–$C_6$ alkoxy group, or a $C_1$–$C_4$ alkylsulfenyl group;

$T^4$, $T^5$ and $T^6$ each independently represent H, a $C_1$–$C_6$ alkyl group, a $C_1$–$C_6$ alkenyl group, a $C_3$–$C_6$ cycloalkyl group optionally substituted by a $C_1$–$C_3$ alkyl group, or a benzyl group; or any two of $T^4$, $T^5$ and $T^6$ may form , together with the nitrogen atom to which they are bonded, a 5-, 6-, 7- or 8-membered cyclic group optionally containing oxygen, nitrogen and/or sulfur atoms;

X and Z are independently substituents selected from the group consisting of a halogen atom, a $C_1$–$C_4$ alkyl group, a $C_1$–$C_4$ haloalkyl group, a $C_1$–$C_4$ alkoxy group, a $C_1$–$C_4$ haloalkoxy group, a $C_1$–$C_4$ alkylsulfenyl group, a $C_1$–$C_4$ alkylsulfinyl group, a $C_1$–$C_4$ alkylsulfonyl group, a $C_2$–$C_5$ alkenylsulfenyl group, a $C_2$–$C_5$ alkenylsulfinyl group, a $C_2$–$C_5$ alkenylsulfonyl group, a $C_1$–$C_4$ haloalkylsulfenyl group, a $C_1$–$C_4$ haloalkylsulfinyl group, a $C_1$–$C_4$ haloalkylsulfonyl group, $NO_2$, CN, CHO, OH, —$NU^1U^2$, a phenyl group, a phenoxy group, and a $C_2$–$C_5$ alkoxycarbonyl group, provided that when the substituent is two or more, then said substituents may be the same or different, and the number of the substituent, X and Z, is 1,2,3, 4 or 5 each;

$T^7$ and $T^8$ each independently represent H, or a phenyl, benzyl, or a $C_1$–$C_6$ alkyl group, or $T^7$ and $T^8$ may, together with the carbon atom to which they are bonded, form a 5-, 6-, 7-, or 8-membered ring;

$U^1$ and $U^2$ each independently represent H, a $C_1$–$C_6$ alkyl, a $C_2$–$C_6$ alkylcarbonyl, phenyl or benzyl group, or $U^1$ and $U^2$ may, together with the nitrogen atom to which they are bonded, form a 5-, 6-, 7-, or 8-membered ring.

2. A compound as claimed in claim 1, wherein:

A represents a phenyl group optionally substituted by W, a naphthyl group optionally substituted by W, or a heterocyclic group optionally substituted by Y, wherein said heterocyclic group is selected from the group consisting of a thienyl, furyl, pyrrolyl, oxazolyl, isoxazolyl, thiazolyl, isothiazolyl, pyrazolyl, imidazolyl, 1,3,4-oxadiazolyl, 1,2,4-oxadiazolyl, 1,3,4-thiadiazolyl, 1,2,4-thiadiazolyl, 1,2,3-thiadiazolyl, 1,2, 4-triazolyl, 1,2,3-triazolyl, 1,2,3,4-tetrazolyl, pyridinyl, pyrimidinyl, pyrazinyl, pyridazinyl, 1,3,5-triazinyl, 1,2,4-triazinyl, pyrazolinyl, and imidazolinyl groups;

B represents H, a $C_1$–$C_4$ alkyl group, a $C_1$–$C_4$ haloalkyl group, a $C_2$–$C_4$ alkoxyalkyl group, $CH_3OC_2H_4OCH_2$, a $C_1$–$C_4$ alkylsulfonyl group, a phenylsulfonyl group optionally substituted by a halogen or a $C_1$–$C_4$ alkyl group, —$SO_2CF_3$, a $C_2$–$C_8$ dialkylaminosulfonyl group, a $C_2$–$C_9$ dialkylaminothiocarbonyl group, a $C_3$–$C_9$ alkoxycarbonylalkyl group, —C(=O)$T^1$, —P(=O)$T^2T^3$, —P(=S)$T^2T^3$, an alkali metal atom, an alkaline earth metal atom, or $NHT^4T^5T^6$; and $T^1$ represents a $C_1$–$C_{20}$ alkyl group, a $C_2$–$C_6$ alkenyl group, a $C_1$–$C_4$ haloalkyl group, a $C_1$–$C_4$ alkoxy-$C_1$–$C_4$ alkyl group, a $C_1$–$C_4$ alkyl group substituted by a phenyl group optionally substituted by a halogen or a $C_1$–$C_4$ alkyl group, a $C_3$–$C_6$ halocycloalkyl group, a $C_3$–$C_6$ cycloalkyl group optionally substituted by a $C_1$–$C_3$ alkyl group, a cycloalkyl group substituted by a phenyl group optionally substituted by a halogen or a $C_1$–$C_4$ alkyl group, a cyclopropyl group substituted-by both a phenyl group optionally substituted by a halogen or a $C_1$–$C_4$ alkyl group and a $C_1$–$C_4$ alkyl group, a $C_3$–$C_4$ cycloalkyl group substituted by both a phenyl group optionally substituted by a halogen or a $C_1$–$C_4$ alkoxy group and a halogen, a cyclopropyl group substituted by both a $C_2$–$C_4$ alkenyl group optionally substituted by a halogen and a $C_1$–$C_4$ alkyl group, a $C_2$–$C_4$ alkenyl group substituted by a phenyl group optionally substituted by a halogen or a $C_1$–$C_4$ alkyl group, a $C_1$–$C_{12}$ alkoxy group, a $C_1$–$C_4$ haloalkoxy group, a $C_2$–$C_5$ alkenyloxy group, a $C_3$–$C_6$ cycloalkoxy group optionally substituted by a $C_1$–$C_3$ alkyl group, a benzyloxy group, a $C_2$–$C_5$ alkoxycarbonyl group, a phenyl group optionally substituted by Z, a phenoxy group optionally substituted by Z, a phenylthio group, a naphthyl group, or a heterocyclic group optionally substituted by Z wherein said heterocyclic group is selected from the group consisting of a thienyl, furyl, oxazolyl, thiazolyl, pyrazolyl, and pyridinyl groups.

3. Ethylene derivatives as claimed in claim 2,
wherein Q is a heterocyclic group optionally substituted by R, said heterocyclic group being

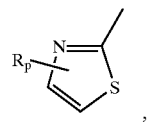
Q-12

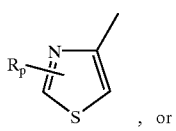
Q-13
, or

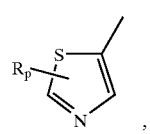
Q-14

A is a phenyl group optionally substituted by W, a naphthyl group optionally substituted by W, or a heterocyclic group optionally substituted by Y, said heterocyclic group being

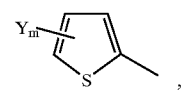
A-1

A-2

A-3

A-4

A-5

A-6

A-7

A-8

A-9

A-10

A-11

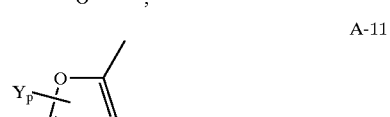
A-12

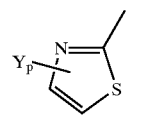

-continued
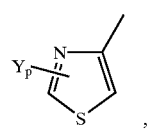 A-13
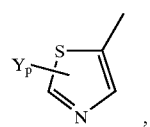 A-14
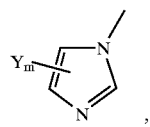 A-15
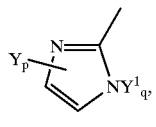 A-16
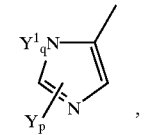 A-17
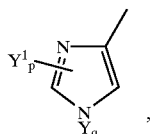 A-18
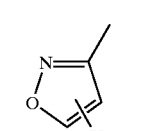 A-19
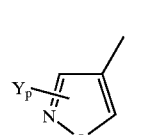 A-20
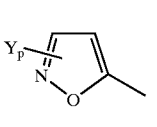 A-21
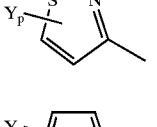 A-22
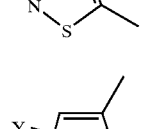 A-23
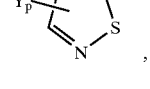 A-24
-continued
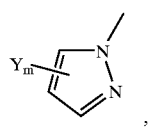 A-25
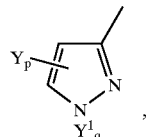 A-26
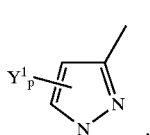 A-27
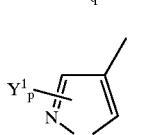 A-28
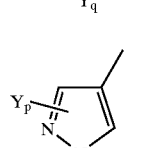 A-29
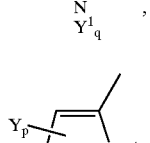 A-30
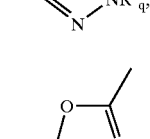 A-31
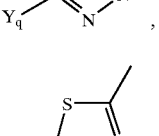 A-32
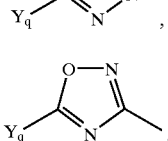 A-33
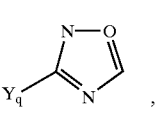 A-34
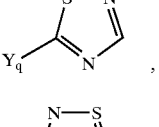 A-35
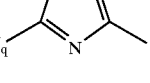 A-36

-continued
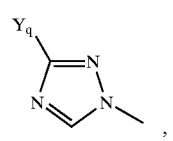, A-37
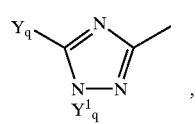, A-38
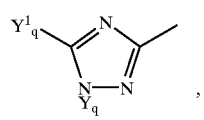, A-39
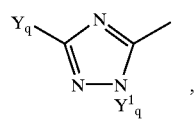, A-40
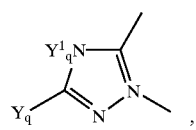, A-41
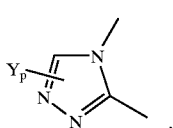, A-42
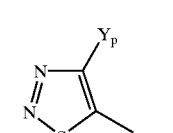, A-43
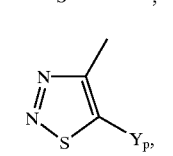, A-44
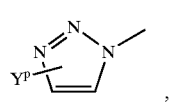, A-45
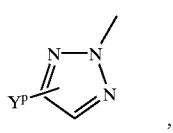, A-46
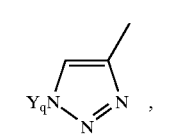, A-47
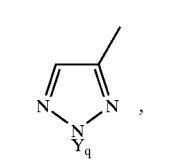, A-48
-continued
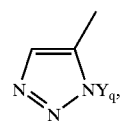, A-49
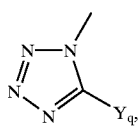, A-50
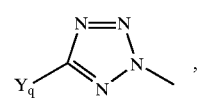, A-51
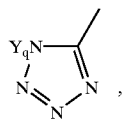, A-52
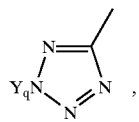, A-53
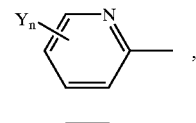, A-54
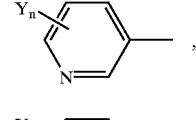, A-55
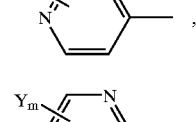, A-56
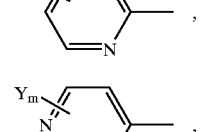, A-57
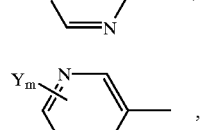, A-58
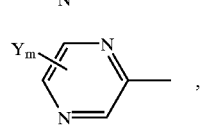, A-59
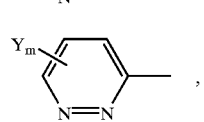, A-60
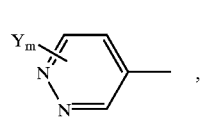, A-61
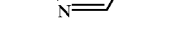, A-62

-continued

A-63 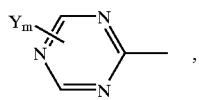

A-64 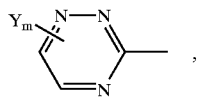

A-65 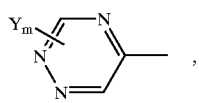

A-66 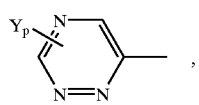

A-67 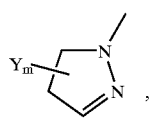

A-68 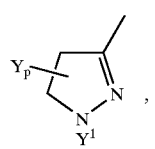

A-69 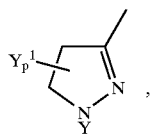

A-70 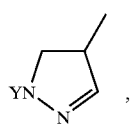

A-71 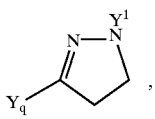

A-72 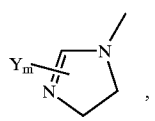

A-73 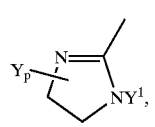

A-74 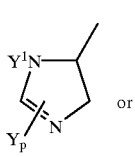 or

-continued

A-75 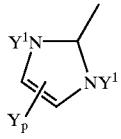

provided that, when Q is Q-12, then A is a naphthyl group optionally substituted by W, or a heterocyclic group optionally substituted by Y, (said heterocyclic group being any of A-1, A-2, A-3, A-4, A-5, A-6, A-7, A-8, A-9, A-10, A-11, A-12, A-13, A-14, A-15, A-16, A-17, A-18, A-19, A-20, A-21, A-22, A-23, A-24, A-25, A-26, A-27, A-28, A-29, A-30, A-31, A-32, A-33, A-34, A-35, A-36, A-37, A-38, A-39, A-40, A-41, A-42, A-43, A-44, A-45, A-46, A-47, A-48, A-49, A-50, A-51, A-52, A-53, A-54, A-55, A-56, A-57, A-58, A-59, A-60, A-61, A-62, A-63, A-64, A-65, A-66, A-67, A-68, A-69, A-70, A-71, A-72, A-73, A-74 or A-75), $R^1$ is selected from a halogen atom, a $C_1$–$C_{10}$ alkyl group, a $C_2$–$C_6$ alkenyl group, a $C_2$–$C_6$ alkynyl group, a $C_1$–$C_6$ haloalkyl group, a $C_1$–$C_6$ alkoxy group, a $C_2$–$C_6$ alkenyloxy group, $NO_2$, CN, —$NU^1U^2$, OH, a $C_2$–$C_7$ alkoxycarbonyl group, a $C_2$–$C_4$ alkoxyalkyl group, a $C_2$–$C_4$ alkylcarbonyl group, a phenyl group optionally substituted by X, a pyridyl group optionally substituted by X, a thienyl group optionally substituted by X, and —N=$CT^7T^8$; or may, together with the adjacent R, form a 5-, 6-, 7- or 8-membered ring as an alkylene group;

$Y^1$ is selected from a halogen atom, a $C_1$–$C_{10}$ alkyl group, a $C_1$–$C_6$ haloalkyl group, a $C_1$–$C_6$ alkoxy group, a $C_2$–$C_6$ alkenyloxy group, $NO_2$, CN, —$NU^1U^2$, OH, a $C_2$–$C_7$ alkoxycarbonyl group, a $C_2$–$C_4$ alkoxyalkyl group, a phenyl group optionally substituted by X, and —N=$CT^7T^8$; or may, together with the adjacent $Y^1$, form a 5-, 6-, 7- or 8-membered ring as an alkylene group;

X is a substituent of which the number is from 1 to 4 and which is freely selected from a halogen atom, a $C_1$–$C_4$ alkyl group, a $C_1$–$C_4$ haloalkyl group, a $C_1$–$C_4$ alkoxy group, a $C_1$–$C_4$ haloalkoxy group, a $C_1$–$C_4$ alkylsulfenyl group, a $C_1$–$C_4$ alkylsulfinyl group, a $C_1$–$C_4$ alkylsulfonyl group, a $C_2$–$C_5$ alkylsulfenyl group, a $C_2$–$C_5$ alkylsulfinyl group, a $C_2$–$C_5$ alkenylsulfonyl group, a $C_1$–$C_4$ haloalkylsulfenyl group, a $C_1$–$C_4$ haloalkylsulfinyl group, a $C_1$–$C_4$ haloalkylsulfonyl group, $NO_2$, CN, CHO, OH, —$NU^1U^2$, a phenyl group, a phenoxy group, and a $C_2$–$C_5$ alkoxycarbonyl group, (provided that when the substituent is two or more then said substituents may be the same or different);

Z is a substituent of which the number is from 1 to 4 and which is freely selected from a halogen atom, a $C_1$–$C_4$ alkyl group, a $C_1$–$C_4$ haloalkyl group, a $C_1$–$C_4$ alkoxy group, a $C_1$–$C_4$ haloalkoxy group, a $C_1$–$C_4$ alkylsulfenyl group, a $C_1$–$C_4$ alkylsulfinyl group, a $C_1$–$C_4$ alkylsulfonyl group, a $C_1$–$C_4$ alkenylsulfenyl group, a $C_1$–$C_4$ alkenylsulfinyl group, a $C_1$–$C_4$ alkenylsulfonyl group, $NO_2$, CN, —$NU^1U^2$, a phenyl group, a phenoxy group, and a $C_2$–$C_5$ alkoxycarbonyl group, (provided that when the substituent is two or more, then said substituents may be the same or different);

m indicates the number of the substituents, and is 0, 1, 2 or 3;

n indicates the number of the substituents, and is 0, 1, 2, 3, or 4;

p indicates the number of the substituents, and is 0, 1 or 2;

q indicates the number of the substituents, and is 0 or 1;

(provided that when m, n and p each are an integer of 2 or more, the substituents may be the same or different).

4. A compound as claimed in claim 2, wherein A represents a phenyl group optionally substituted by W, a thiazolyl group optionally substituted by Y, a pyrazolyl group optionally substituted by Y, a pyridinyl group optionally substituted by Y, or a pyrimidinyl group optionally substituted by Y.

5. Ethylene derivatives as claimed in claim 3, wherein Q is

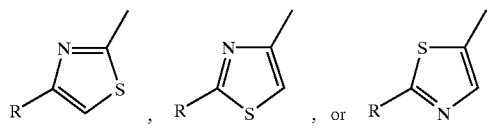

A is

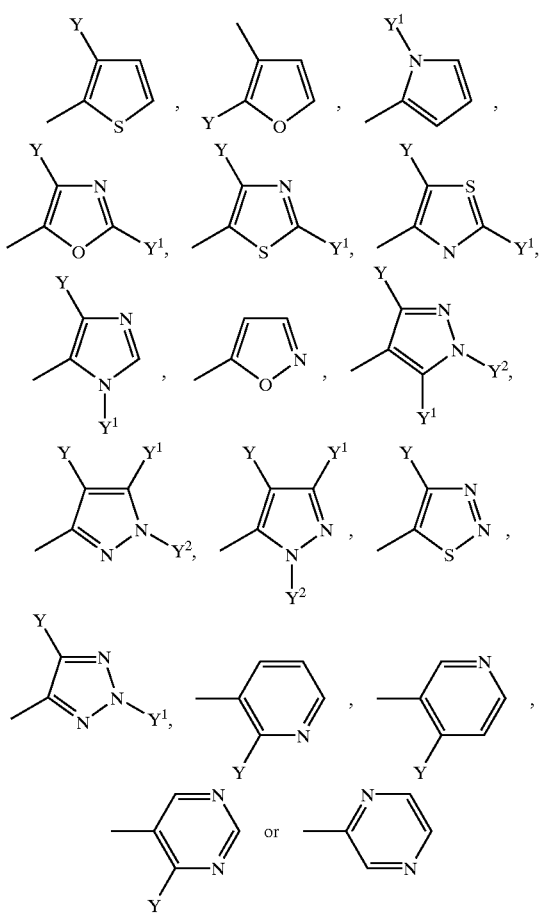

$Y^2$ is a halogen atom, a $C_1-C_4$ alkyl group, a $C_1-C_4$ a haloalkyl group, a $C_1-C_4$ alkoxy group, $NO_2$, CN, or a $C_2-C_5$ alkoxycarbonyl group; and $Y^3$ is a halogen atom, a $C_1-C_4$ alkyl group, a $C_1-C_6$ haloalkyl group, a $C_2-C_4$ alkoxyalkyl group, or a phenyl group optionally substituted by X.

6. A compound as claimed in claim 1, wherein the thiazolyl group of Q is selected from the group consisting of thiazol-2-yl, thiazol-4-yl, or thiazol-5-yl.

7. A compound as claimed in claim 1, wherein A is selected from the group consisting of a phenyl group optionally substituted by W and a heterocyclic group optionally substituted by Y, wherein the heterocyclic group is selected from the group consisting of a thienyl group, a furyl group, a pyrrolyl group, an oxazolyl group, an isoxazolyl group, a thiazolyl group, an isothiazolyl group, a pyrazolyl group, an imidazolyl group, a 1,3,4-oxadiazolyl group, a 1,2,4-oxadiazolyl group, a 1,3,4-thiadiazolyl group, a 1,2,4-thiadiazolyl group, a 1,2,3-thiadiazolyl group, a 1,2,4-triazolyl group, a 1,2,3-triazolyl group, a 1,2,3,4-tetrazolyl group, a pyridinyl group, a pyrimidinyl group, a pyrazinyl group, a pyridazinyl group, a 1,3,5-triazinyl group, and a 1,2,4-triazinyl group.

8. A compound as claimed in claim 1, wherein A is selected from the group consisting of a phenyl group optionally substituted by W and a heterocyclic group optionally substituted by Y, wherein the heterocyclic group is selected from the group consisting of a thienyl group, a furyl group, a pyrrolyl group, an oxazolyl group, an isoxazolyl group, a thiazolyl group, a pyrazolyl group, an imidazolyl group, 1,2,3-thiadiazolyl group, a 1,2,3-triazolyl group, a pyridinyl group, a pyrimidinyl group, a pyrazinyl group, and a pyridazinyl group.

9. A compound as claimed in claim 1, wherein A is selected from the group consisting of a phenyl group optionally substituted by W, a thiazolyl group optionally substituted by Y, a pyrazolyl group optionally substituted by Y, a pyridinyl group optionally substituted by Y, and a pyrimidinyl group optionally substituted by Y.

10. A compound as claimed in claim 1 wherein A is selected from the group consisting of a thiazolyl group optionally substituted by Y, a pyrazolyl group optionally substituted by Y, and a pyridinyl group optionally substituted by Y.

11. A compound as claimed in claim 1, wherein A is a thiazolyl group optionally substituted by Y.

12. A compound as claimed in claim 1, wherein A is a pyrazolyl group optionally substituted by Y.

13. A compound as claimed in claim 1, wherein A is a pyridinyl group optionally substituted by Y.

14. A compound as claimed in claim 1, wherein B is selected from the group consisting of H, a $C_1-C_4$ alkyl group, a $C_1-C_4$ haloalkyl group, a $C_2-C_4$ alkoxyalkyl group, $CH_3OC_2H_4OCH_2$, a $C_1-C_4$ alkylsulfonyl group, a phenylsulfonyl group optionally substituted by a halogen or a $C_1-C_4$ alkyl group, —$SO_2CF_3$, a $C_2-C_8$ dialkylaminosulfonyl group, a $C_3-C_9$ dialkylaminothiocarbonyl group, a $C_3-C_9$ alkoxycarbonylalkyl group, —C(=O)$T^1$, —P(=O)$T^2T^3$, —P(=S)$T^2T^3$, an alkali metal atom, an alkaline earth metal atom, or NH$T^4T^5T^6$.

15. A compound as claimed in claim 1, wherein B is selected from the group consisting of H, a $C_1-C_4$ alkyl group, a $C_1-C_4$ haloalkyl group, a $C_2-C_4$ alkoxyalkyl group, $CH_3OC_2H_4OCH_2$, a $C_1-C_4$ alkylsulfonyl group, —$SO_2CF_3$, —C(=O)$T^1$, an alkali metal atom, an alkaline earth metal atom, or NH$T^4T^5T^6$.

16. A compound as claimed in claim 1, wherein B is selected from the group consisting of H, a $C_2-C_4$ alkoxyalkyl group, a $C_1-C_4$ alkylsulfonyl group, —$SO_2CF_3$, —C(=O)$T^1$, an alkali metal atom, an alkaline earth metal atom, or NH$T^4T^5T^6$.

17. A compound as claimed in claim 1, wherein B is selected from the group consisting of a $C_2-C_4$ alkoxyalkyl group, a $C_1-C_4$ alkylsulfonyl group, —$SO_2CF_3$, —C(=O)$T^1$, an alkali metal atom, an alkaline earth metal atom, or NH$T^4T^5T^6$.

18. A compound as claimed in claim 1, wherein R is selected from the group consisting of a halogen atom, a $C_1$–$C_6$ alkyl group, a $C_1$–$C_3$ alkyl group substituted by a phenyl group optionally substituted by a halogen or a $C_1$–$C_4$ alkyl group, a $C_1$–$C_6$ haloalkyl group, a $C_3$–$C_6$ cycloalkyl group optionally substituted by a $C_1$–$C_3$ alkyl group, a $C_1$–$C_4$ alkoxy group, a $C_2$–$C_4$ alkenyloxy group, a $C_2$–$C_4$ alkynyloxy group, a $C_1$–$C_4$ haloalkoxy group, a $C_2$–$C_4$ haloalkenyloxy group, a $C_2$–$C_4$ haloalkynyloxy group, a $C_1$–$C_4$ alkylsulfenyl group, a $C_1$–$C_4$ alkylsulfinyl group, a $C_1$–$C_4$ alkylsulfonyl group, a $C_2$–$C_4$ alkenylsulfenyl group, a $C_2$–$C_4$ alkenylsulfinyl group, a $C_2$–$C_4$ alkenylsulfonyl group, a $C_2$–$C_4$ alkynylsulfenyl group, a $C_2$–$C_4$ alkynylsulfinyl group, a $C_2$–$C_4$ alkynylsulfonyl group, a $C_1$–$C_4$ haloalkylsulfenyl group, a $C_1$–$C_4$ haloalkylsulfinyl group, a $C_1$–$C_4$ haloalkylsulfonyl group, a $C_2$–$C_4$ haloalkenylsulfenyl group, a $C_2$–$C_4$ haloalkenylsulfinyl group, a $C_2$–$C_4$ haloalkenylsulfonyl group, $NO_2$, CN, —$NU^1U^2$, a naphthyl group, a $C_2$–$C_4$ alkoxycarbonyl group, a $C_2$–$C_4$ alkoxyalkyl group, a phenyl group optionally substituted by X, a pyridyl group optionally substituted by X, and a thienyl group optionally substituted by X, provided that when the substituent is two or more, then said substituents may be the same or different, and the number of the substituent, R, is 1, 2 or 3, or R is an alkylene group as bonded to the adjacent substituting positions to form a 5-, 6-, 7- or 8-membered ring.

19. A compound as claimed in claim , wherein R is selected from the group consisting of a halogen atom, a $C_1$–$C_6$ alkyl group, a $C_1$–$C_3$ alkyl group substituted by a phenyl group optionally substituted by a halogen or a $C_1$–$C_4$ alkyl group, a $C_1$–$C_4$ haloalkyl group, a $C_3$–$C_6$ cycloalkyl group optionally substituted by a $C_1$–$C_3$ alkyl group, $NO_2$, CN, —$NU^1U^2$, a naphthyl group, a $C_2$–$C_4$ alkoxycarbonyl group, a $C_2$–$C_4$ alkoxyalkyl group, a phenyl group optionally substituted by X, and a pyridyl group optionally substituted by X, provided that when the substituent is two or more, then said substituents may be the same or different, and the number of the substituent, R, is 1, 2 or 3.

20. A compound as claimed in claim 1, wherein R is selected from the group consisting of a halogen atom, a $C_1$–$C_6$ alkyl group, a $C_1$–$C_3$ alkyl group substituted by a phenyl group optionally substituted by a halogen or a $C_1$–$C_4$ alkyl group, a $C_1$–$C_4$ haloalkyl group, a $C_3$–$C_6$ cycloalkyl group optionally substituted by a $C_1$–$C_3$ alkyl group, $NO_2$, CN, —$NU^1U^2$, a naphthyl group, a $C_2$–$C_4$ alkoxycarbonyl group, a phenyl group optionally substituted by X, and a pyridyl group optionally substituted by X, provided that when the substituent is two or more, then said substituents may be the same or different, and the number of the substituent, R, is 1 or 2.

21. A compound as claimed in claim 1, wherein Y is selected from the group consisting of a halogen atom, a $C_1$–$C_6$ alkyl group, a $C_1$–$C_4$ haloalkyl group, a $C_1$–$C_4$ alkoxy group, a $C_2$–$C_4$ alkenyloxy group, a $C_2$–$C_4$ alkynyloxy group, a $C_1$–$C_4$ haloalkoxy group, a $C_2$–$C_4$ haloalkenyloxy group, a $C_2$–$C_4$ haloalkynyloxy group, a $C_1$–$C_4$ alkylsulfenyl group, a $C_1$–$C_4$ alkylsulfinyl group, a $C_1$–$C_4$ alkylsulfonyl group, a $C_2$–$C_4$ alkenylsulfenyl group, a $C_2$–$C_4$ alkenylsulfinyl group, a $C_2$–$C_4$ alkenylsulfonyl group, a $C_2$–$C_4$ alkynylsulfenyl group, a $C_2$–$C_4$ alkynylsulfinyl group, a $C_2$–$C_4$ alkynylsulfonyl group, a $C_1$–$C_4$ haloalkylsulfenyl group, a $C_1$–$C_4$ haloalkylsulfinyl group, a $C_1$–$C_4$ haloalkylsulfonyl group, a $C_2$–$C_4$ haloalkenylsulfenyl group, a $C_2$–$C_4$ haloalkenylsulfinyl group, a $C_2$–$C_4$ haloalkenylsulfonyl group, a $C_2$–$C_4$ haloalkynylsulfenyl group, a $C_2$–$C_4$ haloalkynylsulfinyl group, a $C_2$–$C_4$ haloalkynylsulfonyl group, $NO_2$, CN, —$NU^1U^2$, a $C_2$–$C_4$ alkoxycarbonyl group, a $C_2$–$C_4$ alkoxyalkyl group, a $C_2$–$C_4$ alkylcarbonyloxy group, a $C_2$–$C_4$ haloalkylcarbonyloxy group, and a phenyl group optionally substituted by X, provided that when the substituent is two or more, then said substituents may be the same or different, and the number of the substituent, Y, is 1, 2, or 3.

22. A compound as claimed in claim 1, wherein Y is selected from the group consisting of a halogen atom, a $C_1$–$C_4$ alkyl group, a $C_1$–$C_4$ haloalkyl group, a $C_1$–$C_4$ alkoxy group, a $C_1$–$C_4$ alkylsulfenyl group, a $C_1$–$C_4$ alkylsulfinyl group, a $C_1$–$C_4$ alkylsulfonyl group, a $C_1$–$C_4$ haloalkylsulfenyl group, a $C_1$–$C_4$ haloalkylsulfinyl group, a $C_1$–$C_4$ haloalkylsulfonyl group, $NO_2$, CN, a $C_2$–$C_4$ alkoxycarbonyl group, and a phenyl group optionally substituted by X, provided that when the substituent is two or more, then said substituents may be the same or different, and the number of the substituent, Y, is 1, 2, or 3.

23. A compound as claimed in claim 1, wherein $T^1$ is selected from the group consisting of a $C_1$–$C_{18}$ alkyl group, a $C_2$–$C_6$ alkenyl group, a $C_1$–$C_4$ haloalkyl group, a $C_1$–$C_4$ alkoxy-$C_1$–$C_4$ alkyl group, a $C_1$–$C_4$ alkyl group substituted by a phenyl group optionally substituted by a halogen or a $C_1$–$C_4$ alkyl group, a $C_3$–$C_6$ halocycloalkyl group, a $C_3$–$C_6$ cycloalkyl group optionally substituted by a $C_1$–$C_3$ alkyl group, a cycloalkyl group substituted by a phenyl group optionally substituted by a halogen or a $C_1$–$C_4$ alkyl group, a $C_2$–$C_4$ alkenyl group substituted by a phenyl group optionally substituted by a halogen or a $C_1$–$C_4$ alkyl group, a $C_1$–$C_{10}$ alkoxy group, a $C_1$–$C_4$ haloalkoxy group, a $C_2$–$C_5$ alkenyloxy group, a $C_3$–$C_6$ cycloalkoxy group optionally substituted by a $C_1$–$C_3$ alkyl group, a benzyloxy group, a $C_2$–$C_5$ alkoxycarbonyl group, —$NU^1U^2$, a phenyl group optionally substituted by Z, a phenoxy group optionally substituted by Z, a phenylthio group optionally substituted by Z, a naphthyl group, and a heterocyclic group optionally substituted by Z wherein said heterocyclic group is selected from the group consisting of a thienyl, furyl, pyrrolyl, oxazolyl, isoxazolyl, thiazolyl, pyrazolyl, imidazolyl, 1,3,4-oxadiazolyl, 1,2,4-oxadiazolyl, 1,3,4-thiadiazolyl, 1,2,4-thiadiazolyl, 1,2,3-thiadiazolyl, 1,2,4-triazolyl, 1,2,3-triazolyl, 1,2,3,4-tetrazolyl, pyridinyl, pyrimidinyl, pyrazinyl, pyridazinyl, 1,3,5-triazinyl, and 1,2,4-triazinyl groups.

24. A compound as claimed in claim 1, wherein $T^1$ is selected from the group consisting of a $C_1$–$C_{18}$ alkyl group, a $C_2$–$C_6$ alkenyl group, a $C_1$–$C_4$ haloalkyl group, a $C_2$–$C_4$ alkoxyalkyl group, a $C_1$–$C_4$ alkyl group substituted by a phenyl group optionally substituted by a halogen or a $C_1$–$C_4$ alkyl group, a $C_3$–$C_6$ cycloalkyl group optionally substituted by a $C_1$–$C_3$ alkyl group, a cycloalkyl group substituted by a phenyl group optionally substituted by a halogen or a $C_1$–$C_4$ alkyl group, a $C_2$–$C_4$ alkenyl group substituted by a phenyl group optionally substituted by a halogen or a $C_1$–$C_4$ alkyl group, a $C_1$–$C_{10}$ alkoxy group, a $C_1$–$C_4$ haloalkoxy group, a $C_2$–$C_5$ alkenyloxy group, a $C_3$–$C_6$ cycloalkoxy group, a benzyloxy group, a $C_2$–$C_5$ alkoxycarbonyl group, a phenyl group optionally substituted by Z, a phenoxy group optionally substituted by Z, a phenylthio group, a naphthyl group, and a heterocyclic group optionally substituted by Z wherein said heterocyclic group is selected from the group consisting of a thienyl, furyl, oxazolyl, thiazolyl, pyrazolyl, and pyridinyl groups.

25. A compound as claimed in claim 1, wherein T¹ is selected from the group consisting of a $C_1$–$C_{17}$ alkyl group, a $C_2$–$C_6$ alkenyl group, a $C_1$–$C_4$ haloalkyl group, a $C_2$–$C_4$ alkoxyalkyl group, a $C_1$–$C_4$ alkyl group substituted by a phenyl group, a $C_3$–$C_6$ cycloalkyl group optionally substituted by a $C_1$–$C_3$ alkyl group, a cycloalkyl group substituted by a phenyl group, a $C_2$–$C_4$ alkenyl group substituted by a phenyl group, a $C_1$–$C_8$ alkoxy group, a $C_1$–$C_4$ haloalkoxy group, a $C_2$–$C_5$ alkenyloxy group, a $C_3$–$C_6$ cycloalkoxy group, a benzyloxy group, a $C_2$–$C_5$ alkoxycarbonyl group, a phenyl group optionally substituted by Z, a phenoxy group optionally substituted by Z, a phenylthio group, a naphthyl group, a pyrazolyl group optionally substituted by Z, and a pyridinyl group optionally substituted by Z.

26. A compound as claimed in claim 2, wherein R is tert-butyl.

27. A compound as claimed in claim 1, wherein Q is

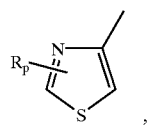

wherein p indicates the number of substituents and is 0, 1 or 2.

28. A compound as claimed in claim 1, wherein B is

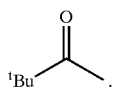

29. A compound as claimed in claim 1, wherein A is

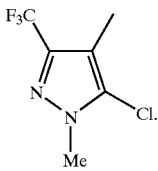

30. A compound as claimed in claim 1, wherein

Q is represented by the following formula:

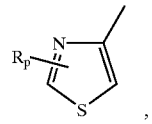

wherein p indicates the number of substituents and is 0, 1 or 2;

R is tert-butyl;

A is represented by the following formula:

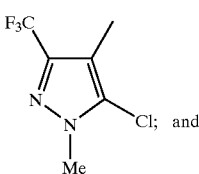

is represented by the following formula:

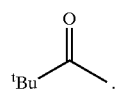

31. A composition comprising a carrier and, as an active ingredient, one or more compounds of claim 1.

32. A method for controlling insects, acari, nematodes, herbs or fungi, comprising applying a composition comprising a carrier and, as an active ingredient, one or more compounds of claim 1.

* * * * *